(12) United States Patent
Muhsin et al.

(10) Patent No.: US 11,901,070 B2
(45) Date of Patent: *Feb. 13, 2024

(54) SYSTEM FOR DISPLAYING MEDICAL MONITORING DATA

(71) Applicant: Masimo Corporation, Irvine, CA (US)

(72) Inventors: Bilal Muhsin, Irvine, CA (US); Massi Joe E. Kiani, Laguna Niguel, CA (US); Peter Scott Housel, Irvine, CA (US); Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/811,994

(22) Filed: Jul. 12, 2022

(65) Prior Publication Data

US 2023/0033122 A1 Feb. 2, 2023

Related U.S. Application Data

(63) Continuation of application No. 15/902,382, filed on Feb. 22, 2018, now Pat. No. 11,417,426.

(Continued)

(51) Int. Cl.
*A61B 5/00* (2006.01)
*G16H 40/63* (2018.01)
(Continued)

(52) U.S. Cl.
CPC ............. *G16H 40/63* (2018.01); *A61B 5/002* (2013.01); *A61B 5/0205* (2013.01); *A61B 5/743* (2013.01);
(Continued)

(58) Field of Classification Search
CPC ....... G16H 40/60; G16H 10/60; A61B 5/7445
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |

(Continued)

FOREIGN PATENT DOCUMENTS

| | | |
|---|---|---|
| CA | 2 994 172 | 2/2017 |
| CN | 102165452 | 8/2011 |

(Continued)

OTHER PUBLICATIONS

US 2022/0192529 A1, 06/2022, Al-Ali et al. (withdrawn)

(Continued)

*Primary Examiner* — Benyam Haile
(74) *Attorney, Agent, or Firm* — Knobbe, Martens, Olson & Bear, LLP

(57) ABSTRACT

A patient monitoring hub can communicate bidirectionally with external devices such as a board-in-cable or a dongle. Medical data can be communicated from the patient monitoring hub to the external devices to cause the external devices to initiate actions. For example, an external device can perform calculations based on data received from the patient monitoring hub, or take other actions (for example, creating a new patient profile, resetting baseline values for algorithms, calibrating algorithms, etc.). The external device can also communicate display characteristics associated with its data to the monitoring hub. The monitoring hub can calculate a set of options for combined layouts corresponding to different external devices or parameters. A display option may be selected for arranging a display screen estate on the monitoring hub.

16 Claims, 113 Drawing Sheets

Related U.S. Application Data

(60) Provisional application No. 62/594,504, filed on Dec. 4, 2017, provisional application No. 62/594,398, filed on Dec. 4, 2017, provisional application No. 62/463,614, filed on Feb. 25, 2017, provisional application No. 62/463,452, filed on Feb. 24, 2017.

(51) Int. Cl.
| | |
|---|---|
| *G16H 40/60* | (2018.01) |
| *A61B 5/0205* | (2006.01) |
| *G06F 21/84* | (2013.01) |
| *G16H 50/30* | (2018.01) |
| *G08B 21/02* | (2006.01) |
| *G16H 10/60* | (2018.01) |
| *A61M 5/14* | (2006.01) |
| *G08B 29/06* | (2006.01) |

(52) U.S. Cl.
CPC .......... *A61B 5/744* (2013.01); *A61B 5/7435* (2013.01); *A61B 5/7445* (2013.01); *G06F 21/84* (2013.01); *G08B 21/02* (2013.01); *G16H 40/60* (2018.01); *G16H 50/30* (2018.01); *A61B 5/746* (2013.01); *A61B 2560/045* (2013.01); *A61B 2562/222* (2013.01); *A61B 2562/225* (2013.01); *A61M 5/14* (2013.01); *A61M 2205/18* (2013.01); *A61M 2205/3561* (2013.01); *A61M 2205/505* (2013.01); *A61M 2205/52* (2013.01); *G08B 29/06* (2013.01); *G16H 10/60* (2018.01)

(56) References Cited

U.S. PATENT DOCUMENTS

| | | |
|---|---|---|
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |

(56) References Cited

U.S. PATENT DOCUMENTS

| | | |
|---|---|---|
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,847,336 B1 | 1/2005 | Lemelson et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,858,012 B2 | 2/2005 | Burns et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,306,560 B2 | 12/2007 | Iliff |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |

(56) References Cited

U.S. PATENT DOCUMENTS

| | | |
|---|---|---|
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,004,396 B2 * | 8/2011 | Liu ................... H04L 12/2825 340/506 |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,177,704 B1 | 5/2012 | Mohl et al. |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,521,558 B2 | 8/2013 | Malave et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |

(56) References Cited

U.S. PATENT DOCUMENTS

| | | |
|---|---|---|
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | Macneish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,743,148 B2 | 6/2014 | Gegner et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |

(56) References Cited

U.S. PATENT DOCUMENTS

| | | |
|---|---|---|
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,501,613 B1 | 11/2016 | Hanson et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| 9,629,570 B2 | 4/2017 | Bar-Tal |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,700,218 B2 | 7/2017 | Boyer |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,757,020 B2 | 9/2017 | Elazar et al. |
| 9,770,203 B1 | 9/2017 | Berme et al. |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,892,564 B1 | 2/2018 | Cvetko et al. |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,958,681 B2 | 5/2018 | Ko et al. |
| 9,959,620 B2 | 5/2018 | Merlet |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,010,379 B1 | 7/2018 | Gibby et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,080,530 B2 | 9/2018 | Cheng et al. |
| 10,086,138 B1 | 10/2018 | Novak, Jr. |
| 10,092,200 B2 | 10/2018 | Al-Ali et al. |
| 10,092,213 B2 | 10/2018 | Gossler et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,690 B2 | 4/2019 | Bhuruth et al. |

(56) References Cited

U.S. PATENT DOCUMENTS

| | | |
|---|---|---|
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,304,206 B2 | 5/2019 | Nakazato et al. |
| 10,304,251 B2 | 5/2019 | Pahud et al. |
| 10,305,775 B2 | 5/2019 | Lamego et al. |
| 10,307,111 B2 | 6/2019 | Muhsin et al. |
| 10,318,811 B1 | 6/2019 | Gold et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,292 B1 | 6/2019 | Arnicar et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,403,047 B1 | 9/2019 | Comer et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali et al. |
| 10,471,159 B1 | 11/2019 | Lapotko et al. |
| 10,478,107 B2 | 11/2019 | Kiani et al. |
| 10,503,379 B2 | 12/2019 | Al-Ali et al. |
| 10,505,311 B2 | 12/2019 | Al-Ali et al. |
| 10,512,436 B2 | 12/2019 | Muhsin et al. |
| 10,524,706 B2 | 1/2020 | Telfort et al. |
| 10,524,738 B2 | 1/2020 | Olsen |
| 10,531,811 B2 | 1/2020 | Al-Ali et al. |
| 10,531,819 B2 | 1/2020 | Diab et al. |
| 10,531,835 B2 | 1/2020 | Al-Ali et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,548,561 B2 | 2/2020 | Telfort et al. |
| 10,555,678 B2 | 2/2020 | Dalvi et al. |
| 10,568,514 B2 | 2/2020 | Wojtczuk et al. |
| 10,568,553 B2 | 2/2020 | O'Neil et al. |
| RE47,882 E | 3/2020 | Al-Ali |
| 10,575,779 B2 | 3/2020 | Poeze et al. |
| 10,582,886 B2 | 3/2020 | Poeze et al. |
| 10,588,518 B2 | 3/2020 | Kiani |
| 10,588,553 B2 | 3/2020 | Poeze et al. |
| 10,588,554 B2 | 3/2020 | Poeze et al. |
| 10,588,556 B2 | 3/2020 | Kiani et al. |
| 10,595,747 B2 | 3/2020 | Al-Ali et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,803,608 B1 | 10/2020 | Na et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| 10,856,796 B1 | 12/2020 | Berme et al. |
| D906,970 S | 1/2021 | Forrest et al. |
| D908,213 S | 1/2021 | Abdul-Hafiz et al. |
| 10,885,530 B2 | 1/2021 | Mercury et al. |
| 10,888,402 B2 | 1/2021 | Kim et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| 11,307,653 B1 | 4/2022 | Qian et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |

(56) References Cited

U.S. PATENT DOCUMENTS

| | | |
|---|---|---|
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| 11,766,198 B2 | 9/2023 | Pauley et al. |
| D1,000,975 S | 10/2023 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0120310 A1 | 8/2002 | Linden et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0102683 A1 | 5/2004 | Khanuja et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2005/0254134 A1 | 11/2005 | Yamamoto |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0241792 A1 | 10/2006 | Pretlove et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0015015 A1 | 1/2008 | Walker et al. |
| 2008/0064965 A1 | 3/2008 | Jay et al. |
| 2008/0081982 A1 | 4/2008 | Simon et al. |
| 2008/0094228 A1 | 4/2008 | Welch et al. |
| 2008/0103375 A1 | 5/2008 | Kiani |
| 2008/0183074 A1 | 7/2008 | Carls et al. |
| 2008/0183190 A1 | 7/2008 | Adcox et al. |
| 2008/0221418 A1 | 9/2008 | Al-Ali et al. |
| 2008/0270188 A1 | 10/2008 | Garg et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0311655 A1 | 12/2009 | Karkanias et al. |
| 2009/0312660 A1 | 12/2009 | Guarino et al. |
| 2010/0004518 A1 | 1/2010 | Vo et al. |
| 2010/0030040 A1 | 2/2010 | Poeze et al. |
| 2010/0048134 A1 | 2/2010 | McCarthy et al. |
| 2010/0099964 A1 | 4/2010 | O'Reilly et al. |
| 2010/0199232 A1 | 8/2010 | Mistry et al. |
| 2010/0234718 A1 | 9/2010 | Sampath et al. |
| 2010/0249540 A1 | 9/2010 | Lisogurski |
| 2010/0270257 A1 | 10/2010 | Wachman et al. |
| 2010/0274099 A1 | 10/2010 | Telfort et al. |
| 2010/0298656 A1 | 11/2010 | McCombie et al. |
| 2011/0021140 A1 | 1/2011 | Binier |
| 2011/0022981 A1 | 1/2011 | Mahajan et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0066007 A1 | 3/2011 | Banet et al. |
| 2011/0082711 A1 | 4/2011 | Poeze et al. |
| 2011/0087081 A1 | 4/2011 | Kiani et al. |
| 2011/0105854 A1* | 5/2011 | Kiani ............... G16Z 99/00 600/300 |
| 2011/0118561 A1 | 5/2011 | Tari et al. |
| 2011/0124996 A1 | 5/2011 | Reinke et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0202084 A1 | 8/2011 | Hoem et al. |
| 2011/0208015 A1 | 8/2011 | Welch et al. |
| 2011/0230733 A1 | 9/2011 | Al-Ali |
| 2011/0257552 A1 | 10/2011 | Banet et al. |
| 2011/0295301 A1 | 12/2011 | Hoem et al. |
| 2011/0295302 A1 | 12/2011 | Mohl |
| 2012/0003933 A1 | 1/2012 | Baker et al. |
| 2012/0005624 A1 | 1/2012 | Vesely |
| 2012/0054691 A1 | 3/2012 | Nurmi |
| 2012/0109676 A1 | 5/2012 | Landau |
| 2012/0113140 A1 | 5/2012 | Hilliges et al. |
| 2012/0123231 A1 | 5/2012 | O'Reilly |
| 2012/0124506 A1 | 5/2012 | Stuebe et al. |
| 2012/0157806 A1 | 6/2012 | Steiger et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0249741 A1 | 10/2012 | Maciocci et al. |
| 2012/0283524 A1 | 11/2012 | Kiani et al. |
| 2012/0317167 A1 | 12/2012 | Rahman et al. |
| 2012/0319816 A1 | 12/2012 | Al-Ali |
| 2013/0009993 A1 | 1/2013 | Horseman |
| 2013/0017791 A1 | 1/2013 | Wang et al. |
| 2013/0023214 A1 | 1/2013 | Wang et al. |
| 2013/0023215 A1 | 1/2013 | Wang |
| 2013/0023775 A1 | 1/2013 | Lamego et al. |
| 2013/0041591 A1 | 2/2013 | Lamego |
| 2013/0050258 A1 | 2/2013 | Liu et al. |
| 2013/0050432 A1 | 2/2013 | Perez et al. |
| 2013/0060147 A1 | 3/2013 | Welch et al. |
| 2013/0078977 A1 | 3/2013 | Anderson et al. |
| 2013/0096405 A1 | 4/2013 | Garfio |
| 2013/0096936 A1 | 4/2013 | Sampath et al. |
| 2013/0147838 A1 | 6/2013 | Small et al. |
| 2013/0149684 A1 | 6/2013 | Ezzell et al. |
| 2013/0162632 A1 | 6/2013 | Varga et al. |
| 2013/0234934 A1 | 9/2013 | Champion et al. |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267792 A1 | 10/2013 | Petersen et al. |
| 2013/0293530 A1 | 11/2013 | Perez et al. |
| 2013/0294969 A1 | 11/2013 | Chen et al. |
| 2013/0296672 A1 | 11/2013 | O'Neil et al. |
| 2013/0296713 A1 | 11/2013 | Al-Ali et al. |
| 2013/0316652 A1 | 11/2013 | Wang et al. |
| 2013/0324808 A1 | 12/2013 | Al-Ali et al. |
| 2013/0331660 A1 | 12/2013 | Al-Ali et al. |
| 2013/0337842 A1 | 12/2013 | Wang et al. |
| 2013/0345921 A1 | 12/2013 | Al-Ali et al. |
| 2014/0012100 A1 | 1/2014 | Al-Ali et al. |
| 2014/0012509 A1 | 1/2014 | Barber |
| 2014/0035925 A1 | 2/2014 | Muranjan et al. |
| 2014/0051953 A1 | 2/2014 | Lamego et al. |

(56) References Cited

U.S. PATENT DOCUMENTS

| | | |
|---|---|---|
| 2014/0065972 A1 | 3/2014 | Wang |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129493 A1 | 5/2014 | Leopold |
| 2014/0135588 A1 | 5/2014 | Al-Ali et al. |
| 2014/0163344 A1 | 6/2014 | Al-Ali |
| 2014/0163376 A1 | 6/2014 | Caluser |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0207489 A1 | 7/2014 | Wartena et al. |
| 2014/0213864 A1 | 7/2014 | Abdul-Hafiz et al. |
| 2014/0222462 A1 | 8/2014 | Shakil et al. |
| 2014/0225918 A1 | 8/2014 | Mittal et al. |
| 2014/0232747 A1 | 8/2014 | Sugimoto et al. |
| 2014/0235166 A1 | 8/2014 | Molettiere et al. |
| 2014/0249431 A1 | 9/2014 | Banet et al. |
| 2014/0266790 A1 | 9/2014 | Al-Ali et al. |
| 2014/0266983 A1 | 9/2014 | Christensen |
| 2014/0267419 A1 | 9/2014 | Ballard et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0285521 A1 | 9/2014 | Kimura |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323818 A1 | 10/2014 | Axelgaard et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0342766 A1 | 11/2014 | Wang |
| 2014/0357966 A1 | 12/2014 | Al-Ali et al. |
| 2014/0368532 A1 | 12/2014 | Keane et al. |
| 2014/0368539 A1 | 12/2014 | Yeh |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0067516 A1 | 3/2015 | Park et al. |
| 2015/0067580 A1 | 3/2015 | Um et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0088546 A1 | 3/2015 | Balram et al. |
| 2015/0091943 A1 | 4/2015 | Lee et al. |
| 2015/0094546 A1 | 4/2015 | Al-Ali |
| 2015/0097701 A1 | 4/2015 | Muhsin et al. |
| 2015/0099458 A1 | 4/2015 | Weisner et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0119733 A1 | 4/2015 | Grubis |
| 2015/0125832 A1 | 5/2015 | Tran |
| 2015/0150518 A1 | 6/2015 | Cremades Peris et al. |
| 2015/0153571 A1 | 6/2015 | Ballard et al. |
| 2015/0157326 A1 | 6/2015 | Schiemanck et al. |
| 2015/0165312 A1 | 6/2015 | Kiani |
| 2015/0186602 A1 | 7/2015 | Pipke et al. |
| 2015/0196249 A1 | 7/2015 | Brown et al. |
| 2015/0205931 A1 | 7/2015 | Wang et al. |
| 2015/0212576 A1 | 7/2015 | Ambrus et al. |
| 2015/0215925 A1 | 7/2015 | Wang et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0261291 A1 | 9/2015 | Mikhailov et al. |
| 2015/0272514 A1 | 10/2015 | Kiani et al. |
| 2015/0277699 A1 | 10/2015 | Algreatly |
| 2015/0286515 A1 | 10/2015 | Monk |
| 2015/0301597 A1 | 10/2015 | Rogers et al. |
| 2015/0351697 A1 | 12/2015 | Weber et al. |
| 2015/0356263 A1 | 12/2015 | Chatterjee et al. |
| 2015/0359429 A1 | 12/2015 | Al-Ali et al. |
| 2015/0366507 A1 | 12/2015 | Blank et al. |
| 2016/0019352 A1 | 1/2016 | Cohen et al. |
| 2016/0027216 A1 | 1/2016 | da Veiga et al. |
| 2016/0029906 A1 | 2/2016 | Tompkins et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0066868 A1 | 3/2016 | Mensinger et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0116979 A1 | 4/2016 | Border |
| 2016/0124501 A1 | 5/2016 | Lam et al. |
| 2016/0135516 A1 | 5/2016 | Cobbett et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0180044 A1 | 6/2016 | Delisle et al. |
| 2016/0183836 A1 | 6/2016 | Muuranto et al. |
| 2016/0189082 A1 | 6/2016 | Garrish et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0225192 A1 | 8/2016 | Jones et al. |
| 2016/0228043 A1 | 8/2016 | O'Neil et al. |
| 2016/0228640 A1 | 8/2016 | Pindado et al. |
| 2016/0233632 A1 | 8/2016 | Scruggs et al. |
| 2016/0234944 A1 | 8/2016 | Schmidt et al. |
| 2016/0235323 A1 | 8/2016 | Tadi et al. |
| 2016/0239252 A1 | 8/2016 | Nakagawa et al. |
| 2016/0270735 A1 | 9/2016 | Diab et al. |
| 2016/0274358 A1 | 9/2016 | Yajima et al. |
| 2016/0278644 A1 | 9/2016 | He |
| 2016/0283665 A1 | 9/2016 | Sampath et al. |
| 2016/0287090 A1 | 10/2016 | Al-Ali et al. |
| 2016/0287207 A1 | 10/2016 | Xue |
| 2016/0287470 A1 | 10/2016 | Lewis et al. |
| 2016/0287786 A1 | 10/2016 | Kiani |
| 2016/0296143 A1 | 10/2016 | Hayes et al. |
| 2016/0296169 A1 | 10/2016 | McHale et al. |
| 2016/0310005 A1 | 10/2016 | Pekander et al. |
| 2016/0310047 A1 | 10/2016 | Pekander et al. |
| 2016/0310052 A1 | 10/2016 | Al-Ali et al. |
| 2016/0314260 A1 | 10/2016 | Kiani |
| 2016/0314624 A1 | 10/2016 | Li et al. |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0330573 A1 | 11/2016 | Masoud et al. |
| 2016/0331332 A1 | 11/2016 | Al-Ali |
| 2016/0335403 A1 | 11/2016 | Mabotuwana et al. |
| 2016/0335800 A1 | 11/2016 | DeStories |
| 2016/0351776 A1 | 12/2016 | Schneider et al. |
| 2016/0357491 A1 | 12/2016 | Oya |
| 2016/0367173 A1 | 12/2016 | Dalvi et al. |
| 2016/0371886 A1 | 12/2016 | Thompson et al. |
| 2017/0000394 A1 | 1/2017 | Al-Ali et al. |
| 2017/0000422 A1 | 1/2017 | Moturu et al. |
| 2017/0004106 A1 | 1/2017 | Joshua et al. |
| 2017/0007134 A1 | 1/2017 | Al-Ali et al. |

(56) References Cited

U.S. PATENT DOCUMENTS

| | | |
|---|---|---|
| 2017/0007198 A1 | 1/2017 | Al-Ali et al. |
| 2017/0010850 A1 | 1/2017 | Kobayashi et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0046872 A1 | 2/2017 | Geselowitz et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0065379 A1 | 3/2017 | Cowburn et al. |
| 2017/0069120 A1 | 3/2017 | Benner et al. |
| 2017/0079594 A1 | 3/2017 | Telfort et al. |
| 2017/0083104 A1 | 3/2017 | Namba et al. |
| 2017/0086723 A1 | 3/2017 | Al-Ali et al. |
| 2017/0092002 A1 | 3/2017 | Mullins et al. |
| 2017/0111824 A1 | 4/2017 | Wang et al. |
| 2017/0140101 A1 | 5/2017 | Anderson et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0161455 A1 | 6/2017 | Grady et al. |
| 2017/0172415 A1 | 6/2017 | Wik et al. |
| 2017/0172515 A1 | 6/2017 | Banet et al. |
| 2017/0172696 A1 | 6/2017 | Saget et al. |
| 2017/0173632 A1 | 6/2017 | Al-Ali |
| 2017/0177816 A1 | 6/2017 | Ribble et al. |
| 2017/0178356 A1 | 6/2017 | Bhuruth et al. |
| 2017/0181645 A1 | 6/2017 | Mahalingam et al. |
| 2017/0186157 A1 | 6/2017 | Boettger et al. |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0200296 A1 | 7/2017 | Jones et al. |
| 2017/0202490 A1 | 7/2017 | Al-Ali et al. |
| 2017/0206676 A1 | 7/2017 | Nakazato et al. |
| 2017/0215261 A1 | 7/2017 | Potucek et al. |
| 2017/0215388 A1 | 8/2017 | Delecroix |
| 2017/0216524 A1 | 8/2017 | Haider et al. |
| 2017/0224262 A1 | 8/2017 | Al-Ali |
| 2017/0228516 A1 | 8/2017 | Sampath et al. |
| 2017/0242480 A1 | 8/2017 | Dees et al. |
| 2017/0244796 A1 | 8/2017 | Liu et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0255838 A1 | 9/2017 | Norieda et al. |
| 2017/0258403 A1 | 9/2017 | Abdul-Hafiz et al. |
| 2017/0262064 A1 | 9/2017 | Ofir et al. |
| 2017/0300824 A1 | 10/2017 | Peng et al. |
| 2017/0311851 A1 | 11/2017 | Schurman et al. |
| 2017/0311891 A1 | 11/2017 | Kiani et al. |
| 2017/0315774 A1 | 11/2017 | Meerbeek et al. |
| 2017/0316561 A1 | 11/2017 | Helm et al. |
| 2017/0323479 A1 | 11/2017 | Mokuya |
| 2017/0325684 A1 | 11/2017 | Vartiovaara |
| 2017/0325728 A1 | 11/2017 | Al-Ali et al. |
| 2017/0329480 A1 | 11/2017 | Ishikawa et al. |
| 2017/0332976 A1 | 11/2017 | Al-Ali |
| 2017/0340293 A1 | 11/2017 | Al-Ali et al. |
| 2017/0351909 A1 | 12/2017 | Kaehler |
| 2017/0357397 A1 | 12/2017 | Masumoto |
| 2017/0359467 A1 | 12/2017 | Norris et al. |
| 2017/0360310 A1 | 12/2017 | Kiani |
| 2017/0367632 A1 | 12/2017 | Al-Ali et al. |
| 2017/0367771 A1 | 12/2017 | Tako et al. |
| 2018/0000415 A1 | 1/2018 | Gupta et al. |
| 2018/0005424 A1 | 1/2018 | Niinuma et al. |
| 2018/0008146 A1 | 1/2018 | Al-Ali et al. |
| 2018/0014752 A1 | 1/2018 | Al-Ali et al. |
| 2018/0024630 A1 | 1/2018 | Goossens |
| 2018/0025116 A1 | 1/2018 | Carrington et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0059812 A1 | 3/2018 | Inomata et al. |
| 2018/0064381 A1 | 3/2018 | Shakespeare et al. |
| 2018/0069776 A1 | 3/2018 | Lamego et al. |
| 2018/0074332 A1 | 3/2018 | Li et al. |
| 2018/0075658 A1 | 3/2018 | Lanier et al. |
| 2018/0078316 A1 | 3/2018 | Schaewe et al. |
| 2018/0080774 A1 | 3/2018 | Sink et al. |
| 2018/0082480 A1 | 3/2018 | White et al. |
| 2018/0084224 A1 | 3/2018 | McNelley et al. |
| 2018/0088682 A1 | 3/2018 | Tsang |
| 2018/0103874 A1 | 4/2018 | Lee et al. |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0139203 A1 | 5/2018 | Dolan et al. |
| 2018/0140362 A1 | 5/2018 | Cali et al. |
| 2018/0144497 A1 | 5/2018 | Hirota et al. |
| 2018/0146901 A1 | 5/2018 | Al-Ali et al. |
| 2018/0146902 A1 | 5/2018 | Kiani et al. |
| 2018/0147024 A1 | 5/2018 | Kall et al. |
| 2018/0153442 A1 | 6/2018 | Eckerbom et al. |
| 2018/0153445 A1 | 6/2018 | Noda et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0157344 A1 | 6/2018 | Toff |
| 2018/0160881 A1 | 6/2018 | Okabe et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0181810 A1 | 6/2018 | Jhawar et al. |
| 2018/0182484 A1 | 6/2018 | Sampath et al. |
| 2018/0184917 A1 | 7/2018 | Kiani |
| 2018/0188807 A1 | 7/2018 | Cimenser et al. |
| 2018/0188831 A1 | 7/2018 | Lyons |
| 2018/0189556 A1 | 7/2018 | Shamir et al. |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0200018 A1 | 7/2018 | Silva et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0217734 A1 | 8/2018 | Koenig et al. |
| 2018/0218792 A1 | 8/2018 | Muhsin et al. |
| 2018/0225960 A1 | 8/2018 | Al-Ali et al. |
| 2018/0225993 A1 | 8/2018 | Buras et al. |
| 2018/0235478 A1 | 8/2018 | Khachaturian et al. |
| 2018/0238718 A1 | 8/2018 | Dalvi |
| 2018/0242853 A1 | 8/2018 | Al-Ali |
| 2018/0242920 A1 | 8/2018 | Hresko et al. |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247024 A1 | 8/2018 | Divine et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0250510 A1 | 9/2018 | Ziv |
| 2018/0251230 A1 | 9/2018 | Chavez et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0261329 A1 | 9/2018 | Blander et al. |
| 2018/0264945 A1 | 9/2018 | Torii |
| 2018/0275837 A1 | 9/2018 | Getz et al. |

(56) References Cited

U.S. PATENT DOCUMENTS

| | | |
|---|---|---|
| 2018/0279947 A1 | 10/2018 | Ummat |
| 2018/0285094 A1 | 10/2018 | Housel et al. |
| 2018/0286132 A1 | 10/2018 | Cvetko et al. |
| 2018/0289325 A1 | 10/2018 | Poeze et al. |
| 2018/0289337 A1 | 10/2018 | Al-Ali et al. |
| 2018/0293802 A1 | 10/2018 | Hendricks et al. |
| 2018/0296161 A1 | 10/2018 | Shreim et al. |
| 2018/0300031 A1 | 10/2018 | Parkinson |
| 2018/0300919 A1 | 10/2018 | Muhsin et al. |
| 2018/0303558 A1 | 10/2018 | Thomas |
| 2018/0310822 A1 | 11/2018 | Indorf et al. |
| 2018/0310823 A1 | 11/2018 | Al-Ali et al. |
| 2018/0315490 A1 | 11/2018 | Jaruzel, II |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2018/0333643 A1 | 11/2018 | Luisi et al. |
| 2018/0342079 A1 | 11/2018 | Yaguchi et al. |
| 2018/0344308 A1 | 12/2018 | Nawana et al. |
| 2018/0365897 A1 | 12/2018 | Pahud et al. |
| 2019/0000317 A1 | 1/2019 | Muhsin et al. |
| 2019/0000362 A1 | 1/2019 | Kiani et al. |
| 2019/0005724 A1 | 1/2019 | Pahud et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0033989 A1 | 1/2019 | Wang et al. |
| 2019/0034076 A1 | 1/2019 | Vinayak et al. |
| 2019/0038143 A1 | 2/2019 | Al-Ali |
| 2019/0043259 A1 | 2/2019 | Wang et al. |
| 2019/0053855 A1 | 2/2019 | Siemionow et al. |
| 2019/0058280 A1 | 2/2019 | Al-Ali et al. |
| 2019/0058281 A1 | 2/2019 | Al-Ali et al. |
| 2019/0064520 A1 | 2/2019 | Christensen |
| 2019/0066538 A1 | 2/2019 | Chao et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0079156 A1 | 3/2019 | Krellmann |
| 2019/0080515 A1 | 3/2019 | Geri et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0121522 A1 | 4/2019 | Davis et al. |
| 2019/0122763 A1 | 4/2019 | Sampath et al. |
| 2019/0133525 A1 | 5/2019 | Al-Ali et al. |
| 2019/0138183 A1 | 5/2019 | Rosas et al. |
| 2019/0141291 A1 | 5/2019 | McNelley et al. |
| 2019/0142283 A1 | 5/2019 | Lamego et al. |
| 2019/0142344 A1 | 5/2019 | Telfort et al. |
| 2019/0146578 A1 | 5/2019 | Ikuta et al. |
| 2019/0149797 A1 | 5/2019 | Casas |
| 2019/0150800 A1 | 5/2019 | Poeze et al. |
| 2019/0150856 A1 | 5/2019 | Kiani et al. |
| 2019/0155382 A1 | 5/2019 | Ikuta et al. |
| 2019/0167161 A1 | 6/2019 | Al-Ali et al. |
| 2019/0175019 A1 | 6/2019 | Al-Ali et al. |
| 2019/0183577 A1 | 6/2019 | Fahim et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0206104 A1 | 7/2019 | Rahman |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216370 A1 | 7/2019 | Schurman et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0231436 A1 | 8/2019 | Panse et al. |
| 2019/0239787 A1 | 8/2019 | Pauley et al. |
| 2019/0239824 A1 | 8/2019 | Muhsin et al. |
| 2019/0240508 A1 | 8/2019 | Friman et al. |
| 2019/0243138 A1 | 8/2019 | Peltola et al. |
| 2019/0250873 A1 | 8/2019 | Blume et al. |
| 2019/0254578 A1 | 8/2019 | Lamego |
| 2019/0254754 A1 | 8/2019 | Johnson et al. |
| 2019/0261857 A1 | 8/2019 | Al-Ali |
| 2019/0272029 A1 | 9/2019 | Fein et al. |
| 2019/0320906 A1 | 10/2019 | Olsen |
| 2019/0333276 A1 | 10/2019 | Brown et al. |
| 2019/0340434 A1 | 11/2019 | Chiu et al. |
| 2019/0340827 A1 | 11/2019 | Abercromie et al. |
| 2019/0348169 A1 | 11/2019 | Gibby et al. |
| 2019/0355182 A1 | 11/2019 | Nozaki et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0380792 A1 | 12/2019 | Poltaretskyi et al. |
| 2019/0387102 A1 | 12/2019 | Norris et al. |
| 2020/0004328 A1 | 1/2020 | Blume et al. |
| 2020/0005542 A1 | 1/2020 | Kocharlakota et al. |
| 2020/0046473 A1 | 2/2020 | Kim et al. |
| 2020/0051448 A1 | 2/2020 | Welch et al. |
| 2020/0060869 A1 | 2/2020 | Telfort et al. |
| 2020/0074740 A1 | 3/2020 | Singh |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0125322 A1 | 4/2020 | Wilde |
| 2020/0129136 A1 | 4/2020 | Harding et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0175609 A1 | 6/2020 | Zolotow et al. |
| 2020/0187901 A1 | 6/2020 | Suresh et al. |
| 2020/0188028 A1 | 6/2020 | Feiner et al. |
| 2020/0196877 A1 | 6/2020 | Vo et al. |
| 2020/0210679 A1 | 7/2020 | Kusens et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0319770 A1 | 10/2020 | Varga et al. |
| 2020/0321099 A1 | 10/2020 | Holladay et al. |
| 2020/0321793 A1 | 10/2020 | Al-Ali et al. |
| 2020/0327670 A1 | 10/2020 | Connor |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2020/0372714 A1 | 11/2020 | Soryal et al. |
| 2020/0405151 A1 | 12/2020 | Berger et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0169578 A1 | 6/2021 | Calloway et al. |
| 2021/0223855 A1 | 7/2021 | Gibby et al. |
| 2021/0236729 A1 | 8/2021 | Kiani et al. |
| 2021/0251538 A1 | 8/2021 | Muhsin et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |

(56) References Cited

U.S. PATENT DOCUMENTS

| | | |
|---|---|---|
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0295048 A1 | 9/2021 | Buras et al. |
| 2021/0296008 A1 | 9/2021 | Novak, Jr. |
| 2021/0298868 A1 | 9/2021 | Rydberg |
| 2021/0327304 A1 | 10/2021 | Buras et al. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0172797 A1 | 6/2022 | Xie |
| 2022/0214743 A1 | 7/2022 | Dascola et al. |
| 2022/0218244 A1 | 7/2022 | Kiani et al. |
| 2022/0283647 A1 | 9/2022 | Qian et al. |
| 2022/0287574 A1 | 9/2022 | Telfort et al. |
| 2022/0293262 A1 | 9/2022 | Beck et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |

FOREIGN PATENT DOCUMENTS

| | | |
|---|---|---|
| CN | 103415852 | 11/2013 |
| CN | 103782649 | 5/2014 |
| CN | 103930029 | 7/2014 |
| CN | 104011764 | 8/2014 |
| CN | 105745855 | 7/2016 |
| JP | 2002-535026 | 10/2002 |
| JP | 2002-153426 | 8/2008 |
| JP | 2011-519607 | 7/2011 |
| JP | 2012-519547 | 4/2013 |
| JP | 2014-208255 | 11/2014 |
| JP | 2014-533997 | 12/2014 |
| JP | 2016-512965 | 5/2016 |
| JP | 2016-532467 | 10/2016 |
| JP | 2016-187561 | 11/2016 |
| JP | 2016-189860 | 11/2016 |
| JP | 2017-035466 | 2/2017 |
| KR | 10-2005-0055072 | 6/2005 |
| WO | WO 2010/031070 | 3/2010 |
| WO | WO 2011/069122 | 6/2011 |
| WO | WO 2012/085762 | 6/2012 |
| WO | WO 2014/051563 | 4/2014 |
| WO | WO 2018/156804 | 8/2018 |
| WO | WO 2018/156809 | 8/2018 |
| WO | WO 2018/208616 | 11/2018 |

OTHER PUBLICATIONS

Allen et al., "Object Tracking Using CamShift Algorithm and Multiple Quantized Feature Spaces", VIP '05: Proceedings of the Pan-Sydney area workshop on Visual information processing, Jun. 2004, pp. 3-7.

International Search Report and Written Opinion from corresponding International Patent Application No. PCT/US2018/019288, dated May 30, 2018, in 10 pages.

International Search Report and Written Opinion from corresponding International Patent Application No. PCT/US2018/031198, dated Aug. 29, 2018, in 12 pages.

International Preliminary Report on Patentability and Written Opinion in corresponding International Patent Application No. PCT/US2018/019283, dated Sep. 6, 2019, in 9 pages.

International Search Report and Written Opinion from corresponding International Patent Application No. PCT/US2018/019283, dated Jul. 27, 2018, in 14 pages.

\* cited by examiner

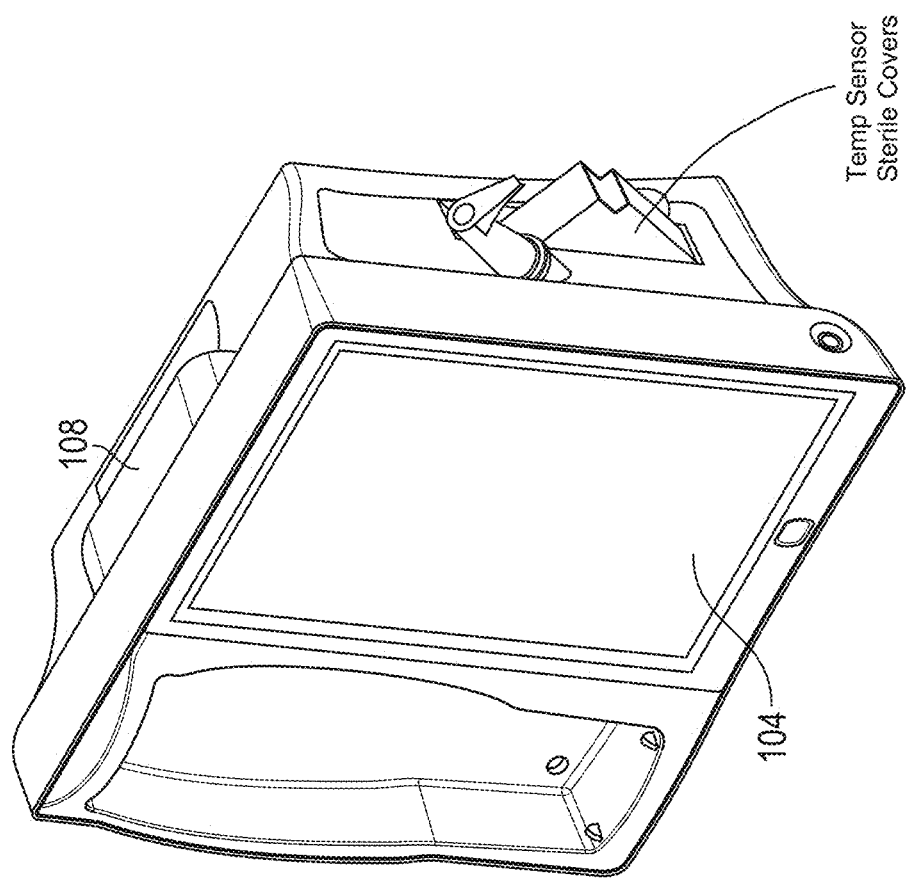
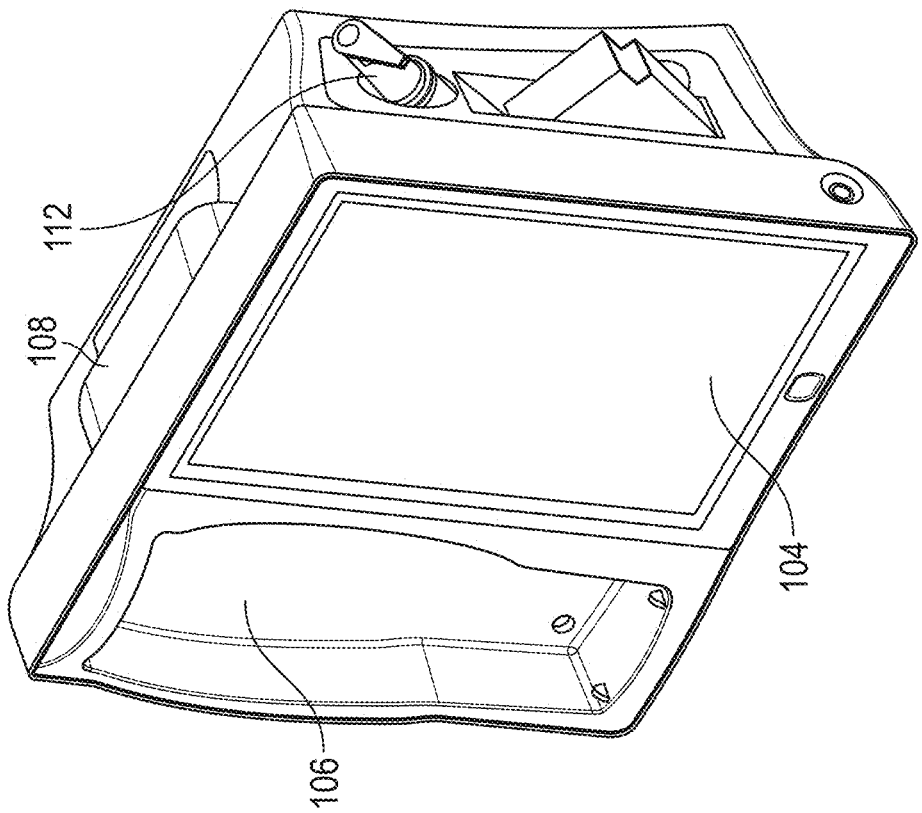
FIG. 1C

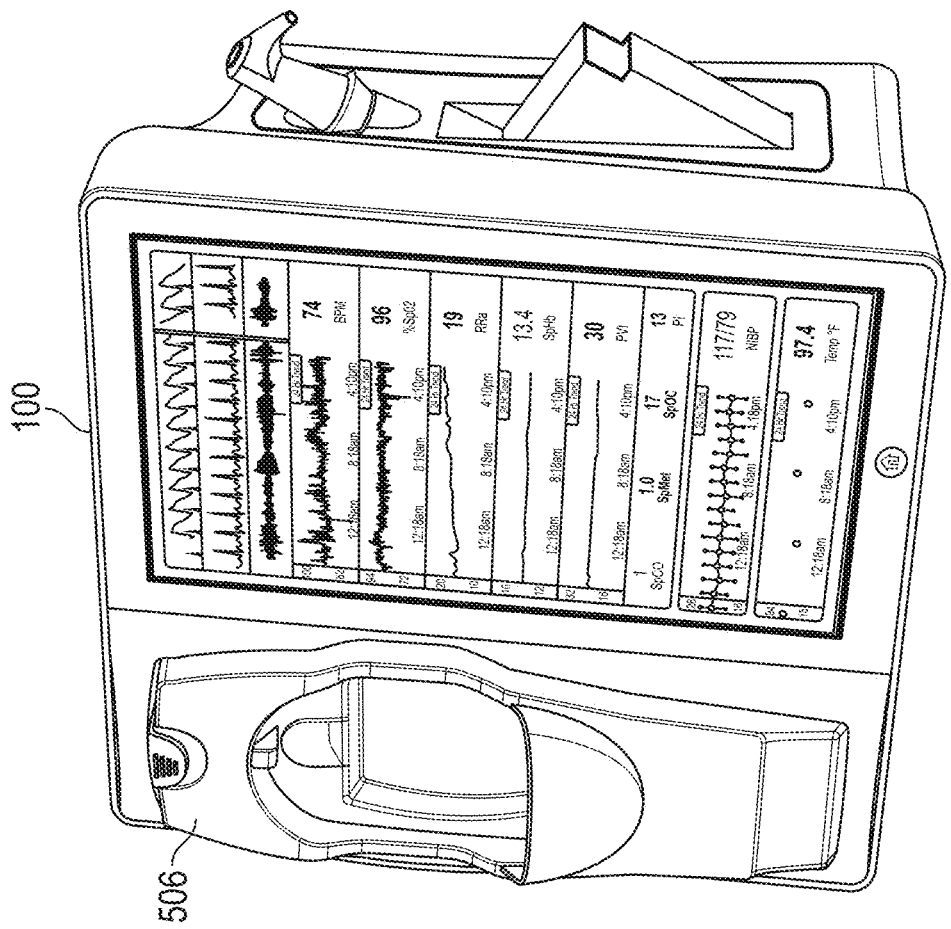
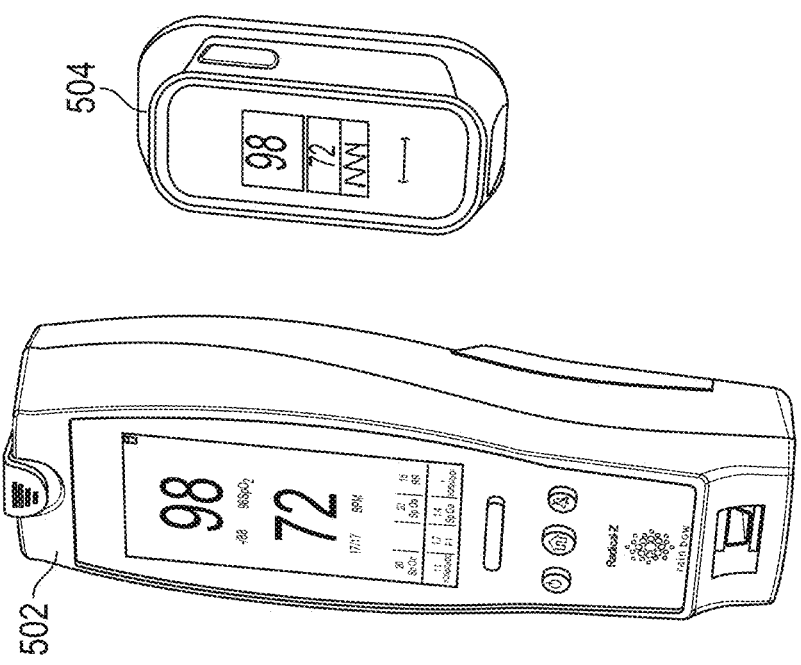
FIG. 5

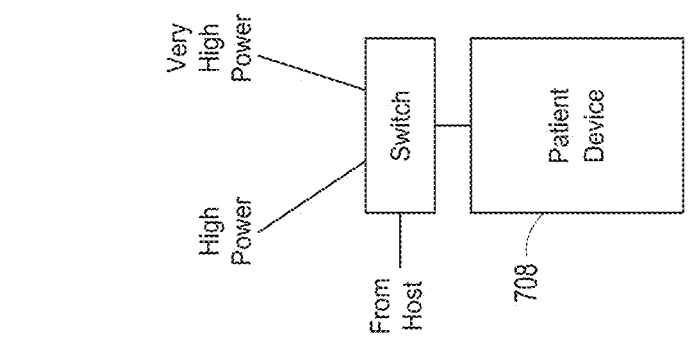
FIG. 7B
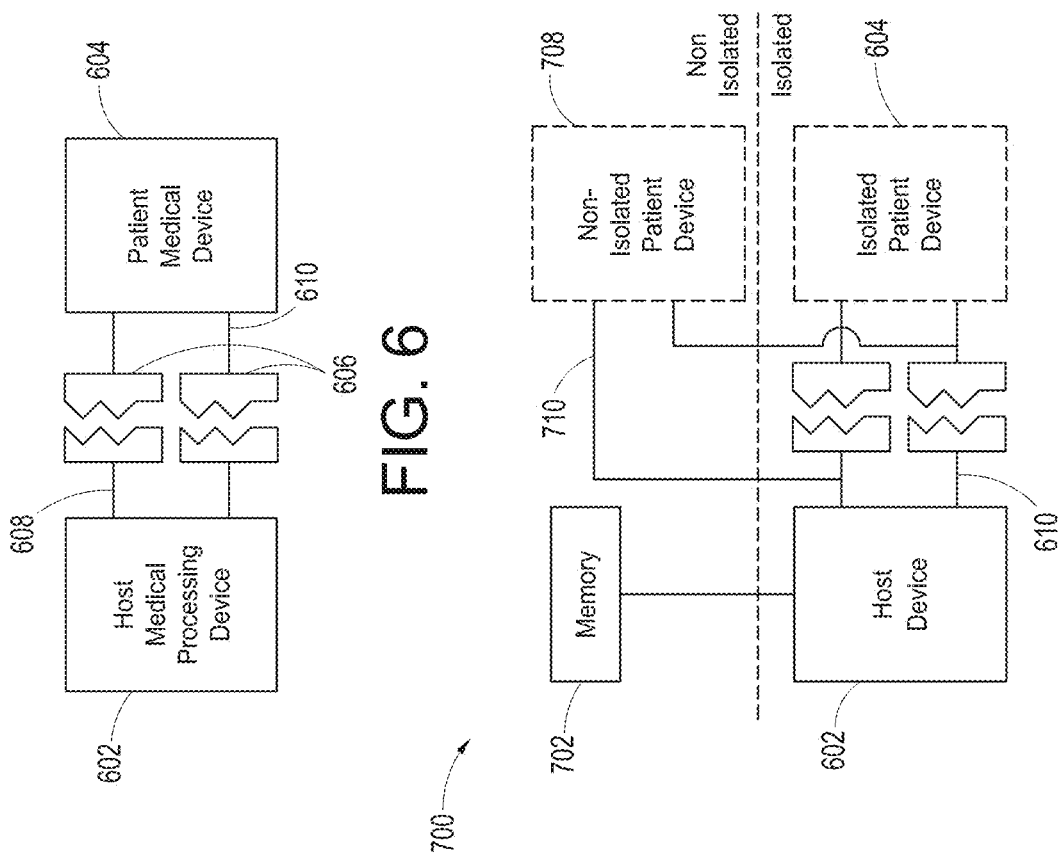
FIG. 6
FIG. 7A

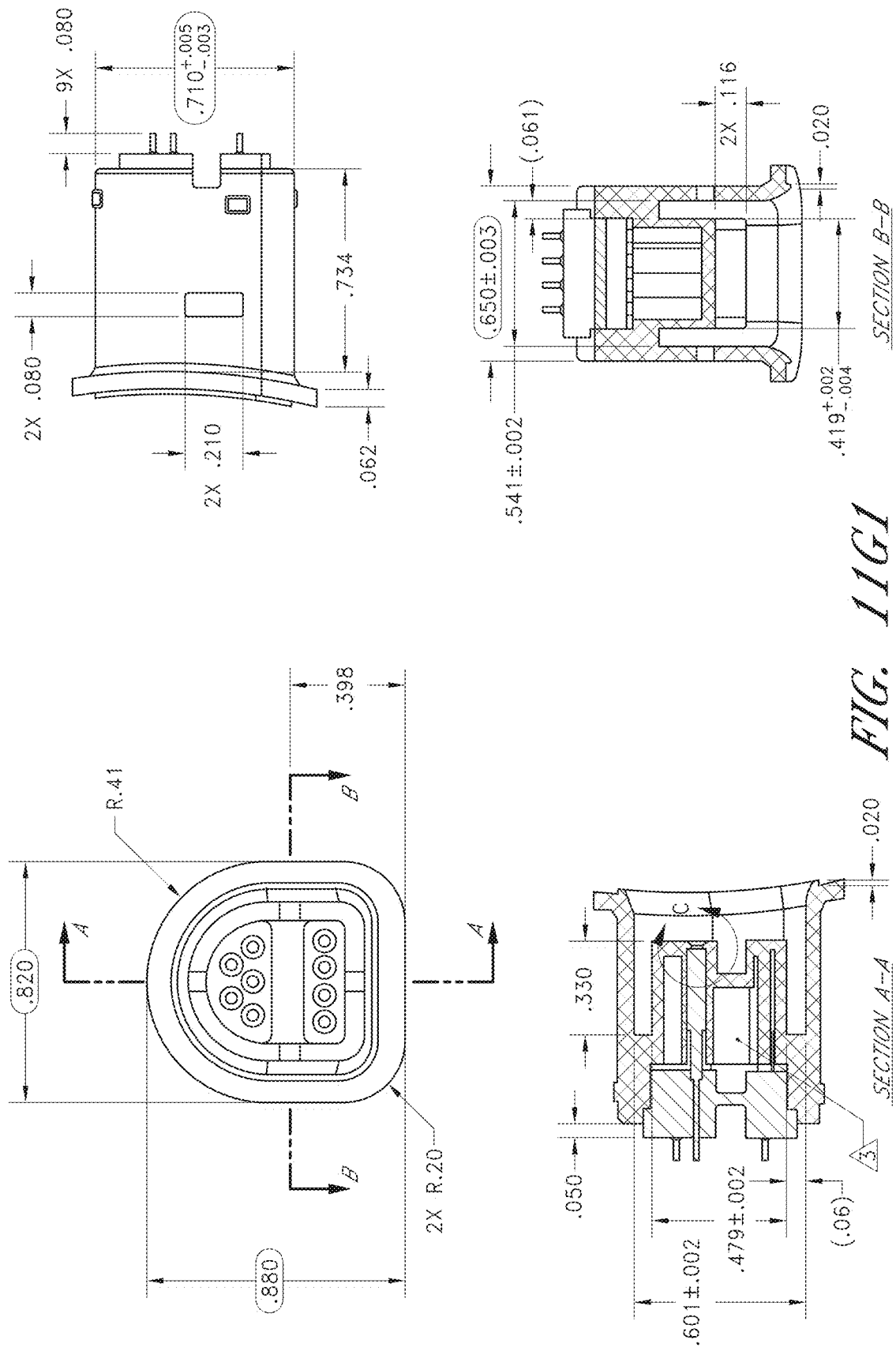

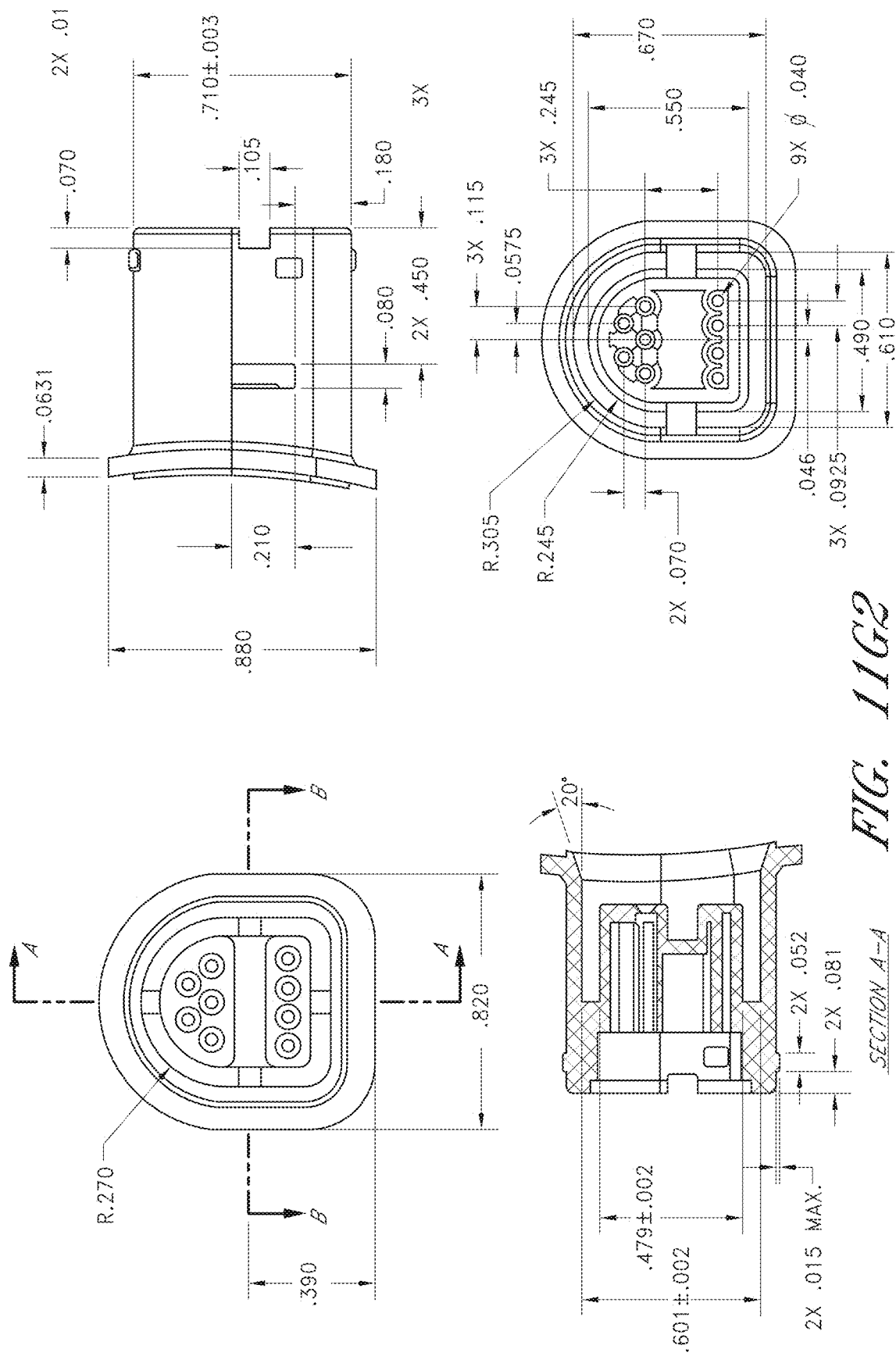
FIG. 11G2

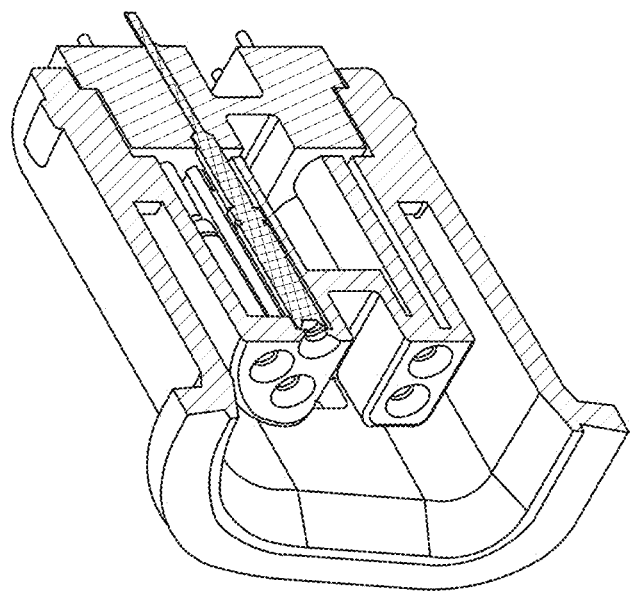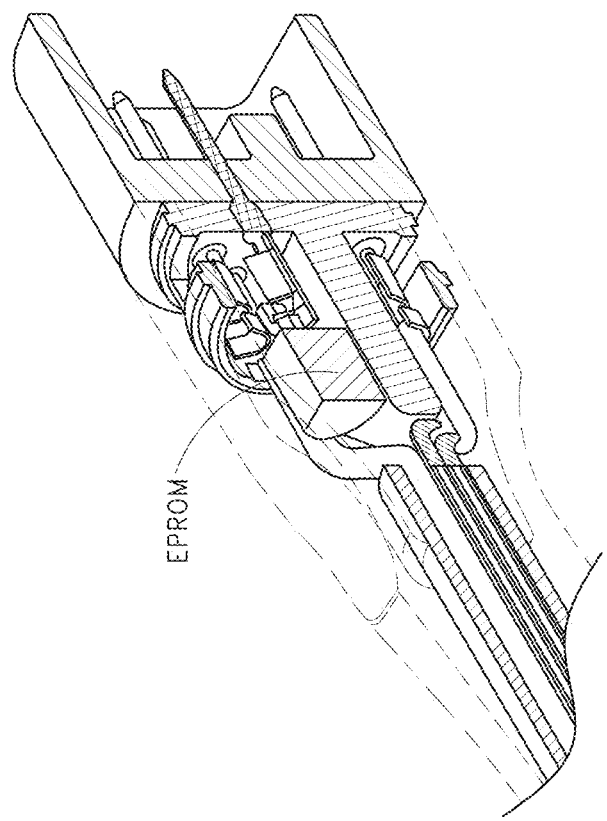
FIG. 11H

```
<SB>
MSH^~|\&^VAFC PIMS^50^NPTF-508^200^20091120104609-0600^^ADT^A01^58103^P^^^^^USA<CR>
EVN^A01^20091120104517-0600^^^05<CR>
PID^1^5000000003V302090^11~7~M10^^^LONG~BRIAN^^^19800401^M^^^^~~~0005~| ~CDC^^^^^~""~P~~~~
~~~~&~|~~~~~VACE~""~""~~~VACA~""~""~~~VACAA~""~""~~~VACM~""~""~~~VACAC~""~""
~^^^~0189~""~~~CDC^ <CR>                        ~~~~&~|~~~~~VACM~""~""~~~VACA0~""~""~~~&~~~~~29^^^^
PD1^^^SOFTWARE SERVICE~~050^""<CR>
ZPD^1^^""^^^^""^^^^^^^^""^^^^^^^""^""""^""""^^^^^^""^""""0^""^""""<CR>
PV1^1^I^PSYCH-304~1^^^^^^^""^""~""^^^^^^^^25~WESSELHOFT~MEGAN^^^""^^^^^^^^^^^^^^^^^^^^^^^^^^
(OTHER)^^^25^^^^^^^^^^^^^^^^^^^^^20091120104517-0600^^^^^^18<CR>                              ~""~""~""~""~SSA<CR>
ROL^18-
25~1^CO^""^^^^^""""""~""~""^^^^^T^""~VA01^25&50~WESSELHOFT~MEGAN~""~""~""~""~""~""~""~VA200|""~""~""~""~""~SSA<CR>
ROL^18-
25*2^CO^""^^^^^""""""~""~""^^^^^A^""~VA01^25&50~WESSELHOFT~MEGAN~""~""~""~""~""~""~""~VA200|""~""~""~""~""~SSA<CR>
DG1^1^^^IBS<CR>
ZSP^1^0^""""""N""""""<CR>
ZEL^1^8-~~~^^^^^^^^^^^^^^^0^NON-VETERAN (OTHER)^^^^^^^^^^^^^^^^^^^^^^^^^<CR>
ZCT^1^1^^^^^^^^^^^^""^^^^^^^^^^^^0^NON-VETERAN^^<CR>
ZEM^1^1^^^^^^^^""^^^;;<CR>
ZIR^<CR>
ZEN^1<CR>
<EB><CR>
```

FIG. 41A

```xml
<?xml version="1.0" encoding="UTF-8" standalone="no" ?>
  <ev7>
    <MSH>
      <MSH.1>^</MSH.1>
      <MSH.2>~|\&</MSH.2>
      <MSH.3>VAFC PIMS</MSH.3>
      <MSH.4>50</MSH.4>
      <MSH.5>NPTF-508</MSH.5>
      <MSH.6>200</MSH.6>
      <MSH.7>20091120104609-0600</MSH.7>
      <MSH.9>
         <component n="1">ADT</component>
         <component n="2">ADT</component>
      <MSH.9>
      <MSH.10>58103</MSH.10>
      <MSH.11>P</MSH.11>
      <MSH.17>USA</MSH.17>
    </MSH>
    <EVN>
      <EVN.1>A01</EVN.1>
      <EVN.2>20091120104517-0600</EVN.2>
      <EVN.4>05</EVN.4>
    </EVN>
    ...
  <ev7>
```

FIG. 41B

```xml
<?xml version="1.0" encoding="UTF-8"?>
<ADT_A01>
  <MSH>
    <MSH.1>^</MSH.1>
    <MSH.2>~|\&</MSH.2>
    <MSH.3>
       <HD.1>VAFC PIMS</HD.1>
    </MSH.3>
    <MSH.4>
       <HD.1>50</HD.1>
    </MSH.4>
    <MSH.5>
       <HD.1>NPTF-508</HD.1>
    </MSH.5>
    <MSH.6>
       <HD.1>200</HD.1>
    </MSH.6>
    <MSH.7>
       <TS.1>20091120104609-0600</TS.1>
    </MSH.7>
    <MSH.9>
       <MSG.1>ADT</MSG.1>
       <MSG.2>A01</MSG.2>
    </MSH.9>
    <MSH.10>58103</MSH.10>
    <MSH.11>
       <PT.1>P</PT.1>
    </MSH.11>
    <MSH.17>USA</MSH.17>
  </MSH>
```

FIG. 41C

```
<output-message>
  <ACK>
    <MSH>
      <MSH.1>^</MSH.1>
      <MSH.2>~|\&</MSH.2>
      <MSH.3>
         <HD.1>NPTF-508</HD.1>
      </MSH.3>
      <MSH.4>
         <HD.1>200</HD.1>
      </MSH.4>
      <MSH.5>
         <HD.1>VAFC PIMS</HD.1>
      </MSH.5>
      <MSH.6>
         <HD.1>50</HD.1>
      </MSH.6>
      <MSH.7>
         <TS.1>20091120104609-0600</TS.1>
      </MSH.7>
      <MSH.9>
         <MSG.1>ACK</MSG.1>
         <MSG.3>ACK</MSG.2>
      </MSH.9>
      <MSH.10>856bc9bd-97c8-4aa5-b411-3cd6fe2edd86</MSH.10>
    <MSH>
    <MSA>
       <MSA.1>AA</MSA.1>
       <MSA.2>58103</MSA.2>
    </MSA>
  </ACK>
</output-message>
```

FIG. 41D

EXAMPLE DISPLAY LAYOUT MANAGER (CONT'D)

EXAMPLES OF CONFIGURABLE HUB DISPLAY

EXAMPLES OF CONFIGURABLE HUB DISPLAY

SYSTEM FOR DISPLAYING MEDICAL MONITORING DATA

INCORPORATION BY REFERENCE TO ANY PRIORITY APPLICATIONS

Any and all applications, if any, for which a foreign or domestic priority claim is identified in the Application Data Sheet of the present application are hereby incorporated by reference under 37 CFR 1.57.

BACKGROUND

Today's patient monitoring environments are crowded with sophisticated and often electronic medical devices servicing a wide variety of monitoring and treatment endeavors for a given patient. Generally, many if not all of the devices are from differing manufactures, and many may be portable devices. The devices may not communicate with one another and each may include its own control, display, alarms, configurations and the like. Complicating matters, caregivers often desire to associate all types of measurement and use data from these devices to a specific patient. Thus, patient information entry often occurs at each device. Sometimes, the disparity in devices leads to a need to simply print and store paper from each device in a patient's file for caregiver review.

The result of such device disparity is often a caregiver environment scattered with multiple displays and alarms leading to a potentially chaotic experience. Such chaos can be detrimental to the patient in many situations including surgical environments where caregiver distraction is unwanted, and including recovery or monitoring environments where patient distraction or disturbance may be unwanted.

Various manufacturers produce multi-monitor devices or devices that modularly expand to increase the variety of monitoring or treatment endeavors a particular system can accomplish. However, as medical device technology expands, such multi-monitor devices begin to be obsolete the moment they are installed.

SUMMARY

In some aspects, a medical device cable can be configured to be connectable to a patient monitoring hub. The medical device cable can comprise: a main cable portion; a board-in-cable device without a display, the board-in-cable device connected to the main cable portion and configured to couple with a sensor configured to obtain physiological information from a patient; a connector connected to the main cable portion, the connector configured to connect to a patient monitoring hub; the board-in-cable device comprising a hardware processor configured to: calculate a first physiological parameter based on the physiological information; receive a second physiological parameter from the patient monitoring hub, the second physiological parameter provided by a second board-in-cable device of a second medical device cable also connected to the patient monitoring hub; process the first and second physiological parameters to generate a third physiological parameter; and communicate the third physiological parameter to the patient monitoring hub so that the patient monitoring hub is configured to output the third physiological parameter on a display of the patient monitoring hub.

The medical device cable in the preceding paragraph can also include one or more of the following features. The third physiological parameter can represent a wellness index. The hardware processor can further be configured to: determine a display characteristic associated with the third physiological parameter, wherein the display characteristic comprises a display layout associated with the third physiological parameter; and communicate the display characteristic to the patient monitoring hub. The communication of the display characteristic to the medical monitoring hub can cause the patient monitoring hub to override a native display characteristic with the display characteristic. The hardware processor can further be configured to access an application programming interface associated with the patient monitoring hub to cause the patient monitoring hub to output a settings user interface. The settings user interface can be user-selectable to cause the board-in-cable device to receive an updated setting from the settings user interface. The updated setting can comprise adjusting a limit of an alarm. The updated setting can comprise enabling a function of the board-in-cable device. The hardware processor can further be configured to receive an indication from the patient monitoring hub that a new patient has connected with the patient monitoring hub. The hardware processor can further be configured to do one or more of the following responsive to receiving the indication: reset a parameter calculation algorithm and reset a baseline calculation.

In some aspects, a method of sharing data between connected medical devices is described. The method can be performed under control of a hardware processor of a first medical device cable. The method can comprise: calculating a first physiological parameter based on physiological information received from a sensor coupled with the medical device cable; receiving a second physiological parameter from a patient monitoring hub connected to the first medical device cable, the second physiological parameter calculated by either the patient monitor or by a second medical device cable also connected to the patient monitoring hub; processing the first and second physiological parameters to generate a third physiological parameter; and communicating the third physiological parameter to the patient monitoring hub so that the medical monitoring hub can output the third physiological parameter on a display.

The method of the preceding paragraph can also include one or more of the following features. The third physiological parameter can represent a wellness index. The method can further comprise sending a function call to the patient monitoring hub to cause the patient monitoring hub to output a settings user interface. The method can further comprise receiving a setting from the settings user interface. The setting can comprise: an adjusted alarm limit or a toggle to enable a function of the medical device cable. The method can further comprise receiving an indication from the patient monitoring hub that a new patient has connected with the patient monitoring hub. The method can further comprise adjusting a parameter calculation algorithm based on the indication.

In some aspects, a method of controlling an operation of an external device connected to a patient monitoring hub is described. The method can be performed under control of a hardware processor of a patient monitoring hub connectable to a plurality of external devices to the patient monitoring hub, the external devices comprising a wireless dongle, a board-in-cable, or both. The method can comprise: receiving device information of a first one of the external devices at the patient monitoring hub, the device information comprising a display characteristic associated with a patient parameter monitored by the first external device; establishing a connection between the patient monitoring hub and the first external device; generating, based at least in part on the display characteristic, a user interface element for managing the patient parameter at the patient monitoring hub; detecting an actuation of the user interface element on a display of the patient monitoring hub; determining one or more adjustments associated with the patient parameter in response to the actuation of the user interface element; and communicating the one or more adjustments to the patient parameter to the first external device, causing the first external device to automatically update its operation based on the one or more adjustments.

The method of the preceding paragraph can also include one or more of the following features. The display characteristic can comprise an instruction to call a graphics library on the patient monitoring hub to draw the user interface element. The device information can comprise at least one of: a measurement channel supported by the first external device, measured parameters, or display layouts for the measured parameters. The one or more adjustments associated with the patient parameter can comprise an adjustment to a value which can trigger an alarm associated with the patient parameter. The one or more adjustments to the patient parameter can further cause the first external device to enable or disable a function associated with the patient parameter. The method can further comprise: detecting a triggering event for updating a setting of the external device and communicate information of the triggering event to the first external device which causes the external device to automatically change the setting in response. The method can further comprise: sending data of another parameter to the first external device, the other parameter being acquired by a second one of the external devices, wherein the data of another parameter automatically can trigger the second external device to perform a second operation. The second operation performed can comprise calibrating an algorithm for calculating the patient parameter at the second external device.

In some aspects, a patient monitoring hub connectable to a plurality of sensors, the patient monitoring hub can comprise: a plurality of ports operable to be in communication with a plurality of sensors; a display; and a hardware processor configured to: identify a plurality of parameters to be displayed by the patient monitoring hub based at least in part on the sensors connected to the patient monitoring hub; determine display characteristics corresponding to the plurality of parameters; generate a set of display layout options based on the display characteristics corresponding to the plurality of parameters; automatically populate a display layout manager with the set of display layout options; receive a user selection of one of the display layout options; and output the plurality of parameters on the display according to the selected display layout option.

The patient monitoring hub of the preceding paragraph can also include one or more of the following features. The hardware processor can further be configured to: detect a change to the plurality of medical devices or the plurality of parameters; and automatically update the set of display layout options and the display layout manager based at least in part on the change. The change can comprise an addition or a removal of a sensor or a parameter. The display characteristics can be automatically provided to the patient monitoring hub by the sensor while the sensor and the patient monitoring hub are establishing a connection. The display characteristics can comprise at least one of: an instruction to call a graphics library on the patient monitoring hub to draw the user interface element; a set of preconfigured display layouts for a parameter; layout restrictions for displaying information of the parameter; or images or texts associated with displaying the parameter. The plurality of parameters can comprise a parameter calculated by the patient monitoring hub. The display can be divided into a plurality of subdivisions wherein each subdivision comprises one or more parameters. The hardware processor can be further configured to: receive a user input for adjusting a size or location of a subdivision; and automatically update displays of parameters in the plurality of subdivisions in response to the user input. The hardware processor can be further configured to automatically select a display layout option among the set of display layout options and automatically render information of the plurality of parameters in accordance with the selected display layout option.

In some aspects, a method of managing displays of a patient monitoring hub is described. The method can be performed under control of a hardware processor of a patient monitoring hub comprising a display. The method can comprise: identifying a plurality of medical devices connected to a patient monitoring hub; identify a plurality of parameters to be displayed by the patient monitoring hub based at least in part on information of the plurality of medical devices; determining display characteristics corresponding to the plurality of parameters; generating a set of display layout options based on the display characteristics corresponding to the plurality of parameters; automatically populating a display layout manager with the set of display layout options; and rendering the display layout manager with the set of display layout options on the display of the medical monitoring hub.

The method of the preceding paragraph can also include one or more of the following features. The method can further comprise detecting a change to the plurality of medical devices or the plurality of parameters; and automatically updating the set of display layout options and the display layout manager based at least in part on the change. The change can comprise an addition or a removal of a medical device or a parameter. The display characteristics can be automatically provided to the patient monitoring hub by the medical device while the medical device and the patient monitoring hub are establishing a connection. The display characteristics can comprise at least one of: an instruction to call a graphics library on the patient monitoring hub to draw the user interface element; a set of preconfigured display layouts for a parameter; layout restrictions for displaying information of the parameter; or images or texts associated with displaying the parameter. The plurality of parameters can comprise a parameter calculated by the patient monitoring hub. The display can be divided into a plurality of subdivisions wherein each subdivision comprises one or more parameters. The method can further comprise receiving a user input for adjusting a size or location of a subdivision; and automatically updating displays of parameters in the plurality of subdivisions in response to the user input. The method can further comprise: automatically selecting a display layout option among the set of display layout options; and automatically rendering information of the plurality of parameters in accordance with the selected display layout option. A parameter can be displayed with a user interface element for managing a feature on a medical device which can provide data of the parameter to the monitoring hub, and the method can further comprise receiving a user input for the user interface element and communicate to the medical device of the user input to manage the feature on the medical device.

For purposes of summarizing the disclosure, certain aspects, advantages and novel features are discussed herein.

It is to be understood that not necessarily all such aspects, advantages or features will be embodied in any particular example of the invention and an artisan would recognize from the disclosure herein a myriad of combinations of such aspects, advantages or features.

BRIEF DESCRIPTION OF THE DRAWINGS

The following drawings and the associated descriptions are provided to illustrate examples of the present disclosure and do not limit the scope of the claims.

FIGS. 1A-1C illustrate perspective views of an example medical monitoring hub. For example, FIG. 1A illustrates the hub with an example docked portable patient monitor, FIG. 1B illustrates the hub with a set of medical ports and a noninvasive blood pressure input, and FIG. 1C illustrates the hub with various example temperature sensors attached thereto.

FIG. 5 illustrates a perspective view of example portable patient monitors undocked from the hub of FIG. 1. Moreover, FIG. 5 illustrates an example alternative docking station.

FIG. 6 illustrates a simplified block diagram of traditional patient device electrical isolation principles.

FIG. 7A illustrates a simplified block diagram of an example optional patient device isolation system of the disclosure, while FIG. 7B adds example optional non-isolation power levels for the system of FIG. 7A.

FIGS. 9A-9B, 10, 11A-11F, 11G1-11G2, and 11H-11K illustrate simplified block diagrams of example universal medical connectors having a size and shape smaller in cross section than tradition isolation requirements.

FIG. 10 illustrates a perspective view of a side of the hub of FIG. 1, showing example instrument-side channel inputs for example universal medical connectors.

FIGS. 11A-11F, 11G1-11G2, and 11H-11K illustrate various views of example male and mating female universal medical connectors.

FIG. 41A illustrates an example input message received by the translation module.

FIG. 41B illustrates an example message header segment of an input message that has been parsed into fields.

FIG. 41C illustrates an example encoded version of the parsed message header segment of FIG. 41B.

FIG. 41D illustrates an example output message of the translation module based on the input message of FIG. 41A.

FIGS. 46-71 illustrate additional example hub displays, including displays of measurement data.

Figure 1A:
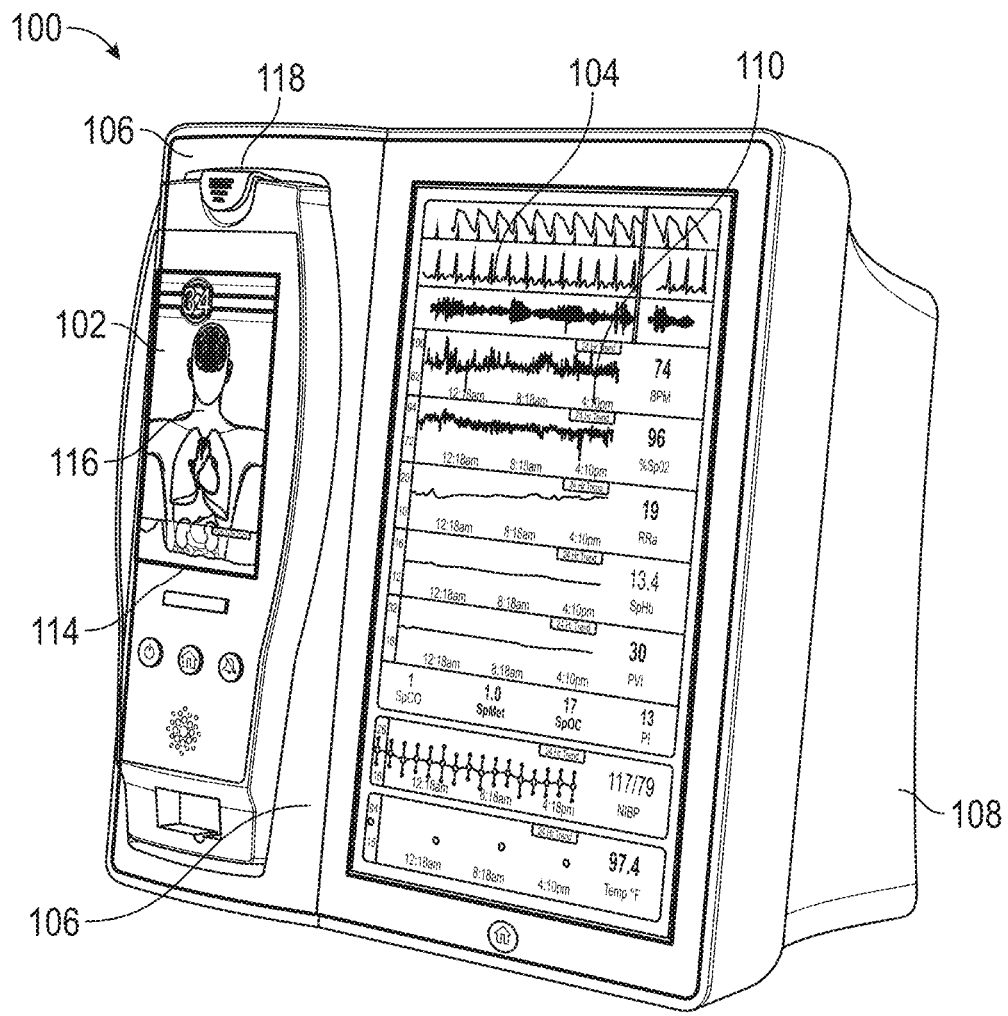

While the foregoing "Brief Description of the Drawings" references generally various examples of the disclosure, an artisan will recognize from the disclosure herein that such examples are not mutually exclusive. Rather, the artisan would recognize a myriad of combinations of some or all of such examples.

DETAILED DESCRIPTION

I. Introduction

Based on at least the foregoing, a solution is needed that coordinates the various medical devices treating or monitoring a patient Such a solution can provide patient identification seamlessly across the device space and such a solution can expand for future technologies without necessarily requiring repeated software upgrades. In addition, such a solution may include patient electrical isolation where desired.

Therefore, the present disclosure relates to a patient monitoring hub that is the center of patient monitoring and treatment activities for a given patient. The patient monitoring hub can interface with legacy devices without necessitating legacy reprogramming, provide flexibility for interfacing with future devices without necessitating software upgrades, and offer optional patient electrical isolation. The hub may include a large display dynamically providing information to a caregiver about a wide variety of measurement or otherwise determined parameters. Additionally or optionally, the hub can include a docking station for a portable patient monitor. The portable patient monitor may communicate with the hub through the docking station or through various wireless paradigms known to an artisan from the disclosure herein, including WiFi, Bluetooth, Zigbee, or the like.

The portable patient monitor can modify its screen when docked. The undocked display indicia is in part or in whole transferred to a large dynamic display of the hub and the docked display presents one or more anatomical graphics of monitored body parts. For example, the display may present a heart, lungs, a brain, kidneys, intestines, a stomach, other organs, digits, gastrointestinal systems or other body parts when it is docked. The anatomical graphics may advantageously be animated. The animation may generally follow the behavior of measured parameters, such as, for example, the lungs may inflate in approximate correlation to the measured respiration rate and/or the determined inspiration portion of a respiration cycle, and likewise deflate according to the expiration portion of the same. The heart may beat according to the pulse rate, may beat generally along understood actual heart contraction patterns, and the like. Moreover, when the measured parameters indicate a need to alert a caregiver, a changing severity in color may be associated with one or more displayed graphics, such as the heart, lungs, brain, or the like. The body portions may include animations on where, when or how to attach measurement devices to measurement sites on the patient. For example, the monitor may provide animated directions for CCHD screening procedures or glucose strip reading protocols, the application of a forehead sensor, a finger or toe sensor, one or more electrodes, an acoustic sensor, and ear sensor, a cannula sensor or the like.

The present disclosure relates to a medical monitoring hub configured to be the center of monitoring activity for a given patient. The hub can comprise a large easily readable display, such as an about ten (10) inch display dominating the majority of real estate on a front face of the hub. The display could be much larger or much smaller depending upon design constraints. However, for portability and current design goals, the preferred display is roughly sized proportional to the vertical footprint of one of the dockable portable patient monitors. Other considerations are recognizable from the disclosure herein by those in the art.

The display can provide measurement data for a wide variety of monitored parameters for the patient under observation in numerical or graphic form, and can be automatically configured based on the type of data and information being received at the hub. The hub can be moveable, portable, and mountable so that it can be positioned to convenient areas within a caregiver environment. For example, the hub can be collected within a singular housing.

The hub may advantageously receive data from a portable patient monitor while docked or undocked from the hub. Typical portable patient monitors, such as oximeters or co-oximeters can provide measurement data for a large number of physiological parameters derived from signals output from optical and/or acoustic sensors, electrodes, or the like. The physiological parameters include, but not limited to oxygen saturation, carboxy hemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, combinations of the same or the like, to name a few. The hub may output data sufficient to accomplish closed-loop drug administration in combination with infusion pumps or the like.

The hub can communicate with other devices in a monitoring environment that are interacting with the patient in a number of ways. For example, the hub advantageously receives serial data from other devices without necessitating their reprogramming or that of the hub. Such other devices include pumps, ventilators, all manner of monitors monitoring any combination of the foregoing parameters, ECG/EEG/EKG devices, electronic patient beds, and the like. Moreover, the hub advantageously receives channel data from other medical devices without necessitating their reprogramming or that of the hub. When a device communicates through channel data, the hub may advantageously alter the large display to include measurement information from that device. Additionally, the hub accesses nurse call systems to ensure that nurse call situations from the device are passed to the appropriate nurse call system.

The hub also communicates with hospital systems to advantageously associate incoming patient measurement and treatment data with the patient being monitored. For example, the hub may communicate wirelessly or otherwise to a multi-patient monitoring system, such as a server or collection of servers, which in turn many communicate with a caregiver's data management systems, such as, for example, an Admit, Discharge, Transfer ("ADT") system and/or an Electronic Medical Records ("EMR") system. The hub advantageously associates the data flowing through it with the patient being monitored thereby providing the electronic measurement and treatment information to be passed to the caregiver's data management systems without the caregiver associating each device in the environment with the patient.

The hub may advantageously include a reconfigurable and removable docking station. The docking station may dock additional layered docking stations to adapt to different patient monitoring devices. Additionally, the docking station itself is modularized so that it may be removed if the primary dockable portable patient monitor changes its form factor. Thus, the hub is flexible in how its docking station is configured.

The hub may include a large memory for storing some or all of the data it receives, processes, and/or associates with the patient, and/or communications it has with other devices and systems. Some or all of the memory may advantageously comprise removable SD memory.

The hub communicates with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, (6) other wired or wireless communication mechanisms known to an artisan. The universal medical connectors advantageously provide optional electrically isolated power and communications, are designed to be smaller in cross section than isolation requirements. The connectors and the hub communicate to advantageously translate or configure data from other devices to be usable and displayable for the hub. A software development kit ("SDK") can be provided to a device manufacturer to establish or define the behavior and meaning of the data output from their device. When the output is defined, the definition is programmed into a memory residing in the cable side of the universal medical connector and supplied as an original equipment manufacture ("OEM") to the device provider. When the cable is connected between the device and the hub, the hub understands the data and can use it for display and processing purposes without necessitating software upgrades to the device or the hub. The hub can negotiate the schema and even add additional compression and/or encryption. Through the use of the universal medical connectors, the hub organizes the measurement and treatment data into a single display and alarm system effectively and efficiently bringing order to the monitoring environment.

As the hub receives and tracks data from other devices according to a channel paradigm, the hub may advantageously provide processing to create virtual channels of patient measurement or treatment data. A virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub also receives serial data through serial communication ports, such as RJ connectors. The serial data is associated with the monitored patient and passed on to the multi-patient server systems and/or caregiver backend systems discussed above. Through receiving the serial data, the caregiver advantageously associates devices in the caregiver environment, often from varied manufactures, with a particular patient, avoiding a need to have each individual device associated with the patient and possible communicating with hospital systems. Such association is vital as it reduces caregiver time spent entering biographic and demographic information into each device about the patient. Moreover, through the SDK, the device manufacturer may advantageously provide information associated with any measurement delay of their device, thereby further allowing the hub to advantageously time-wise synchronize serial incoming data and other data associated with the patient.

When a portable patient monitor is docked, and it includes its own display, the hub effectively increases its display real estate. For example, the portable patient monitor may simply continue to display its measurement and/or treatment data, which may be now duplicated on the hub display, or the docked display may alter its display to provide additional information. The docked display, when docked, can present anatomical graphical data of, for example, the heart, lungs, organs, the brain, or other body parts being measured and/or treated. The graphical data may advantageously animate similar to and in concert with the measurement data. For example, lungs may inflate in approximate correlation to the measured respiration rate and/or the determined inspiration/expiration portions of a respiration cycle, the heart may beat according to the pulse rate, may beat generally along understood actual heart contraction patterns, the brain may change color or activity based on varying depths of sedation, or the like. When the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. The body portions may include animations on where, when or how to attach measurement devices.

The hub may also advantageously overlap parameter displays to provide additional visual information to the caregiver. Such overlapping may be user definable and configurable. The display may also incorporate analog-appearing icons or graphical indicia.

The hub of the present disclosure can be highly configurable and capable of communicating with previously unknown medical systems. The connectable medical systems can be a dongle with a built-in processor providing specialized software processing capabilities that can expand the capabilities of the hub. Optionally, the connected medical systems can be medical devices communicating via a communication cable with the hub. The cable can include a processing board in the cable. Optionally, the processor on the medical device itself can communicate directly with the hub.

When a medical system is initially connected, for example, using a wired connection such as a cable or dongle device, an EPROM on the cable or dongle device initially describes the necessary physical communication parameters for speaking with the medical system's processor. For example, the EPROM can provide parameters including ISO/non-ISO communication requirements, baud rates, etc.

Once initial communication parameters are established, the hub can begin communicating with the processor of the medical system. The medical system then describes itself and its capabilities to the hub. For example, the self-description can include the measurement channels supported by the device; the measured parameters (metrics) supported by each channel, including, but not limited to: names, relationship to metrics and coding systems defined by standards bodies, valid ranges and units of measure, body sites involved, parameter exceptions, visual presentation requirements and characteristics; alarm limits and other parameter settings; alarm, alert and other event conditions; actions that can be performed by the device (such as requests to begin performing measurements); patient demographics and externally-measured metrics needed by the device to perform its computations; manufacturer branding information; or other information as would be desired for patient monitoring.

The "self-describing" nature of the platform can permit a high degree of flexibility, allowing the protocol and its capabilities to evolve while maintaining compatibility across protocol and software versions. For example, the platform can be a patient hub device (or just "hub") that communicates with a third-party device (which may be an external device or a medical device) to receive patient data from the third-party device and display the patient data on a screen of the hub. The third-party device can communicate with the hub by accessing a library of code, represented by an application programming interface ("API"), which may be stored at the hub or in a dongle or cable connected to the hub. The code library can provide functionality that enables creating user interface controls on the hub that can be used to control aspects of the third-party device.

For example, sliders could be provided as user interface controls on the hub, which allow a user to adjust alarm limits or other settings of the third-party device. Upon receipt of an updated setting, the hub can communicate this setting update to the third-party device (for example, over a cable, a network, or the like). The third-party device can know how to read the setting update because the third-party device can include code that can interpret the settings update from the hub (for example, the hub can format the settings update in a way that the third-party device can understand it). Similarly, the hub can send patient data obtained from any sensor connected to the hub (such as an SpO2 or pulse rate sensor) and send that patient data (such as SpO2% or pulse rate) to the third-party device, which may use this data to update its algorithms or for other purposes.

Moreover, when a new patient connects to the hub, the hub can report that a new patient has connected to the third-party device. That way, the third-party device can know to restart a measurement or treatment algorithm, for example, by resetting a baseline for the new patient. Without this feature, when a new patient connected to the hub, the third-party device may have continued to measure or treat the patient using old baseline data about the patient (which in fact would have referred to a previous patient).

The medical systems, once connected to the hub, can then pull from or push to the hub any information. For example, a connected Medical System A can pull measured parameters from connected Medical System B. Medical System A can then use that information to generate a new measured parameter which can then be pushed to the platform for display or use by other connected medical systems.

The data obtained from the various connected medical system can be time-stamped using the hub's system clock. Time-stamping can allow various measurements to be synchronized with other measurements. Synchronization can aid with display of the data and further calculations using the data.

The third-party device can perform calculations based on patient data and communicate the results of the calculations to the hub. For example, the third-party device can calculate a wellness index based on patient parameter data received from the hub or other third-party devices. The third-party device may be a board-in-cable configured to perform the calculations. For example, the third-party device can execute algorithms to calculate a patient's parameter(s) based on data acquired from a sensor connected to the board-in-cable.

The platform can provide standardized graphical interfaces depending on the display characteristics of the medical systems. For example, the medical systems can self-define to a numerical readout, a graph, or other specified display options which can be self-defined. Optionally, the attached medical device can provide image data used by the hub to provide display graphics.

The third-party device can also control at least a portion of the display settings on the hub. For example, the third-party device can communicate the display characteristics or the self-defined display options of a medical system to the hub, which can override or supplement the display on the hub that is associated with the data provided by the medical system. The self-describing features as well as other functions and communications of the third-party device described herein can be programmed with a software development kit (SDK). The SDK can be provided by a supplier of the hub to a supplier of the third-party device, which can allow the supplier of the third-party device to create customized functions and to interface with the hub.

In the interest of clarity, not all features of an actual implementation are described in this specification. An artisan will of course be appreciate that in the development of any such actual implementation (as in any development project), numerous implementation-specific decisions must be made to achieve a developers' specific goals and sub-goals, such as compliance with system- and business-related constraints, which will vary from one implementation to another. Moreover, it will be appreciated that such a development effort might be complex and time-consuming, but would nevertheless be a routine undertaking of device engineering for those of ordinary skill having the benefit of this disclosure.

To facilitate a complete understanding of the disclosure, the remainder of the detailed description describes the disclosure with reference to the drawings, wherein like reference numbers are referenced with like numerals throughout.

II. Examples of a Medical Monitoring Hub

FIG. 1A illustrates a monitoring environment including a perspective view of an example medical monitoring hub 100 with an example docked portable patient monitor 102. The hub 100 can include a display 104, and a docking station 106, which can be configured to mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes.

The display 104 may present a wide variety of measurement and/or treatment data in numerical, graphical, waveform, or other display indicia 110. The display 104 can occupy much of a front face of the housing 108, although an artisan will appreciate the display 104 may comprise a tablet or tabletop horizontal configuration, a laptop-like configuration or the like. The display 104 may include communicating display information and data to a table computer, smartphone, television, or any display system recognizable to an artisan. The upright inclined configuration of FIG. 1A can present display information to a caregiver in an easily viewable manner.

Figure 1B:
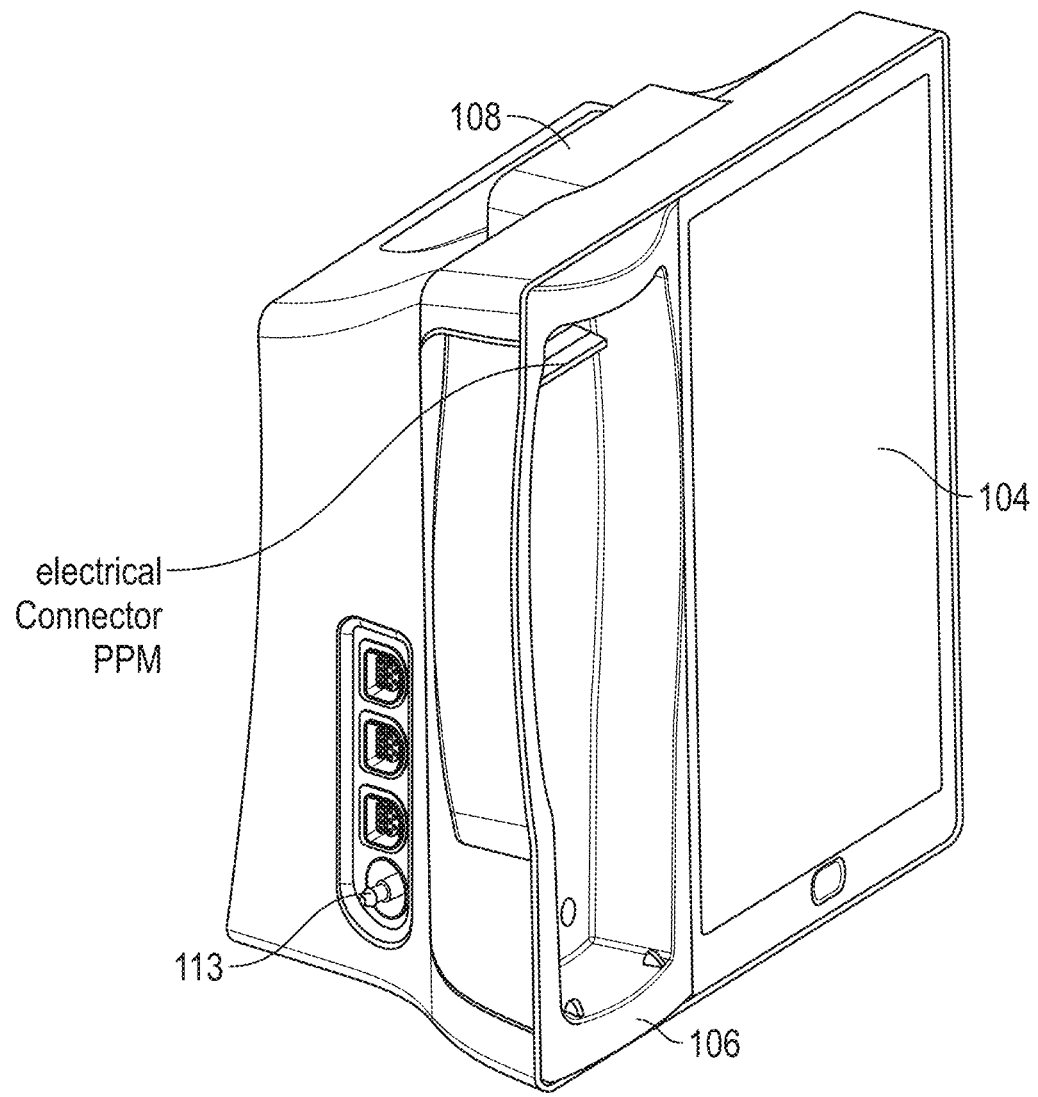

FIG. 1B shows a perspective side view of the hub 100 including the housing 108, the display 104, and the docking station 106 without a portable monitor docked. Also shown is a connector for noninvasive blood pressure.

The housing 108 may also include pockets or indentations to hold additional medical devices, such as, for example, a blood pressure monitor or temperature sensor 112, such as that shown in FIG. 1C.

The portable patient monitor 102 of FIG. 1A may advantageously comprise an oximeter, co-oximeter, respiratory monitor, depth of sedation monitor, noninvasive blood pressure monitor, vital signs monitor or the like, such as those commercially available from Masimo Corporation of Irvine, CA, and/or disclosed in U.S. Pat. Pub. Nos. 2002/0140675, 2010/0274099, 2011/0213273, 2012/0226117, 2010/0030040; U.S. Pat. App. Ser. Nos. 61/242,792, 61/387,457, 61/645,570, Ser. No. 13/554,908 and U.S. Pat. Nos. 6,157,850, 6,334,065, and the like. The monitor 102 may communicate with a variety of noninvasive and/or minimally invasive devices such as optical sensors with light emission and detection circuitry, acoustic sensors, devices that measure blood parameters from a finger prick, cuffs, ventilators, and the like. The monitor 102 may include its own display 114 presenting its own display indicia 116, discussed below with reference to FIGS. 19A-19J. The display indicia may advantageously change based on a docking state of the monitor 102. When undocked, the display indicia may include parameter information and may alter orientation based on, for example, a gravity sensor or accelerometer.

The docking station 106 of the hub 100 includes a mechanical latch 118, or mechanically releasable catch to ensure that movement of the hub 100 doesn't mechanically detach the monitor 102 in a manner that could damage the same.

Although disclosed with reference to particular portable patient monitors 102, an artisan will recognize from the disclosure herein a large number and wide variety of medical devices that may advantageously dock with the hub 100. Moreover, the docking station 106 may advantageously electrically and not mechanically connect with the monitor 102, and/or wirelessly communicate with the same.

Figure 2:
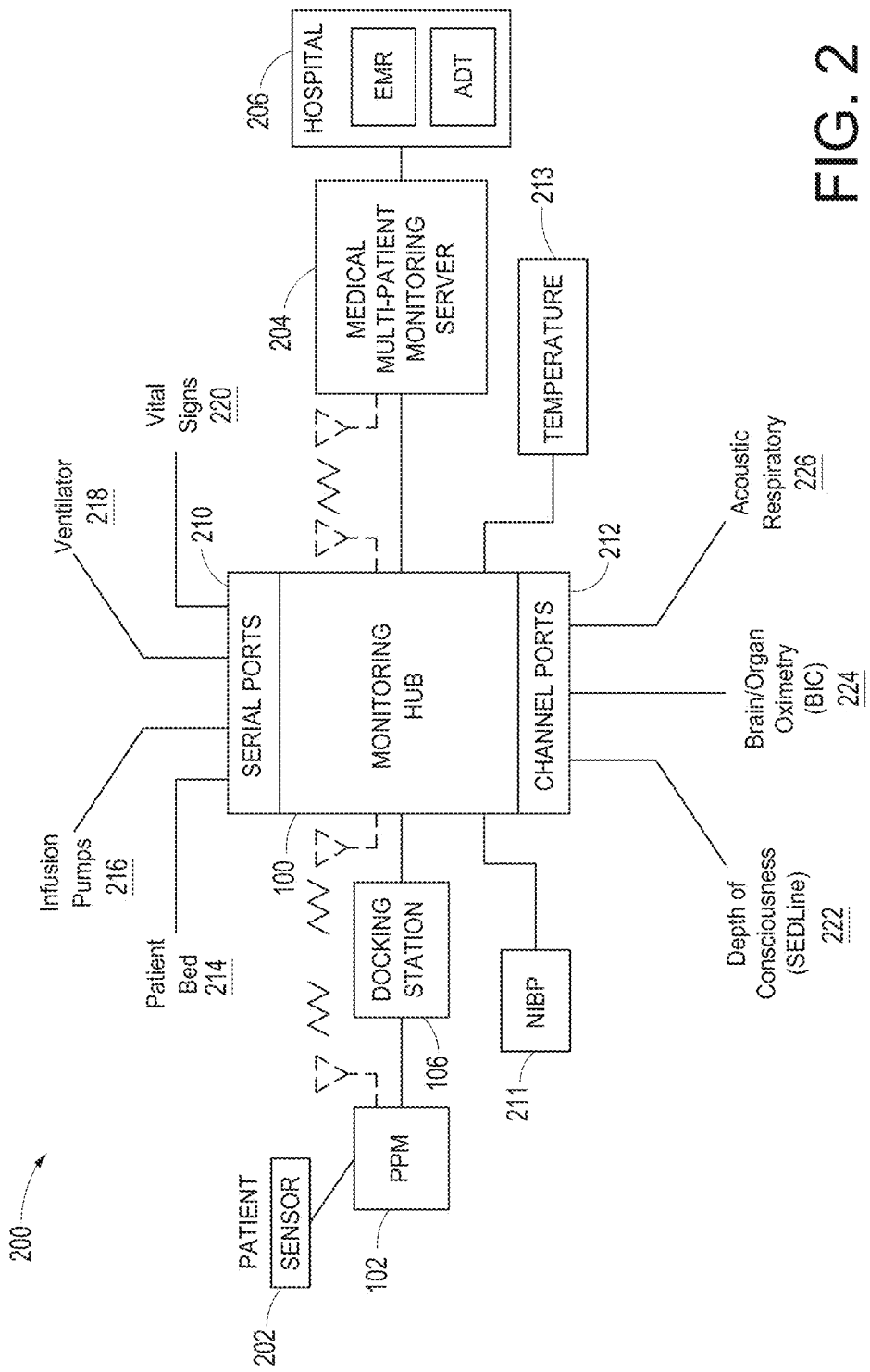
FIG. 2 illustrates a simplified block diagram of an example monitoring environment including the hub of FIG. 1.

FIG. 2 illustrates a simplified block diagram of an example monitoring environment 200 including the hub 100 of FIG. 1. As shown in FIG. 2, the environment may include the portable patient monitor 102 communicating with one or more patient sensors 202, such as, for example, oximetry optical sensors, acoustic sensors, blood pressure sensors, respiration sensors or the like. Additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

As disclosed, the portable patient monitor 102 can communicate with the hub 100, through the docking station 106 when docked and, wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140. In general, the server 204 communicates with caregiver backend systems 206 such as EMR and/or ADT systems. The server 204 may advantageously obtain through push, pull or combination technologies patient information entered at patient admission, such as demographical information, billing information, and the like. The hub 100 accesses this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SEDLine, brain or other organ oximeter devices 224, noninvasive blood pressure or acoustic devices 226, or the like. A channel device may include board-in-cable ("BIC") solutions where the processing algorithms and the signal processing devices that accomplish those algorithms are mounted to a board housed in a cable or cable connector, which may have no additional display technologies. The BIC solution outputs its measured parameter data to the channel port 212 to be displayed on the display 104 of hub 100. The hub 100 may advantageously be entirely or partially formed as a BIC solution that communicates with other systems, such as, for example, tablets, smartphones, or other computing systems.

Although disclosed with reference to a single docking station 106, the environment 200 may include stacked docking stations where a subsequent docking station mechanically and electrically docks to a first docking station to change the form factor for a different portable patent monitor as discussed with reference to FIG. 5. Such stacking may include more than 2 docking stations, may reduce or increase the form fact for mechanical compliance with mating mechanical structures on a portable device.

Figure 3:
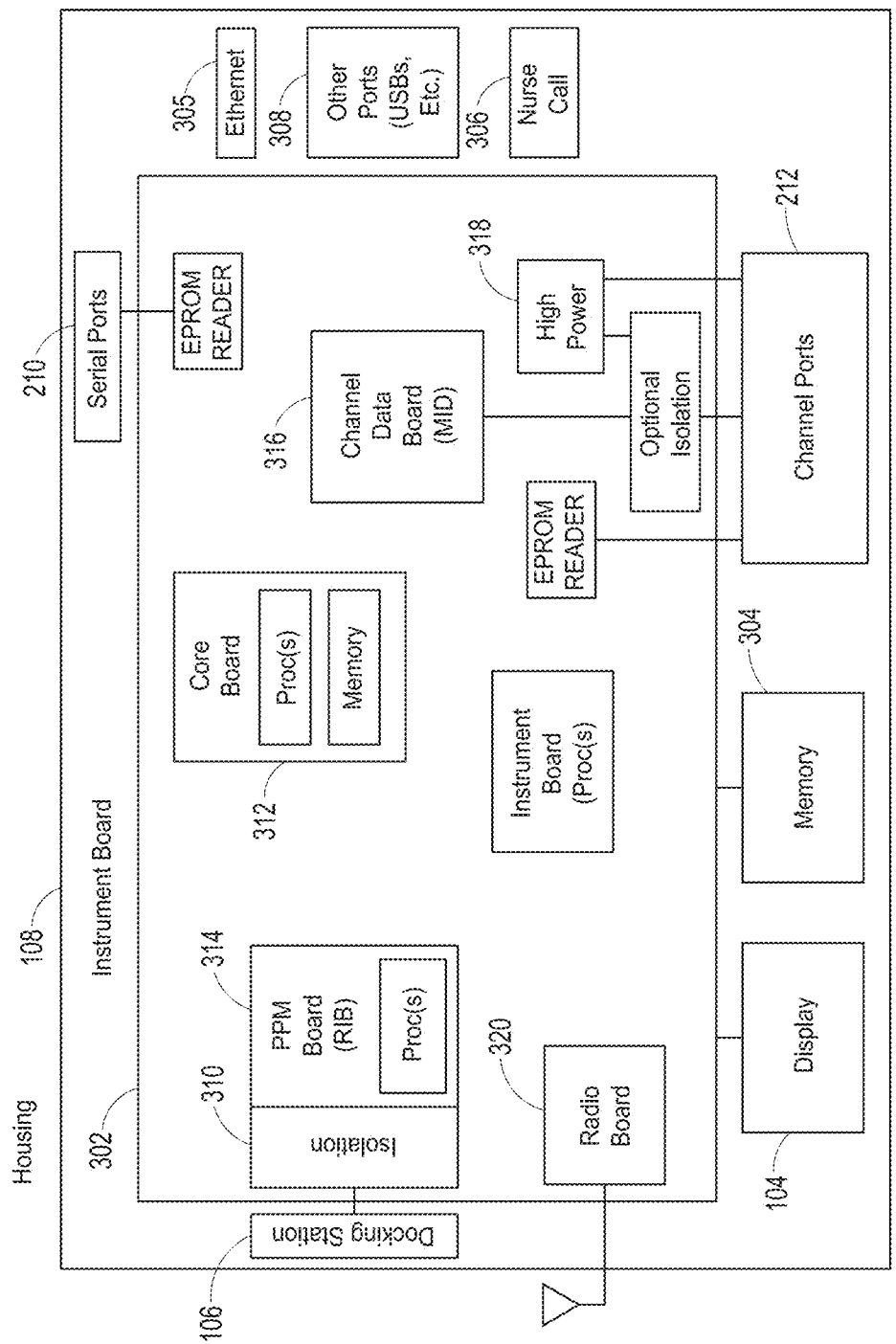
FIG. 3 illustrates a simplified example hardware block diagram of the hub of FIG. 1.

FIG. 3 illustrates a simplified example hardware block diagram of the hub 100 of FIG. 1. As shown in FIG. 3, the housing 108 of the hub 100 positions and/or encompasses an instrument board 302, the display 104, memory 304, and the various communication connections, including the serial ports 210, the channel ports 212, Ethernet ports 305, nurse call port 306, other communication ports 308 including standard USB or the like, and the docking station interface 310. The instrument board 302 comprises one or more substrates including communication interconnects, wiring, ports and the like to enable the communications and functions described herein, including inter-board communications. A core board 312 includes the main parameter, signal, and other processor(s) and memory, a portable monitor board ("RIB") 314 includes patient electrical isolation for the monitor 102 and one or more processors, a channel board ("MID") 316 controls the communication with the channel ports 212 including optional patient electrical isolation and power supply 318, and a radio board 320 includes components configured for wireless communications. Additionally, the instrument board 302 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 may comprise a large number of electronic components organized in a large number of ways. Using different boards such as those disclosed above advantageously provides organization and compartmentalization to the complex system.

Figure 4:
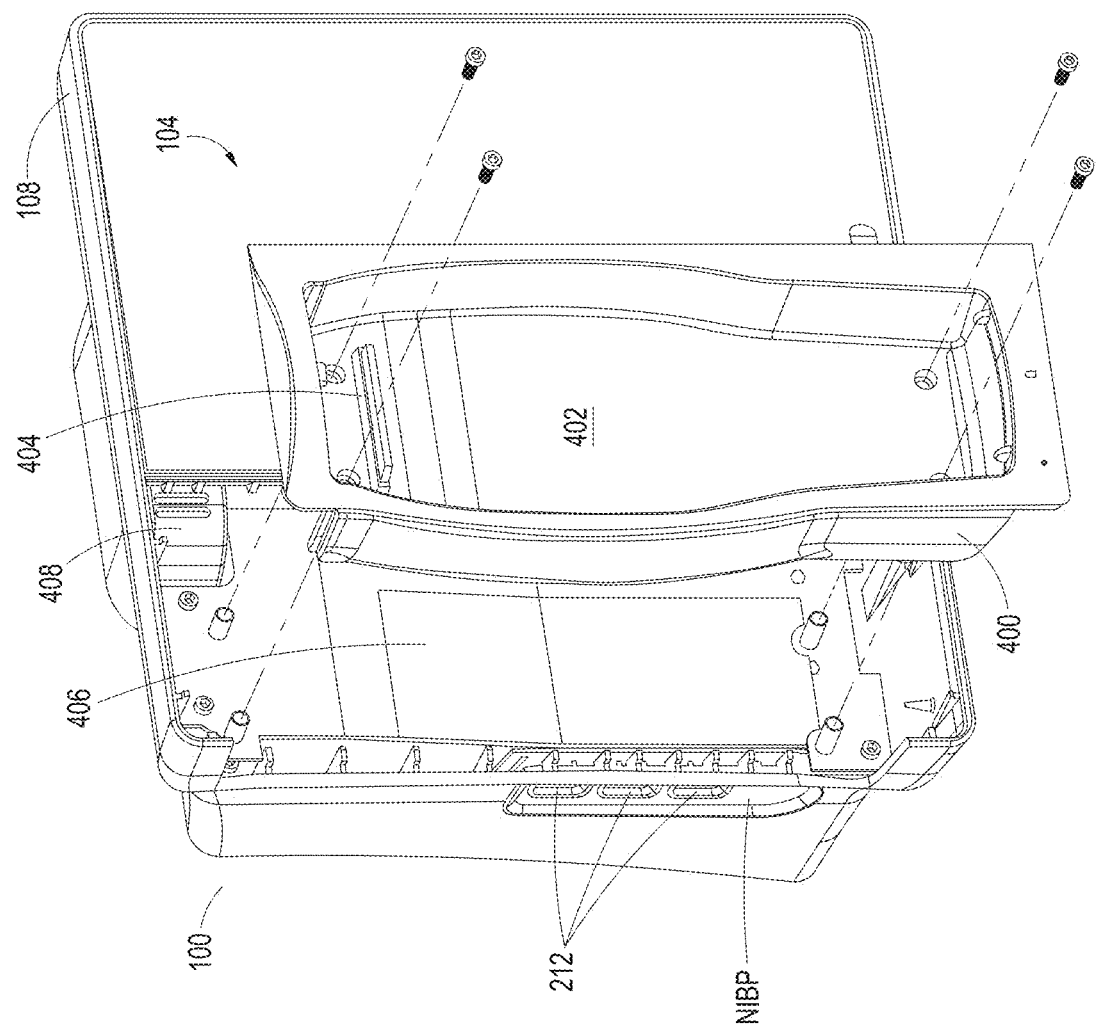
FIG. 4 illustrates a perspective view of an example removable docking station of the hub of FIG. 1.

FIG. 4 illustrates a perspective view of an example removable docking station 400 of the hub 100 of FIG. 1. As shown in FIG. 4, the docking station 400 provides a mechanical mating to portable patient monitor 102 to provide secure mechanical support when the monitor 102 is docked. The docking station 400 includes a cavity 402 shaped similar to the periphery of a housing of the portable monitor 102. The station 400 also includes one or more electrical connectors 404 providing communication to the hub 100. Although shown as mounted with bolts, the docking station 400 may snap fit, may use movable tabs or catches, may magnetically attach, or may employ a wide variety or combination of attachment mechanisms know to an artisan from the disclosure herein. The attachment of the docking station 400 may be sufficiently secure that when docked, the monitor 102 and docking station cannot be accidentally detached in a manner that could damage the instruments, such as, for example, if the hub 100 was accidently bumped or the like, the monitor 102 and docking station 400 can remain intact.

The housing 108 of the hub 100 also includes cavity 406 housing the docking station 400. To the extent a change to the form factor for the portable patient monitor 102 occurs, the docking station 400 is advantageously removable and replaceable. Similar to the docking station 400, the hub 100 includes within the cavity 406 of the housing 108 electrical connectors 408 providing electrical communication to the docking station 400. The docking station 400 can include its own microcontroller and processing capabilities, such as those disclosed in U.S. Pat. Pub. No. 2002/0140675. The docking station 400 can pass communications through to the electrical connector 408.

FIG. 4 also shows the housing 108 including openings for channel ports 212 as universal medical connectors discussed in detail below.

FIG. 5 illustrates a perspective view of example portable patient monitors 502 and 504 undocked from the hub 100 of FIG. 1. As shown in FIG. 5, the monitor 502 may be removed and other monitors, like monitor 504 may be provided. The docking station 106 includes an additional docking station 506 that mechanically mates with the original docking station 106 and presents a form factor mechanically matable with monitor 504. The monitor 504 can mechanically and electrically mate with the stacked docking stations 506 and 106 of hub 100. As can be readily appreciated by and artisan from the disclosure herein, the stackable function of the docking stations provides the hub 100 with an extremely flexible mechanism for charging, communicating, and interfacing with a wide variety of patient monitoring devices. As noted above, the docking stations may be stacked, or removed and replaced.

FIG. 6 illustrates a simplified block diagram of traditional patient electrical isolation principles. As shown in FIG. 6, a host device 602 is generally associated with a patient device 604 through communication and power. As the patient device 604 often comprises electronics proximate or connected to a patient, such as sensors or the like, certain safety requirements dictate that electrical surges of energy from, for example, the power grid connected to the host device, should not find an electrical path to the patient. This is generally referred to a "patient isolation" which is a term known in the art and includes herein the removing of direct uninterrupted electrical paths between the host device 602 and the patient device 604. Such isolation is accomplished through, for example, isolation devices 606 on power conductors 608 and communication conductors 610. Isolation devices 606 can include transformers, optical devices that emit and detect optical energy, and the like. Use of isolation devices, especially on power conductors, can be expensive component wise, expensive size wise, and drain power. Traditionally, the isolation devices were incorporated into the patient device 604, however, the patient devices 604 are trending smaller and smaller and not all devices incorporate isolation.

FIG. 7A illustrates a simplified block diagram of an example optional patient isolation system. As shown in FIG. 7A, the host device 602 communicates with an isolated patient device 604 through isolation devices 606. However, a memory 702 associated with a particular patient device informs the host 602 whether that device needs isolated power. If a patient device 708 does not need isolated power, such as some types of cuffs, infusion pumps, ventilators, or the like, then the host 602 can provide non-isolated power through signal path 710. This power may be much higher that what can cost-effectively be provided through the isolated power conductor 608. The non-isolated patient devices 708 can receive isolated communication as such communication is typically at lower voltages and is not cost prohibitive. An artisan will recognize from the disclosure herein that communication could also be non-isolated. Thus, FIG. 7A shows a patient isolation system 700 that provides optional patient isolation between a host 602 and a wide variety of potential patient devices 604, 708. The hub 100 can include the channel ports 212 incorporating similar optional patient isolation principles.

FIG. 7B adds an example optional non-isolation power levels for the system of FIG. 7A. As shown in FIG. 7B, once the host 602 understands that the patient device 604 comprises a self-isolated patient device 708, and thus does not need isolated power, the host 602 provides power through a separate conductor 710. Because the power is not isolated, the memory 702 may also provide power requirements to the host 602, which may select from two or more voltage or power levels. In FIG. 7B, the host 602 provides either high power, such as about 12 volts, but could have a wide range of voltages or very high power such as about 24 volts or more, but could have a wide range of voltages, to the patient device 708. An artisan will recognize that supply voltages can advantageously be altered to meet the specific needs of virtually any device 708 and/or the memory could supply information to the host 602 which provided a wide range of non-isolated power to the patient device 708.

Moreover, using the memory 702, the host 602 may determine to simply not enable any unused power supplies, whether that be the isolated power or one or more of the higher voltage non-isolated power supplies, thereby increasing the efficiency of the host.

Figure 8:
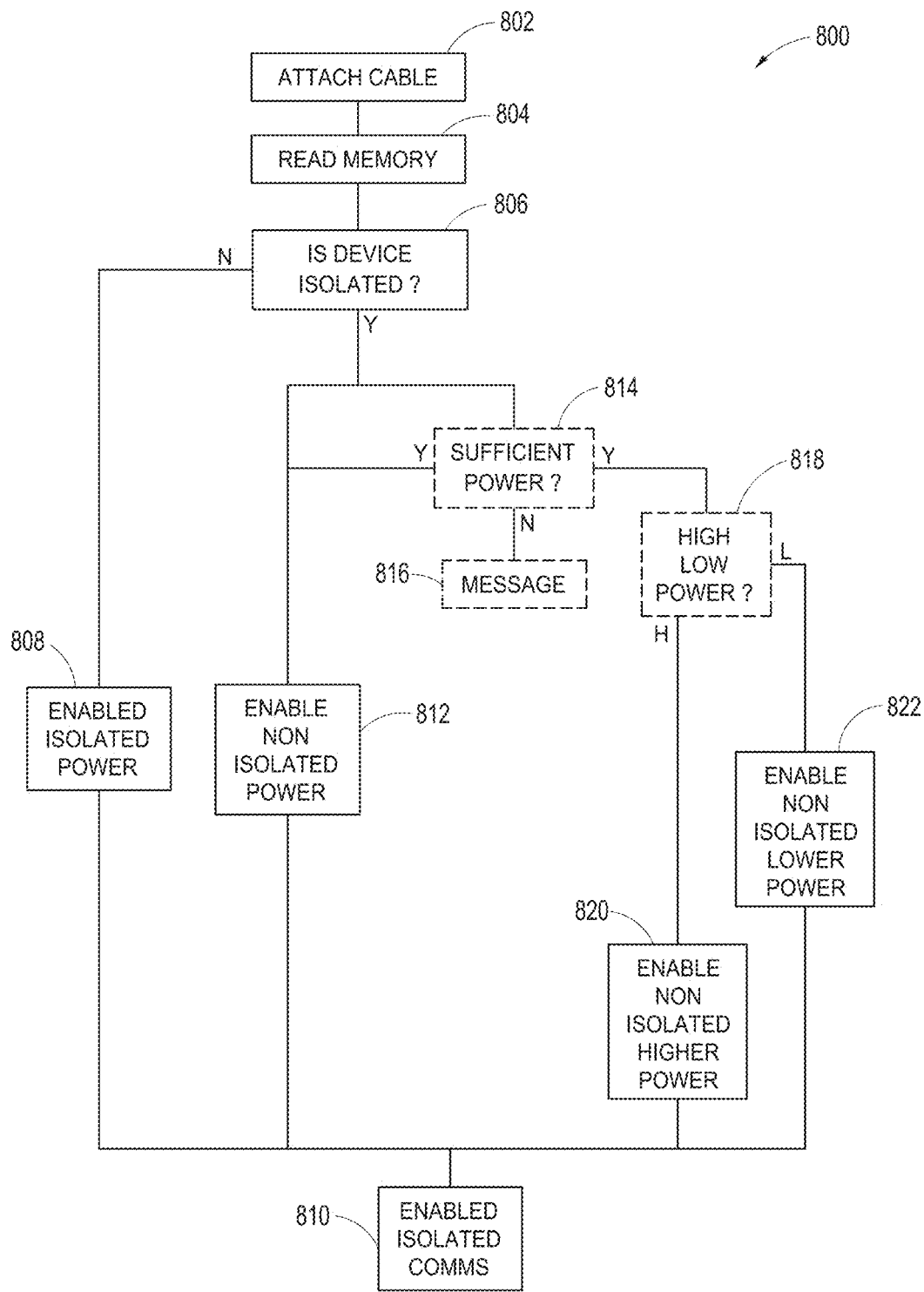
FIG. 8 illustrates a simplified example universal medical connector configuration process.

FIG. 8 illustrates a simplified example universal medical connector configuration process 800. As shown in FIG. 8, the process includes step 802, where a cable is attached to a universal medical connector incorporating optional patient isolation as disclosed in the foregoing. In step 804, the host device 602 or the hub 100, more specifically, the channel data board 316 or EPROM reader of the instrument board, reads the data stored in the memory 702 and in step 806, determines whether the connecting device requires isolated power. In step 808, when the isolated power is required, the hub 100 may advantageously enable isolated power and in step 810, enable isolated communications. In step 806, when isolated power is not needed, the hub 100 may simply in optional step 812 enable non-isolated power and where communications remain isolated, step 810 can enable isolated communications. In step 806, when isolated power is not needed, the hub 100 in step 814 may use information from memory 702 to determine the amount of power needed for the patient device 708. When sufficient power is not available, because for example, other connected devices are also using connected power, in step 816 a message may be displayed indicating the same and power is not provided. When sufficient power is available, optional step 812 may enable non-isolated power. Optionally, optional step 818 may determine whether memory 702 indicates higher or lower power is desired. When higher power is desired, the hub 100 may enable higher power in step 820 and when not, may enable lower power in step 822. The hub 100 in step 810 then enables isolated communication. The hub 100 in step 818 may simply determine how much power is needed and provide at least sufficient power to the self-isolated device 708.

An artisan will recognize from the disclosure herein that hub 100 may not check to see if sufficient power is available or may provide one, two or many levels of non-isolated voltages based on information from the memory 702.

Figure 9A:
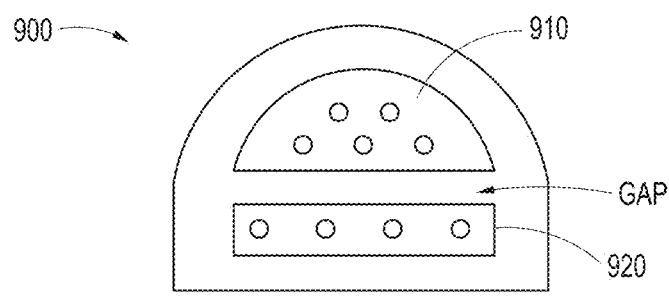
Figure 9B:
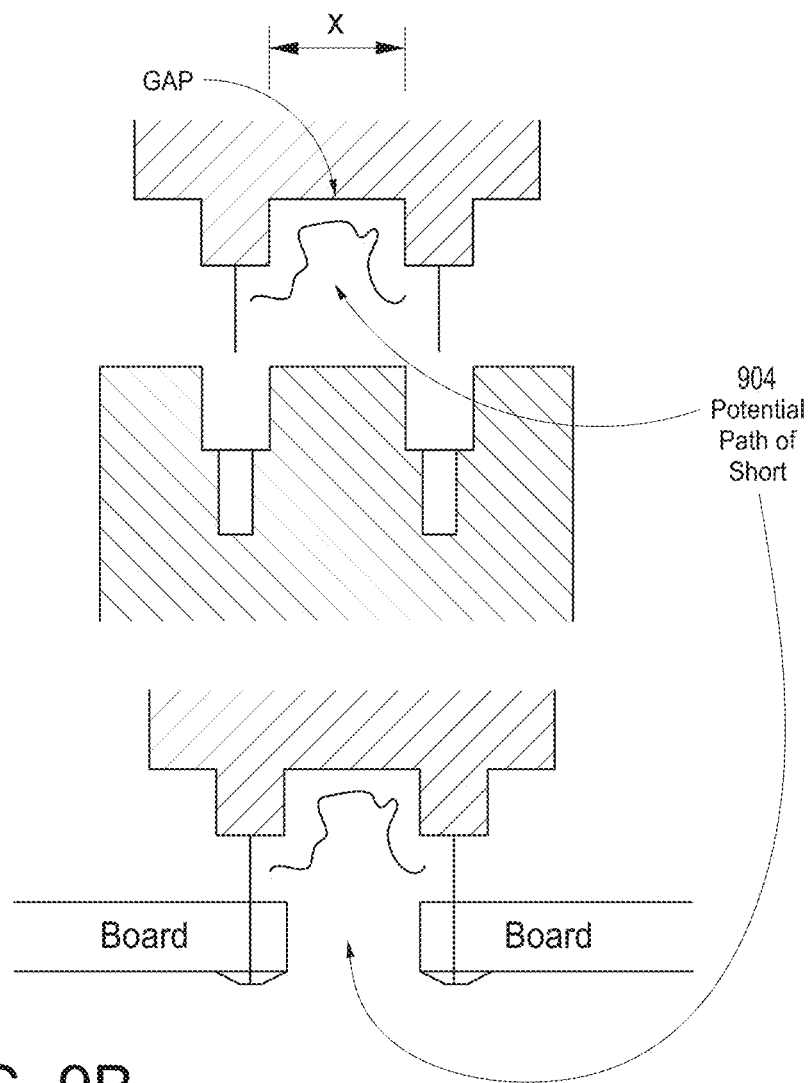

FIGS. 9A and 9B illustrate simplified block diagrams of example universal medical connectors 900 having a size and shape smaller in cross section than tradition isolation requirements. The connector 900 physically separates non-isolated signals on one side 910 from isolated signals on another side 920, although the sides could be reversed. The gap between such separations may be dictated at least in part by safety regulations governing patient isolation. The distance between the sides 910 and 920 may appear to be too small.

As shown from a different perspective in FIG. 9B, the distance between connectors "x" appears small. However, the gap causes the distance to includes a non-direct path between conductors. For example, any short would have to travel path 904, and the distance of such path is within or beyond such safety regulations, in that the distance is greater than "x." It is noteworthy that the non-straight line path 904 occurs throughout the connector, such as, for example, on the board connector side where solder connects various pins to a PCB board.

Figure 10:
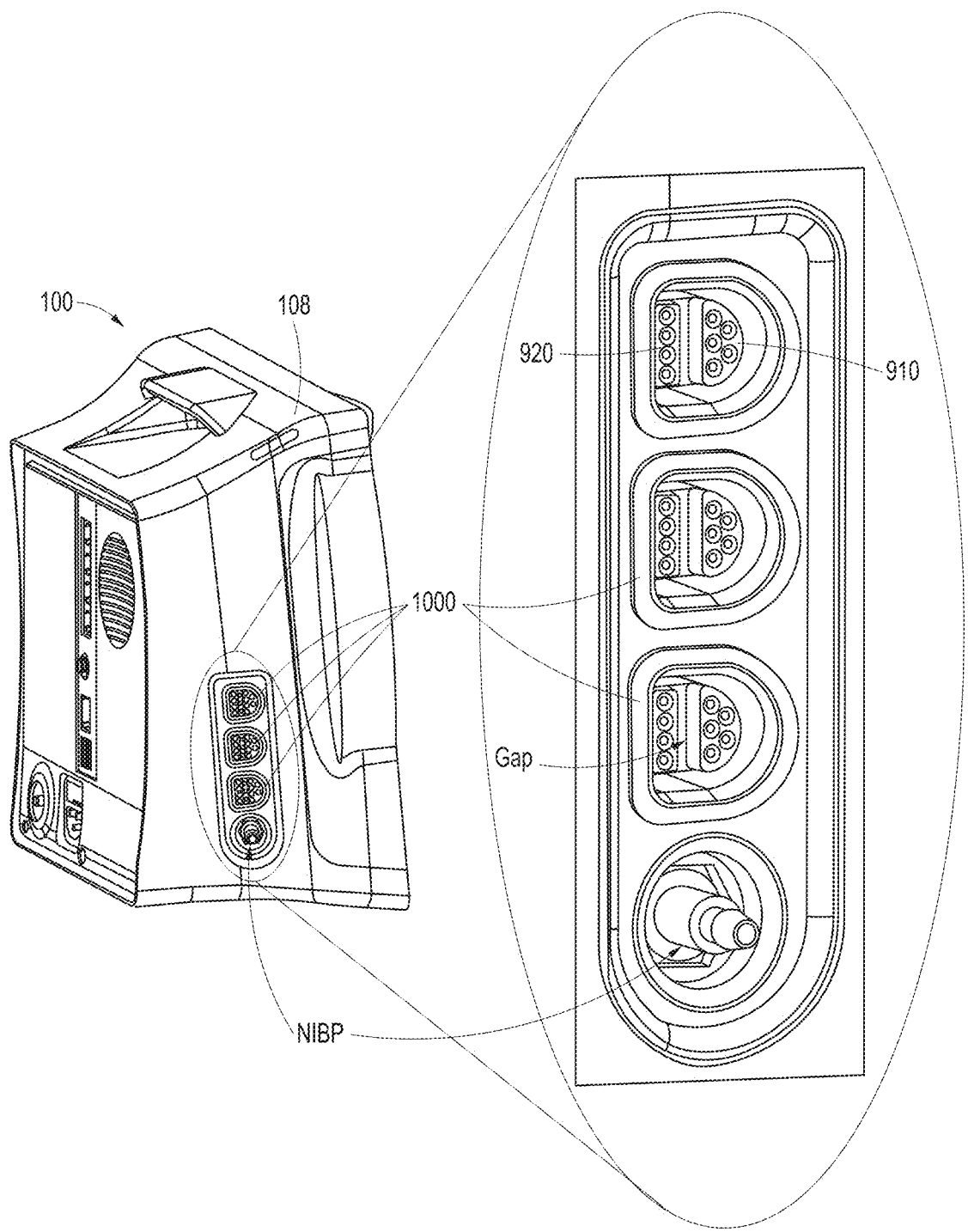

FIG. 10 illustrates a perspective view of a side of the hub 100 of FIG. 1, showing example instrument-side channel inputs 1000 as example universal medical connectors. As shown in FIG. 10, the inputs include the non-isolated side 910, the isolated side 920, and the gap. The memory 710 can communicate through pins on the non-isolated side.

Figure 11A:
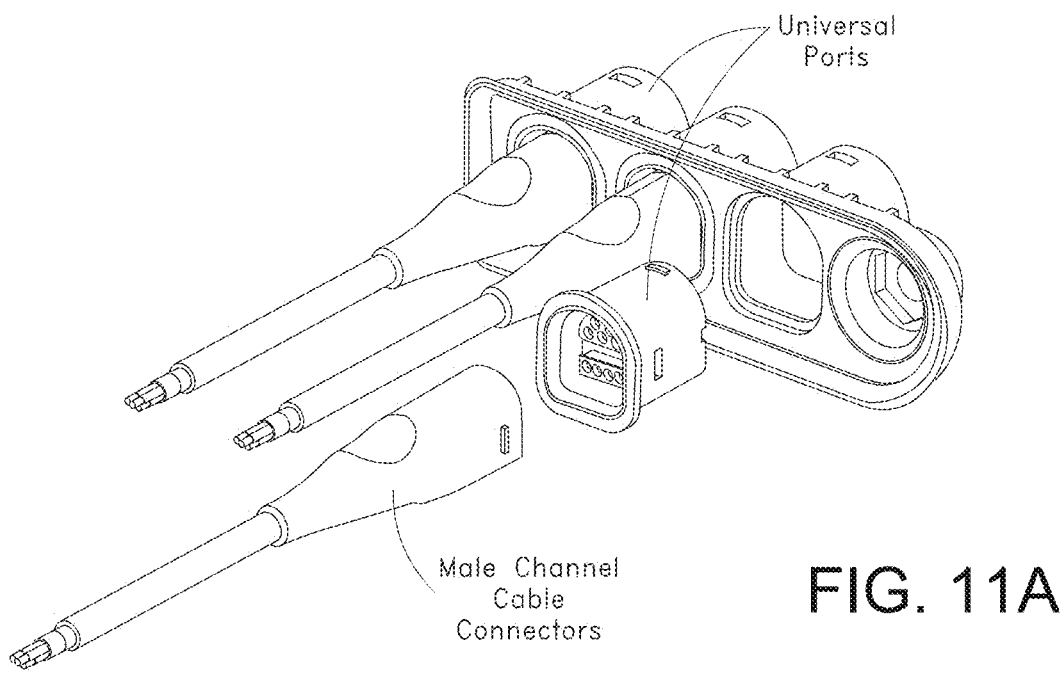
Figure 11B:
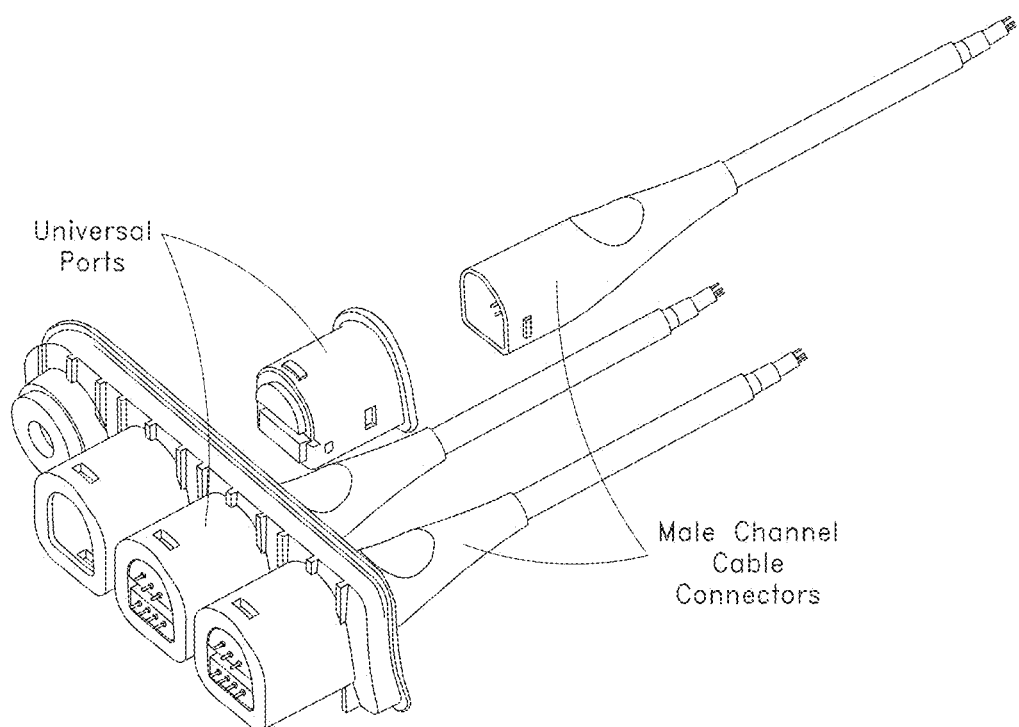
Figure 11C:
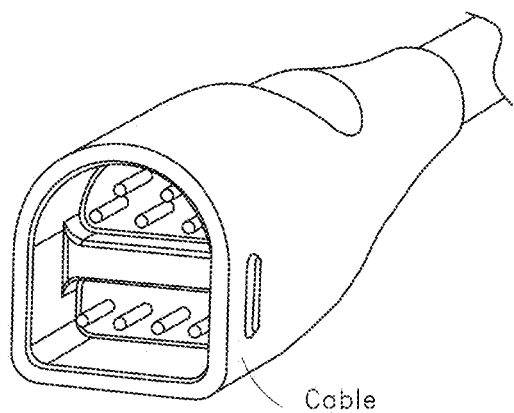
Figure 11D:
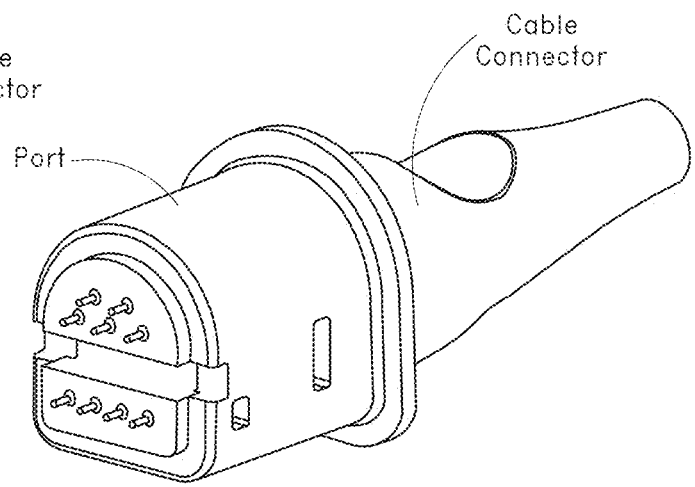
Figure 11E:
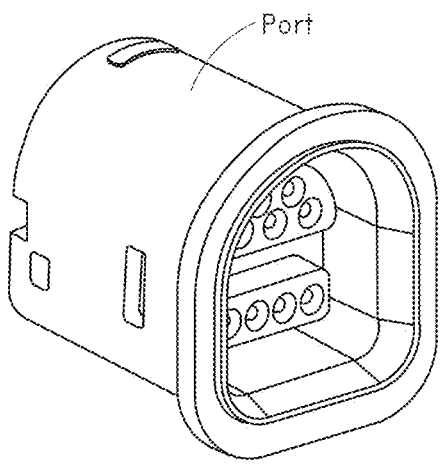
Figure 11F:
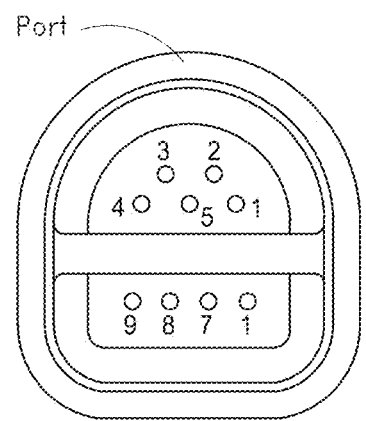
Figure 11J:
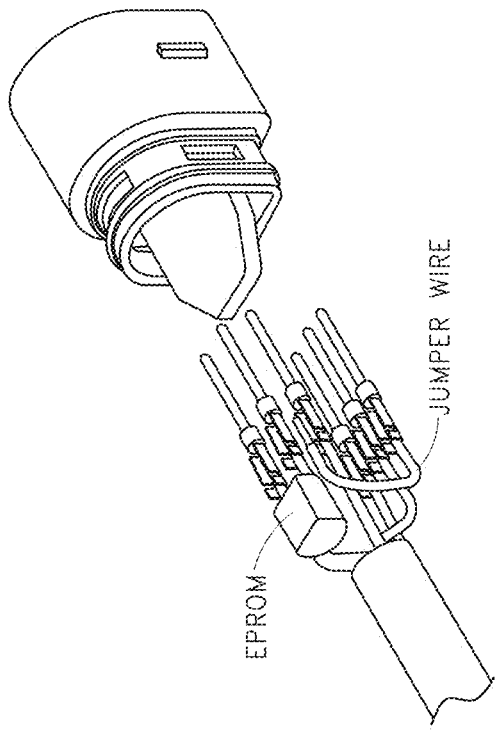
Figure 11I:
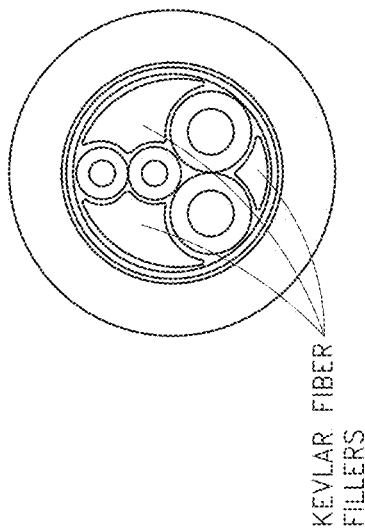
Figure 11K:
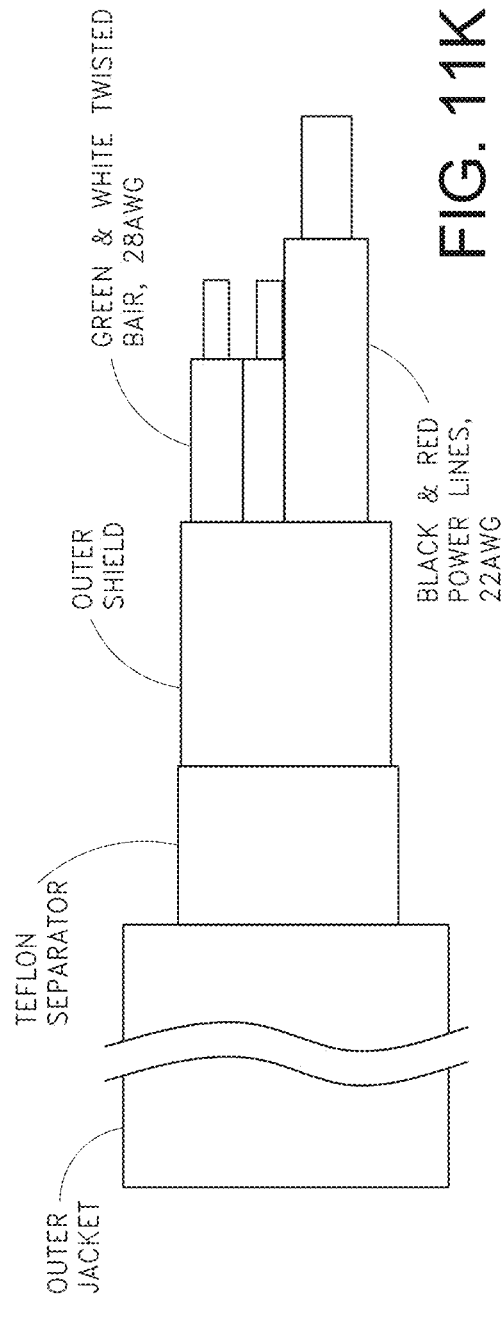

FIGS. 11A-11K illustrate various views of example male and mating female universal medical connectors. For example, FIGS. 11G1 and 11G2 shows various preferred but not required sizing, and FIG. 11H shows incorporation of electronic components, such as the memory 702 into the connectors. FIGS. 11I-11K illustrate wiring diagrams and cabling specifics of the cable itself as it connects to the universal medical connectors.

Figure 12:
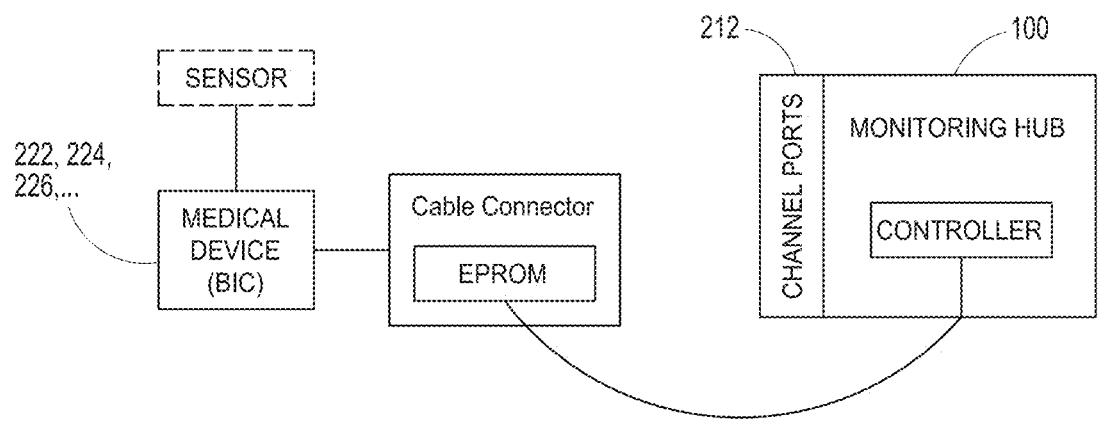
FIG. 12 illustrates a simplified block diagram of a channel system for the hub of FIG. 1.

FIG. 12 illustrates a simplified block diagram of a channel system for the hub of FIG. 1. As shown in FIG. 12, a male cable connector, such as those shown in FIG. 11 above, includes a memory such as an EPROM. The memory advantageously stores information describing the type of data the hub 100 can expect to receive, and how to receive the same. A controller of the hub 100 communicates with the EPROM to negotiate how to receive the data, and if possible, how to display the data on display 104, alarm when needed, and the like. For example, a medical device supplier may contact the hub provider and receive a software development kit ("SDK") that guides the supplier through how to describe the type of data output from their device. After working with the SDK, a map, image, or other translation file may advantageously be loaded into the EPROM, as well as the power requirements and isolation requirements discussed above. When the channel cable is connected to the hub 100 through the channel port 212, the hub 100 reads the EPROM and the controller of the hub 100 negotiates how to handle incoming data.

Figure 13:
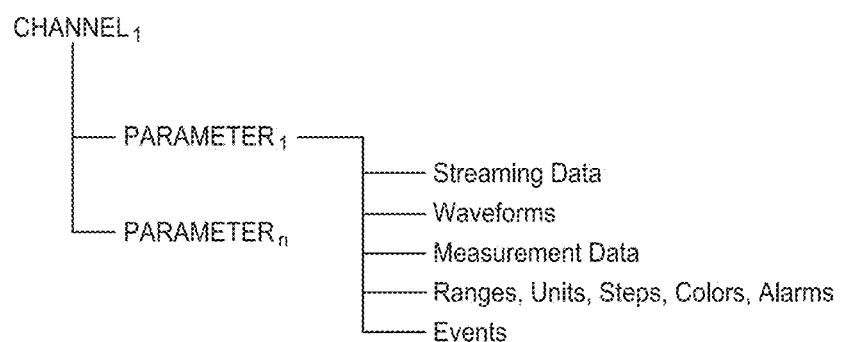
FIG. 13 illustrates an example logical channel configuration.

FIG. 13 illustrates an example logical channel configuration that may be stored in the EPROM of FIG. 12. As shown in FIG. 13, each incoming channel describes one or more parameters. Each parameter describes whatever the hub 100 should know about the incoming data. For example, the hub 100 may want to know whether the data is streaming data, waveform data, already determined parameter measurement data, ranges on the data, speed of data delivery, units of the data, steps of the units, colors for display, alarm parameters and thresholds, including complex algorithms for alarm computations, other events that are parameter value driven, combinations of the same or the like. Additionally, the parameter information may include device delay times to assist in data synchronization or approximations of data synchronization across parameters or other data received by the hub 100. The SDK can present a schema to the device supplier which self-describes the type and order of incoming data. The information may advantageously negotiate with the hub 100 to determine whether to apply compression and/or encryption to the incoming data stream.

Such open architecture advantageously provides device manufacturers the ability to port the output of their device into the hub 100 for display, processing, and data management as disclosed in the foregoing. By implementation through the cable connector, the device manufacturer avoids any reprogramming of their original device; rather, they simply let the hub 100 know through the cable connector how the already existing output is formatted. Moreover, by describing the data in a language already understood by the hub 100, the hub 100 also avoids software upgrades to accommodate data from "new-to-the-hub" medical devices.

Figure 14:
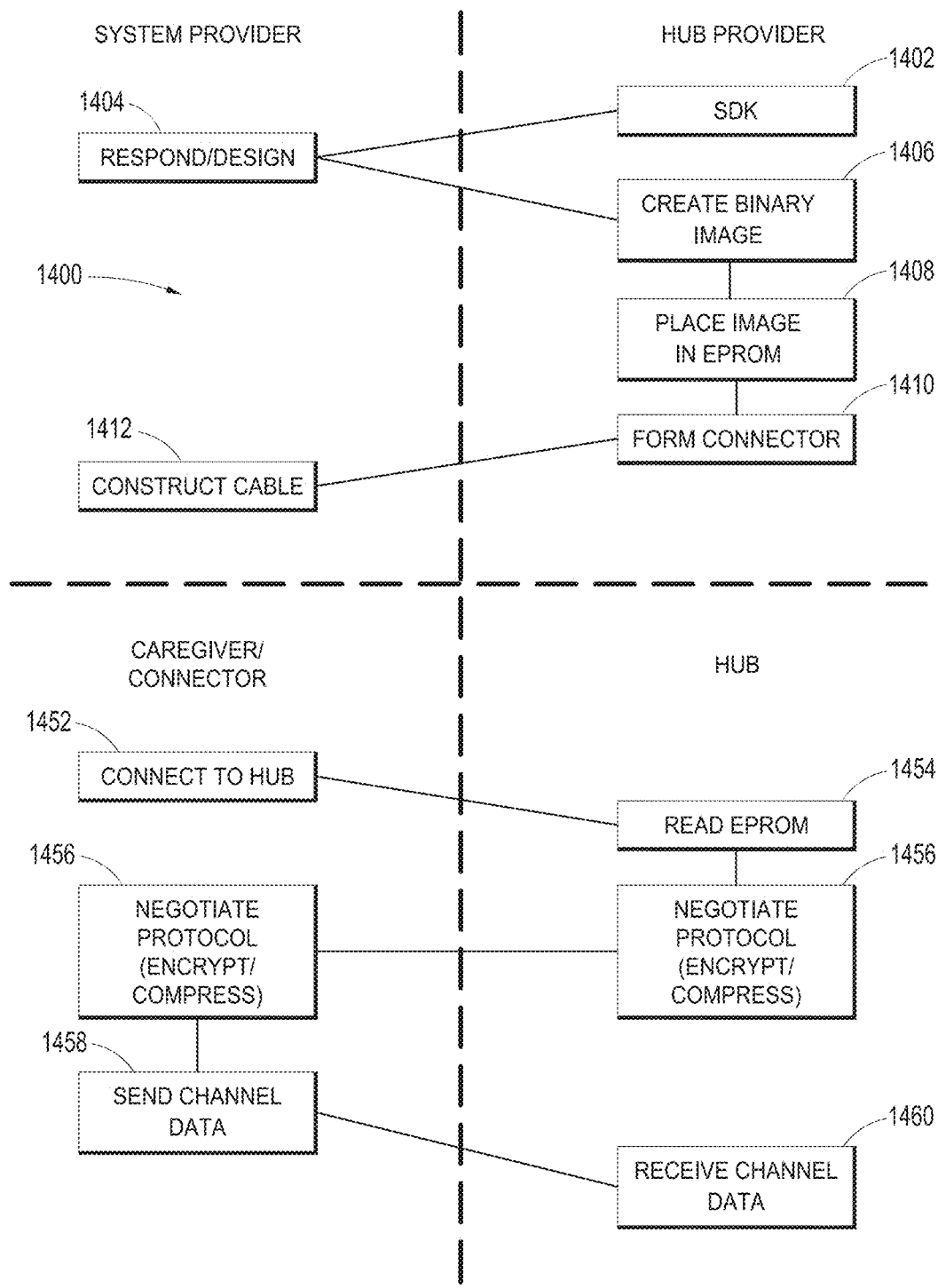
FIG. 14 illustrates a simplified example process for constructing a cable and configuring a channel.

FIG. 14 illustrates a simplified example process for configuring a channel. As shown in FIG. 14, the hub provider provides a device manufacturer with an SDK in step 1402, who in turn uses the SDK to self-describe the output data channel from their device in step 1404. The SDK can include a series of questions that guide the development, The SDK provides a language and schema to describe the behavior of the data.

Once the device provider describes the data, the hub provider creates a binary image or other file to store in a memory within a cable connector in step 1405; however, the SDK may create the image and simply communicated it to the hub provider. The cable connector is provided as an OEM part to the provider in step 1410, who constructs and manufactures the cable to mechanically and electrically mate with output ports on their devices in step 1412.

Once a caregiver has the appropriately manufactured cable, with one end matching the device provider's system and the other OEM'ed to match the hub 100 at its channel ports 212, in step 1452 the caregiver can connect the hub between the devices. In step 1454, the hub 100 reads the memory, provides isolated or non-isolated power, and the cable controller and the hub 100 negotiate a protocol or schema for data delivery. A controller on the cable may negotiate the protocol. The controller of the hub 100 may negotiate with other processors on the hub the particular protocol. Once the protocol is set, the hub 100 can use, display and otherwise process the incoming data stream in an intelligent manner.

Through the use of the universal medical connectors described herein, connection of a myriad of devices to the hub 100 is accomplished through straightforward programming of a cable connector as opposed to necessitating software upgrades to each device.

Figure 15:
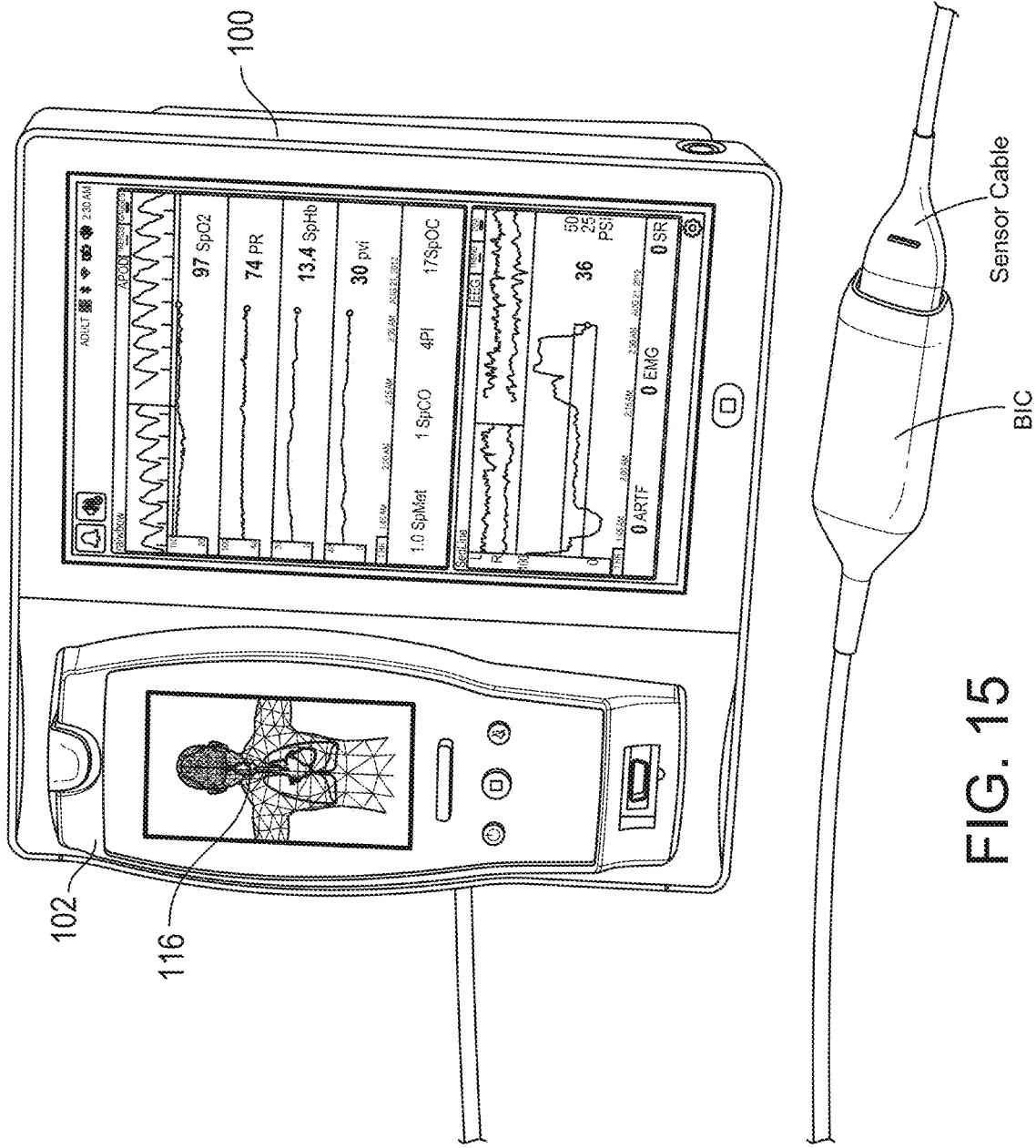
FIG. 15 illustrates a perspective view of the hub of FIG. 1, including an example attached board-in-cable to form an input channel.

FIG. 15 illustrates a perspective view of the hub of FIG. 1 including an example attached board-in-cable ("BIC") to form an input channel. As shown in FIG. 15, a SEDLine depth of consciousness board communicates data from an appropriate patient sensor to the hub 100 for display and caregiver review. As described, the provider of the board need only use the SDK to describe their data channel, and the hub 100 understands how to present the data to the caregiver.

Figure 16:
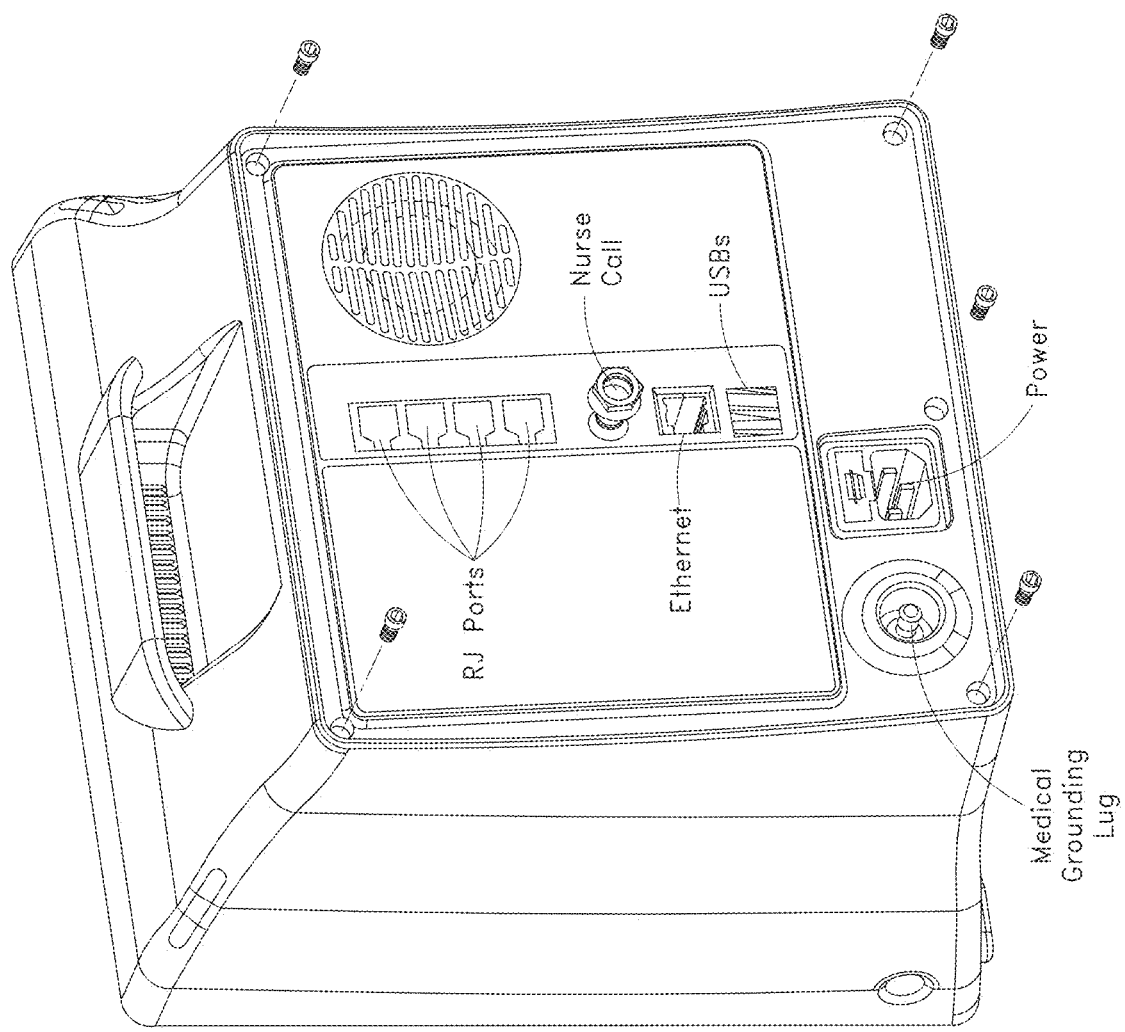
FIG. 16 illustrates a perspective view of a back side of the hub of FIG. 1, showing an example instrument-side serial data inputs.

FIG. 16 illustrates a perspective view of a back side of the hub 100 of FIG. 1, showing an example serial data inputs. The inputs can include such as RJ 45 ports. As is understood in the art, these ports include a data ports similar to those found on computers, network routers, switches and hubs. A plurality of these ports can be used to associate data from various devices with the specific patient identified in the hub 100. FIG. 16 also shows a speaker, the nurse call connector, the Ethernet connector, the USBs, a power connector and a medical grounding lug.

Figure 17A:
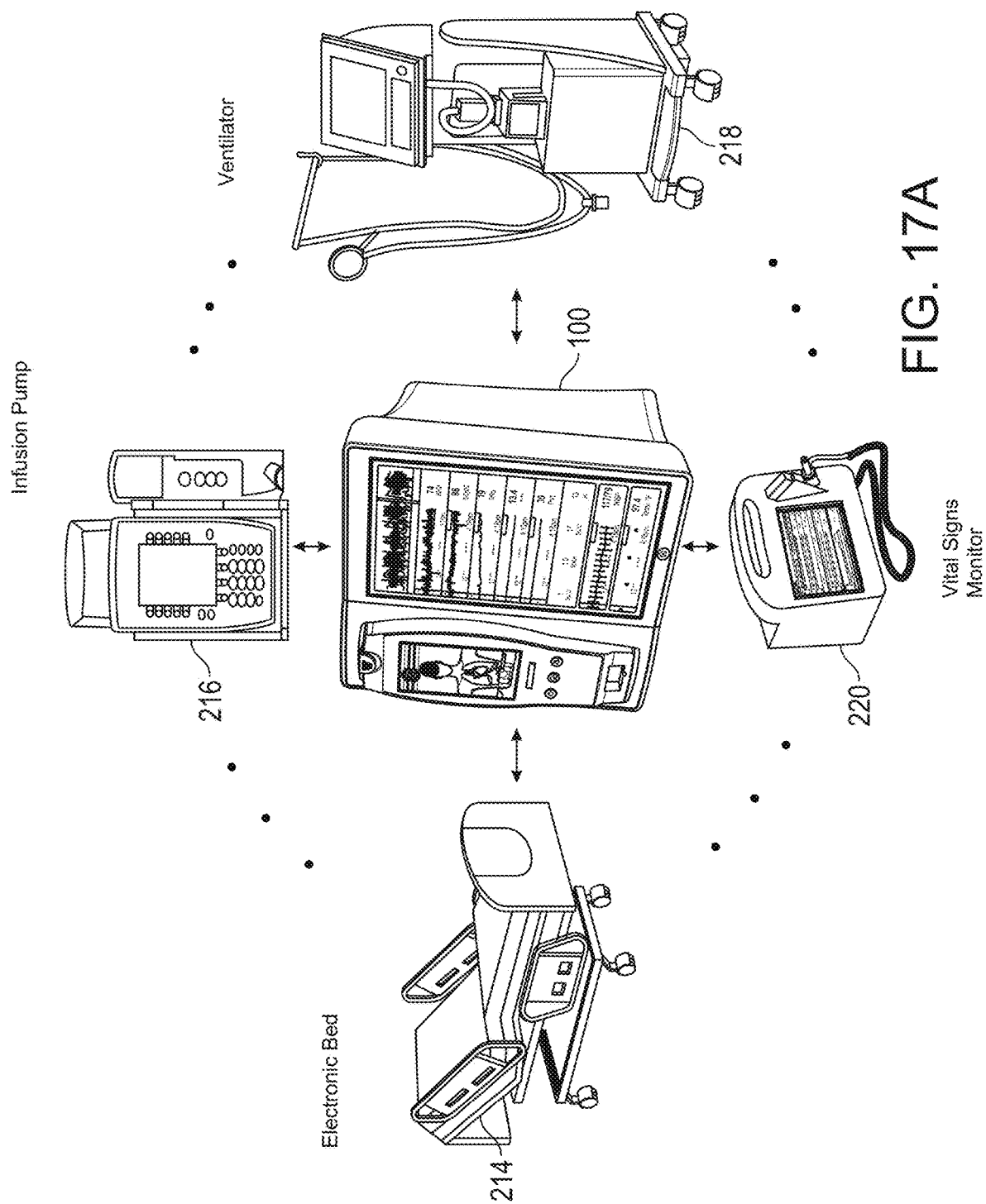
FIG. 17A illustrates an example monitoring environment with communication through the serial data connections of FIG. 16.

FIG. 17A illustrates an example monitoring environment with communication through the serial data connections of the hub 100 of FIG. 1. As shown and as discussed in the foregoing, the hub 100 may use the serial data ports 210 to gather data from various devices within the monitoring environment, including an electronic bed, infusion pumps, ventilators, vital sign monitors, and the like. The difference between the data received from these devices and that received through the channel ports 212 is that the hub 100 may not know the format or structure of this data. The hub 100 may not display information from this data or use this data in calculations or processing. However, porting the data through the hub 100 conveniently associates the data with the specifically monitored patient in the entire chain of caregiver systems, including the foregoing server 214 and backend systems 206. The hub 100 may determine sufficient information about the incoming data to attempt to synchronize it with data from the hub 100.

Figure 17B:
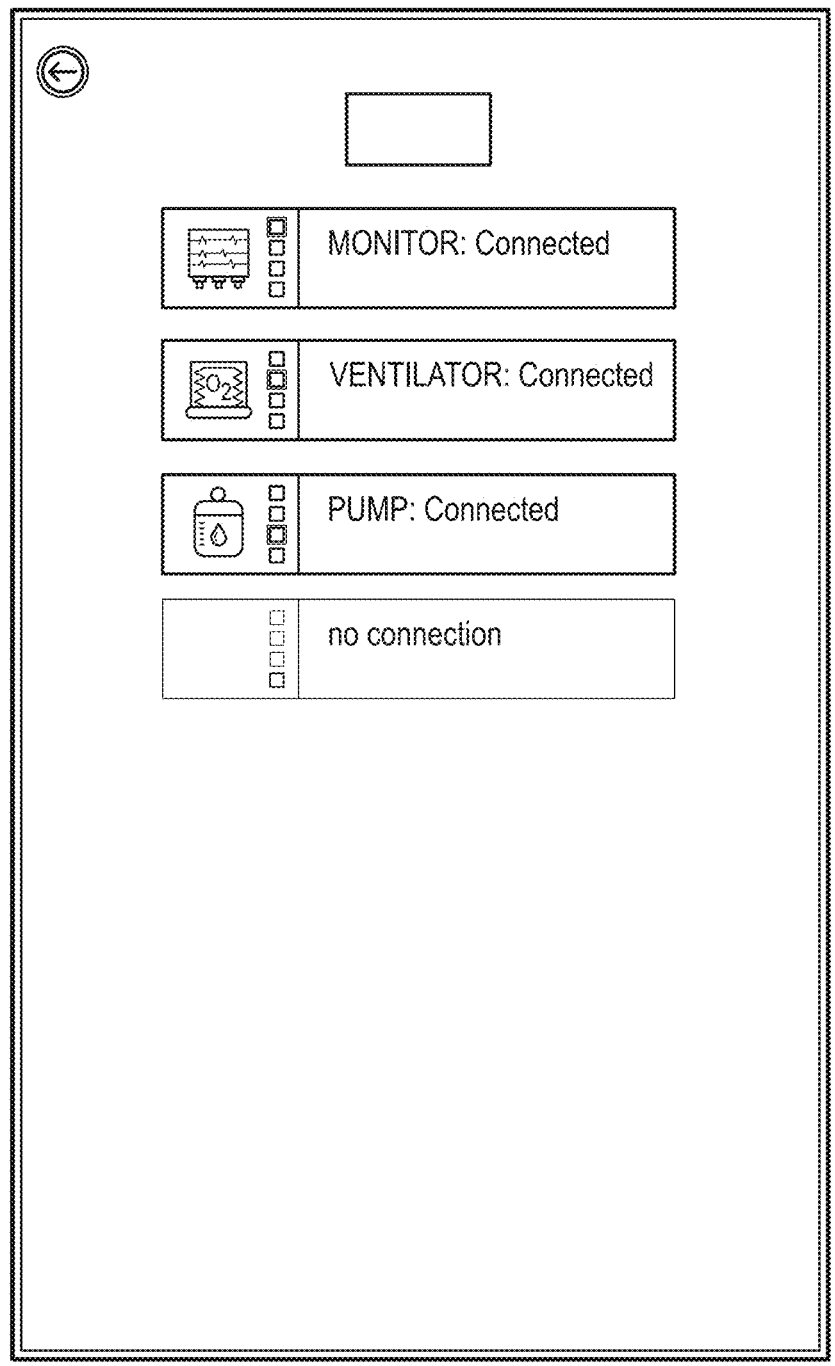
FIG. 17B illustrates an example connectivity display of the hub of FIG. 1.

In FIG. 17B, a control screen may provide information on the type of data being received. A green light next to the data can indicate connection to a device and on which serial input the connection occurs.

Figure 18:
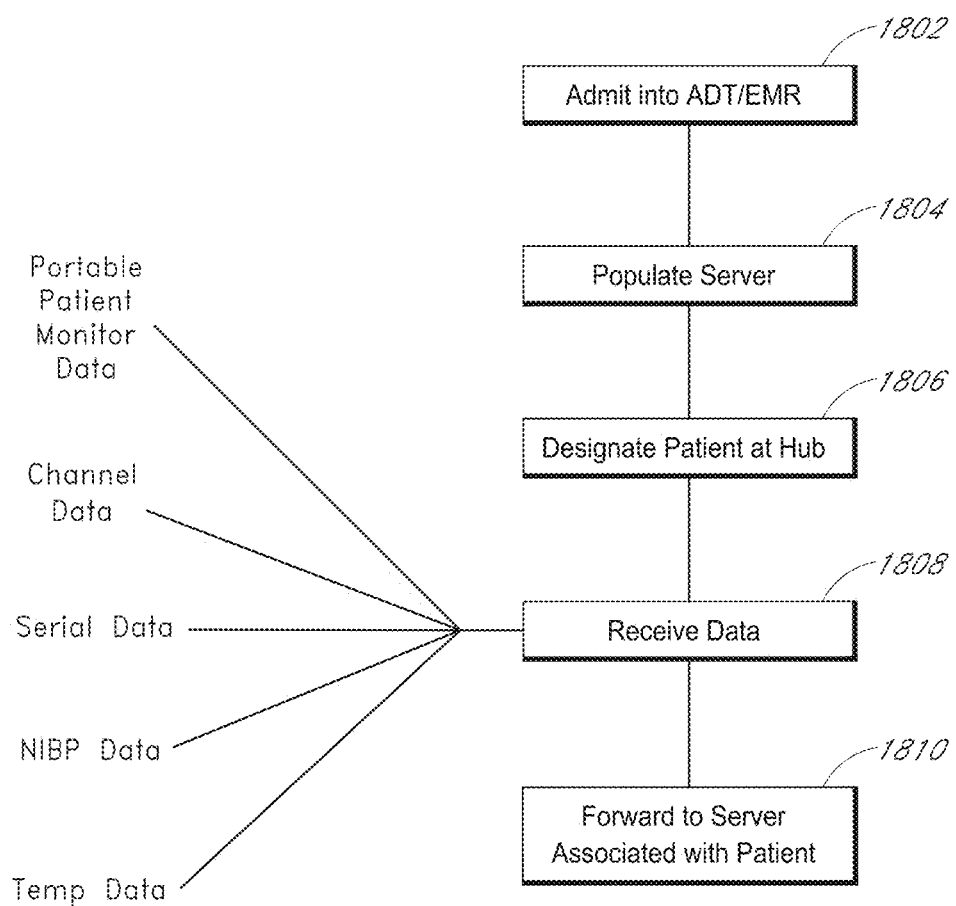
FIG. 18 illustrates a simplified example patient data flow process.

FIG. 18 illustrates a simplified example patient data flow process. As shown, once a patient is admitted into the caregiver environment at step 1802, data about the patient is populated on the caregiver backend systems 206. The server 214 may advantageously acquire or receive this information in step 1804, and then make it accessible to the hub 100. When the caregiver at step 1806 assigns the hub 100 to the patient, the caregiver simply looks at the presently available patient data and selects the particular patient being currently monitored. The hub 100 at step 1808 then associates the measurement, monitoring and treatment data it receives and determines with that patient. The caregiver need not again associate another device with the patient so long as that device is communicating through the hub 100 by way of (1) the docking station, (2) the universal medical connectors, (3) the serial data connectors, or (4) other communication mechanisms known to an artisan. At step 1810, some or the entirety of the received, processed and/or determined data is passed to the server systems discussed above.

Figure 19A:
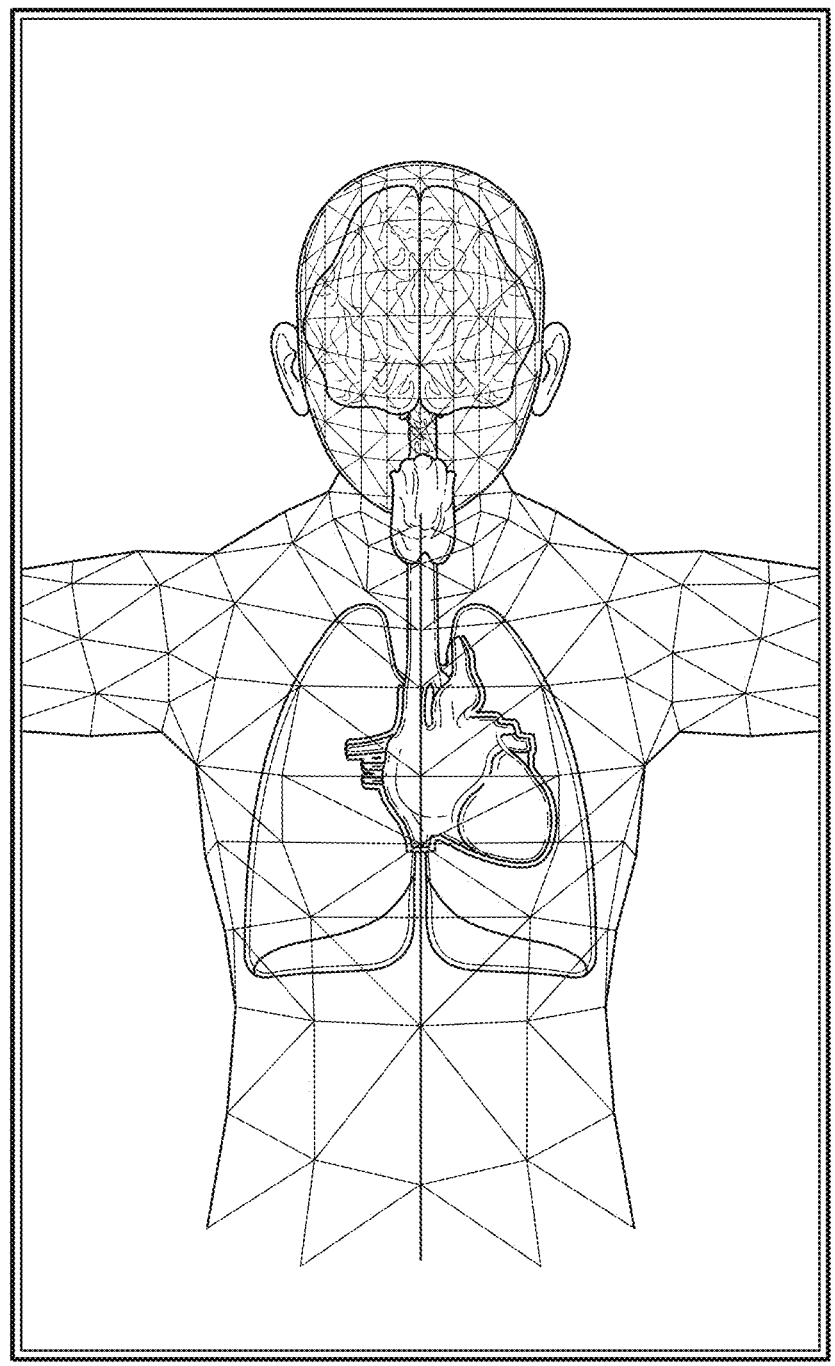
FIGS. 19A-19J illustrate example displays of anatomical graphics for the portable patient monitor of FIG. 1 docked with the hub of FIG. 1.

FIGS. 19A-19J illustrate example displays of anatomical graphics for the portable patient monitor docked with the hub 100 of FIG. 1. As shown in FIG. 19A, the heart, lungs and respiratory system are shown while the brain is not highlighted. Thus, a caregiver can readily determine that depth of consciousness monitoring or brain oximetry systems are not currently communicating with the hub 100 through the portable patient monitor connection or the channel data ports. However, it is likely that acoustic or other respiratory data and cardiac data is being communicated to or measured by the hub 100. Moreover, the caregiver can readily determine that the hub 100 is not receiving alarming data with respect to the emphasized body portions. The emphasized portion may animate to show currently measured behavior or, optionally, animate in a predetermined fashion.

Figure 19B:
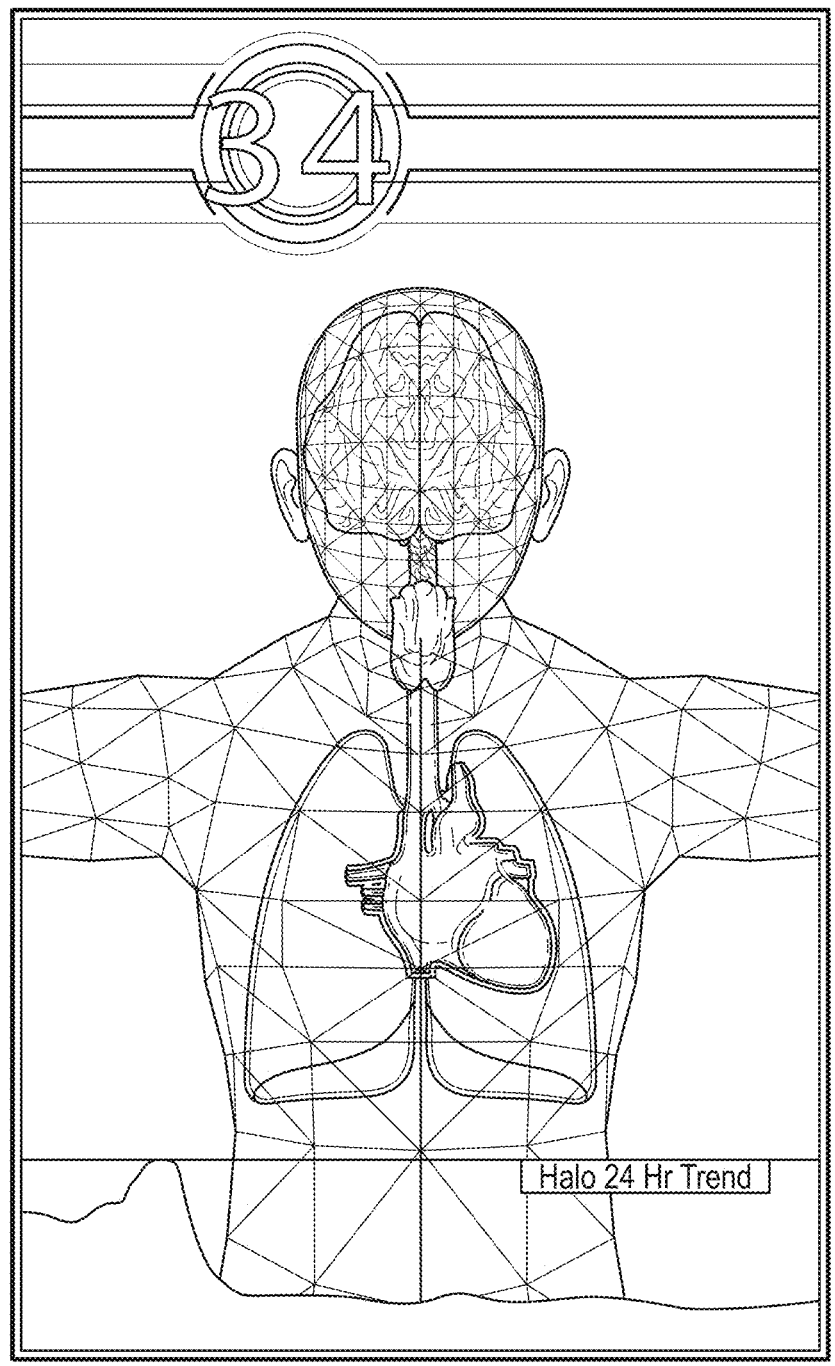
Figure 19C:
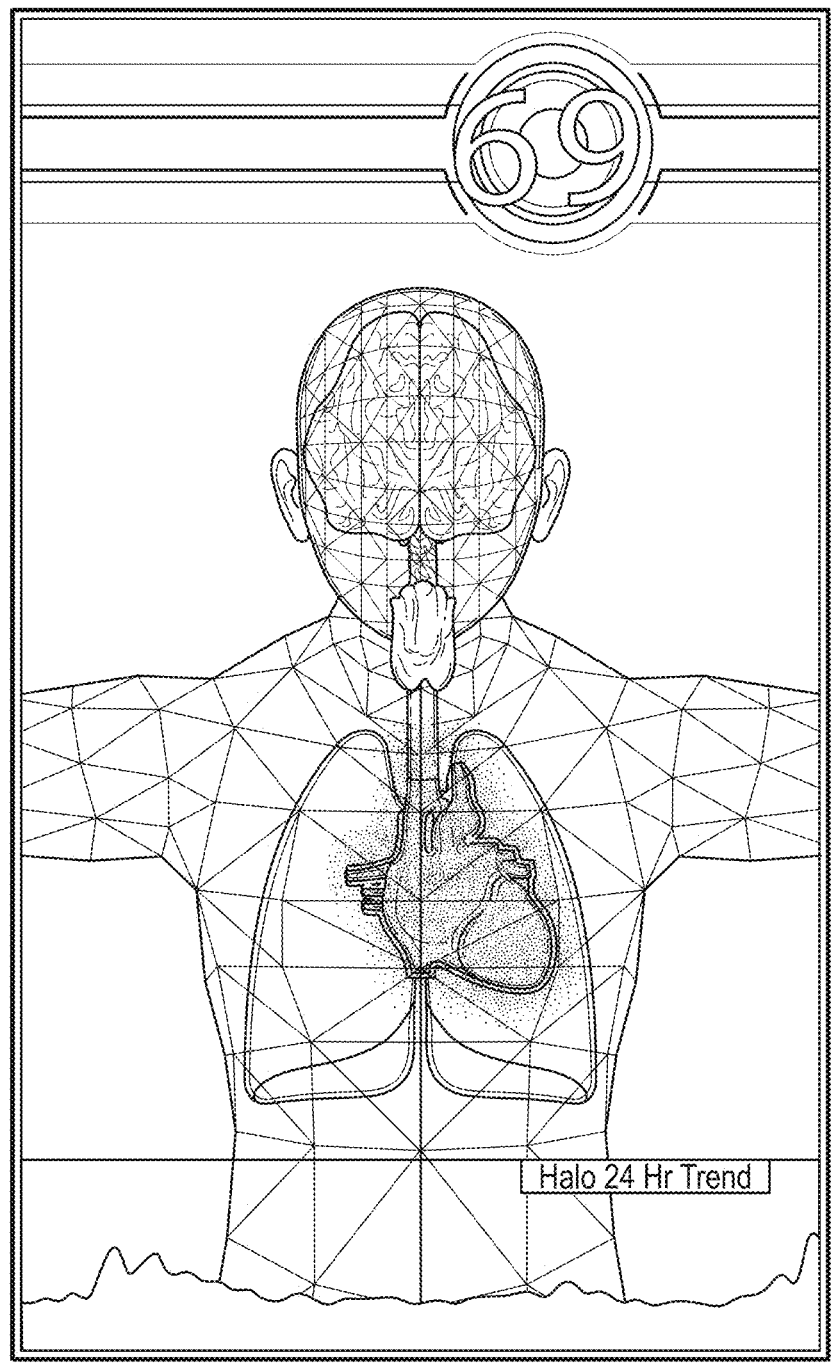

FIG. 19B shows the addition of a virtual channel showing an indication of wellness. As shown in FIG. 19B, the indication is positive as it is a "34" on an increasingly severity scale to "100." The wellness indication may also be shaded to show problems. In contrast to FIG. 19B, FIG. 19C shows a wellness number that is becoming or has become problematic and an alarming heart graphic. Thus, a caregiver responding to a patient alarm on the hub 100 or otherwise on another device or system monitoring or treating the patient can quickly determine that a review of vital signs and other parameters relating to heart function is needed to diagnose and/or treat the patient.

Figure 19D:
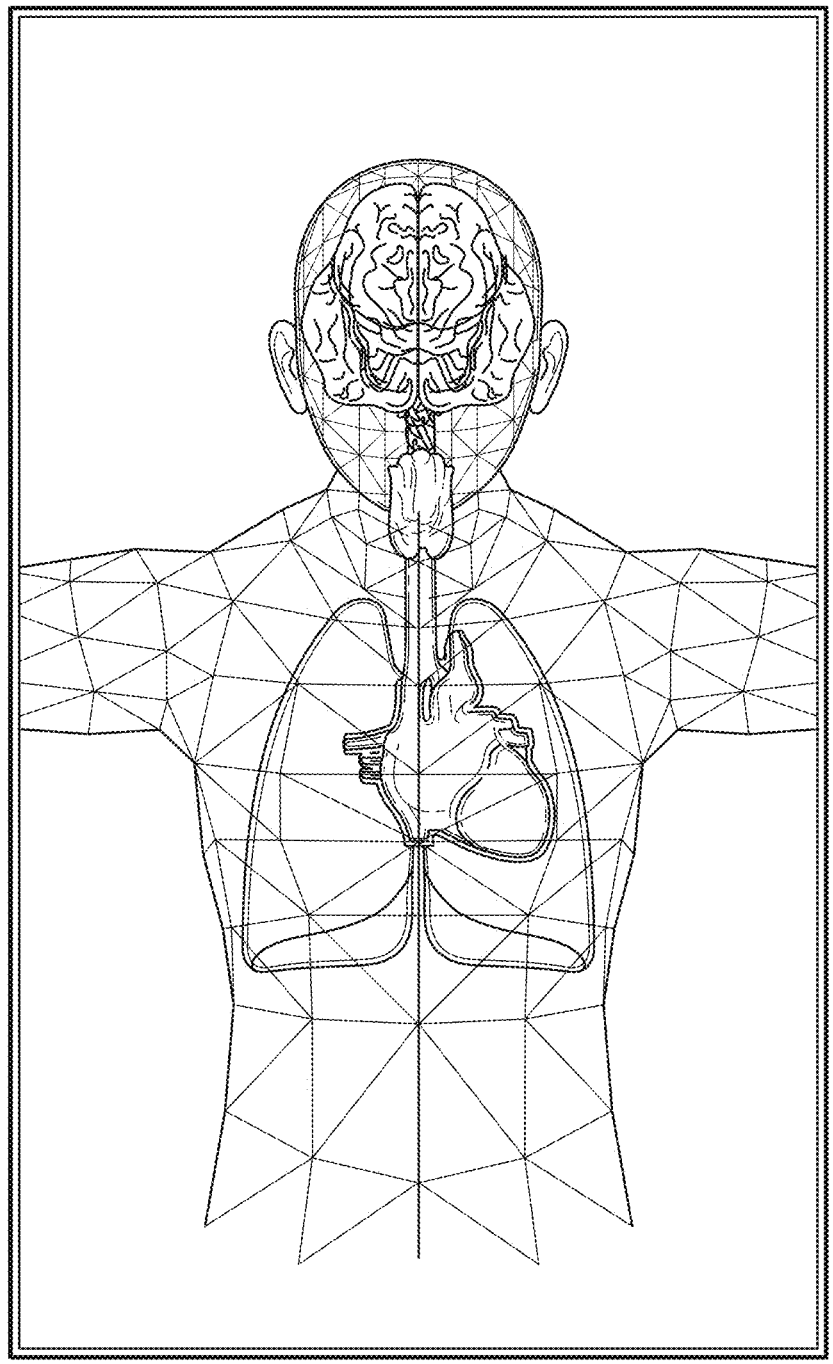
Figure 19E:
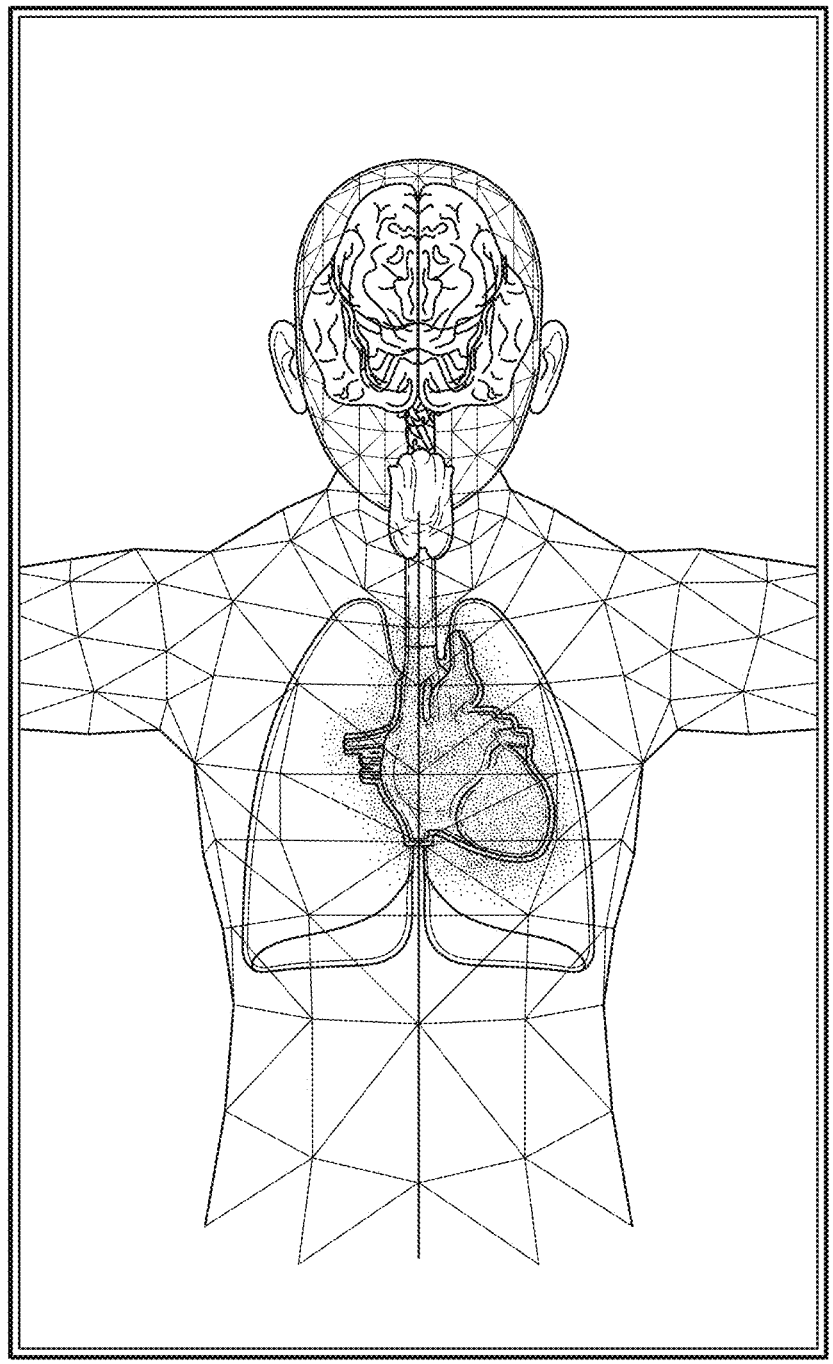

FIGS. 19D and 19E show the brain included in the emphasized body portions meaning that the hub 100 is receiving data relevant to brain functions, such as, for example, depth of sedation data or brain oximetry data. FIG. 19E additionally shows an alarming heart function similar to FIG. 19C.

Figure 19F:
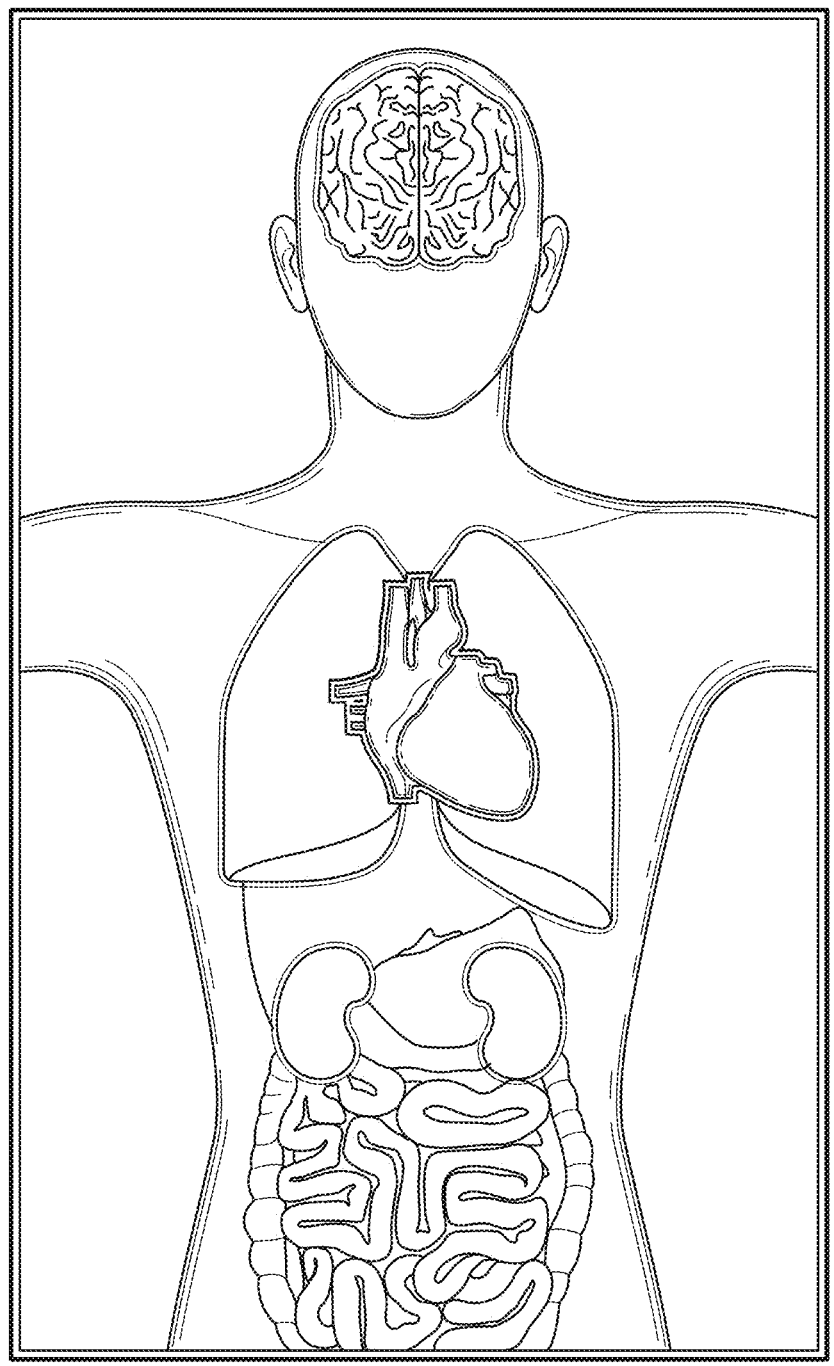
Figure 19G:
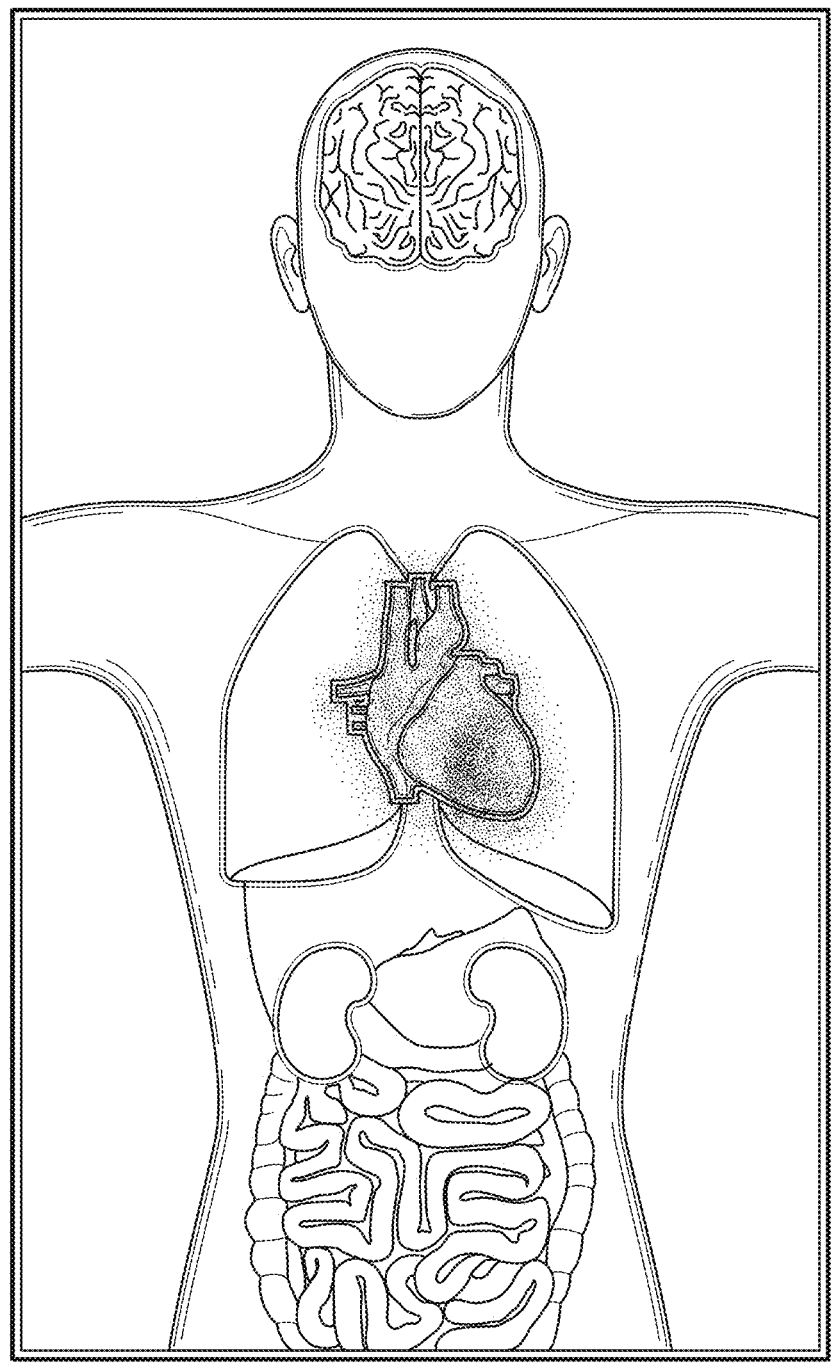
Figure 19H:
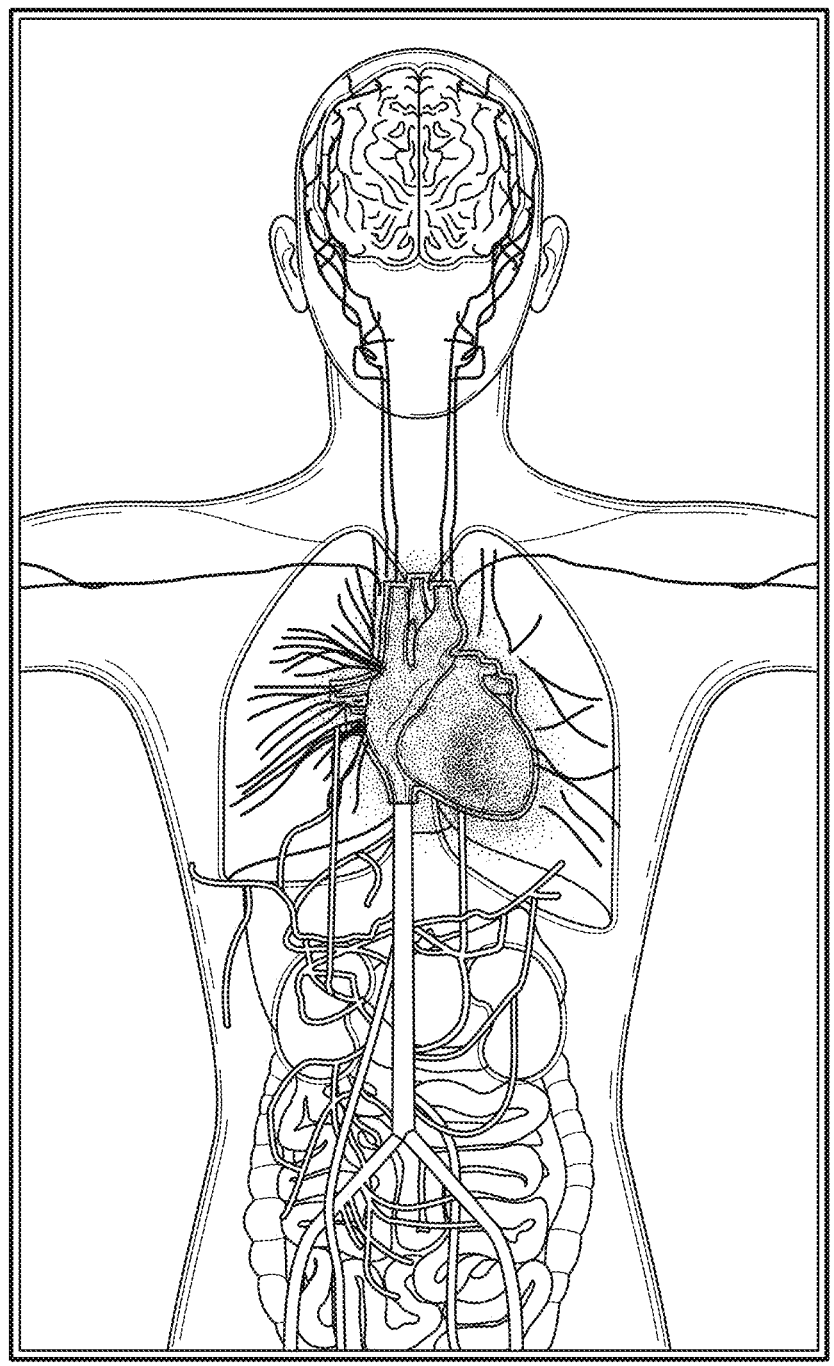
Figure 19I:
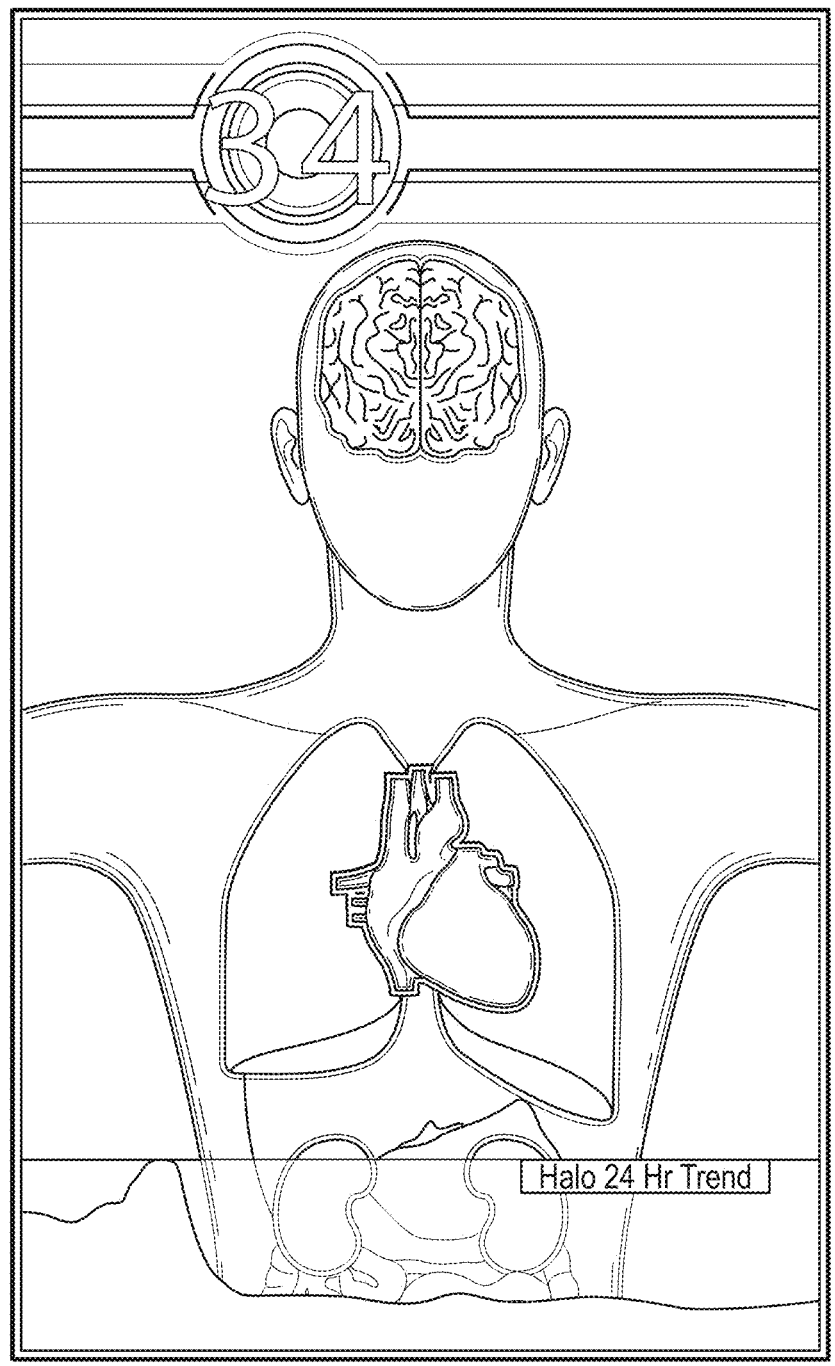
Figure 19J:
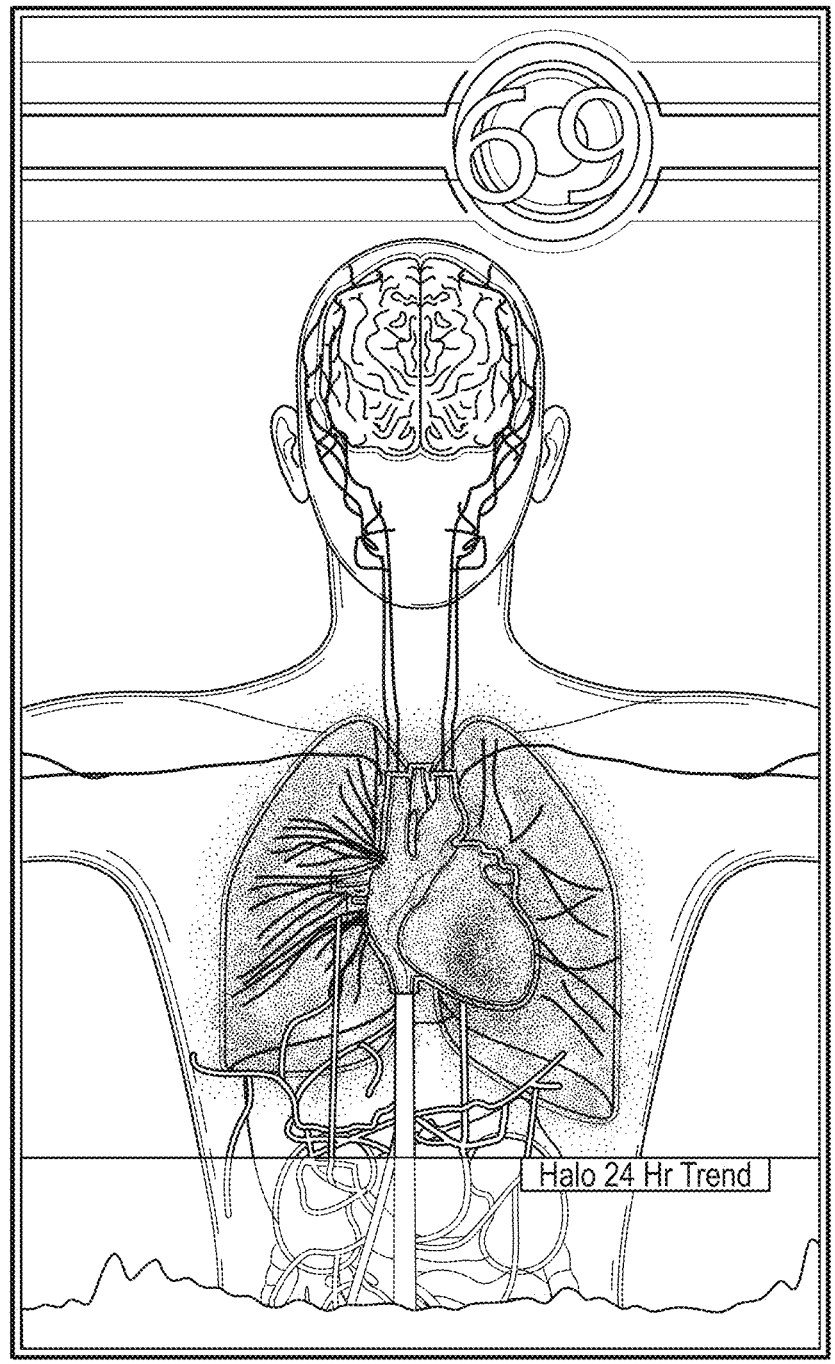

In FIG. 19F, additional organs, such as the kidneys are being monitored, but the respiratory system is not. In FIG. 19G, an alarming hear function is shown, and in FIG. 19H, an alarming circulatory system is being shown. FIG. 19I shows the wellness indication along with lungs, heart, brain and kidneys. FIG. 19J shows alarming lungs, heart, and circulatory system as well as the wellness indication. Moreover, FIG. 19J shows a severity contrast, such as, for example, the heart alarming red for urgent while the circulatory system alarms yellow for caution. An artisan will recognize other color schemes that are appropriate from the disclosure herein.

Figure 20A:
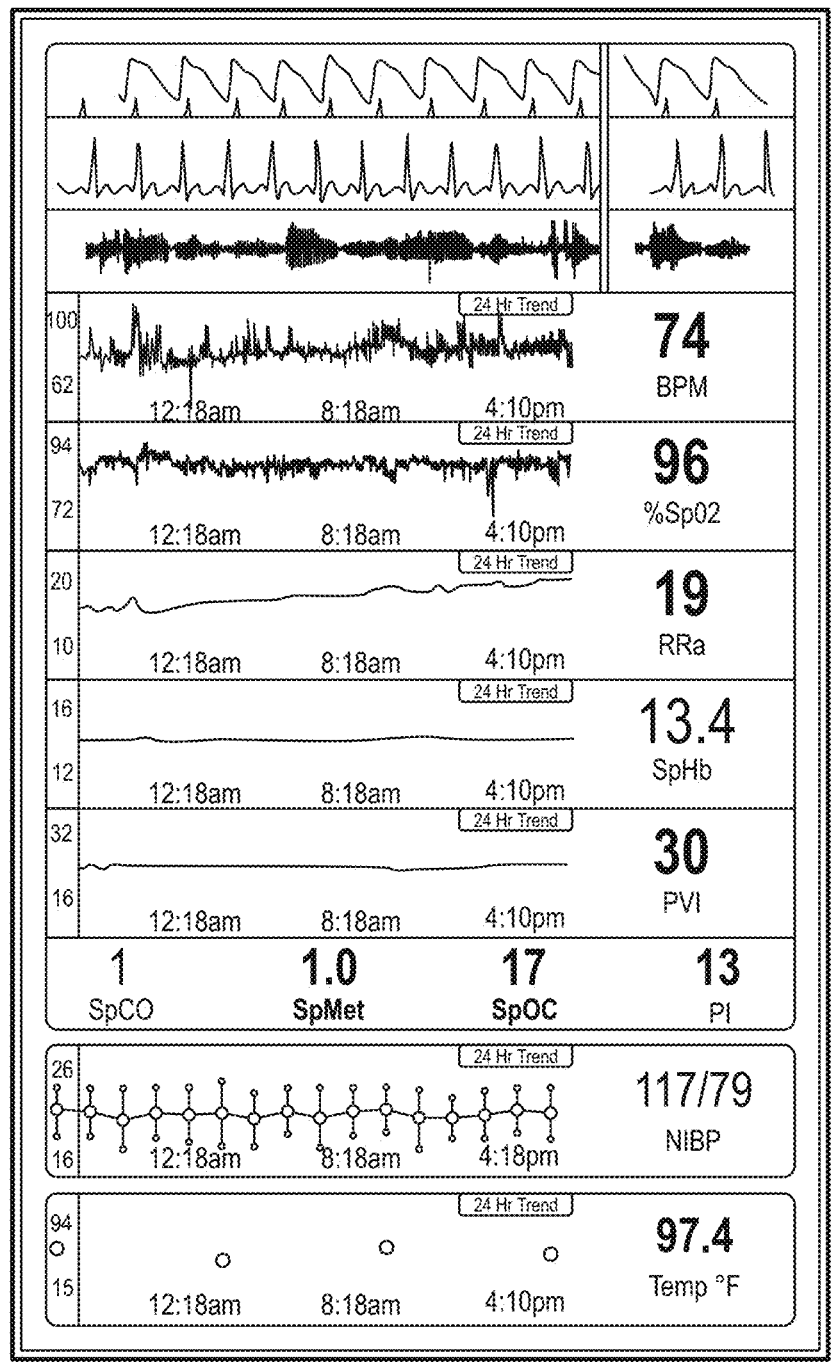
FIGS. 20A-20C illustrate example displays of measurement data showing data separation and data overlap on a display of the hub of FIG. 1, respectively.
Figure 20B:
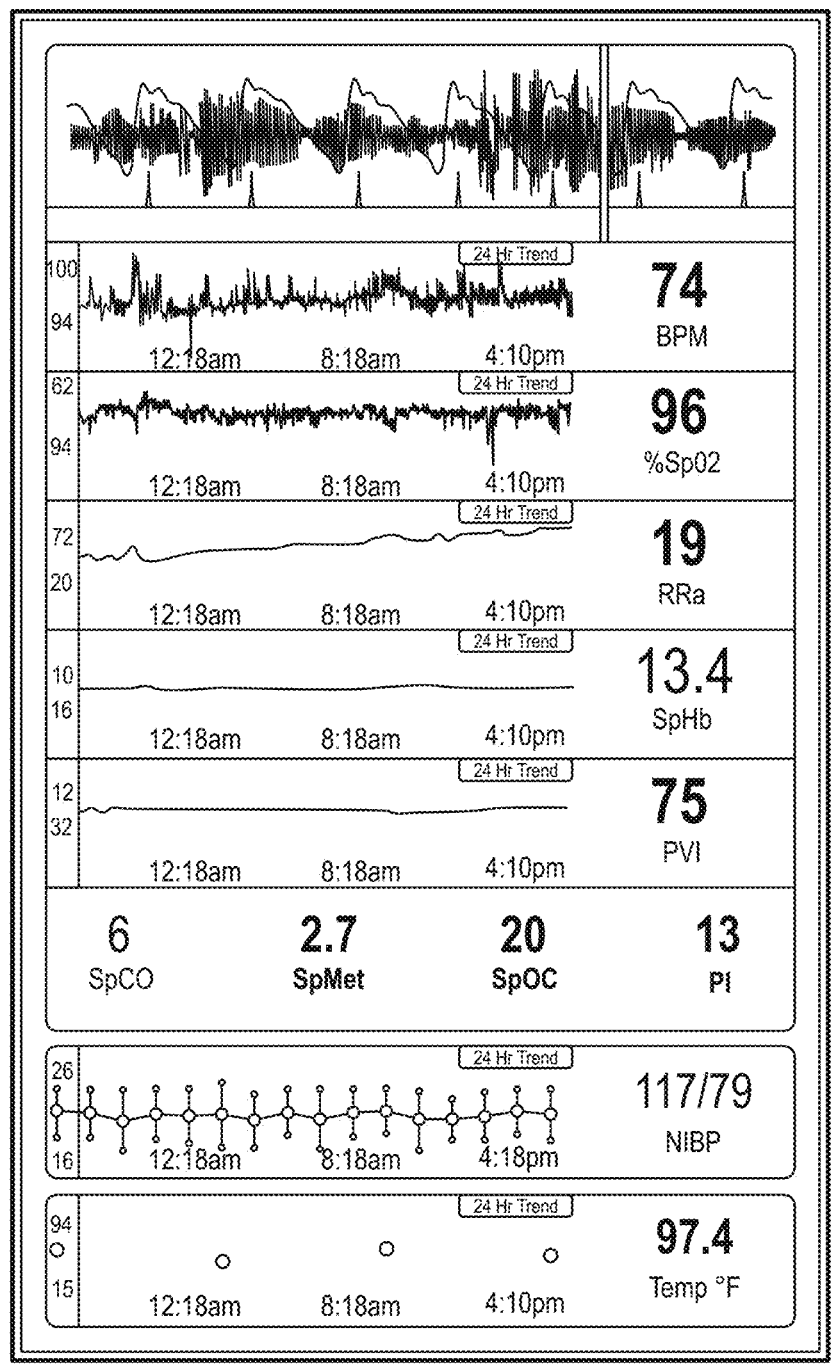
Figure 20C:
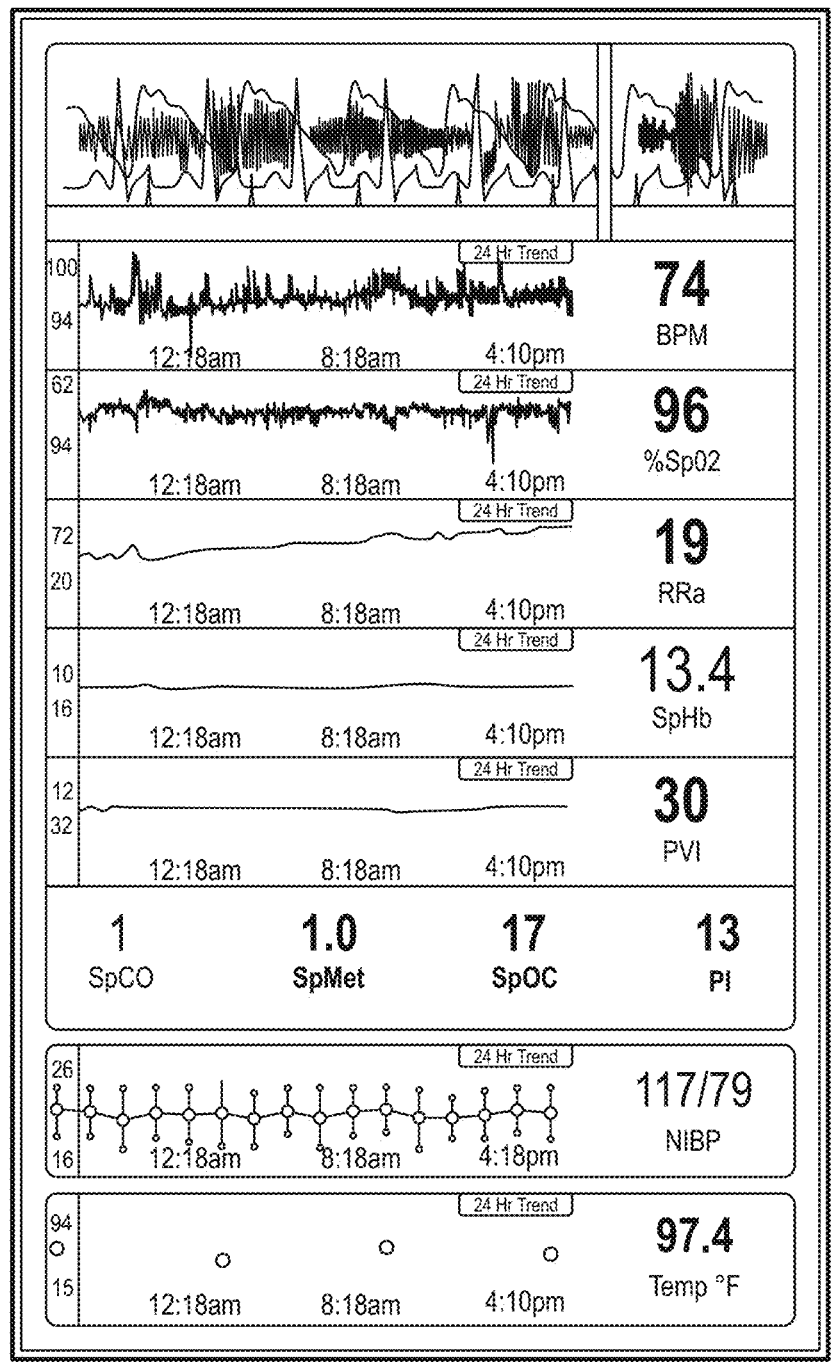
Figure 21A:
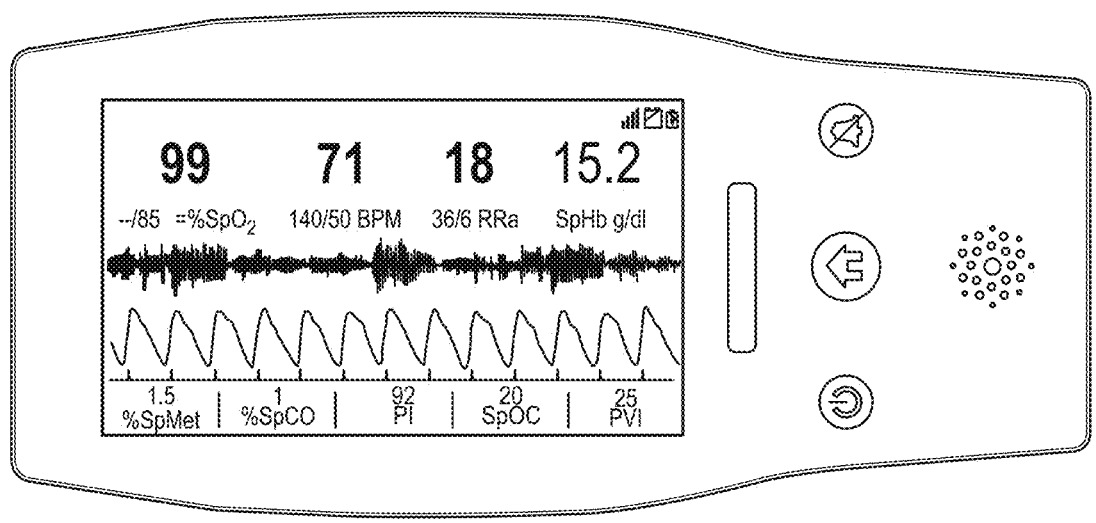
FIGS. 21A and 21B illustrate example displays of measurement data showing data separation and data overlap on a display of the portable patient monitor of FIG. 1, respectively.
Figure 21B:
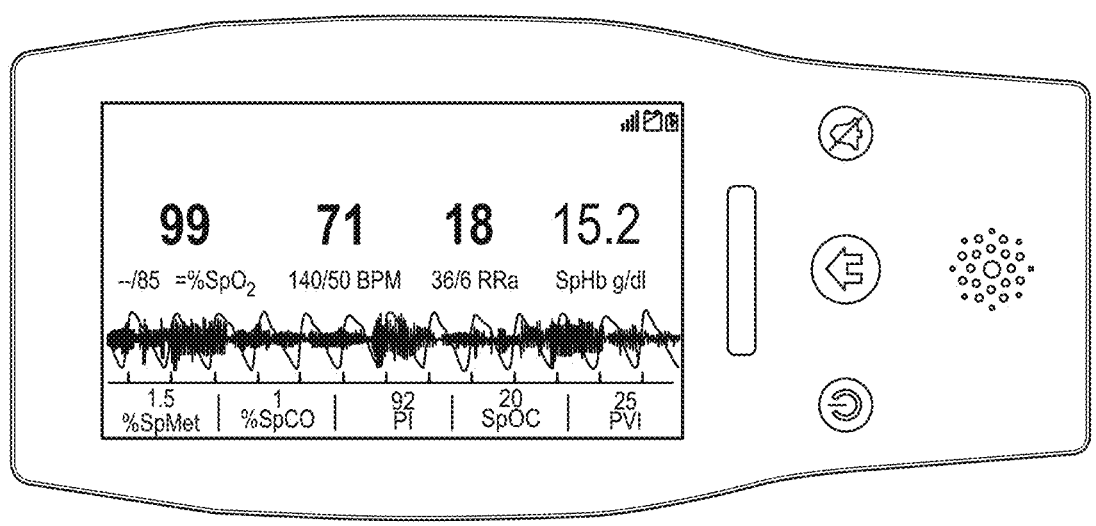

FIGS. 20A-20C illustrate example displays of measurement data showing data separation and data overlap, respectively. FIGS. 21A and 21B illustrate example displays of measurement data also showing data separation and data overlap, respectively.

For example, acoustic data from an acoustic sensor may advantageously provide breath sound data, while the plethysmograph and ECG or other signals can also be presented in separate waveforms (FIG. 20A, top of the screen capture). The monitor may determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases a system monitors other physiological sounds, such as heart rate to help with probe off detection, heart sounds (S1, S2, S3, S4, and murmurs), and change in heart sounds such as normal to murmur or split heart sounds indicating fluid overload.

Providing a visual correlation between multiple physiological signals can provide a number of valuable benefits where the signals have some observable physiological correlation. As one example of such a correlation, changes in morphology (for example, envelope and/or baseline) of the plethysmographic signal can be indicative of patient blood or other fluid levels. And, these changes can be monitored to detect hypovolemia or other fluid-level related conditions. A pleth variability index may provide an indication of fluid levels, for example. And, changes in the morphology of the plethysmographic signal are correlated to respiration. For example, changes in the envelope and/or baseline of the plethysmographic signal are correlated to breathing. This is at least in part due to aspects of the human anatomical structure, such as the mechanical relationship and interaction between the heart and the lungs during respiration.

Thus, superimposing a plethysmographic signal and a respiratory signal (FIG. 20B) can give operators an indication of the validity of the plethysmographic signal or signals derived therefrom, such as a pleth variability index. For example, if bursts in the respiration signal indicative of inhalation and exhalation correlate with changes in peaks and valleys of the plethysmographic envelope, this gives monitoring personnel a visual indication that the plethysmographic changes are indeed due to respiration, and not some other extraneous factor. Similarly, if the bursts in the respiration signal line up with the peaks and valleys in the plethysmographic envelope, this provides monitoring personnel an indication that the bursts in the respiration signal are due to patient breathing sounds, and not some other non-targeted sounds (for example, patient non-breathing sounds or non-patient sounds).

The monitor may also be configured to process the signals and determine whether there is a threshold level of correlation between the two signals, or otherwise assess the correlation. However, by additionally providing a visual indication of the correlation, such as by showing the signals superimposed with one another, the display provides operators a continuous, intuitive and readily observable gauge of the particular physiological correlation. For example, by viewing the superimposed signals, users can observe trends in the correlation over time, which may not be otherwise ascertainable.

The monitor can visually correlate a variety of other types of signals instead of, or in addition to plethysmographic and respiratory signals. For example, FIG. 20C depicts a screen shot of another example monitoring display. As shown in the upper right portion of FIG. 20C, the display superimposes a plethysmographic signal, an ECG signal, and a respiration signal. In other configurations, more than three different types of signals may be overlaid onto one another.

The hub 100 can provide an interface through which the user can move the signals together to overlay on one another. For example, the user may be able to drag the respiration signal down onto the plethysmographic signal using a touch screen interface. Conversely, the user may be able to separate the signals, also using the touch screen interface. The monitor can include a button the user can press, or some other user interface allowing the user to overlay and separate the signals, as desired. FIGS. 21A and 21B show similar separation and joining of the signals.

In certain configurations, in addition to providing the visual correlation between the plethysmographic signal and the respiratory signal, the monitor is additionally configured to process the respiratory signal and the plethysmographic signal to determine a correlation between the two signals. For example, the monitor may process the signals to determine whether the peaks and valleys in the changes in the envelope and/or baseline of the plethysmographic signal correspond to bursts in the respiratory signal. And, in response to the determining that there is or is not a threshold level of correlation, the monitor may provide some indication to the user. For example, the monitor may provide a graphical indication (for example, a change in color of pleth variability index indicator), an audible alarm, or some other indication. The monitor may employ one or more envelope detectors or other appropriate signal processing componentry in making the determination.

The system may further provide an audible indication of the patient's breathing sounds instead of, or in addition to the graphical indication. For example, the monitor may include a speaker, or an earpiece (for example, a wireless earpiece) may be provided to the monitoring personnel providing an audible output of the patient sounds. Examples of sensors and monitors having such capability are described in U.S. Pat. Pub. No. 2011/0172561 and are incorporated by reference herein.

In addition to the above described benefits, providing both the acoustic and plethysmographic signals on the same display in the manner described can allow monitoring personnel to more readily detect respiratory pause events where there is an absence of breathing, high ambient noise that can degrade the acoustic signal, improper sensor placement, etc.

Figure 22A:
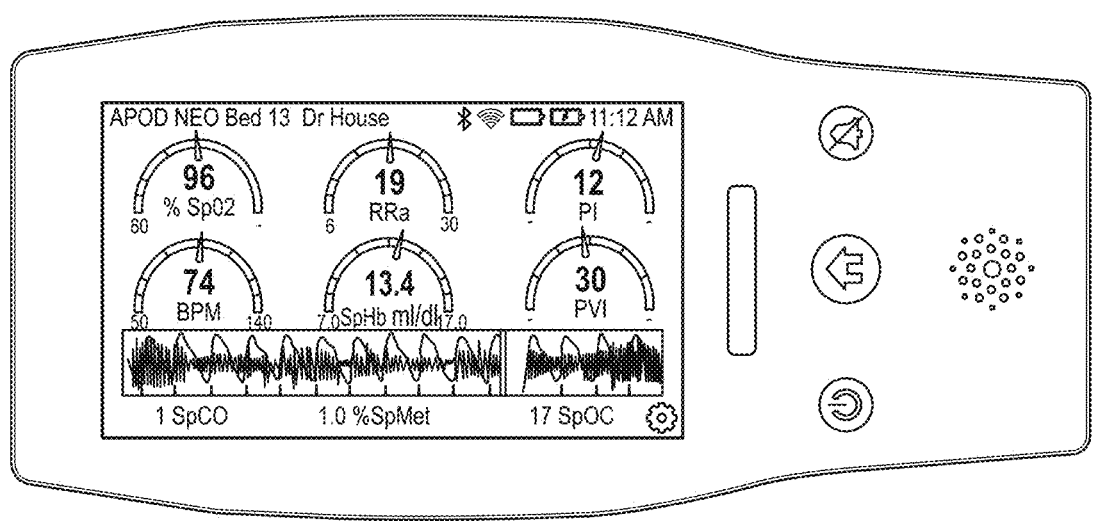
FIGS. 22A and 22B illustrate example analog display indicia.
Figure 22B:
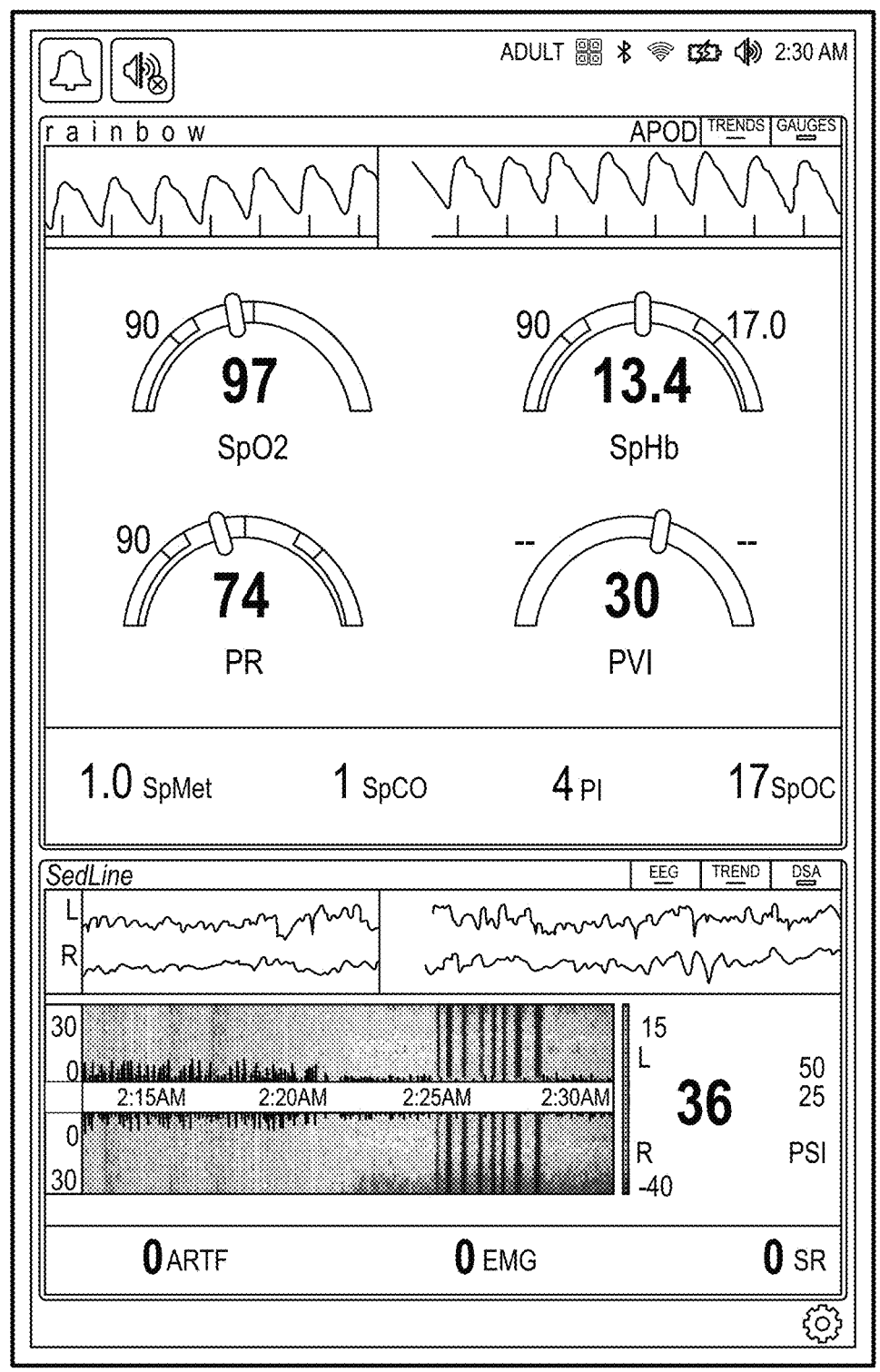

FIGS. 22A-22B illustrate example analog display indicia. As shown in FIGS. 22A and 22B, the screen shots displays health indicators of various physiological parameters, in addition to other data. Each health indicator can include an analog indicator and/or a digital indicator. Where the health indicator includes an analog and a digital indicator, the analog and digital indicators can be positioned in any number of formations, such as side-by-side, above, below, transposed, etc. The analog indicators are positioned above and to the sides of the digital indicators. As shown more clearly in FIG. 22B, the analog displays may include colored warning sections, dashes indicating position on the graph, and digital information designating quantitate information form the graph. In FIG. 22B, for example, the pulse rate PR graph shows that from about 50 to about 140 beats per minute, the graph is either neutral or beginning to be cautionary, whereas outside those numbers the graph is colored to indicate a severe condition. Thus, as the dash moves along the arc, a caregiver can readily see where in the range of acceptable, cautionary, and extreme the current measurements fall.

Each analog indicator of the health indicator can include a dial that moves about an arc based on measured levels of monitored physiological parameters. As the measured physiological parameter levels increase the dial can move clockwise, and as the measured physiological parameter levels decrease, the dial can move counter-clockwise, or vice versa. In this way, a user can quickly determine the patient's status by looking at the analog indicator. For example, if the dial is in the center of the arc, the observer can be assured that the current physiological parameter measurements are normal, and if the dial is skewed too far to the left or right, the observer can quickly assess the severity of the physiological parameter levels and take appropriate action. Normal parameter measurements can be indicated when the dial is to the right or left, etc.

The dial can be implemented as a dot, dash, arrow, or the like, and the arc can be implemented as a circle, spiral, pyramid, or other shape, as desired. Furthermore, the entire arc can be lit up or only portions of the arc can be lit up based on the current physiological parameter measurement level. Furthermore, the arc can turn colors or be highlighted based on the current physiological parameter level. For example, as the dial approaches a threshold level, the arc and/or dial can turn from green, to yellow, to red, shine brighter, flash, be enlarged, move to the center of the display, or the like.

Different physiological parameters can have different thresholds indicating abnormal conditions. For example, some physiological parameters may upper a lower threshold levels, while others only have an upper threshold or a lower threshold. Accordingly, each health indicator can be adjusted based on the physiological parameter being monitored. For example, the SpO2 health indicator can have a lower threshold that when met activates an alarm, while the respiration rate health indicator can have both a lower and upper threshold, and when either is met an alarm is activated. The thresholds for each physiological parameter can be based on typical, expected thresholds and/or user-specified thresholds.

The digital indicator can provide a numerical representation of the current levels of the physiological parameter the digital indicator may indicate an actual level or a normalized level and can also be used to quickly asses the severity of a patient condition. The display can include multiple health indicators for each monitored physiological parameter. The display can include fewer health indicators than the number of monitored physiological parameters. The health indicators can cycle between different monitored physiological parameters.

Figure 23A:
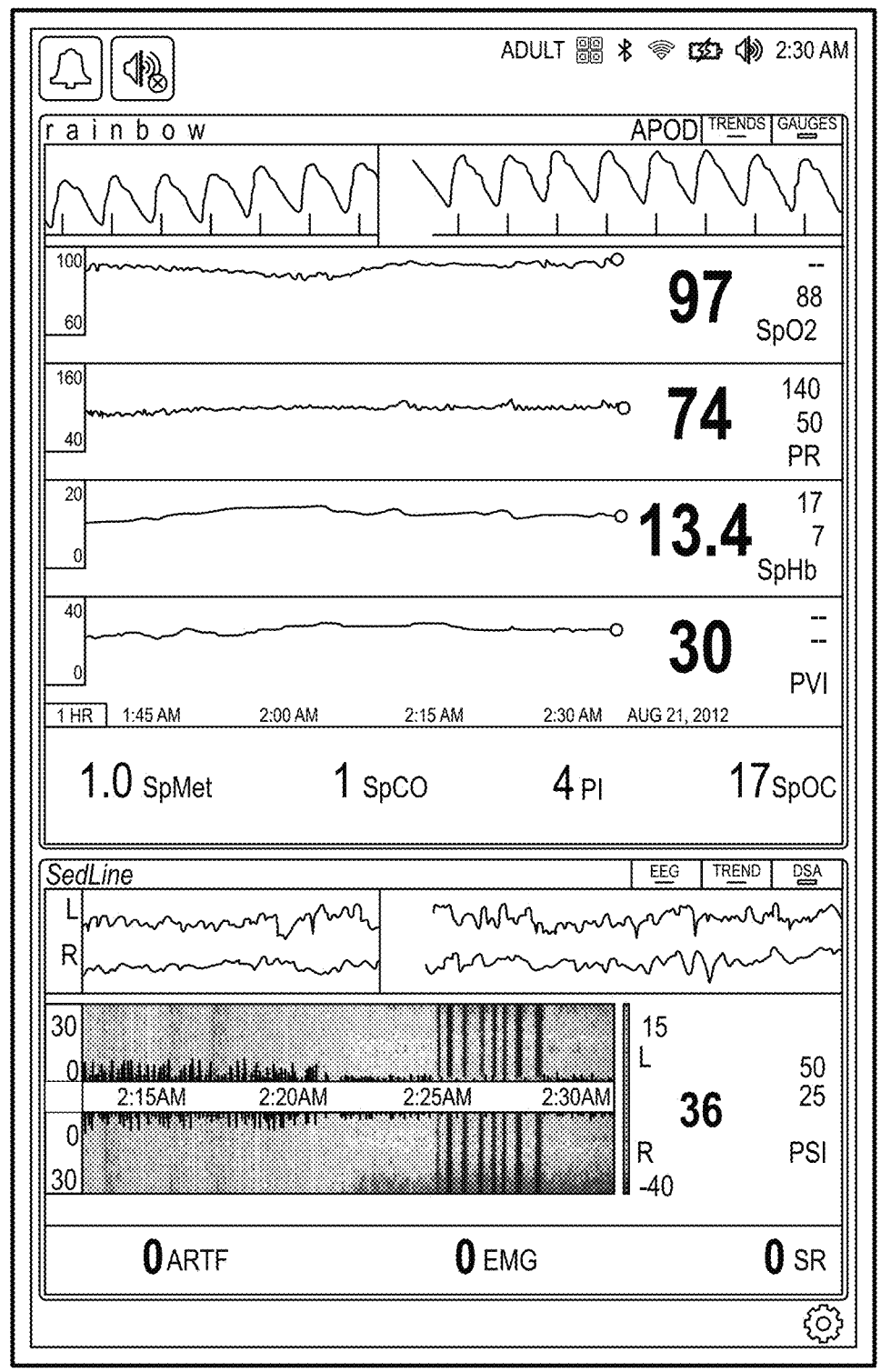
FIGS. 23A-23F illustrate example displays of measurement data showing, for example, data presentation in FIGS. 23A-23D when a depth of consciousness monitor is connected to a channel port of the hub of FIG. 1, data presentation in FIG. 23E when temperature and blood pressure sensors communicate with the hub of FIG. 1 and data presentation in FIG. 23F when an acoustic sensor is also communicating with the hub of FIG. 1.
Figure 23B:
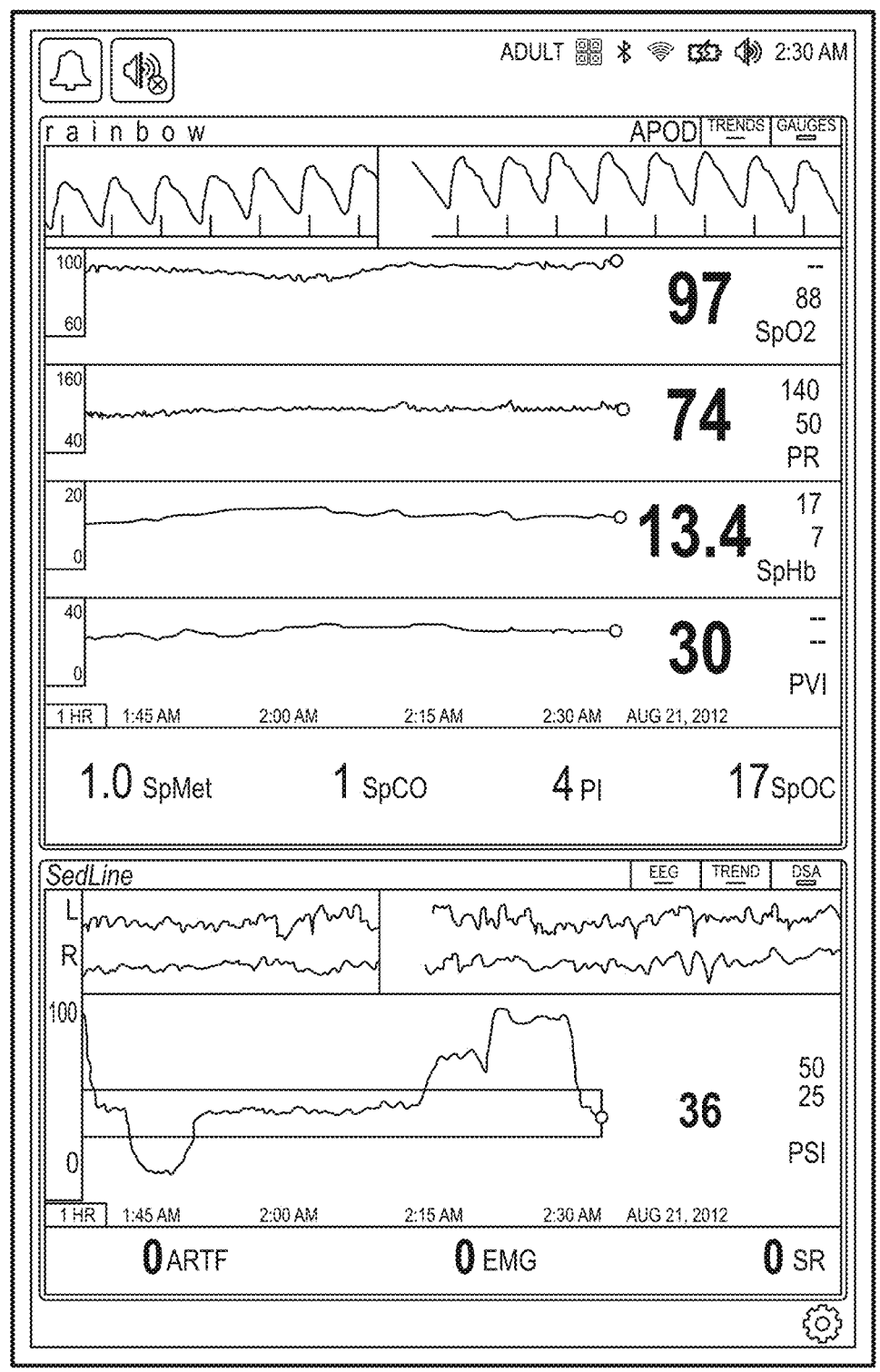
Figure 23C:
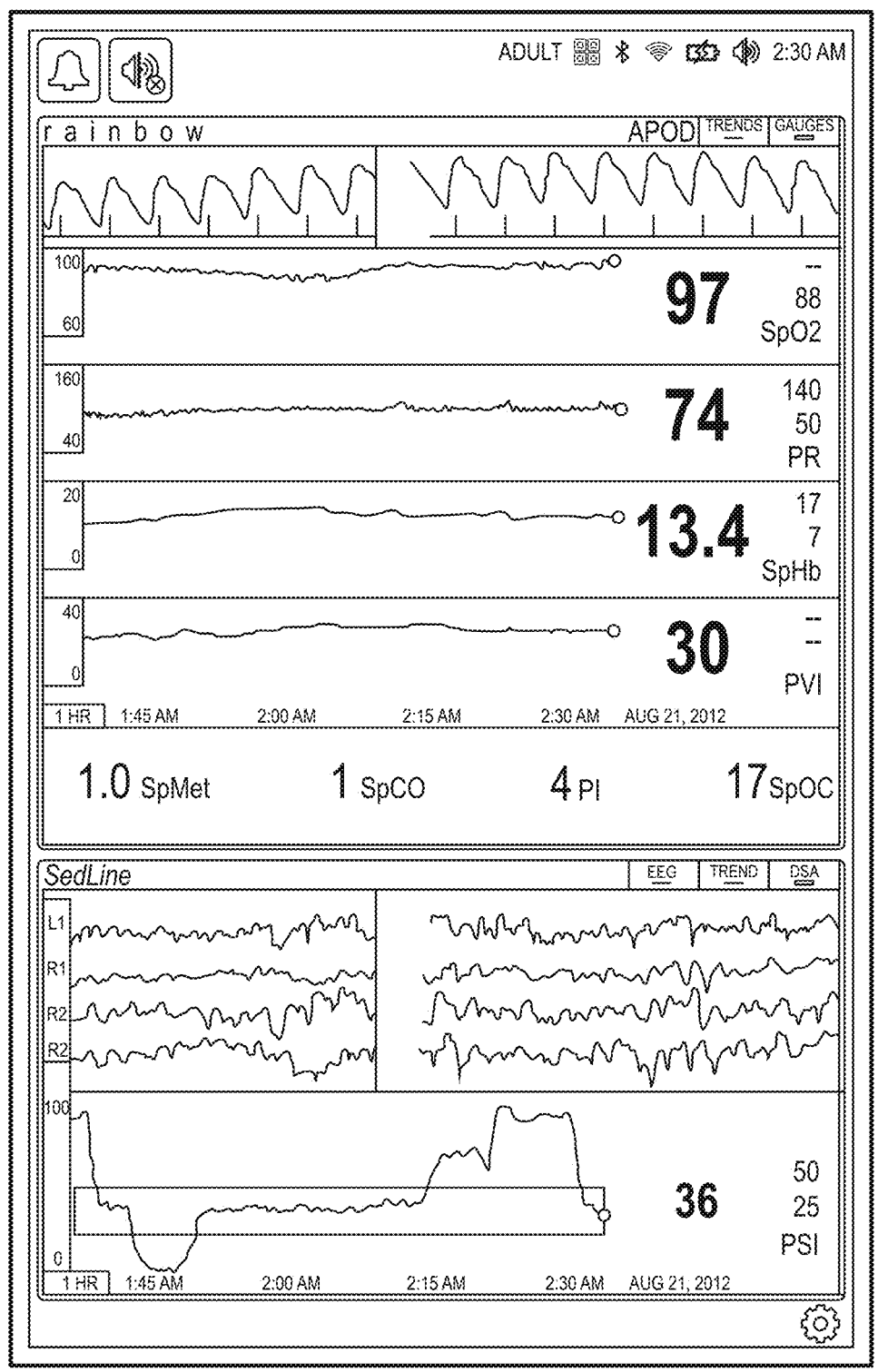
Figure 23D:
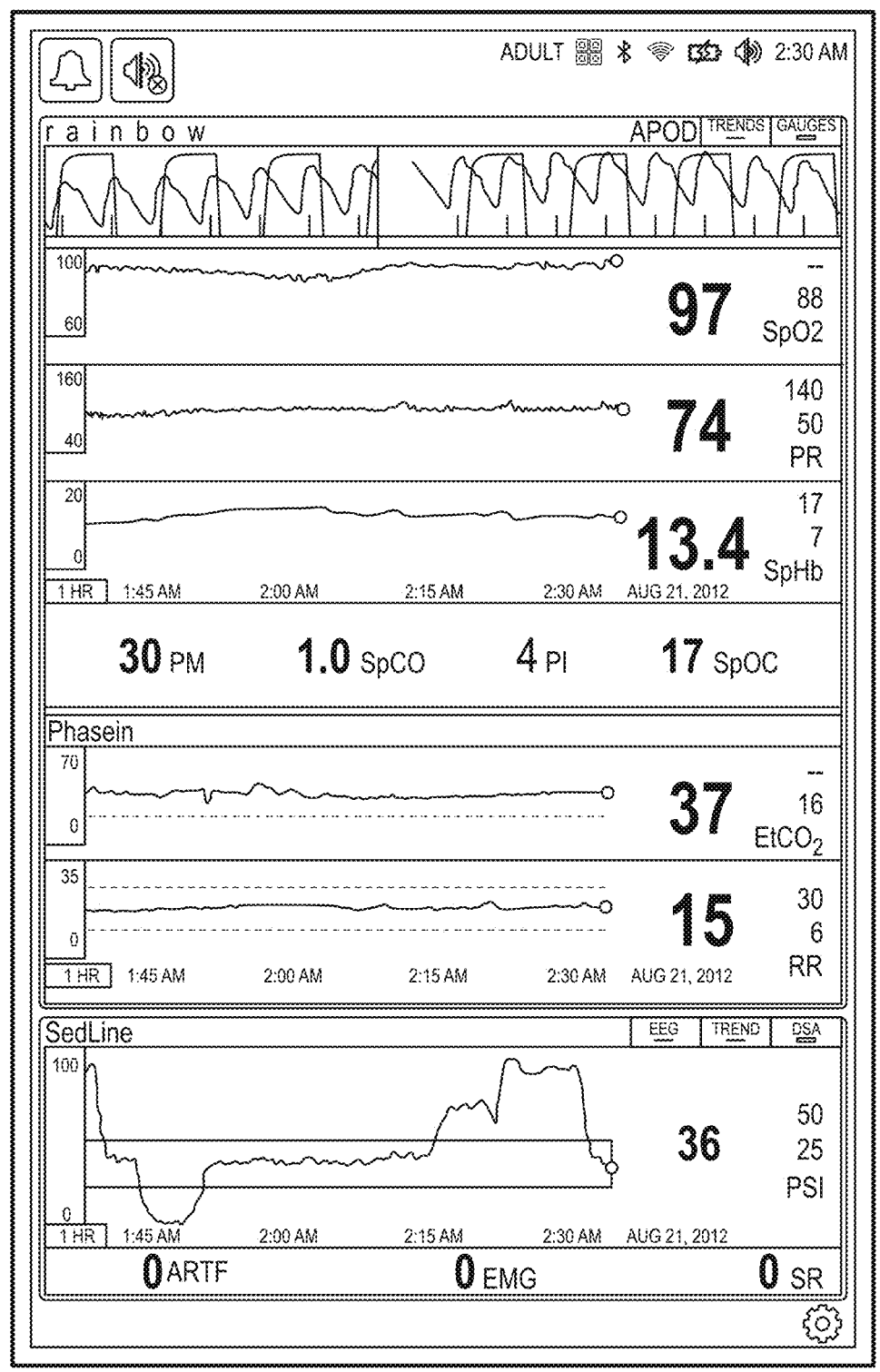
Figure 23E:
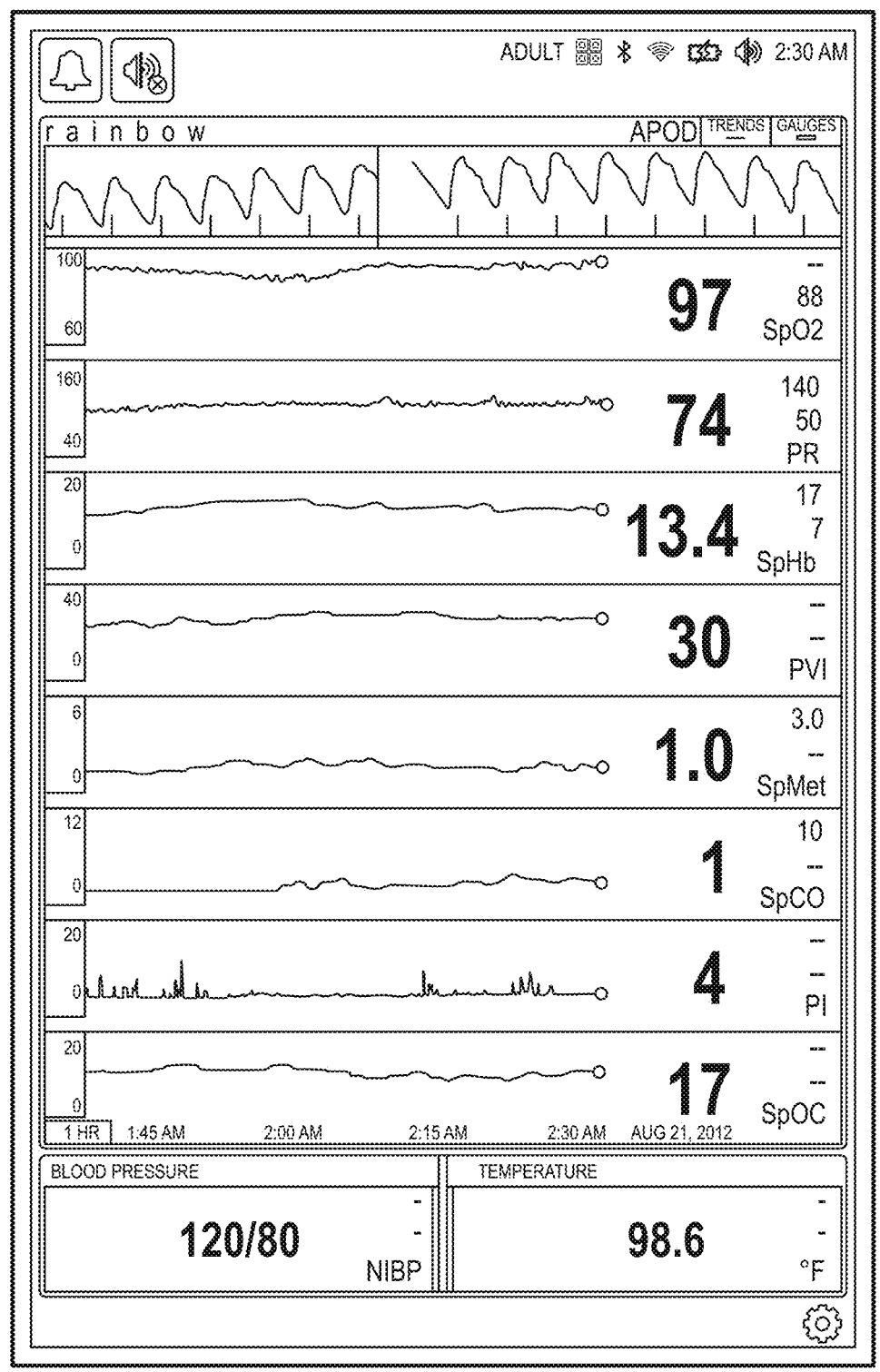
Figure 23F:
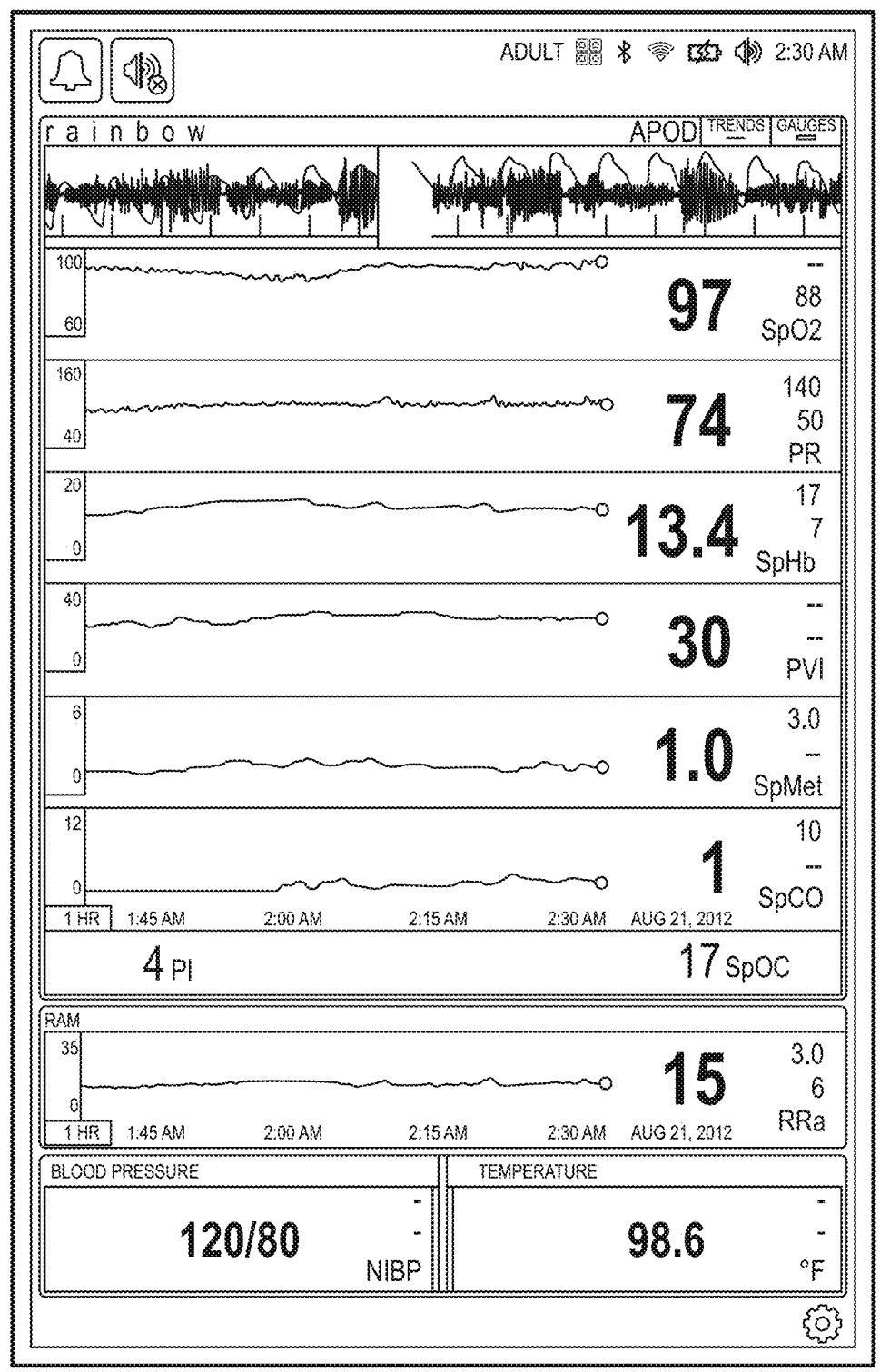

FIGS. 23A-23F illustrate example displays of measurement data showing, for example, data presentation in FIGS. 23A-23D when a depth of consciousness monitor is connected to a channel port of the hub of FIG. 1. As shown in FIGS. 23A-23C, the hub 100 advantageously roughly bifurcates its display 104 to show various information from the, for example, SEDLine device, commercially available from Masimo Corp. of Irvine, CA In FIG. 23D, the hub 100 includes an attached PhaseIn device, commercially available by PHASEIN AB of Sweden, providing, for example, information about the patient's respiration. The hub 100 also includes the SEDLine information, so the hub 100 has divided the display 104 appropriately. In FIG. 23E, temperature and blood pressure sensors communicate with the hub of FIG. 1 and the hub 100 creates display real estate appropriate for the same. In FIG. 23F, an acoustic sensor is also communicating with the hub of FIG. 1, as well as the forgoing blood pressure and temperature sensor. Accordingly, the hub 100 adjust the display real estate to accommodate the data from each attached device.

The term "and/or" herein has its broadest least limiting meaning which is the disclosure includes A alone, B alone, both A and B together, or A or B optionally, but does not require both A and B or require one of A or one of B. As used herein, the phrase "at least one of" A, B, "and" C should be construed to mean a logical A or B or C, using a non-exclusive logical or.

The term "plethysmograph" includes it ordinary broad meaning known in the art which includes data responsive to changes in volume within an organ or whole body (usually resulting from fluctuations in the amount of blood or air it contains).

III. Additional Monitoring Environments

Figure 24:
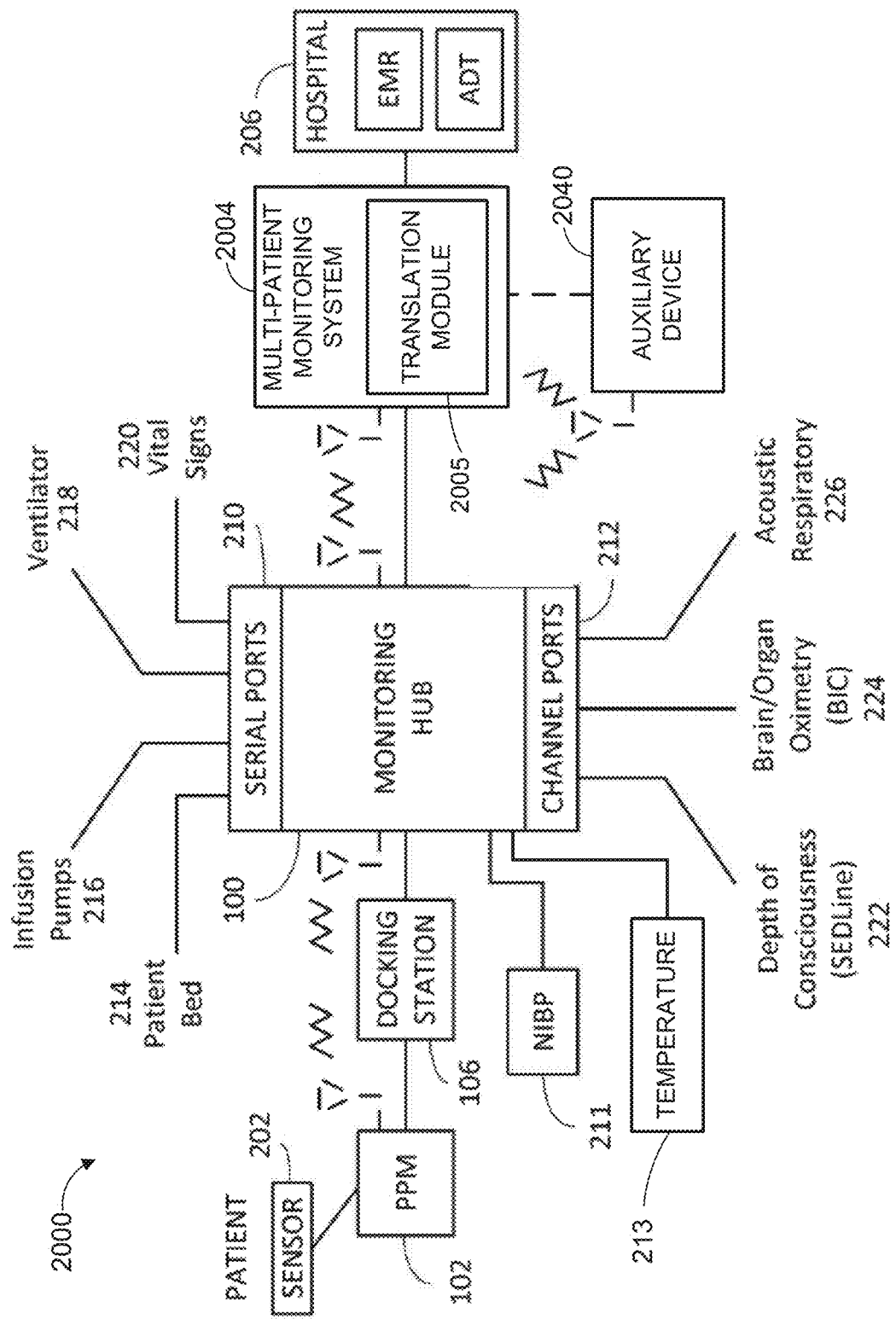
FIG. 24 illustrates another example of a monitoring environment including the hub of FIG. 1.

FIG. 24 illustrates another example of a monitoring environment 2000 including the hub 100 of FIG. 1. The monitoring environment 2000 may include all the features of the monitoring environment 200 of FIG. 2, as well as any of the other features described above. In addition, the monitoring environment 2000 depicts another example of the multi-patient monitoring system 204, namely, the multi-patient monitoring system (MMS) 2004. The MMS 2004 includes a translation module 2005 that can receive serial data, translate the serial data into a format recognizable by the monitoring hub 100, and provide the serial data to the monitoring hub 100 (among possibly other devices). Also shown is an auxiliary device 2040 that may communicate with the MMS 2004, the monitoring hub 100, or the PPM 102, wired or wirelessly.

As described above, the hub 100 may receive serial data from a variety of medical equipment, including the patient's bed 214, infusion pumps 216, a ventilator 218, and other vital signs monitors 220. The hub 100 can pass serial data from these sources on to the MMS 2004. As described above, the MMS 2004 may then store the serial data in a caregiver backend system 206 such as an EMR system or ADT system.

The medical equipment providing this serial data may use a variety of different proprietary protocols, messaging infrastructure, and the like that may not be natively recognizable by the hub 100. Accordingly, the hub 100 may not have native capability to read parameter values or other data from this medical equipment, and as a result, may not have the capability to display parameter values or other data from these devices. Advantageously, however, the translation module 2005 at the MMS 2004 can receive serial data from these devices, translate the serial data into a format recognizable by the monitoring hub 100, and provide the serial data to the monitoring hub 100. The monitoring hub 100 can then read parameter values and other data from the translated information and output these values or data to a display, such as any of the displays described above.

The translation module 2005 can apply one or more translation rules to the serial data to translate or transform the serial data from one format to another format. The serial data may be formatted according to a Health Level Seven ("HL7") protocol. The HL7 protocol has been developed to provide a messaging framework for the communication of clinical messages between medical computer systems and devices. However, the HL7 standard is quite flexible and merely provides a framework of guidelines. Consequently, medical devices or clinical computer systems that are all HL7-compliant may still be unable to communicate with each other. For example, the medical equipment 214-220 may each implement a version of the HL7 protocol, but these implementations may be different from an HL7 protocol implemented by the monitoring hub 100. Accordingly, the monitoring hub 100 may not be able to parse or read messages from the medical equipment 214-220, even though both use the HL7 standard. Further, the translation module 2005 may translate between different implementations of a common standard other than the HL7 protocol implemented by the hub 100 and medical equipment 214-220.

In addition to translating between different implementations of a common electronic medical communication protocol (for example, different formatting of HL7 messages), the translation module 2005 can also translate between input and output messages adhering to different communication protocols. The translation module 2005 can be capable of responding to and translating messages from, for example, one medical communication protocol to a separate medical communication protocol. For example, the translation module 2005 can facilitate communication between messages sent according to the HL7 protocol, the ISO 11073 protocol, other open protocols, or proprietary protocols. Accordingly, the translation module 2005 can translate an input message sent according to the HL7 protocol to an output message according to a different protocol, or vice-versa. The translation module 2005 can implement any of the translation features described below in greater detail under the section entitled "Translation Module Embodiments," as well as further in U.S. application Ser. No. 14/032,132, filed Sep. 19, 2013, titled "Medical Monitoring System," the disclosure of which is hereby incorporated by reference in its entirety.

Advantageously, the translation module 2005 can pass translated serial data back to the hub 100 or PPM 102. Since the translated data is in a format readable by the hub 100 or PPM 102, the hub 100 or PPM 102 can output the data from the medical equipment 214-220 on the display of the hub 100 or PPM 102. In addition, the translation module 2005 can provide the translated data to devices other than the hub 100, including clinician devices (such as cell phones, tablets, or pagers) and an auxiliary device 2040 that will be described below. Moreover, since the serial data provided by the medical equipment 214-220 may include alarm notifications, the translation module 2005 can pass these alarm notifications to the hub 100 or PPM 102. The hub 100 or PPM 102 can therefore generate visual or audible alarms responsive to these alarm notifications. Further, the translation module 2005 can provide the alarm notifications to clinician devices, for example, over a hospital network or wide area network (such as the Internet). In addition, the translation module 2005 can provide the alarm notifications to the auxiliary device 2040.

The translation module 2005 is shown as implemented in the MMS 2004 because it may be beneficial to maintain and update the translation rules of the translation module 2005 in a single location. However, the translation module 2005 may also be (or instead be) implemented in the hub 100 or PPM 102. Accordingly, the hub 100 or PPM 102 can access an internal translation module 2005 to translate serial data for output to the display of the hub 100 or PPM 102.

The auxiliary device 2040 can be a computing device having physical computer hardware, a display, and the like. For example, the auxiliary device 2040 may be a handheld computing device used by a clinician, such as a tablet, laptop, cellphone or smartphone, personal digital assistant (PDA), a wearable computer (such as a smart watch or glasses), or the like. The auxiliary device 2040 may also be simply a display device, such as a computer monitor or digital television. The auxiliary device 2040 can provide a second screen functionality for the hub 100, PPM 102, or MMS 2004. As such, the auxiliary device 2040 can communicate wirelessly or through a wired connection with the hub 100, MMS 2004, or PPM 102.

As a second screen device, the auxiliary device 2040 can depict a copy of at least a portion of the display of the hub 100 (or the PPM 102) or a different version of the hub 100 (or the PPM 102) display. For instance, the auxiliary device 2040 can receive physiological parameter data, trend data, or waveforms from the hub 100, PPM 102, or MMS 2040 and display the parameter data, trend data, or waveforms. The auxiliary device 2040 can output any information available to the hub 100, PPM 102, or MMS 2004. One use of the auxiliary device 2040 is as a clinician device usable by a clinician to view data from the hub 100, PPM 102, or MMS 2004 while away from a patient's room (or even while in a patient's room). A clinician can use the auxiliary device 2040 to view more detailed information about physiological parameters than is displayed on the hub 100 or PPM 102 (see, for example, FIG. 39). For instance, the auxiliary device 2040 may include zoom functionality or the like that enables a clinician to zoom into trends or waveforms to more closely inspect parameter activity.

One example reason for copying at least a portion of the display of the hub 100 or PPM 102 is to enable different clinicians to have the same view of the data during a surgical procedure. In some surgical procedures, for instance, two anesthesiologists monitor a patient, one anesthesiologist monitoring the brain function and brain oxygenation of the patient, while the other monitors peripheral oxygenation of the patient. A brain sensor, such as has been described above, may be attached to the patient and provide brain monitoring and oxygenation data that is output to the hub 100 or the PPM 102 for presentation to the first anesthesiologist. A finger or toe/foot optical sensor can also be attached to the patient and output data to the hub 100 or PPM 102. The hub 100 or PPM 102 can transmit this data to the auxiliary device 2040, which the second anesthesiologist can monitor to observe oxygenation in the patient's peripheral limbs. The second anesthesiologist may also need to know the oxygenation at the brain to help interpret the seriousness or lack thereof of poor peripheral oxygenation values. However, in many surgical procedures, a curtain or screen is placed over the patient as part of the procedure, blocking the second anesthesiologist's view of the hub 100 or PPM 102. Accordingly, the hub 100 or PPM 102 can output a copy of at least a portion of its display to the auxiliary device 2040 so that the second anesthesiologist can monitor brain function or oxygenation.

The auxiliary device has a larger display area than the display of the hub 100. For instance, the hub 100 may have a relatively smaller display, such as about 10 inches, while the auxiliary device 2040 may be a television monitor or the like that has a 40 inch or larger display (although any size display may be used for the auxiliary device 2040). The auxiliary device 2040 as a television can include a hardware module that includes a processor, memory, and a wireless or wired networking interface or the like. The processor can execute programs from the memory, including programs for displaying physiological parameters, trends, and waveforms on the display of the television. Since a television monitor may be larger than the hub 100, the television monitor version of the auxiliary device 2040 can display more fine detail of patient waveforms and trends (see, for example, FIG. 39).

The auxiliary device 2040 may display one portion of any of the displays described herein while the hub 100 displays another portion thereof. For instance, the auxiliary device 2040 may display any of the anatomical graphics described above with respect to FIGS. 19A-19J, while the hub 100 displays any of the parameter displays described above with respect to FIGS. 20A-23F (or vice versa). Likewise, the auxiliary device 2040 may display the translated data received from the translation module 2005 while the hub 100 displays channel data (or vice versa). The auxiliary device 2040 can display both translated data and channel data (see., for example, FIG. 38).

The auxiliary device 2040 can perform at least some processing of physiological parameters, including any of the functionality of the monitoring hub 100. For instance, the auxiliary device 2040 may include the translation module 2005 and perform the features thereof.

Figure 25:
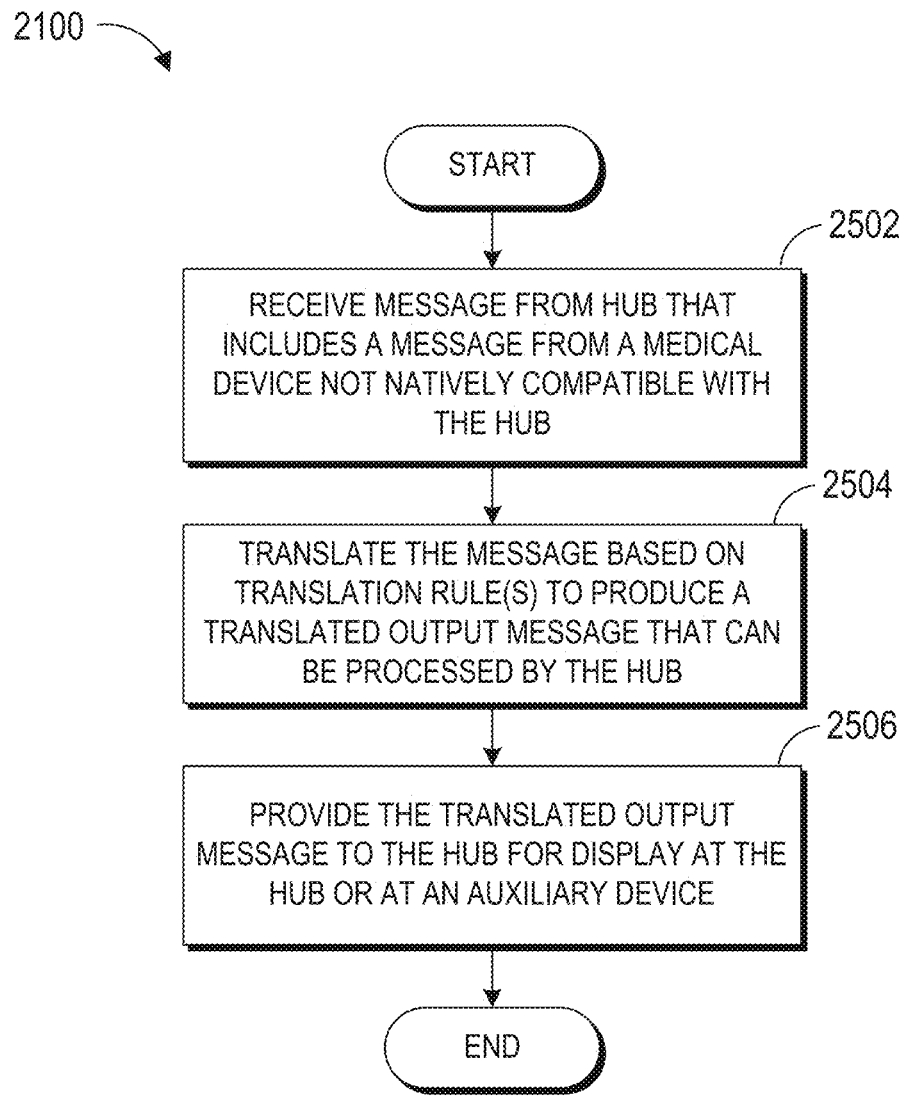
FIG. 25 illustrates a translation message handling process.

FIG. 25 illustrates a translation message handling process 2100. The process 2100 can be implemented by the translation module 2005 described above or by any other computing system. At block 2502, the translation module 2005 receives a message from the hub 100 (or PPM 102) that includes a message from a medical device not natively compatible with the hub 100 (or PPM 102). At block 2504, the translation module 2005 can translate the message based on one or more translation rules to produce a translated output message that can be processed by the hub 100 (or PPM 102). At block 2506, the translation module can provide the translated output message to the hub 100 for display at the hub 100 (or PPM 102) or at an auxiliary device 2040. The hub 100 (or PPM 102) may route the translated data to the auxiliary device 2040, or the auxiliary device 2040 may receive the translated data directly from the translation module 2005.

For example, a first medical device having digital logic circuitry can receive a physiological signal associated with a patient from a physiological sensor, obtains a first physiological parameter value based on the physiological signal, and outputs the first physiological parameter value for display. The first medical device can also receive a second physiological parameter value from a second medical device other than the first medical device, where the second physiological parameter value is formatted according to a protocol not used by the first medical device, such that the first medical device is not able to process the second physiological parameter value to produce a displayable output value. The first medical device can pass the physiological parameter data from the first medical device to a separate translation module, receive translated parameter data from the translation module at the first medical device, where the translated parameter data is able to be processed for display by the first medical device, and output a second value from the translated parameter data for display. The first medical device may be, for example, the hub 100, PPM 102, or MMS 2004, and the second medical device may be the infusion pump 216 or ventilator 218 or the like.

FIGS. 26-38 and 46-71 illustrate additional example hub displays, including displays of measurement data. Each of these displays may be implemented by the auxiliary device 2040, although similar displays may also be output on the hub 100 (or PPM 102) directly. The example Figures shown are depicted as being implemented for a tablet computer that includes touchscreen functionality. Touchscreen functionality is optional and be replaced by other suitable input devices, such as keyboards, mice, track wheels, and the like.

Figure 26:
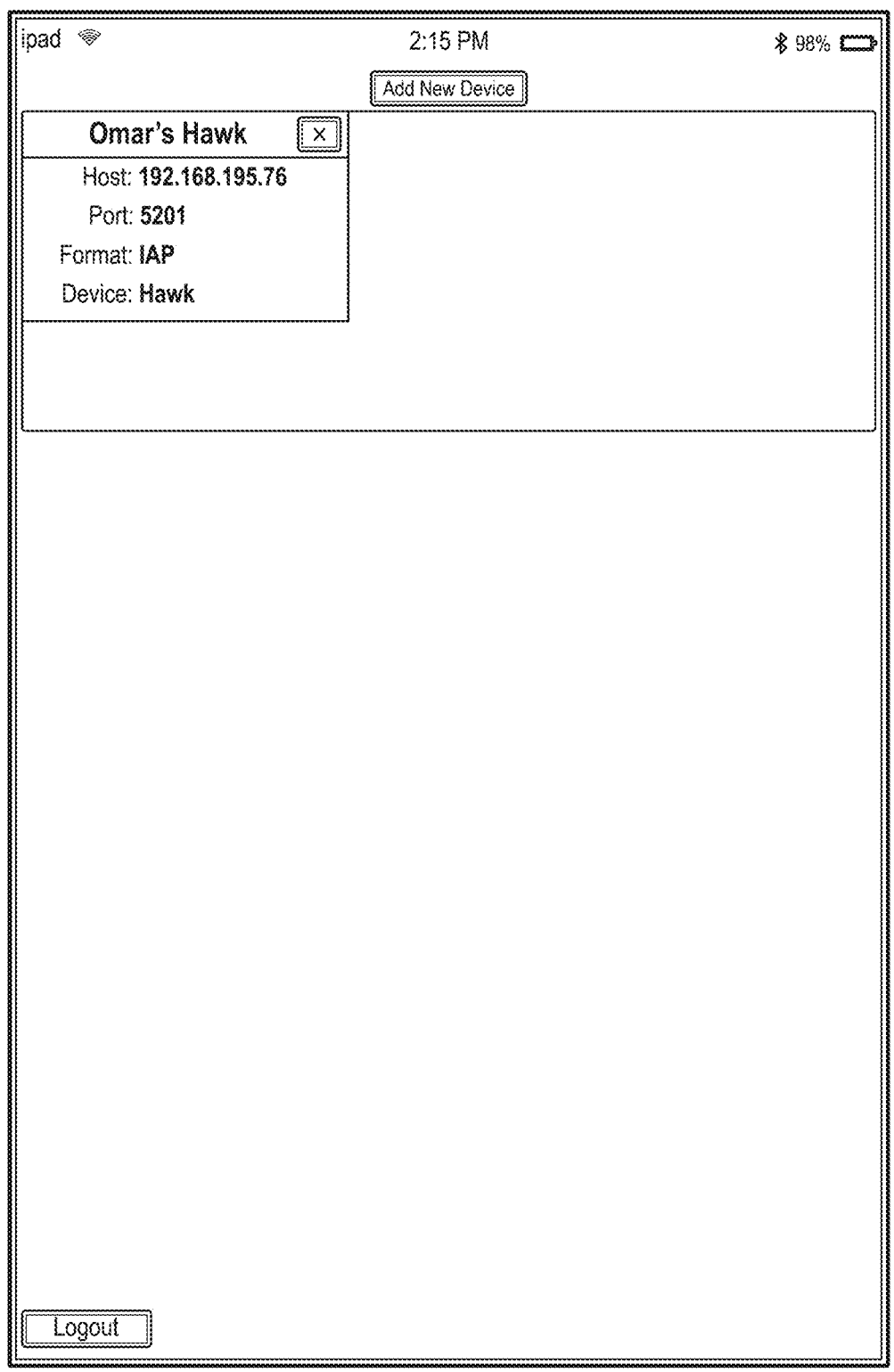
FIGS. 26-39 and 46-71 illustrate additional example hub displays, including displays of measurement data.

Turning to FIG. 26, the user interface shown depicts a device connected to the auxiliary device 2040. The device shown is "Omar's Hawk," which can be the monitoring hub 100. The auxiliary device 2040 is connected wirelessly to the hub 100 so as to receive data from the hub 100. The auxiliary device could also connect wirelessly to the MMS 2004 or PPM 102.

Figure 27:
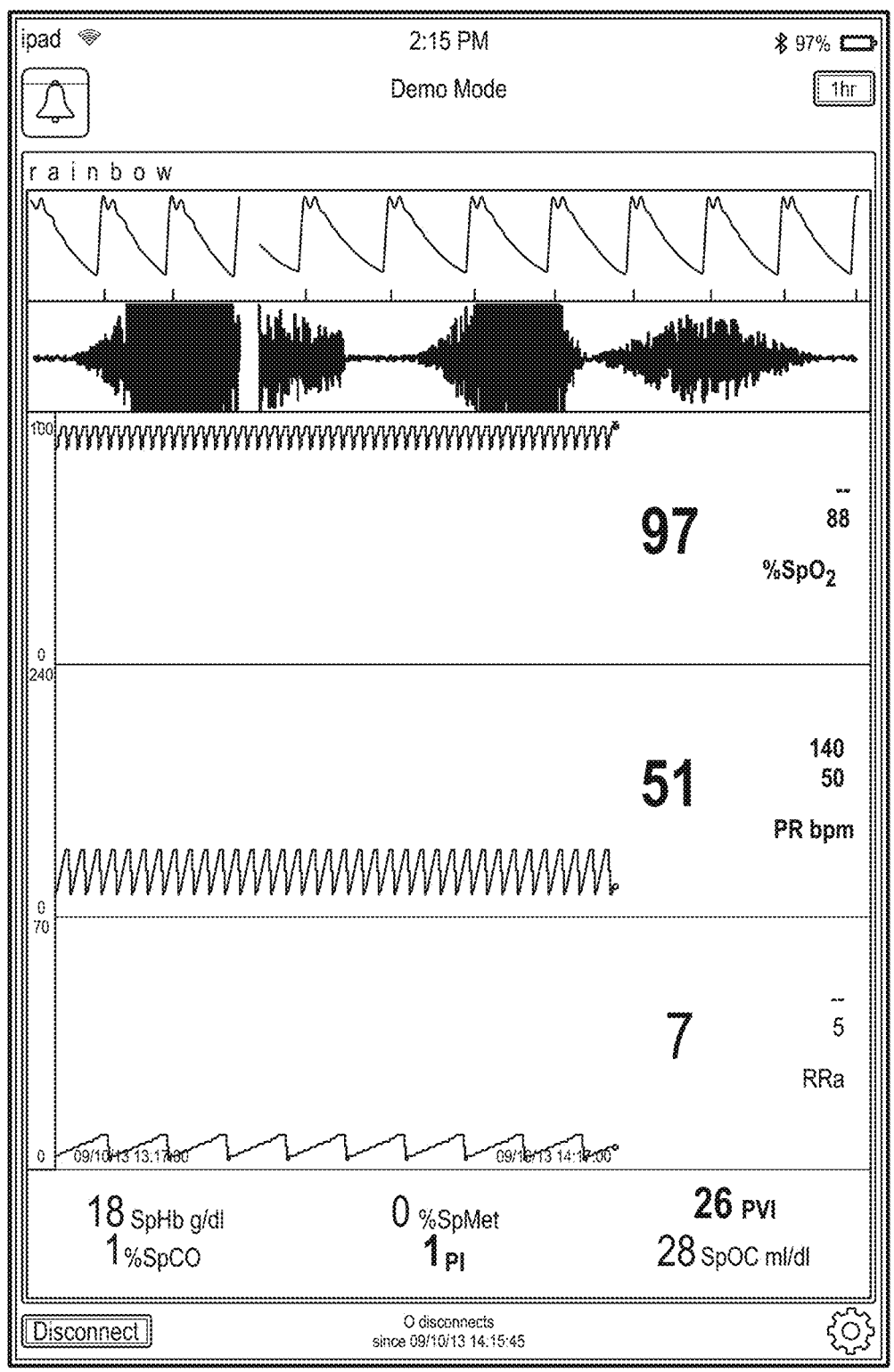
Figure 28:
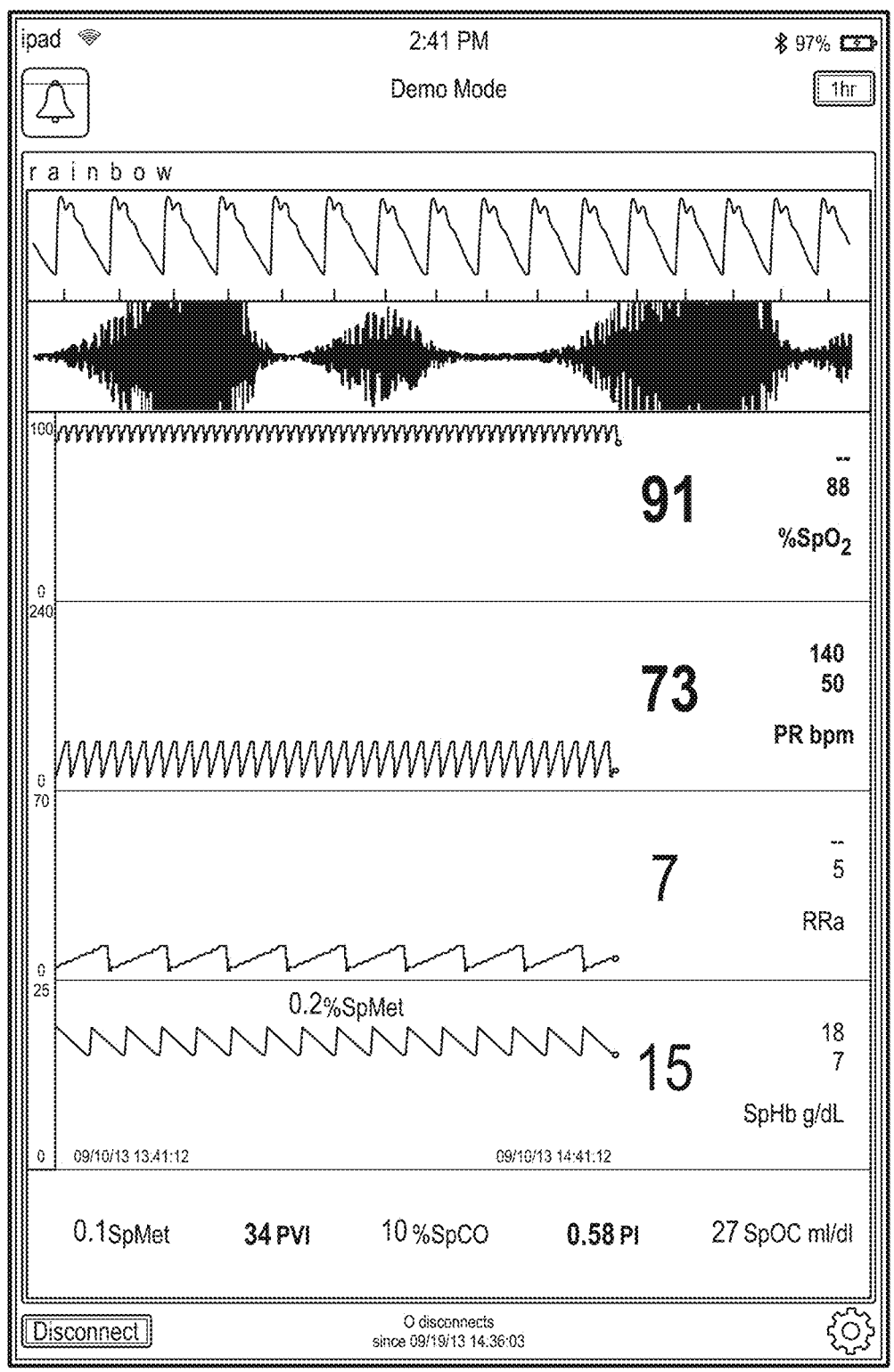

FIG. 27 depicts a default parameter view on the auxiliary device 2040. Parameter values are shown together with waveforms in an upper portion of the display, and other parameters (such as SpHb, SpMet, PVI, etc.) are shown at the bottom of the display without their corresponding waveforms. Any of these parameters at the bottom of the display may be dragged and dropped onto the upper portion of the display to cause their waveforms to be shown. For instance, FIG. 28 depicts a similar display as in FIG. 27 except that the SpHb parameter has been dragged and dropped onto the upper portion of the display, causing the SpHb waveform and additional details on alarm limits (18 and 7) to be shown. Similarly, FIG. 29 shows the same display as FIG. 28 except that the SpMet parameter has been dragged and dropped on the upper portion of the display, causing its waveform and alarm limit (3) to be shown.

Figure 29:
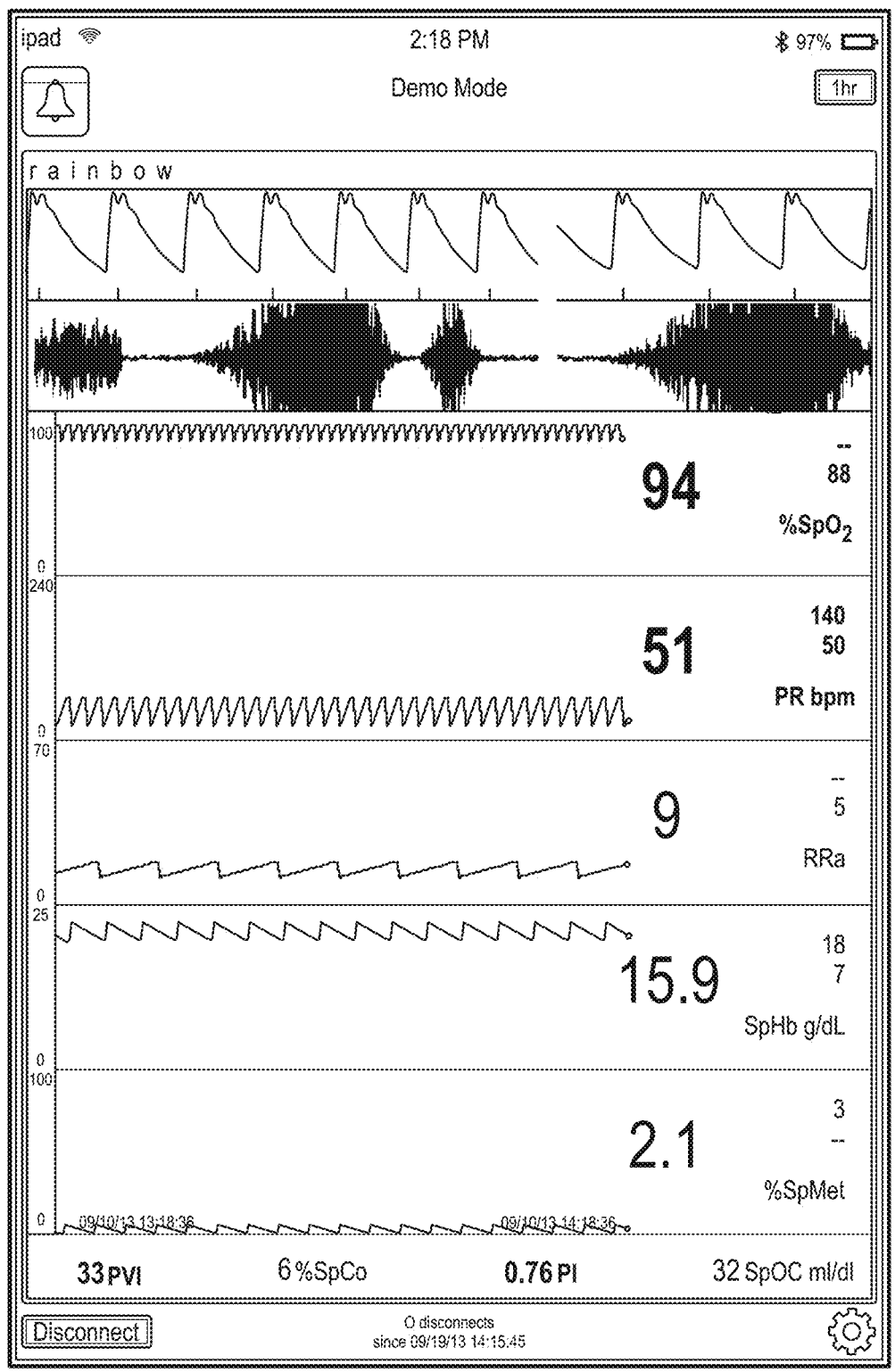
Figure 30:
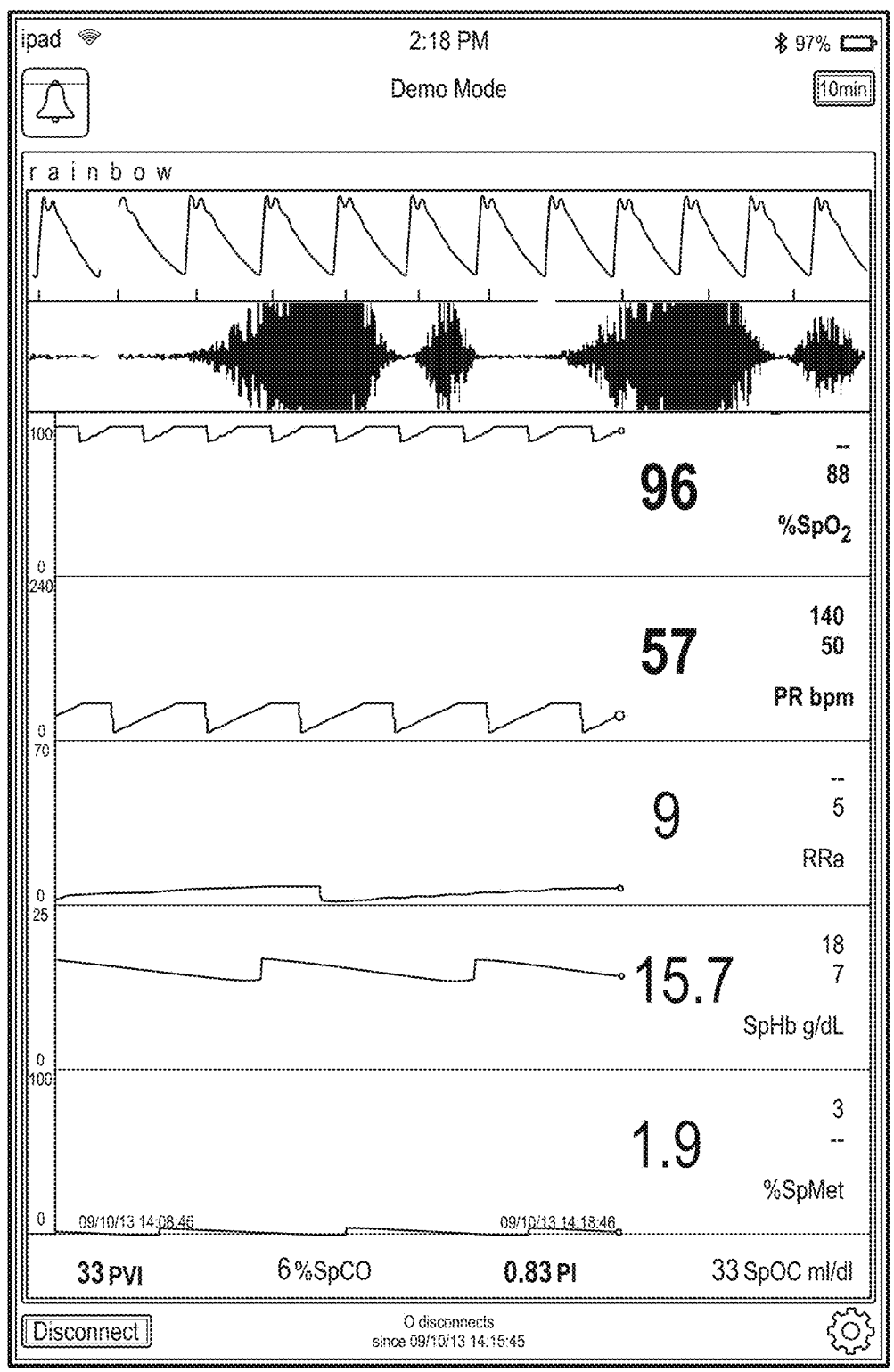

In each of the displays of FIGS. 27-29, a time window button is shown in the upper right corner. This time window button says "1 hr" in FIGS. 27-29 but may be selected by a user to change the time window, which can affect the window of trend or waveform data shown in the display. A user selection of this time window button and change to a 10 minute window is shown in FIG. 30. As can be seen, the waveforms in FIG. 30 are shown in a smaller window of time than in the previous Figures.

Figure 31:
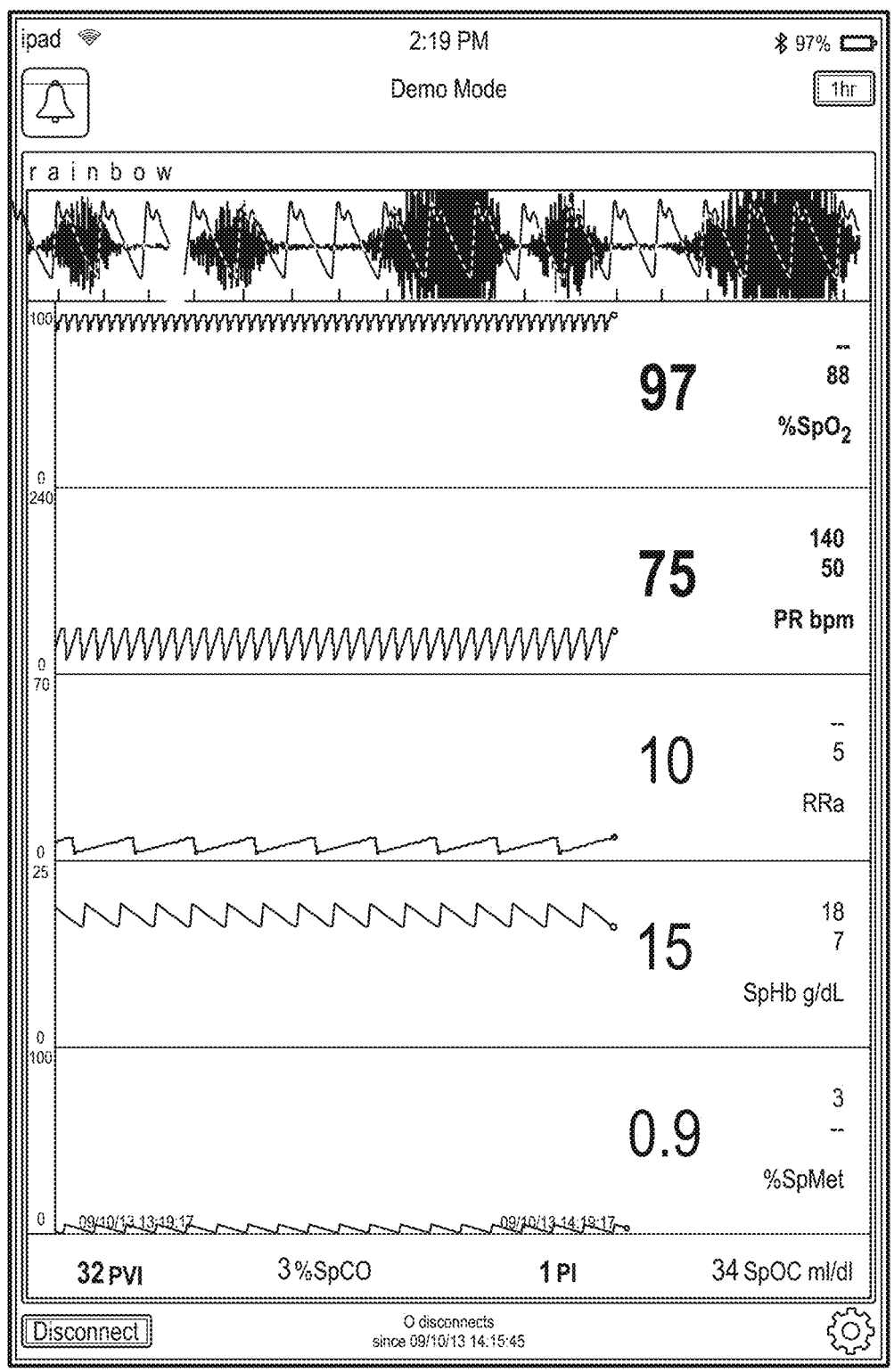
Figure 32:
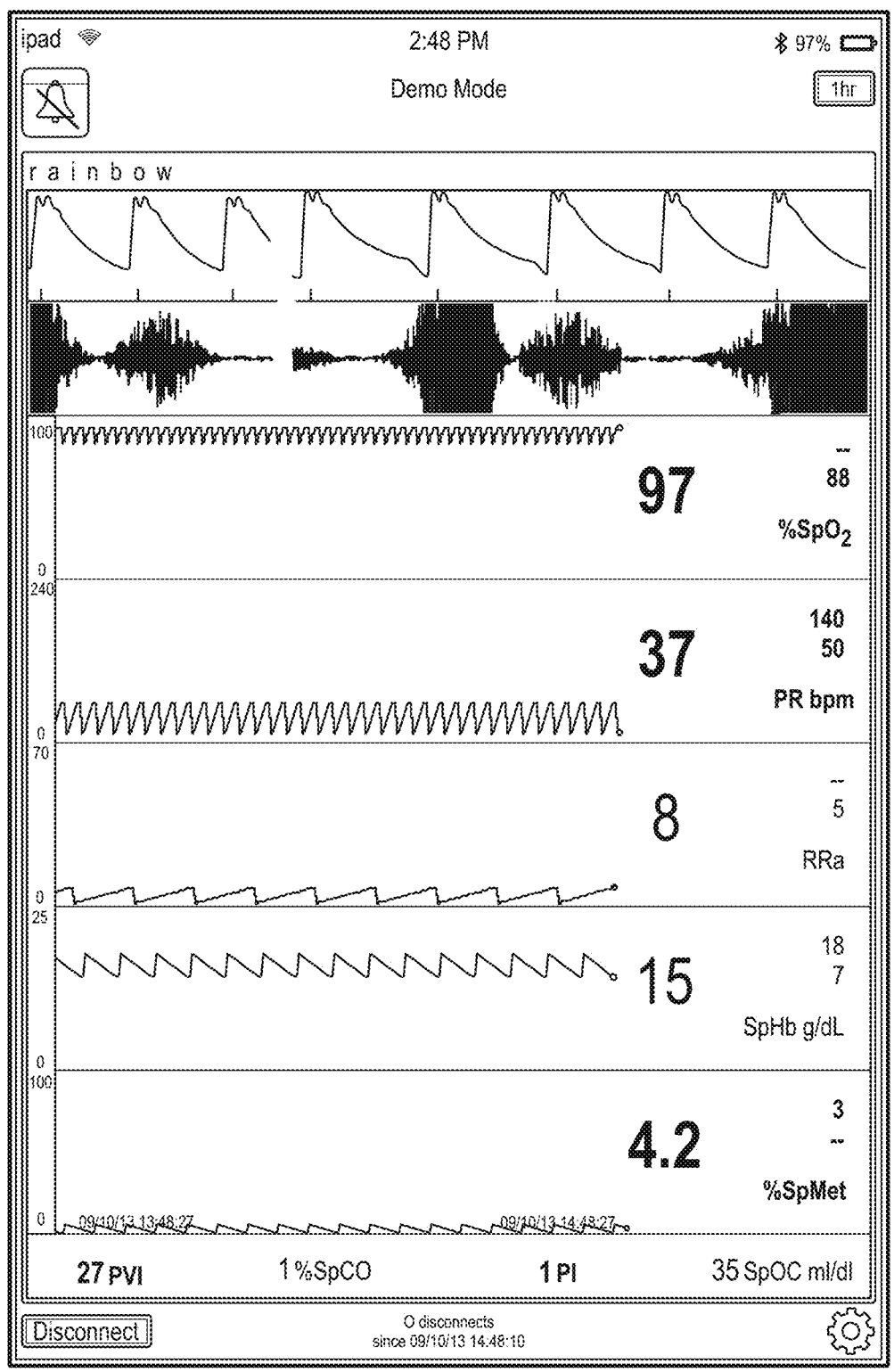

FIG. 31 shows another version of the display of FIG. 29 with stacked waveforms, including a stacked SpO2 and respiratory waveform, similar to other stacked waveforms described elsewhere herein. FIG. 32 shows a similar display to FIG. 29 with the pulse rate (PR) and SpMet (methemoglobin) parameters highlighted as being in alarm condition. The alarm condition can be represented as a red box around the parameter values and waveforms, or with red transparency coloring at least a portion of the box. The red box or transparency may also flash, and an audible alarm may sound. Other ways to represent an alarm condition can also be used.

Figure 33:
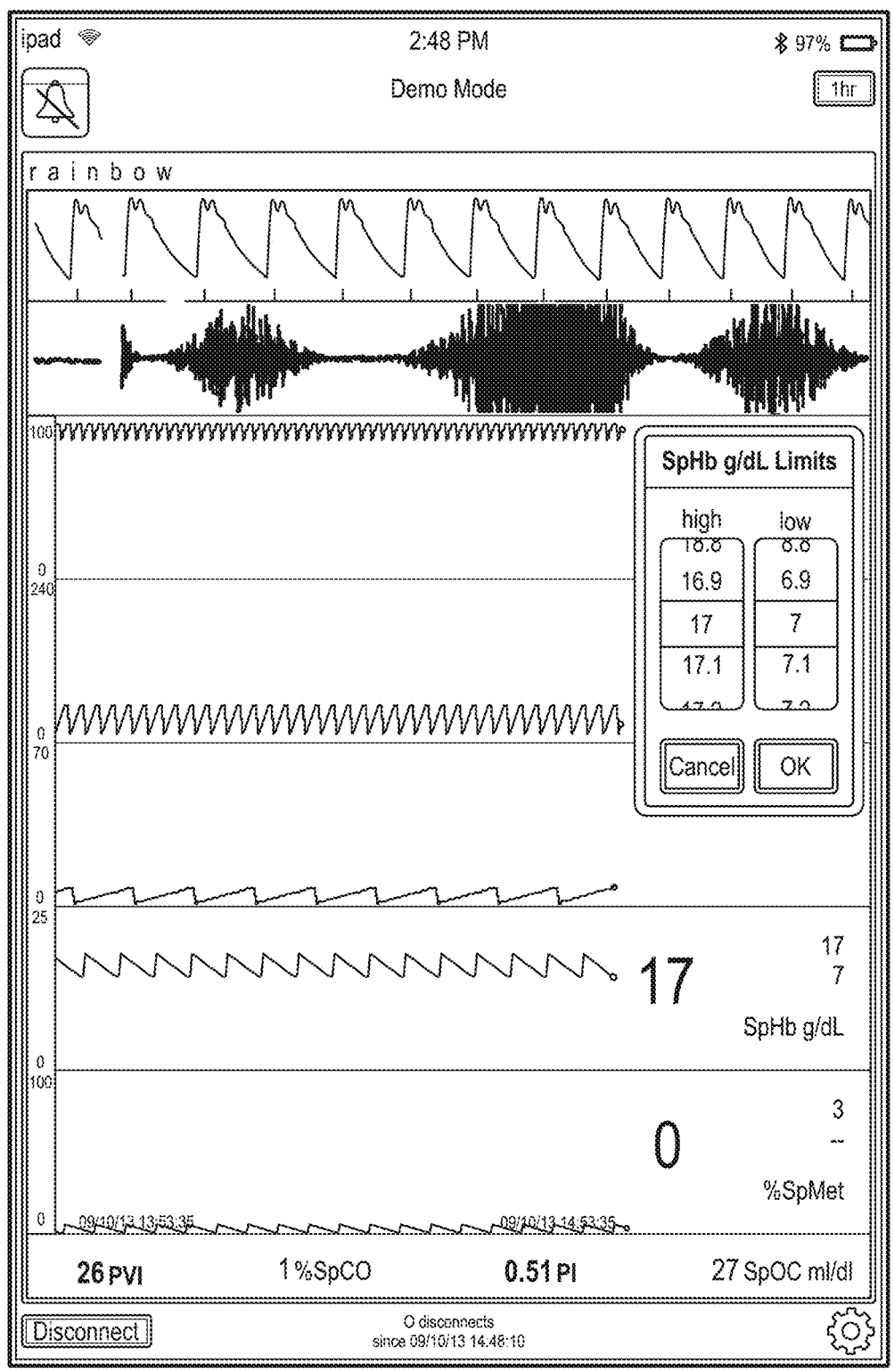

FIG. 33 shows a popup interface that enables a user to adjust alarm limits for a parameter (for example, SpHb or total hemoglobin). The popup interface includes scroll wheels that allow a user to quickly scroll among and select possible parameter limit values.

Figure 34:
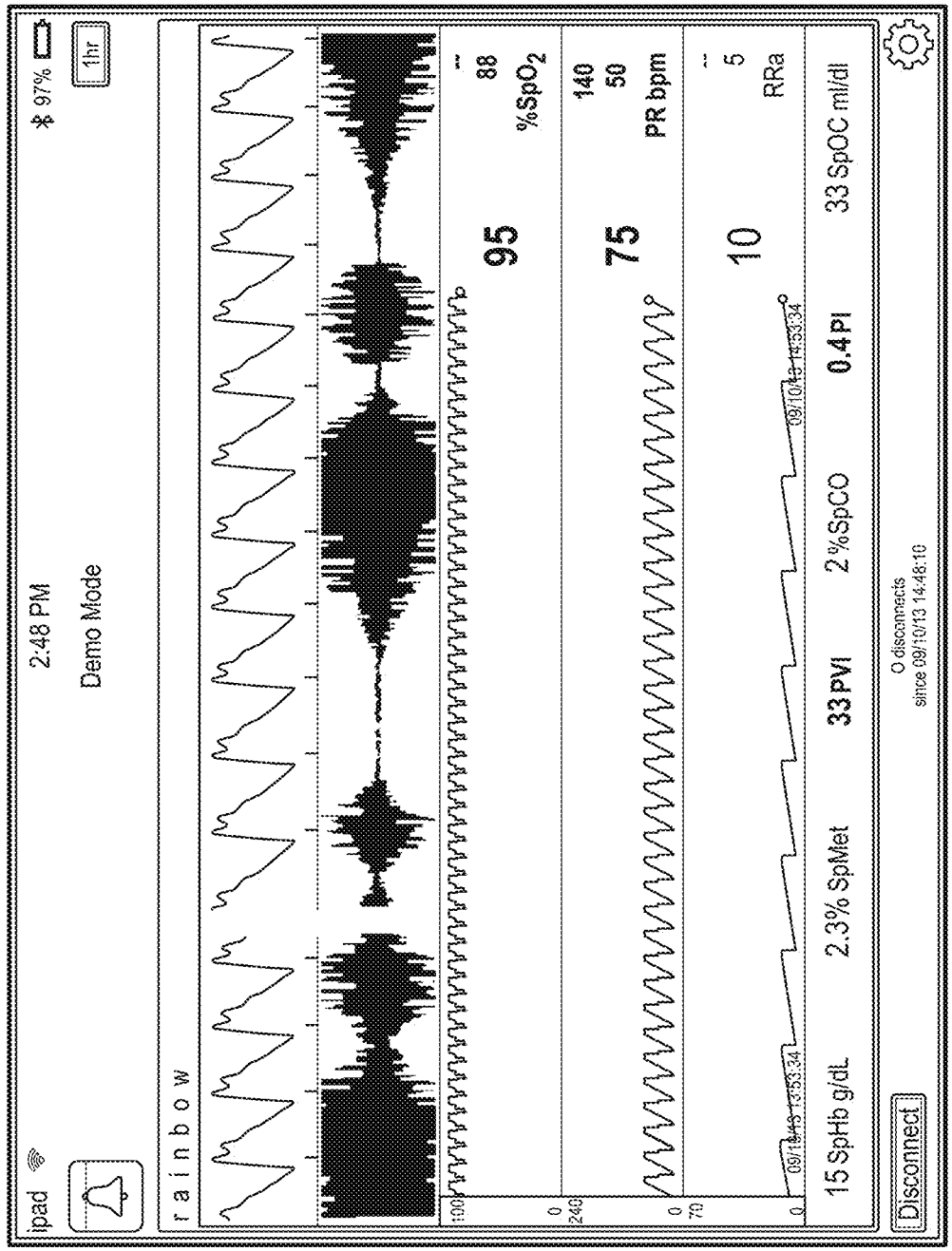
Figure 35:
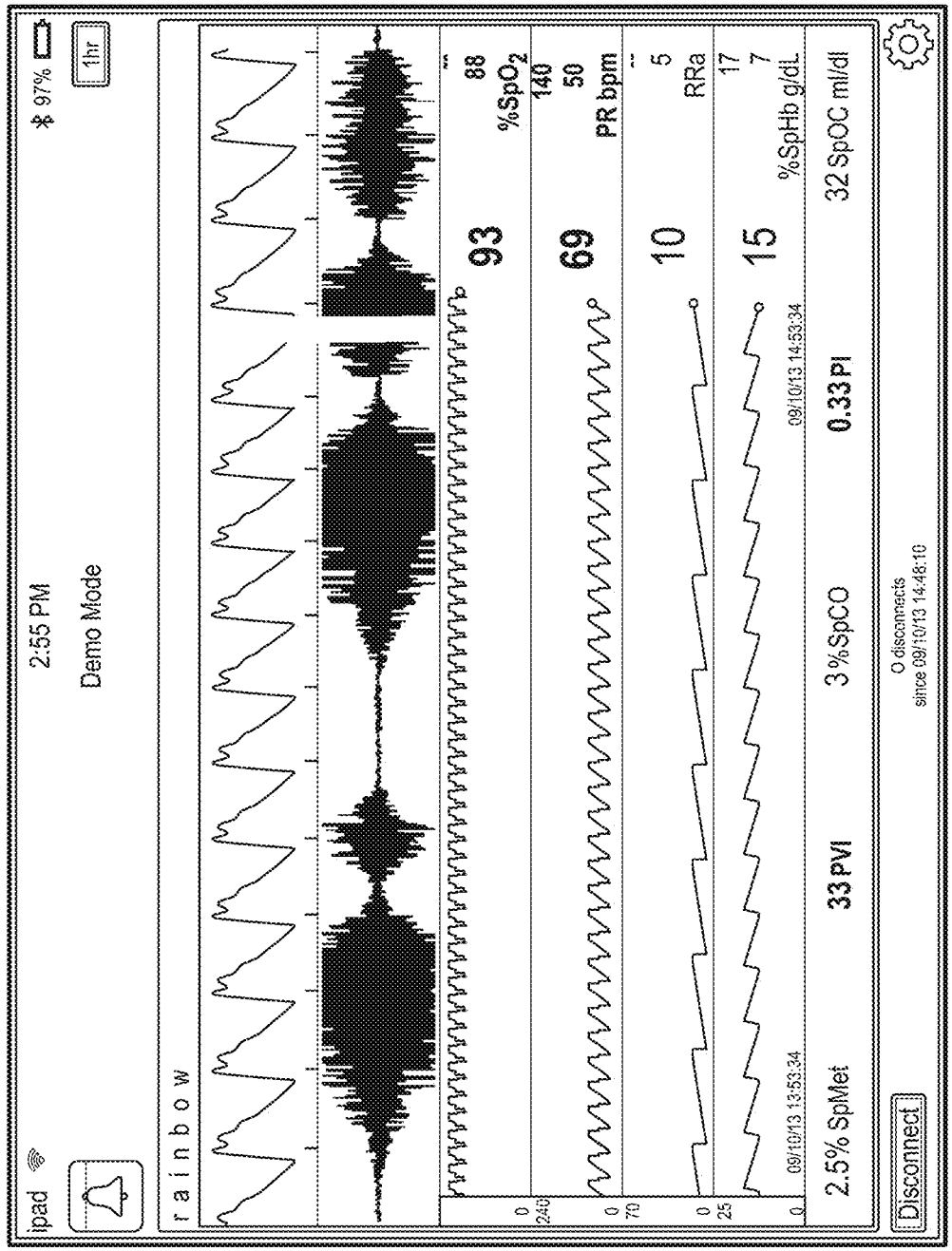
Figure 36:
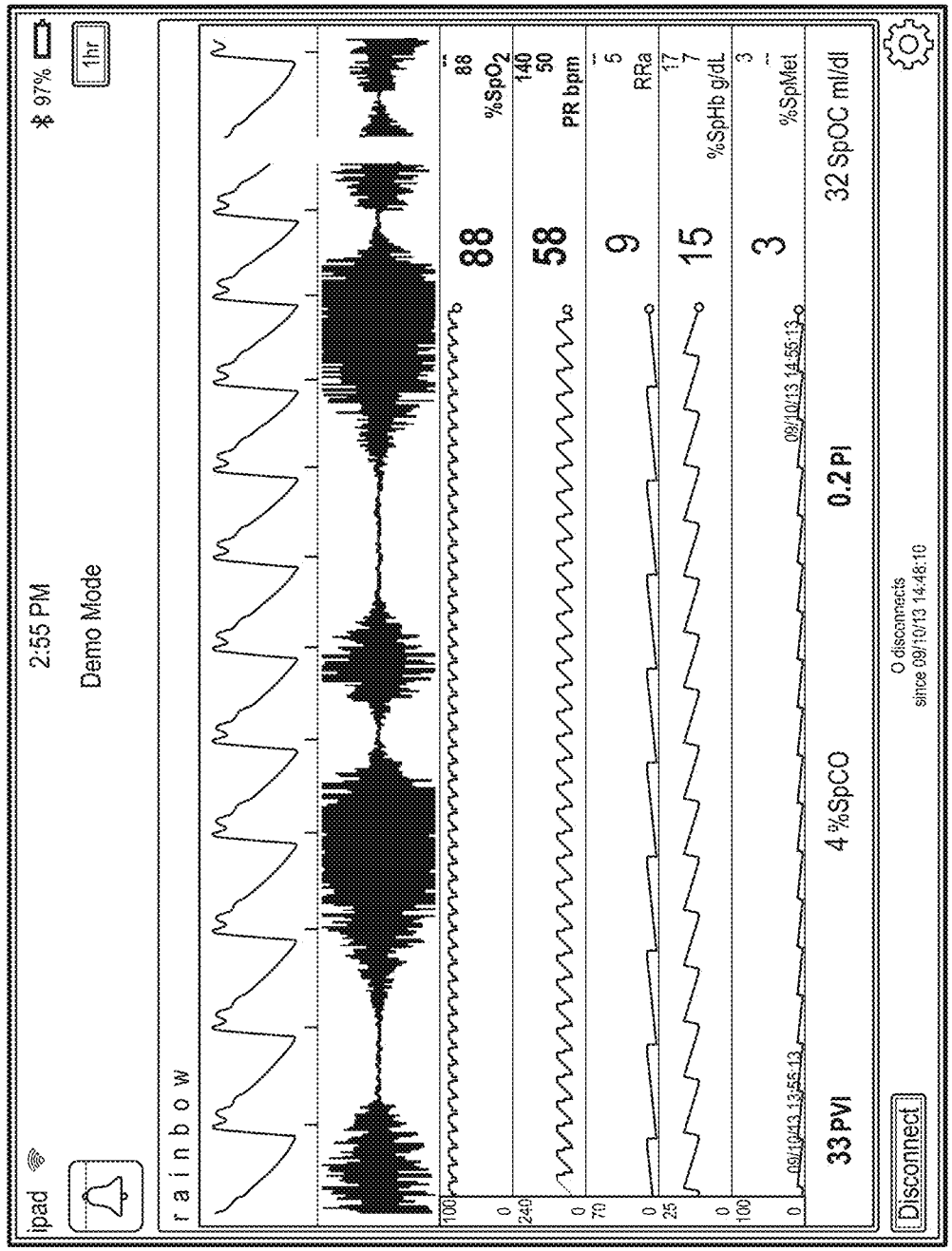
Figure 37:
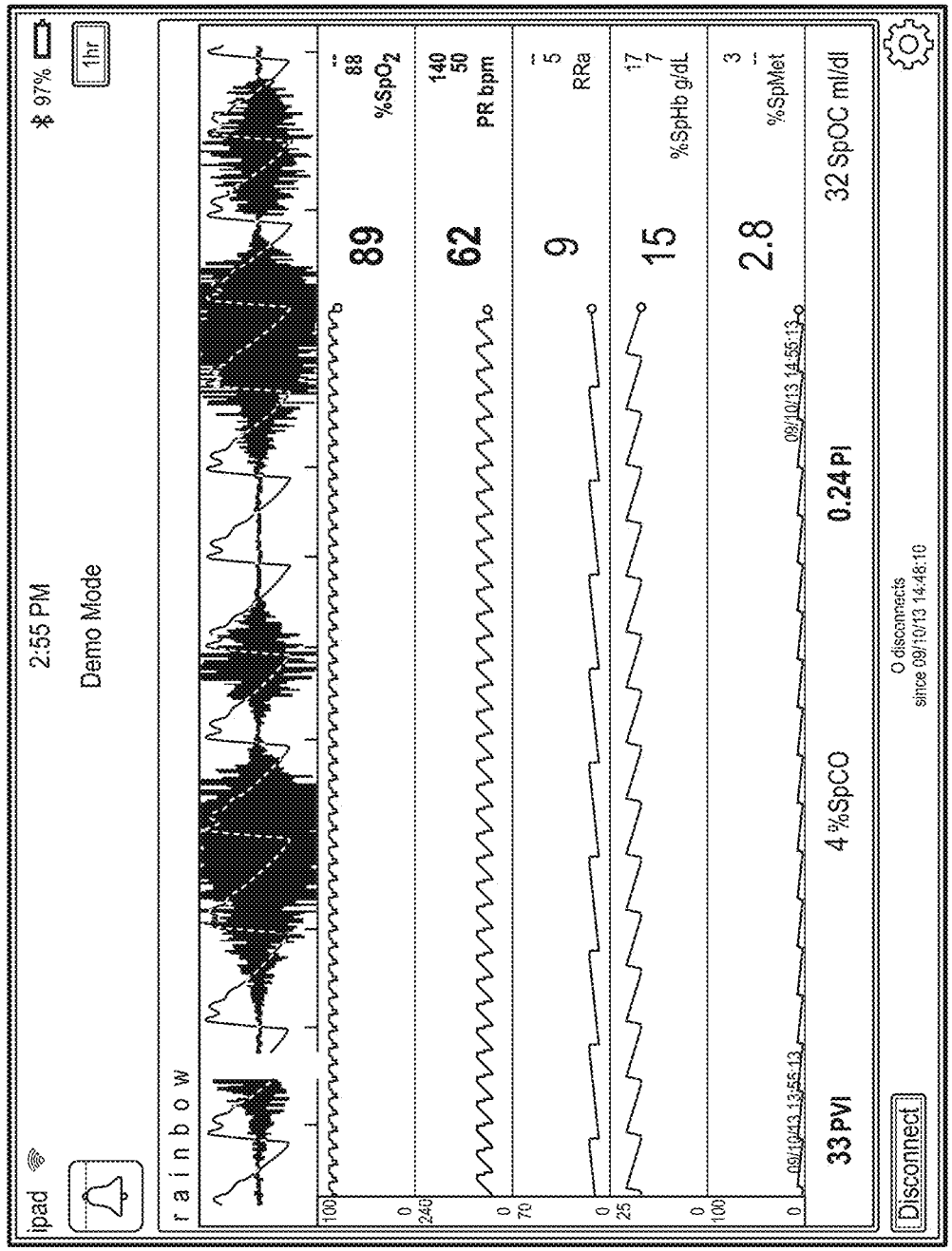
Figure 38:
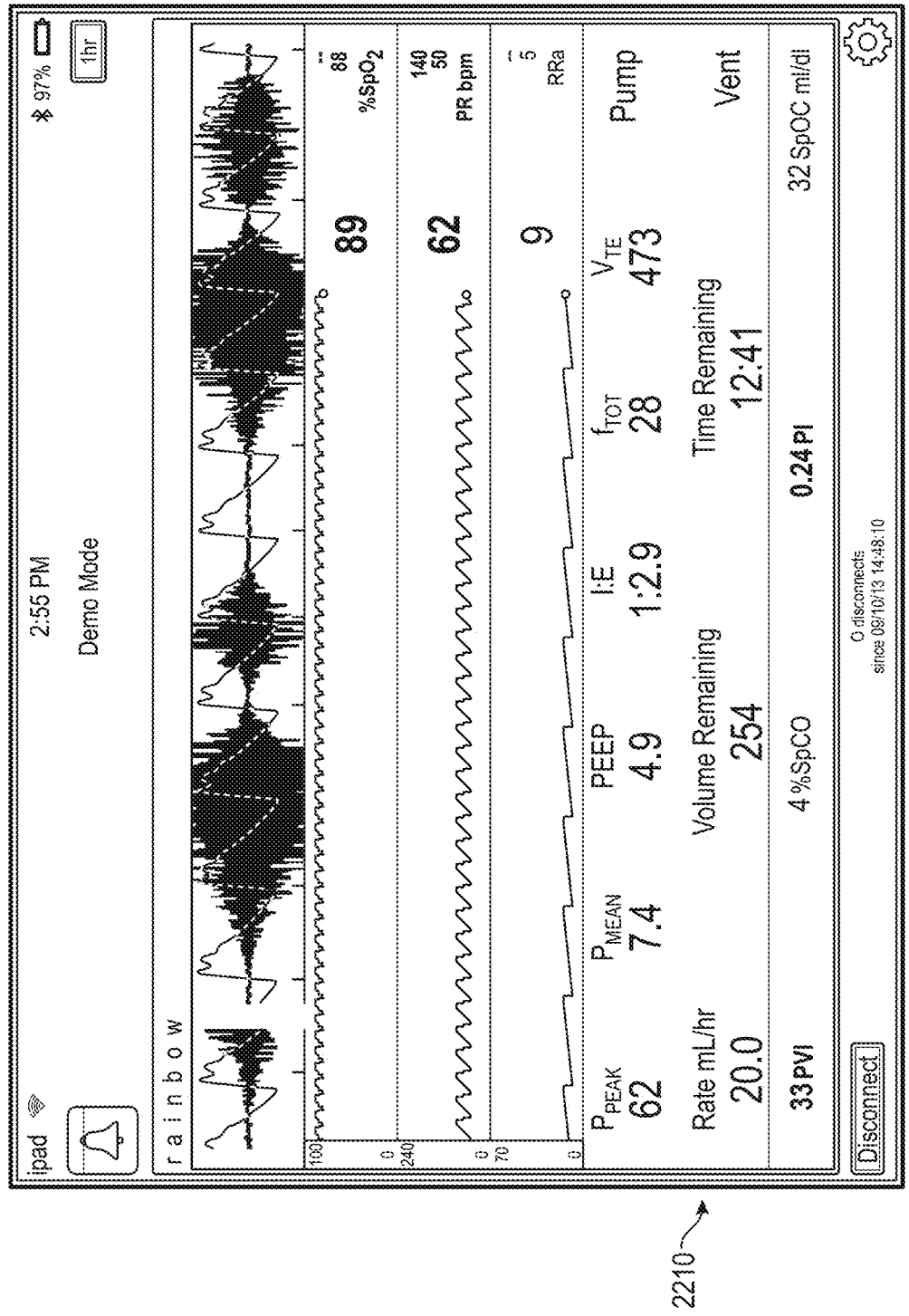

FIGS. 34-38 show landscape display views in contrast to the portrait-oriented displays of FIGS. 26-33. These landscape display views may be accessed by rotating the auxiliary device 2040 (such as tablet etc.) to a landscape orientation. FIG. 34 shows a first set of parameters, while FIGS. 35 and 36 add additional drag-and-dropped parameters with their waveforms and additional alarm limit details, similar to those described above with respect to FIGS. 27-29. FIG. 37 depicts stacked parameter waveforms, stacking SpO2 and respiratory waveforms. FIG. 38 depicts both channel parameters (such as SpO2, PR (pulse rate), and RRa (acousticly-measured respiratory rate)) while also showing translated serial data parameters 2210, including parameters from a pump and a vent. These translated serial data parameters 2210 may have been received from the translation module 2005, either through the hub 100 or directly from the MMS 2004.

Referring again to FIG. 24, as described above, the hub 100 or PPM 102 can output a copy of at least a portion of the display to the auxiliary device 2040. The hub 100 or PPM 102 can output data with respect to a subset of the full parameters shown on the hub 100 or PPM 102 to the auxiliary device 2040. For instance, the hub 100 or PPM 102 may provide functionality for a clinician to select one or more of the parameters displayed thereon to see just that one or more parameters displayed on the auxiliary device 2040. Doing so may allow the auxiliary device 2040 to show more detail about the selected one or more parameters because fewer parameters may be shown on the auxiliary device's 2040 display than on the hub 100 or PPM 102.

Figure 39:
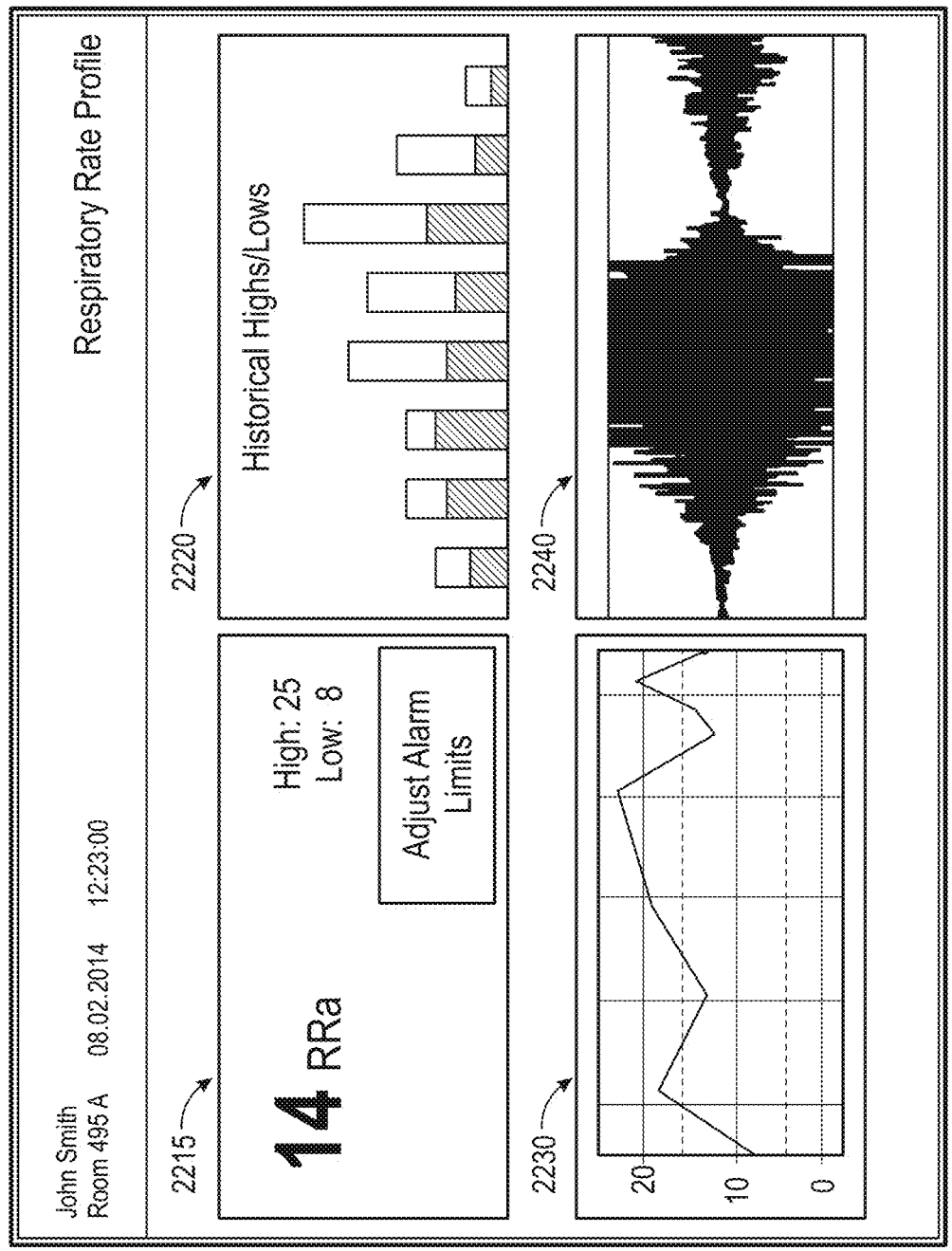

FIG. 39 depicts one example display of an auxiliary device 2040 that depicts data with respect to one parameter, respiratory rate. Unlike the main display of the hub 100 or PPM 102, the display shown in FIG. 39 includes more than just the current value 2215, a recent trend 2230, and small waveform of the respiratory rate. In addition, the display depicts a histogram 2220 of historical highs and lows (for example, for the past several days) of the patient being monitored. In addition, a detailed waveform 2240 is shown, which may be larger than the waveforms shown on the main display of the hub 100 or PPM 102, which may give the user more detailed insight into the patient's respiratory condition. A user may choose to zoom into the waveform 2240 (or other aspects of the display), causing the waveform 2242 to be enlarged to fill the display in place of the other elements of the display, or the like. Other graphs, tables, waveforms, and data may be shown for the respiratory parameter on the auxiliary device display 2040. Of course, parameters other than respiratory rate may also be selected for detailed display on the auxiliary device 2040.

IV. Translation Module

Any of the following features described with respect to FIGS. 40A through 45D can be implemented by the translation module 2005 of FIG. 24 or together with any of the devices described above with respect to FIG. 24.

Healthcare costs have been increasing and the demand for reasonably-priced, high-quality patient care is also on the rise. Health care costs can be reduced by increasing the effectiveness of hospital information systems. One factor which may affect the efficacy of a health institution is the extent to which the various clinical computer systems employed at the health institution can interact with one another to exchange information.

Hospitals, patient care facilities, and healthcare provider organizations typically include a wide variety of different clinical computer systems for the management of electronic healthcare information. Each of the clinical computer systems of the overall IT or management infrastructure can help fulfill a particular category or aspect of the patient care process. For example, a hospital can include patient monitoring systems, medical documentation and/or imaging systems, patient administration systems, electronic medical record systems, electronic practice management systems, business and financial systems (such as pharmacy and billing), and/or communications systems, etc.

The quality of care in a hospital or other patient care facility could be improved if each of the different clinical computer systems across the IT infrastructure (or even within the same hospital room; see, for example, FIGS. 1 and 24) were able to effectively communicate with each other. This could allow for the exchange of patient data that is collected by one clinical computer system with another clinical computer system that could benefit from such patient data. For example, this may allow decisions relating to patient care to be made, and actions to be taken, based on a complete analysis of all the available information.

In current practice, individual clinical computer systems can be, and often are, provided by different vendors. As a result, individual clinical computer systems may be implemented using a proprietary network or communication infrastructure, proprietary communication protocols, etc.; the various clinical computer systems used in the hospital cannot always effectively communicate with each other.

Medical device and medical system vendors sometimes develop proprietary systems that cannot communicate effectively with medical devices and systems of other vendors in order to increase their market share and to upsell additional products, systems, and/or upgrades to the healthcare provider. Thus, healthcare providers are forced to make enterprise or system-wide purchase decisions, rather than selecting the best technology available for each type of individual clinical computer system in use.

One example where this occurs is in the area of life-saving technology available for patient monitoring. For example, many different bedside devices for monitoring various physiological parameters are available from different vendors or providers. One such provider may offer a best-in-class device for monitoring a particular physiological parameter, while another such provider may offer the best-in-class device for another physiological parameter. Accordingly, it may be desirable in some circumstances for a hospital to have the freedom to use monitoring devices from more than one manufacturer, but this may not be possible if devices from different manufacturers are incapable of interfacing and exchanging patient information. Accordingly, the ability to provide reasonably-priced, high-quality patient care can be compromised. In addition, since each hospital or patient care facility may also implement its own proprietary communication protocols for its clinical computer network environment, the exchange of information can be further hindered.

As described above, the Health Level Seven ("HL7") protocol has been developed to provide a messaging framework for the communication of clinical messages between medical computer systems and devices. The HL7 communication protocol specifies a number of standards, guidelines, and methodologies which various HL7-compliant clinical computer systems can use to communicate with each other.

The HL7 communication protocol has been adopted by many medical device manufacturers. However, the HL7 standard is quite flexible, and merely provides a framework of guidelines (for example, the high-level logical structure of the messages); consequently, each medical device or medical system manufacturer or vendor may implement the HL7 protocol somewhat differently while still remaining HL7-compliant. For example, the format of the HL7 messages can be different from implementation to implementation, as described more fully herein. In some cases, the HL7 messages of one implementation can also include information content that is not included in messages according to another HL7 implementation. Accordingly, medical devices or clinical computer systems that are all HL7-compliant still may be unable to communicate with each other.

Consequently, a translation module can be provided that can improve the communication of medical messages between medical devices or systems that use different allowed implementations of an established communication protocol (for example, HL7), thereby increasing the quality of patient care through the integration of multiple clinical computer systems.

Figure 40A:
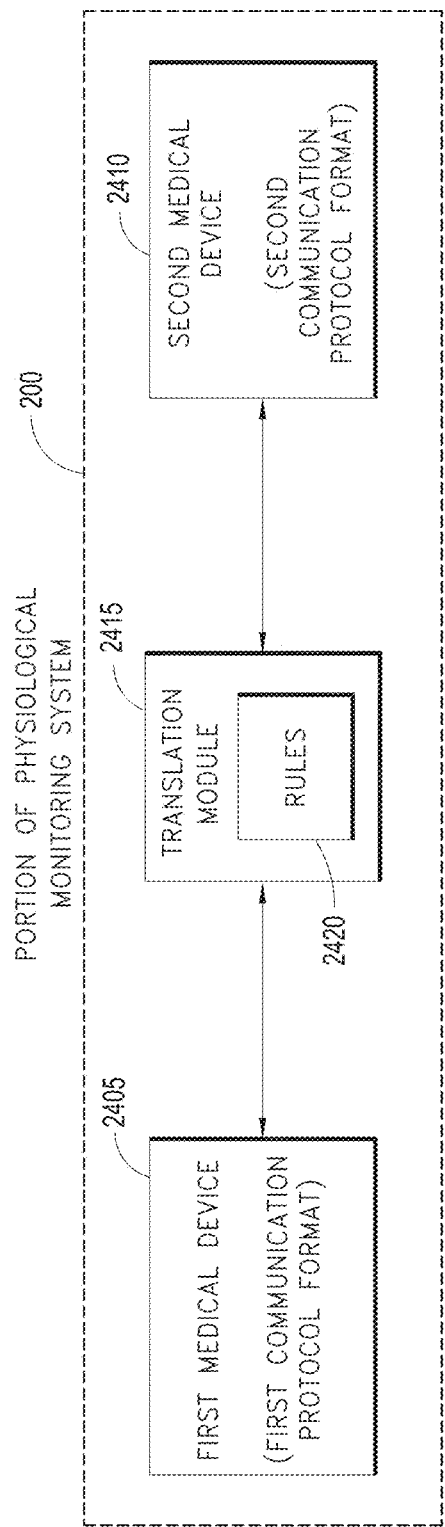
FIG. 40A illustrates an example first medical device and an example second medical device that communicate with one another via a translation module.

FIG. 40A illustrates a first medical device 2405 and a second medical device 2410 that communicate with one another via a translation module 2415. The first medical device 2405 is configured to transmit and receive messages according to a first allowed format or implementation of an accepted electronic medical communication protocol, while the second medical device 2410 is configured to transmit and receive messages according to a second allowed format or implementation of the electronic medical communication protocol. The first and second protocol formats are different implementations of the HL7 communication protocol. Other electronic medical communication protocols besides HL7 can also be used.

The translation module 2415 receives input messages having the first protocol format from the first medical device 2405 and generates output messages to the second medical device 2410 having the second protocol format. The translation module 2415 also receives input messages having the second protocol format from the second medical device 2410 and generates output messages to the first medical device 2405 having the first protocol format. Thus, the translation module 2415 can enable the first and second medical devices 2405, 2410 to effectively and seamlessly communicate with one another without necessarily requiring modification to the communication equipment or protocol implemented by each device.

The translation module 2415 can determine the protocol format expected by an intended recipient of the input message based on, for example, the information in the input message or by referencing a database that stores the protocol format used by various devices, and then generates the output message based on the protocol format used by the intended recipient device or system. The output message can be generated based upon a comparison with, and application of, a set of translation rules 2420 that are accessible by the translation module 2415.

The translation rules 2420 can include rules that govern how to handle possible variations between formatting implementations within a common protocol. Examples of variations in formatting implementation of an electronic medical communication protocol include, for example, the delimiter or separator characters that are used to separate data fields, whether a particular field is required or optional, the repeatability of portions of the message (for example, segments, fields, components, sub-components), the sequence of portions of the message (for example, the order of fields or components), whether a particular portion of a message is included, the length of the message or portions of the message, and the data type used for the various portions of the message.

The translation rules 2420 can define additions, deletions, swappings, and/or modifications that can be performed in order to "translate" an input message that adheres to a first HL7 implementation into an output message that adheres to a second HL7 implementation. The output message can have, for example, different formatting than the input message, while maintaining all, or a portion of, the substance or content of the input message.

In addition to translating between different implementations of a common electronic medical communication protocol (for example, different formatting of HL7 messages), the translation module 2415 can also translate between input and output messages adhering to different communication protocols. The translation module 2415 can be capable of responding to and translating messages from, for example, one medical communication protocol to a separate medical communication protocol. For example, the translation module 2415 can facilitate communication between messages sent according to the HL7 protocol, the ISO 11073 protocol, other open protocols, and/or proprietary protocols. Accordingly, an input message sent according to the HL7 protocol can be translated to an output message according to a different protocol, or vice-versa.

The operation of the translation module 2415 and the translation rules 2420 will be described in more detail below. Various examples of system architectures including the translation module 2415 will now be described.

The first medical device 2405, the second medical device 2410, and the translation module 2415 can be communicatively coupled via connection to a common communications network or directly (via cables or wirelessly), for example, through the hub 100, PPM 102, and/or MMS 2004. The translation module 2415 can be communicatively coupled between the first medical device 2405 and the second medical device 2410 (with or without a communications network) such that all messages between the first and second medical devices 2405, 2410 are routed through the translation module 2415. Other architectures are also possible.

The first and second medical devices 2405, 2410 and the translation module 2415 can be included in, for example, a portion of the monitoring environments of FIG. 1 or 24 described above. The first medical device 2405 may be, for example, the infusion pump(s) 216 or ventilator 218, while the second medical device 2410 may be, for example, the monitoring hub 100, PPM 102, MMS 2004, or auxiliary device 2040. The translation module 2415 is an example implementation of the translation module 2005.

The translation module 2415 can facilitate communication across multiple networks within a hospital environment. Additionally or optionally, the translation module 2415 can facilitate communication of messages across one or more networks extending outside of the hospital or clinical network environment. For example, the translation module 2415 can provide a communications interface with banking institutions, insurance providers, government institutions, outside pharmacies, other hospitals, nursing homes, or patient care facilities, doctors' offices, and the like.

The translation module 2415 of FIG. 40 can be a component of, for example, the environment 2000 described above with respect to FIG. 24. For example, the translation module 2415 can be communicatively coupled with a hospital network or other networks or monitoring environments described above. The translation module 2415 can facilitate the exchange of patient monitoring information, including, for example, physiological parameter measurements, physiological parameter trend information, and physiological parameter alarm conditions between bedside medical monitor devices, nurses' monitoring stations, a Hospital or Clinical Information System (which may store Electronic Medical Records), and/or many other medical devices and systems. The translation module 2415 can enable seamless communication between different medical devices and systems, each of which may use a different implementation of an electronic medical communication protocol such as, for example, the HL7 communication protocol, within a clinical or hospital network environment.

The translation module 2415 can also facilitate communication between a first medical device that is part of the patient monitoring sub-system and a second medical device that is not part of, or is external to, the patient monitoring system 200. As such, the translation module 2415 can be capable of responding to externally-generated medical messages (such as patient information update messages, status query messages, and the like from an HIS or CIS) and generating external reporting messages (such as event reporting messages, alarm notification messages, and the like from patient monitors or nurses' monitoring stations).

The first and second medical devices 2405, 2410 can communicate with each other over a communication bus 2421. Communication bus 2421 can include any one or more of the communication networks, systems, and methods described above, including the Internet, a hospital WLAN, a LAN, a personal area network, etc. For example, any of the networks describe above can be used to facilitate communication between a plurality of medical devices, including first and second medical devices 2405, 2410, discussed above. One such example is illustrated in FIG. 40B.

Figure 40B:
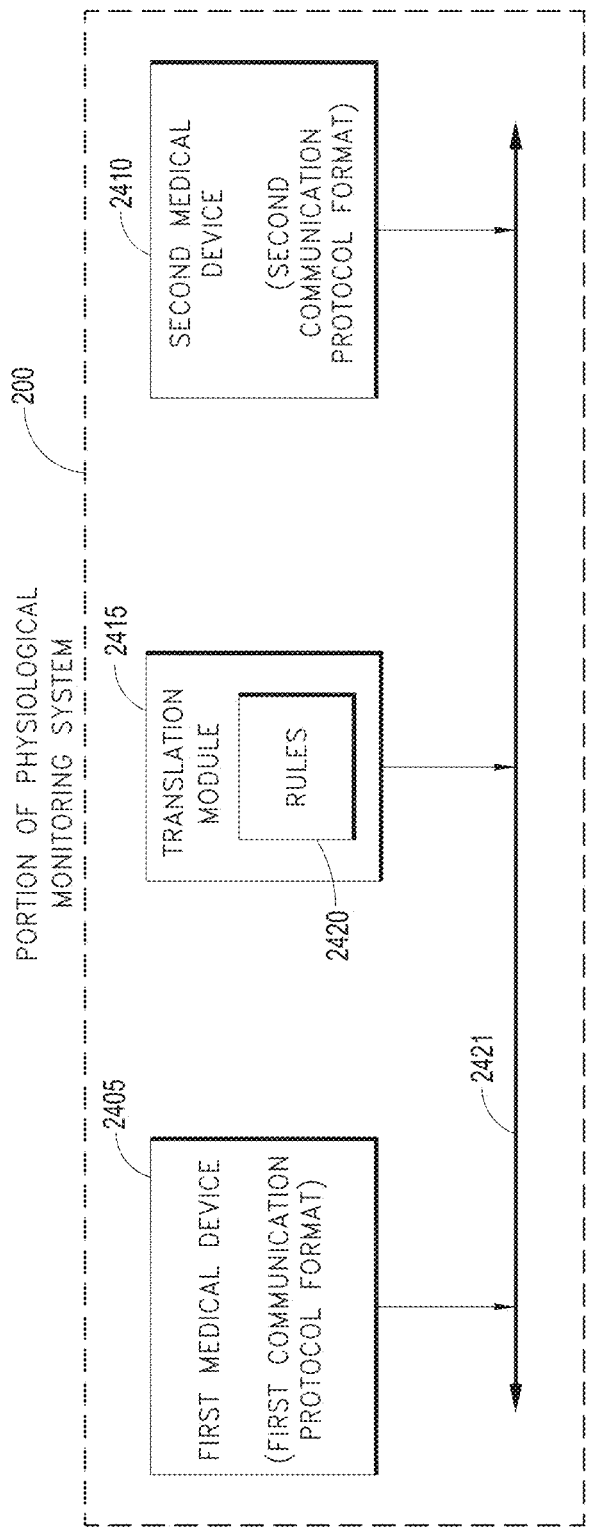
FIG. 40B illustrates an example first medical device and an example second medical device that communicate with one another via a translation module and a communication bus.

In FIG. 40B, first medical device 2405 provides a message to the communication bus 2421. The message is intended for receipt by the second medical device 2410; however, because first and second medical devices 2405, 2410 communicate according to different communication protocol format, second medical device 2410 is unable to process the message.

Translation module 2415 monitors the communication bus 2421 for such messages. Translation module receives the message and determines that first medical device 2405 is attempting to communicate with second medical device 2410. Translation module 2415 determines that message translation would facilitate communication between first and second medical devices 2405, 2410. Translation module 2415 therefore utilizes an appropriate translation rule stored in a translation module 2420. Translation module 2420 can include a memory, EPROM, RAM, ROM, etc.

The translation module 2415 translates the message from the first medical device 2405 according to any of the methods described herein. Once translated, the translation module 2415 delivers the translated message to the communication bus 2421. The second medical device 2410 receives the translated message and responds appropriately. For example, the second medical device may perform a function and/or attempt to communication with the first medical device 2405. The translation module 2415 facilitates communication from the second medical device 2410 to the first medical device 2405 in a similar manner.

The first medical device 2405 and the second medical device 2410 can be, for example, any of the medical devices or systems communicatively coupled to a hospital network or hub 100, PPM 102, and/or MMS 2004. These medical devices or systems can include, for example, point-of-care devices (such as bedside patient monitors), data storage units or patient record databases, hospital or clinical information systems, central monitoring stations (such as a nurses' monitoring station), and/or clinician devices (such as pagers, cell phones, smart phones, personal digital assistants (PDAs), laptops, tablet PCs, personal computers, pods, and the like).

The first medical device 2405 can be a patient monitor for communicatively coupling to a patient for tracking a physiological parameter (for example, oxygen saturation, pulse rate, blood pressure, etc.), and the second medical device 2410 is a hospital information system ("HIS") or clinical information system ("CIS"). The patient monitor can communicate physiological parameter measurements, physiological parameter alarms, or other physiological parameter measurement information generated during the monitoring of a patient to the HIS or CIS for inclusion with the patient's electronic medical records maintained by the HIS or CIS.

The first medical device 2405 can an HIS or CIS and the second medical device 2410 can be a nurses' monitoring station, as described herein. However, the translation module 2415 can facilitate communication between a wide variety of medical devices and systems that are used in hospitals or other patient care facilities. For example, the translation module 2415 can facilitate communication between patient physiological parameter monitoring devices, between a monitoring device and a nurses' monitoring station, etc.

Using the translation module 2415, a patient monitoring sub-system, such as those described herein (for example, physiological monitoring system 200), can push data to the HIS or pull data from the HIS even if the HIS uses a different implementation of the HL7 protocol, or some other electronic medical communication protocol.

The patient monitoring sub-system can be configured to push/pull data at predetermined intervals. For example, a patient monitor or clinician monitoring station can download patient data automatically from the HIS at periodic intervals so that the patient data is already available when a patient is connected to a patient monitor. The patient data sent from the HIS can include admit/discharge/transfer ("ADT") information received upon registration of the patient. ADT messages can be initiated by a hospital information system to inform ancillary systems that, for example, a patient has been admitted, discharged, transferred or registered, that patient information has been updated or merged, or that a transfer or discharge has been canceled.

The patient monitoring sub-system can be configured to push/pull data to/from the HIS only when the HIS is solicited by a query. For example, a clinician may make a request for information stored in a patient's electronic medical records on the HIS.

The patient monitoring sub-system can be configured to push/pull data to/from the HIS in response to an unsolicited event. For example, a physiological parameter of a patient being monitored can enter an alarm condition, which can automatically be transmitted to the HIS for storing in the patient's electronic medical records. Any combination of the above methods or alternative methods for determining when to communicate messages to and from the HIS can be employed.

Example system architectures and example triggers for the communication of messages involving the translation module 2415 have been described. Turning now to the operation of the translation module, FIGS. 25A-25D illustrate an example medical message at different phases or steps of a translation process. The translation process will be described in more detail below in connection with FIGS. 26, 27A and 27B.

FIG. 41A illustrates an example ADT input message 2505 received by the translation module 2415 from an HIS. The ADT input message 2505 is implemented according to the HL7 communication protocol and contains information related to the admission of a patient to a hospital. The ADT message 2505 includes multiple segments, including a message header segment 2506, an event segment, a patient identification segment, a patient visit segment, role segments, a diagnosis segment, and multiple custom segments.

The message header ("MSH") segment 2506 can define how the message is being sent, the field delimiters and encoding characters, the message type, the sender and receiver, etc. The first symbol or character after the MSH string can define the field delimiter or separator (in this message, a "caret" symbol). The next four symbols or characters can define the encoding characters. The first symbol defines the component delimiter ("~"), the second symbol defines the repeatable delimiter ("|"), the third symbol defines the escape delimiter ("\"), and the fourth symbol defines the sub-component delimiter ("&"). All of these delimiters can vary between HL7 implementations.

The example header segment 2506 can further include the sending application ("VAFC PIMS"), the receiving application ("NPTF-508"), the date/time of the message ("20091120104609-0600"), the message type ("ADT~A01"), the message control ID ("58103"), the processing ID ("P"), and the country code ("USA"). As represented by the consecutive caret symbols, the header segment also contains multiple empty fields.

FIG. 41B illustrates the message header segment 2506 after it has been parsed into fields or elements based on an identified field delimiter (the caret symbol). The parsed input message comprises an XML message that is configured to be transformed according to extensible stylesheet language transformation (XSLT) rules.

The parsed input message can be encoded. FIG. 41C illustrates the parsed message header segment of the input message after being encoded (for example, using a Unicode Transformation Format-8 ("UTF-8") encoding scheme).

The encoded message header segment shows some of the various data types that can be used in the message. For example, the sending application ("VAFC PIMS") of the third parsed field and the receiving application ("NPTF-508") of the fifth parsed field are represented using a hierarchic designator ("HD") name data type. The date/time field (the seventh parsed field) is represented using the time stamp ("TS") data type. The processing ID field (the eleventh parsed field) is represented using the processing type ("PT") data type. The fields that do not include a data type identifier are represented using the string ("ST") data type. Other possible data types include, for example, coded element, structured numeric, timing quantity, text data, date, entry identifier, coded value, numeric, and sequence identification. The data types used for the various fields or attributes of the segments can vary between formatting implementations.

FIG. 41D illustrates an example output message 2510 from the translation module 2415 based on the example input message 2505 of FIG. 41A. The output message 2510 includes a message acknowledgement segment 2512.

Turning to the operation of the translation module, the translation module 2415 can, for example, create, generate, or produce an output message that is reflective of the input message based on an application of the set of translation rules 2420. The translation module 2415 can, for example, translate, transform, convert, reformat, configure, change, rearrange, modify, adapt, alter, or adjust the input message based on a comparison with, and application of, the set of translation rules 2420 to form the output message. The translation module 2415 can, for example, replace or substitute the input message with an output message that retains the content of the input message but has a new formatting implementation based upon a comparison with, and application of, the set of translation rules 2420.

Figure 42:
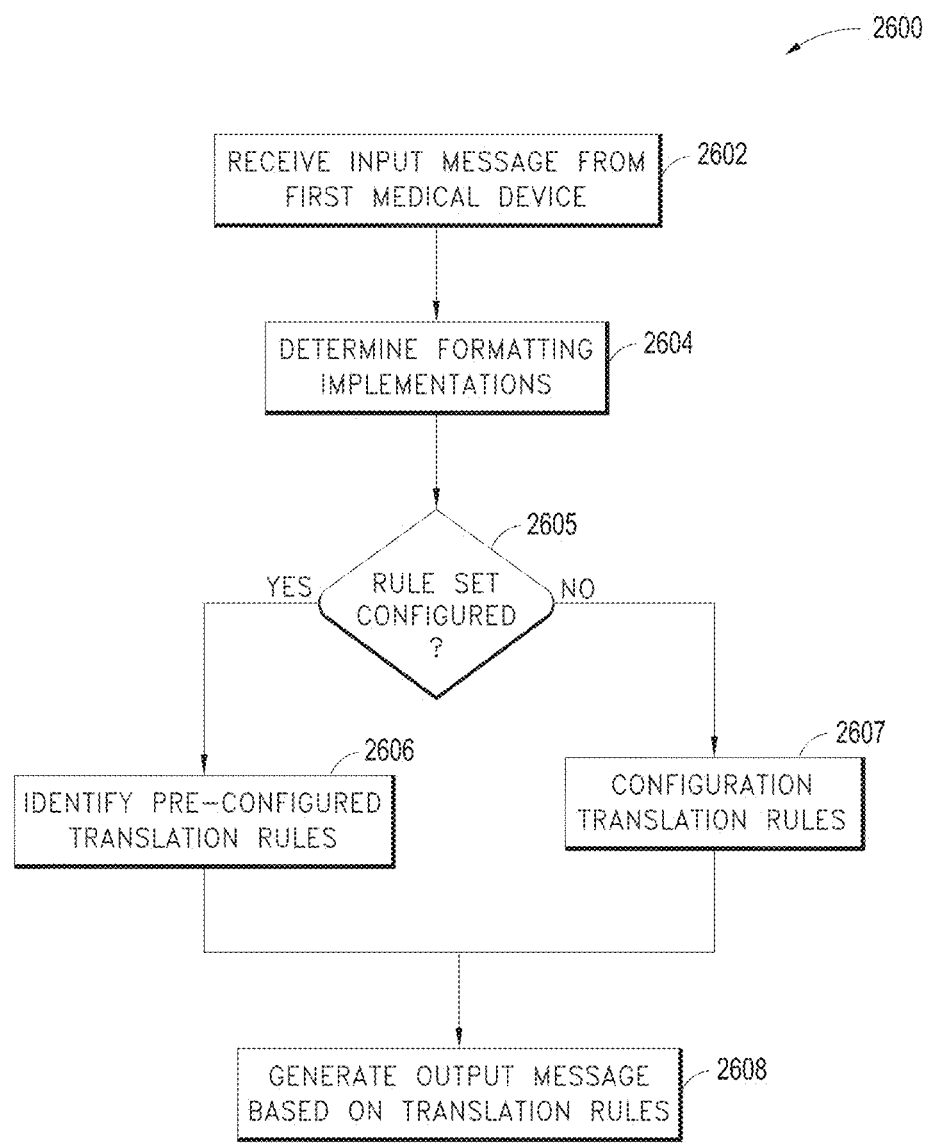
FIG. 42 illustrates an example translation process for generating an output message based on an input message and a comparison with translation rules associated with the translation module.

FIG. 42 illustrates a translation process 2600 for generating an output message based on an input message and a comparison with the set of translation rules 2420 associated with the translation module 2415. The translation process 2600 starts at block 2602 where the translation module 2415 receives an input message from a first medical device.

At block 2604, the translation module 2415 determines the formatting implementation of the input message and the formatting implementation to be used for the output message. The input message can include one or more identifiers indicative of the formatting implementation. The determination of the formatting implementation can be made, for example, by analyzing the message itself by identifying the delimiter or encoding characters used, the field order, the repeatability of segments, fields, or components, the data type of the fields, or other implementation variations. The translation module 2415 can separate or parse out the formatting from the content of the message (as shown in FIG. 41B) to aid in the determination of the formatting implementation. The translation module 2415 can determine the formatting implementation of the input message by referencing a database that stores the implementation used by each device with which the translation module 2415 has been configured to interface.

The determination of the formatting implementation used by the output message can also be determined from the input message. For example, the input message can include a field that identifies the intended recipient application, facility, system, device, and/or destination. The input message can optionally include a field that identifies the type of message being sent (for example, ADT message) and the translation module 2415 can determine the appropriate recipient from the type of message being sent and/or the sending application, device, or system. The translation module 2415 can then determine the formatting implementation required by the intended recipient of the input message.

At decision block 2605, the translation module 2415 determines whether a rule set has been configured for the translation from the identified formatting implementation of the input message to the identified formatting implementation to be used for the output message. The rule set may have been manually configured prior to installation of the translation module software or may have been automatically configured prior to receipt of the input message. If a rule set has already been configured, then the translation process 2600 continues to block 2606. If a rule set has not been configured, then a rule set is configured at block 2607. The configuration of the rule set can be performed as described below in connection with FIGS. 44 and 45A-45D. The translation process 2600 then continues to block 2608.

At block 2606, the translation module 2415 identifies the pre-configured rules from the set of translation rules 2420 that govern translation between the determined formatting implementation of the input message and the formatting implementation of the output message. The identification of the pre-configured rules can be made manually.

At block 2608, the translation module 2415 generates an output message based on the configured rule set(s) of the translation rules 2420. The output message can retain all, or at least a portion of, the content of the input message but has the format expected and supported by the intended recipient of the input message.

The translation rules 2420 can include, for example, unidirectional rules and/or bidirectional rules. A unidirectional rule can be one, for example, that may be applied in the case of a message from a first medical device (for example, 2405) to a second medical device (for example, 2410) but is not applied in the case of a message from the second medical device to the first medical device. For example, a unidirectional rule could handle a difference in the delimiters used between fields for two different formatting implementations of, for example, the HL7 communication protocol. The translation module 2415 can apply a field delimiter rule to determine if the field delimiter is supported by the intended recipient of the input message. If the field delimiter of the input message is not supported by the intended recipient, the field delimiter rule can replace the field delimiter of the input message with a field delimiter supported by the intended recipient.

For example, an input message from an input medical device can include a formatting implementation that uses a "caret" symbol (""") as the field delimiter or separator. However, the formatting implementation recognized by the intended recipient medical device may use a "pipe" symbol ("|") as the field delimiter. The translation module 2415 can identify the field delimiter symbol used in the formatting implementation recognized by the intended recipient medical device from the set of translation rules 2420 and generate an output message based on the input message that uses the pipe field delimiter symbol instead of the caret field delimiter symbol used in the input message. The rule to substitute a pipe symbol for a caret symbol would, in this case, only apply to messages that are sent to a recipient device that recognizes the pipe symbol as a field delimiter. This rule could be accompanied by a complementary rule that indicates that a caret symbol should be substituted for a pipe symbol in the case of a message that is intended for a recipient device that is known to recognize the caret symbol as the field delimiter.

Another unidirectional rule can handle the presence or absence of certain fields between different formatting implementations. For example, an input message from an input medical device can include fields that would not be recognized by the intended recipient medical device. The translation module 2415 can generate an output message that does not include the unrecognized or unsupported fields. In situations where an input message does not include fields expected by the intended recipient medical device, the set of translation rules 2420 can include a rule to insert null entries or empty " " strings in the fields expected by the intended recipient medical device and/or to alert the recipient device of the absence of the expected field. The sender device may also be notified by the translation module 2415 that the recipient device does not support certain portions of the message.

Other unidirectional rules can facilitate, for example, the conversion of one data type to another (for example, string ("ST") to text data ("TX") or structured numeric ("SN") to numeric ("NM")), and the increase or decrease in the length of various portions of the message. Unidirectional rules can also be used to handle variations in repeatability of portions of the message. For example, the translation module 2415 can apply a field repeatability rule to repeated instances of a segment, field, component, or sub-component of the message to determine how many such repeated instances are supported by the recipient device, if any, and deleting or adding any repeated instances if necessary. For example, a phone number field of a patient identification segment can be a repeatable field to allow for entry of home, work, and cell phone numbers.

Bidirectional rules can also be used. Such rules may apply equally to messages between first and second medical devices (for example, 2405, 2410) regardless of which device is the sender and which is the recipient. A bidirectional rule can be used to handle changes in sequence, for example. An input message from an input medical device can include a patient name field, or fields, in which a first name component appears before a last name component. However, the intended recipient medical device may be expecting an implementation where the last name component appears before the first name component. Accordingly, the set of translation rules 2420 can include a bidirectional rule to swap the order of the first and last name components when communicating between the two medical devices, or between the two formatting implementations. In general, field order rules can be applied to determine whether the fields, components, or sub-components are in the correct order for the intended recipient and rearranging them if necessary. Other bidirectional rules can be included to handle, for example, other sequential variations between formatting implementations or other types of variations.

The translation rules 2420 can also include compound rules. For example, a compound rule can include an if-then sequence of rules, wherein a rule can depend on the outcome of another rule. Some translation rules 2420 may employ computations and logic (for example, Boolean logic or fuzzy logic), etc.

Figure 43A:
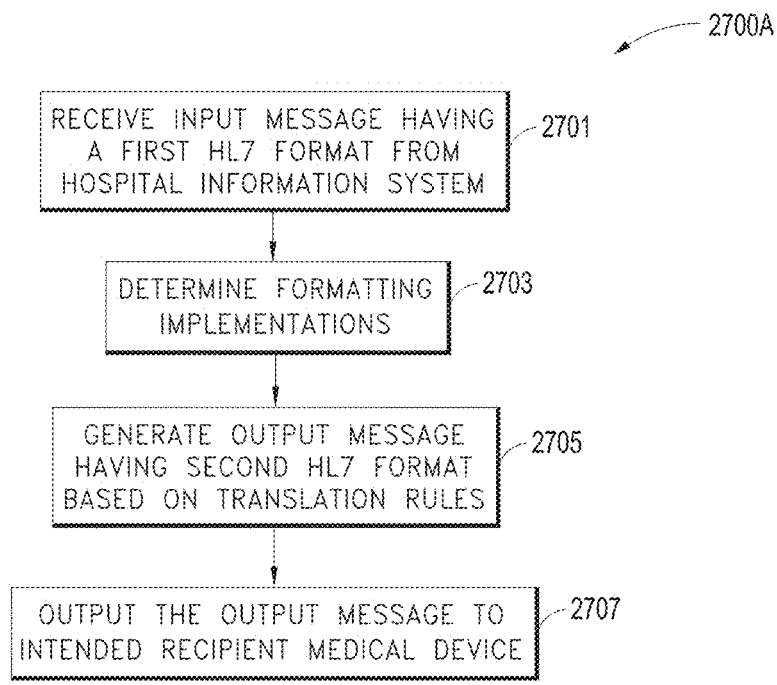
FIG. 43A illustrates an example translation process in which the translation module facilitates communication of an HL7 message from a Hospital Information System ("HIS") having a first HL7 format to an intended recipient medical device having a second HL7 format.
Figure 43B:
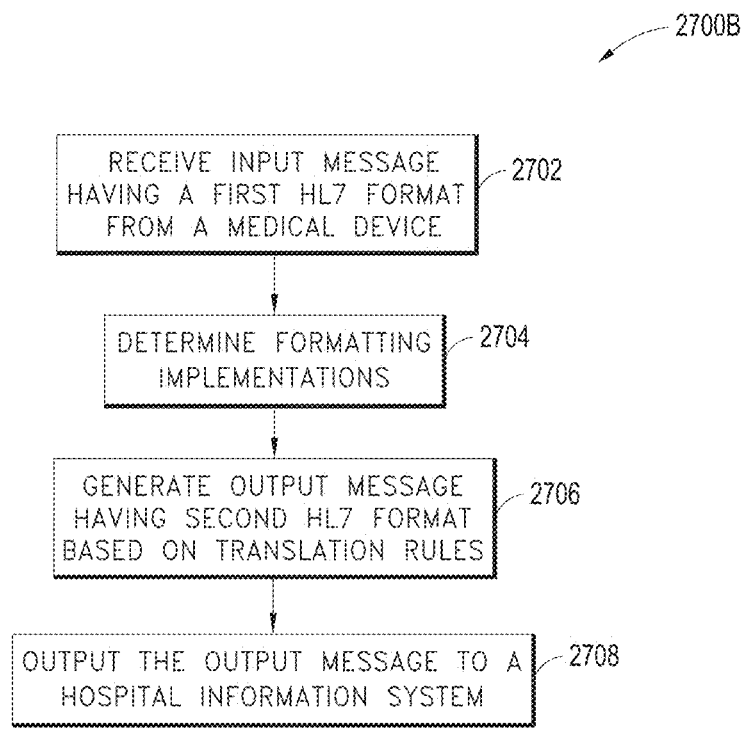
FIG. 43B illustrates an example translation process in which the translation module facilitates communication of an HL7 message from a medical device having a first HL7 format to a HIS having a second HL7 format.

As discussed above, the messages communicated over the hospital-based communication network can employ the HL7 protocol. FIGS. 43A and 43B illustrate translation processes 2700A, 2700B in which HL7 messages are communicated between a HIS and a medical device over a hospital-based communications network or a clinical network. The translation processes 2700A, 2700B will be described with the assumption that the rules governing "translation" between the first and second HL7 formats have already been configured.

FIG. 43A illustrates a translation process 2700A in which the translation module 2415 facilitates communication of an HL7 message, such as the ADT message of FIG. 41A, from an HIS having a first HL7 format to an intended recipient medical device, such as a patient monitor or a clinician monitoring station, having a second HL7 format.

The translation process 2700A starts at block 2701, where the translation module 2415 receives an input message having a first HL7 format from the HIS. The input message includes information regarding, for example, the admission of a patient and/or patient identification and patient medical history information from an electronic medical records database.

At block 2703, the translation module 2415 determines the formatting implementation of the input message and the formatting implementation to be used for the output message. These determinations can be made in a similar manner to the determinations discussed above in connection with block 2604 of FIG. 42.

At block 2705, the translation module 2415 identifies the rules that govern translation between the determined HL7 format of the input message and the HL7 format of the output message and generates an output message having the second HL7 format based on the identified rules. The output message can retain the content of the input message sent by the HIS but can have the format expected and supported by the intended recipient of the input message.

At block 2707, the translation module 2415 can output the output message to the intended recipient over the hospital-based communications network. The intended recipient can transmit an acknowledgement message back to the hospital information system acknowledging successful receipt or reporting that an error occurred.

FIG. 43B illustrates a translation process 2700B in which the translation module 2415 facilitates communication of an HL7 message from a medical device, such as a patient monitor, having a first HL7 format to an HIS having a second HL7 format. For example, the patient monitor can transmit reporting event data m such as patient alarm data, to the HIS to store in the patient's electronic medical records.

The translation process 2700B starts at block 2702, where the translation module 2415 receives an input message having a first HL7 format from the medical device. The input message can include patient monitoring data or alarm data regarding one or more physiological parameters of the patient being monitored for storage in an electronic medical records database associated with the HIS.

At block 2704, the translation module 2415 determines the formatting of the input message and the formatting implementation to be used for the output message. These determinations can be made in a similar manner to the determinations discussed above in connection with block 2604 of FIG. 42.

At block 2706, the translation module 2415 identifies the rules that govern translation between the determined HL7 format of the input message and the HL7 format of the output message and generates an output message having the second HL7 format based on the identified rules. The output message can retain the content of the input message sent by the medical device but can have the format expected and supported by the HIS.

At block 2708, the translation module 2415 can output the output message to the hospital information system over the hospital-based communications network. The HIS can transmit an acknowledgement message back to the medical device acknowledging successful receipt or reporting that an error occurred.

FIGS. 42, 43A and 43B described the operation of the translator module 2415. FIGS. 44 and 45A-45D will be used to illustrate the description of the configuration of the translation rules 2420.

The translation rules 2420 can be implemented as one or more stylesheets, hierarchical relationship data structures, tables, lists, other data structures, combinations of the same, and/or the like. The translation rules 2420 can be stored in local memory within the translation module 2415. The translation rules 2420 can be stored in external memory or on a data storage device communicatively coupled to the translation module 2415.

The translation module 2415 can include a single rule set or multiple rule sets. For example, the translation module 2415 can include a separate rule set for each medical device/system and/or for each possible communication pair of medical devices/systems coupled to the network or capable of being coupled to the network. The translation module 2415 can include a separate rule set for each possible pair of formatting implementations that are allowed under a medical communication protocol such as, for example, the HL7 protocol.

Figure 44:
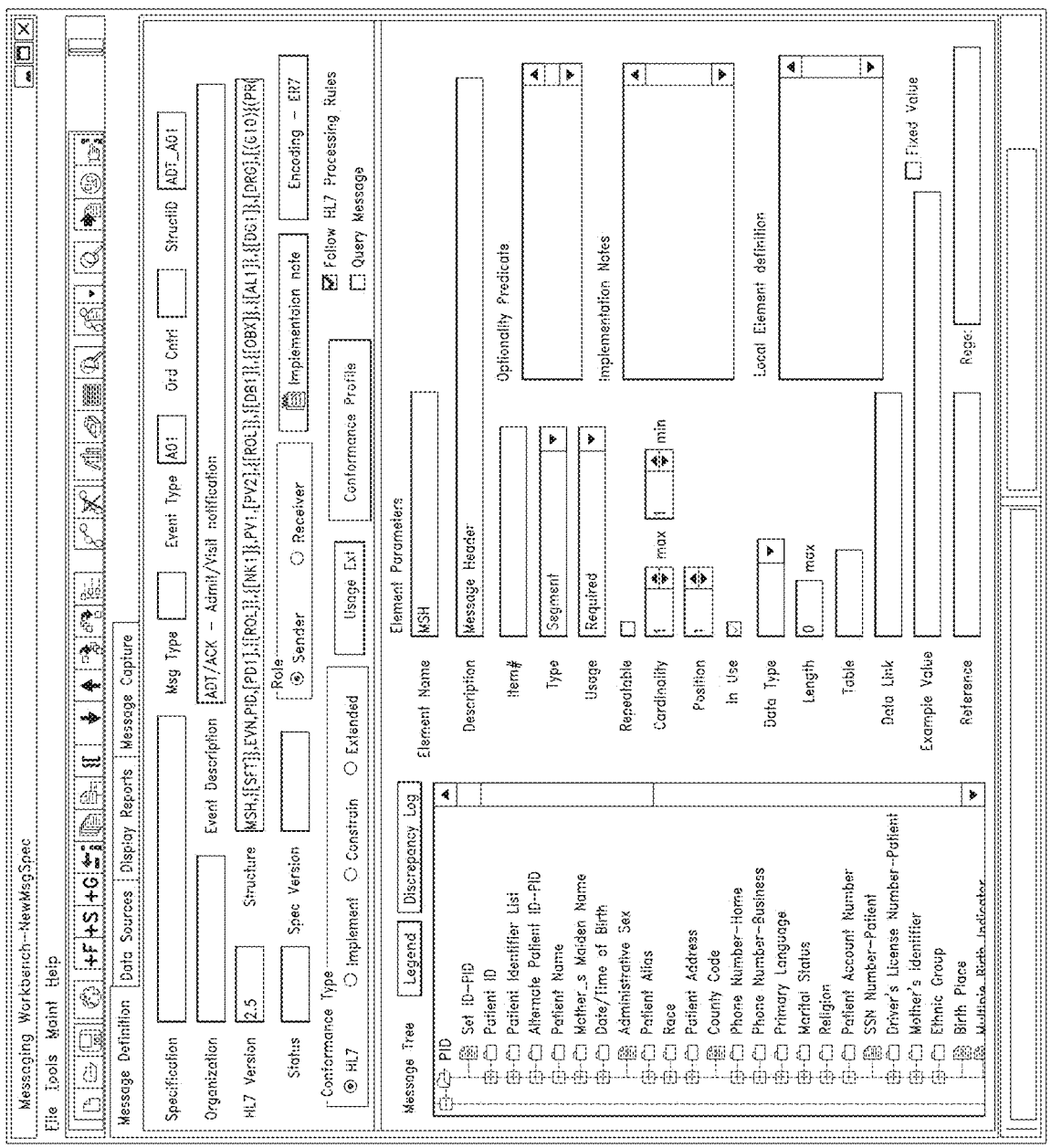
FIG. 44 illustrates an example screenshot from a messaging implementation tool for manually configuring translation rules to be used by the translation module.

The translation rules 2420 can be manually inputted using, for example, the messaging implementation software tool 2800 illustrated in FIG. 44. For example, the software developer for a particular hospital network can determine the protocol message formats used by the devices and/or systems that are or can be coupled to the hospital network and then manually input rules to facilitate "translation" between the various protocol message formats supported or recognized by the devices and/or systems.

FIG. 44 illustrates an example screenshot from a messaging implementation software tool 2800 for manually configuring translation rules 2420 to be used by the translation module 2415. The screenshot from the messaging implementation software tool 2800 illustrates various parameters that may differ between formatting implementations of an electronic medical communication protocol, such as HL7. The screenshot also includes areas where a user can input information that defines, or is used to define, translation rules for converting between different HL7 implementations. The messaging implementation software tool 2800 can store a variety of pre-configured rule sets based, for example, on known communication protocol implementations of various medical devices. A user may configure one or more translation rules 2420 to be used in communications involving such devices by entering identification information, such as the device manufacturer, model number, etc. Based on this identification information, the messaging implementation tool 2800 can identify a pre-configured set of translation rules for communication with that device.

The translation rules 2420 can be automatically generated. For example, the automatic generation of a new set, or multiple sets, of rules can be triggered by the detection of a newly recognized "communicating" medical device or system on a network. The automatic generation of a new set or multiple sets of rules can occur at the time a first message is received from or sent to a new "communicating" medical device or system coupled to the network. The automatic generation of rule sets can include updating or dynamically modifying a pre-existing set of rules.

The automatic generation of translation rule sets can be carried out in a variety of ways. For example, the translation module 2415 can automatically initiate usage of a pre-configured set of translation rules 2420 based upon, for example, the make and model of a new device that is recognized on the network. The translation module 2415 can request one or more messages from the new device or system and then analyze the messages to determine the type of formatting being implemented, as illustrated by the automatic rule configuration process 2900A of FIG. 45A. The automatic rule configuration process 2900A starts at block 2901, where the translation module 2415 receives one or more messages from a detected medical device or system on the network. The messages can be received upon transmission to an intended recipient medical device or system or in response to a query sent by the translation module 2415 or another medical device or system coupled to the network.

At block 2903, the translation module 2415 determines the protocol of the one or more received messages by, for example, analyzing the message or by consulting a database that indicates what communication protocol/format is implemented by each medical device or system on the network. The translation module 2415 can be configured to handle medical messages implemented using a single common protocol, such as HL7. Accordingly, if a determination is made that the received messages are implemented using a non-supported or non-recognized protocol, the translation module can ignore the messages received from the detected medical device or system, output an alert or warning, or allow the messages to be sent without being translated.

At block 2905, the translation module 2415 determines the formatting implementation of the received message(s). The received messages can include one or more identifiers indicative of the formatting implementation. Additionally or optionally, the determination of the formatting implementation can be made, for example, by analyzing the message itself by checking field order, the delimiter or encoding characters used, or other implementation variations. The translation module 2415 can separate or parse out the formatting from the content of the message to aid in the determination of the formatting implementation.

At block 2907, the translation module 2415 configures one or more rules or rule sets to handle messages received from and/or sent to the detected medical device or system. The configuration of the rules may involve the creation or generation of new rules. Additionally or optionally, the configuration of the rules may involve the alteration or updating of existing rules. The configured rules or rule sets can be included with the translation rules 2420. If a set of rules already exists for the formatting implementation used by the new device or system, then the configuration of new translation rules may not be required. Instead, existing translation rules can be associated with the new device or system for use in communication involving that device or system. The translation module 2415 can create a new set of rules geared specifically for the new device or system or can modify an existing set of rules based on subtle formatting variations identified.

The translation module 2415 can generate test message(s) that may be useful in identifying the communication protocol and implementation used by a device or system. For example, the translation module can generate test messages to cause the newly detected device or system to take a particular action (for example, store information) and then query information regarding the action taken by the newly detected device to determine whether or how the test message was understood. This is illustrated by the automatic rule configuration process 2900B of FIG. 45B.

The automatic rule configuration process 2900B starts at block 2902, where the translation module 2415 transmits one or more test, or initialization, messages to a remote device or system detected on a network. The test messages can be configured, for example, to instruct the remote device or system to take a particular action (for example, store patient information). The test messages can be configured to generate a response indicative of the type of formatting recognized or supported by the remote device or system. The test messages can be configured such that only devices or systems supporting a particular formatting implementation will understand and properly act on the test messages.

At block 2904, the translation module 2415 queries the remote device or system to receive information regarding the action taken based on the test message sent to the remote device or system to determine whether the test message was understood. For example, if the test message instructed the remote device or system to store patient information in a particular location, the translation module 2415 can query the information from the location to determine whether the test message was understood. If the test message was not understood, the translation module 2415 can, for example, continue sending test messages of known formatting implementations until a determination is made that the test message has been understood.

At block 2906, the translation module 2415 determines the protocol and formatting implementation based on the information received. As an example, the test message can include an instruction to store patient name information. The test message can include a patient name field having a first name component followed by a surname component. The translation module 2415 can then query the remote device or system to return the patient surname. Depending on whether the patient surname or the first name is returned, this query can be useful in determining information about the order of fields in the formatting implementation being used by the remote device or system. As another example, the test messages can instruct the detected device or system to store repeated instances of a component. The translation module 2415 can then query the device or system to return the repeated instances to see which, if any, were stored. This repeatability information can also be useful in determining whether certain fields are allowed to be repeated in the formatting implementation being used by the remote device for system, and, if so, how many repeated instances are permitted.

At block 2908, the translation module 2415 configures one or more rules to handle messages received from and/or sent to the detected medical device or system. For example, the rules can convert messages from the message format used by a first medical device to that used by a second medical device, as described herein. The configuration of the rules can involve the creation or generation of new rules. Additionally or optionally, the configuration of the rules can involve the alteration or updating of existing rules. If a set of rules already exists for the formatting implementation used by the new device or system, then the configuration of new translation rules may not be required. Instead, existing translation rules can be associated with the new device or system for use in communication involving that device or system.

FIGS. 29C and 29D illustrate automatic rule configuration processes performed by the translation module 2415 for messages utilizing the HL7 protocol. The HL7 protocol can be used, for example, to communicate electronic messages to support administrative, logistical, financial, and clinical processes. For example, HL7 messages can include patient administration messages, such as ADT messages, used to exchange patient demographic and visit information across various healthcare systems.

Figure 45A:
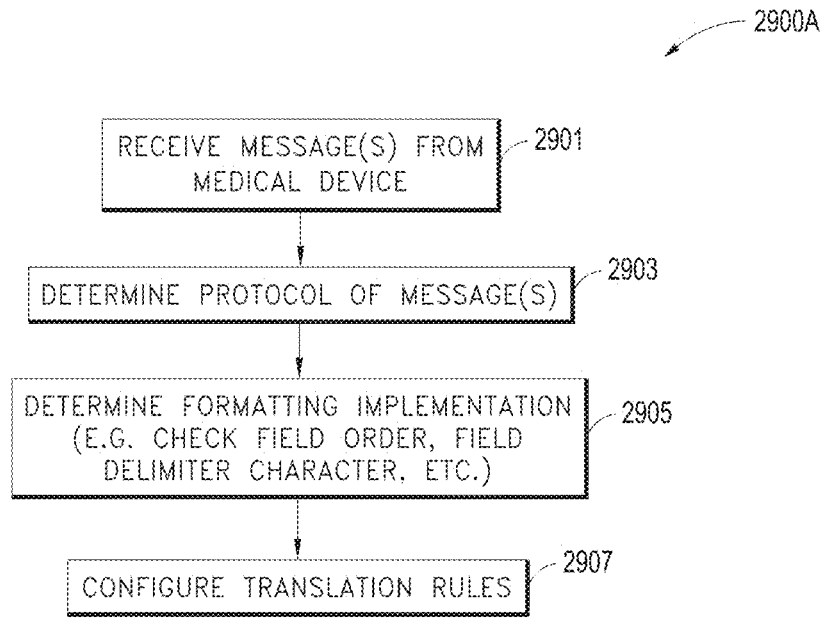
FIGS. 45A and 45B illustrate example automatic rule configuration processes that can be performed by the translation module.
Figure 45B:
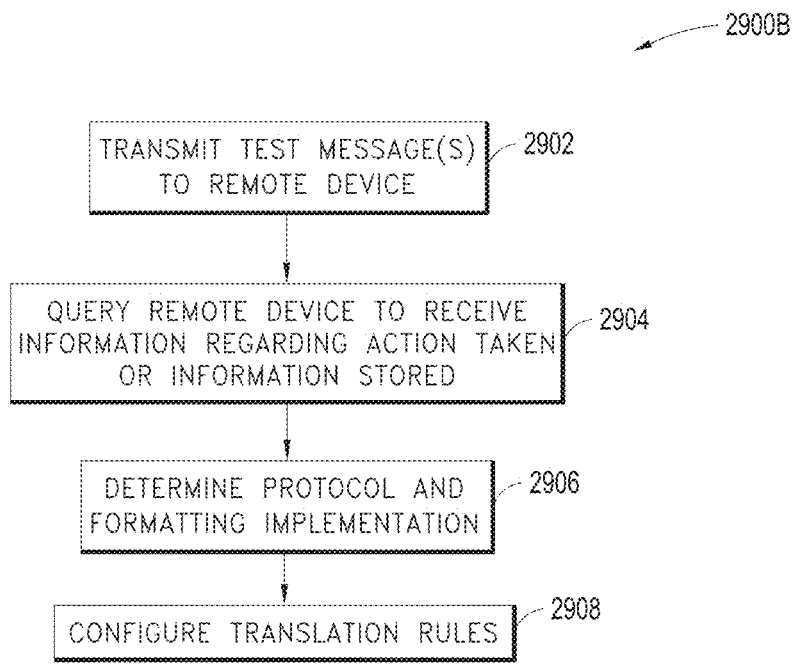
Figure 45C:
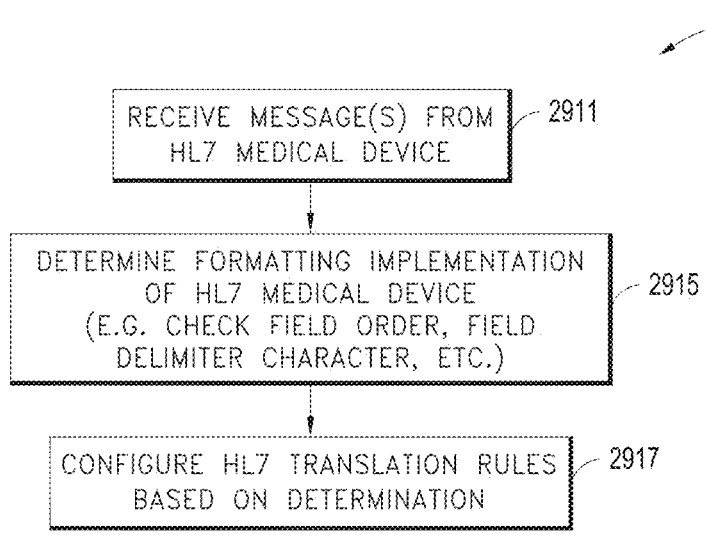
FIGS. 45C and 45D illustrate example automatic rule configuration processes that can be performed by the translation module for messages utilizing the HL7 protocol.

The automatic rule configuration process 2900C illustrated in FIG. 45C is similar to the process 2900A illustrated in FIG. 45A. At block 2911, the translation module 2415 receives one or more messages from an HL7 medical device. At block 2915, the translation module 2415 determines the formatting implementation of the HL7 medical device from the one or more messages received. As discussed above, the determination of the formatting implementation can be made, for example, by checking field order or sequence, field delimiter characters, repeatability, cardinality, and other HL7 implementation variations.

At block 2917, the translation module 2415 configures one or more rules to handle messages received from and/or sent to the HL7 medical device. The configuration of the rules can involve the creation or generation of new rules for the detected formatting implementation. Additionally or optionally, the configuration of the rules involves the dynamic alteration or updating of existing rules. If a set of rules already exists for the formatting implementation used by the new HL7 medical device, then the configuration of new translation rules may not be required. Instead, existing translation rules can be associated with the new HL7 medical device for use in communication involving that device.

Figure 45D:
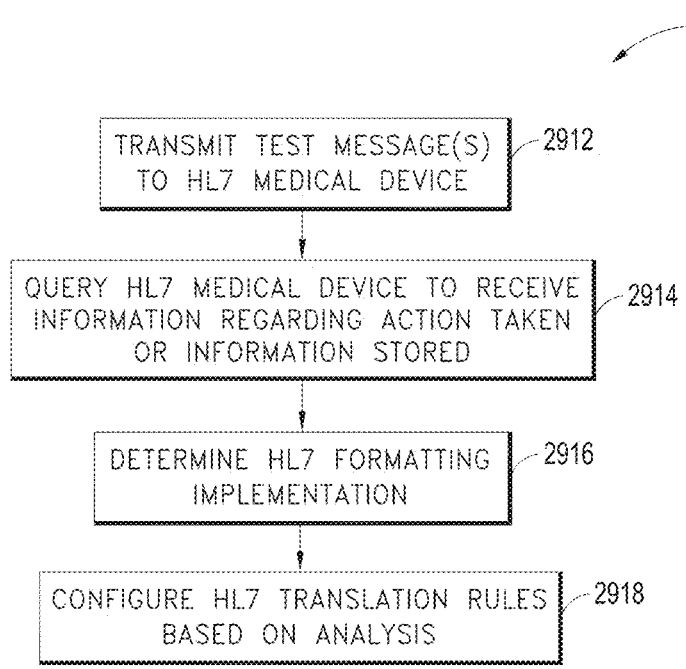
Figure 46:
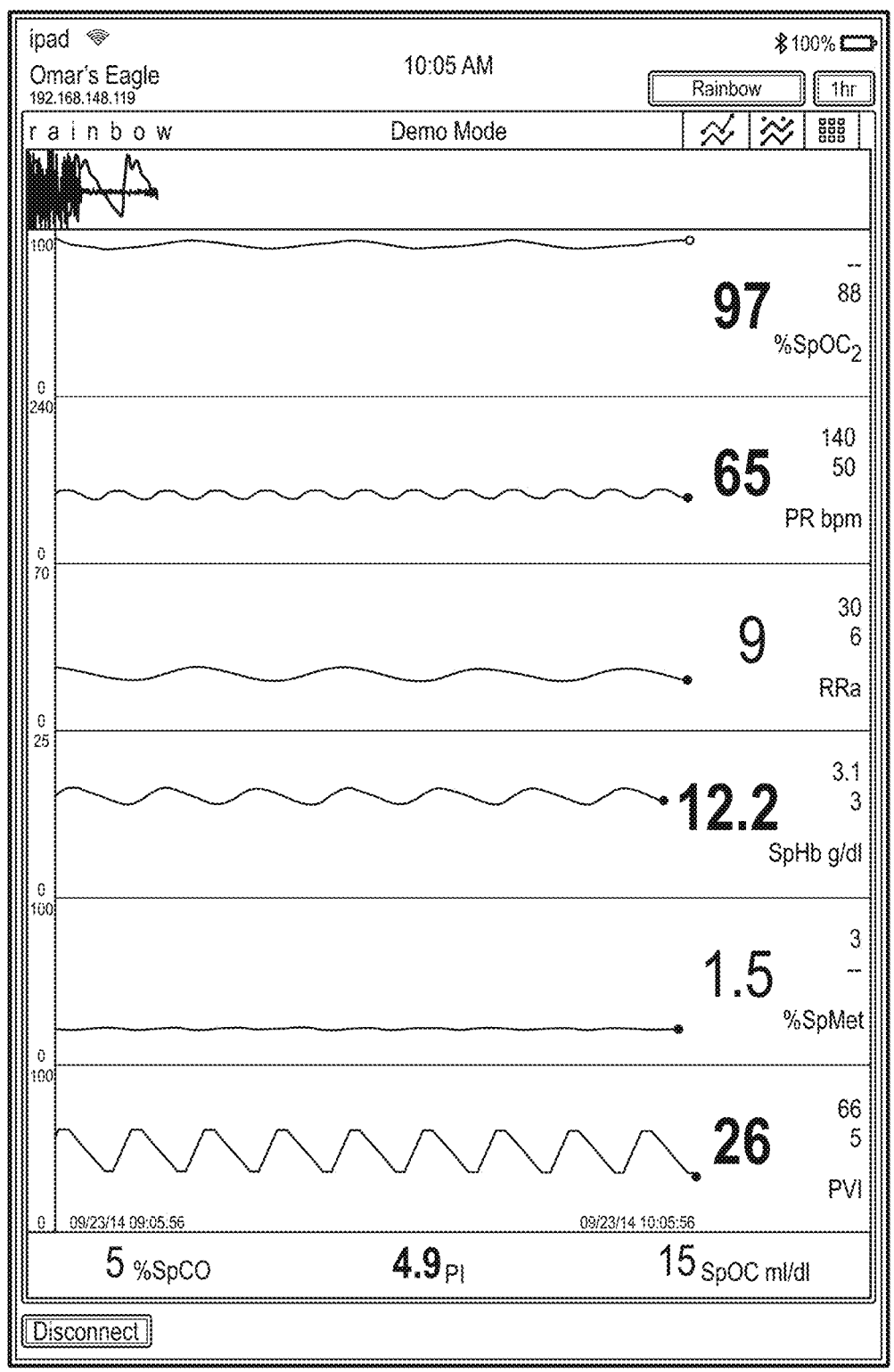
Figure 47:
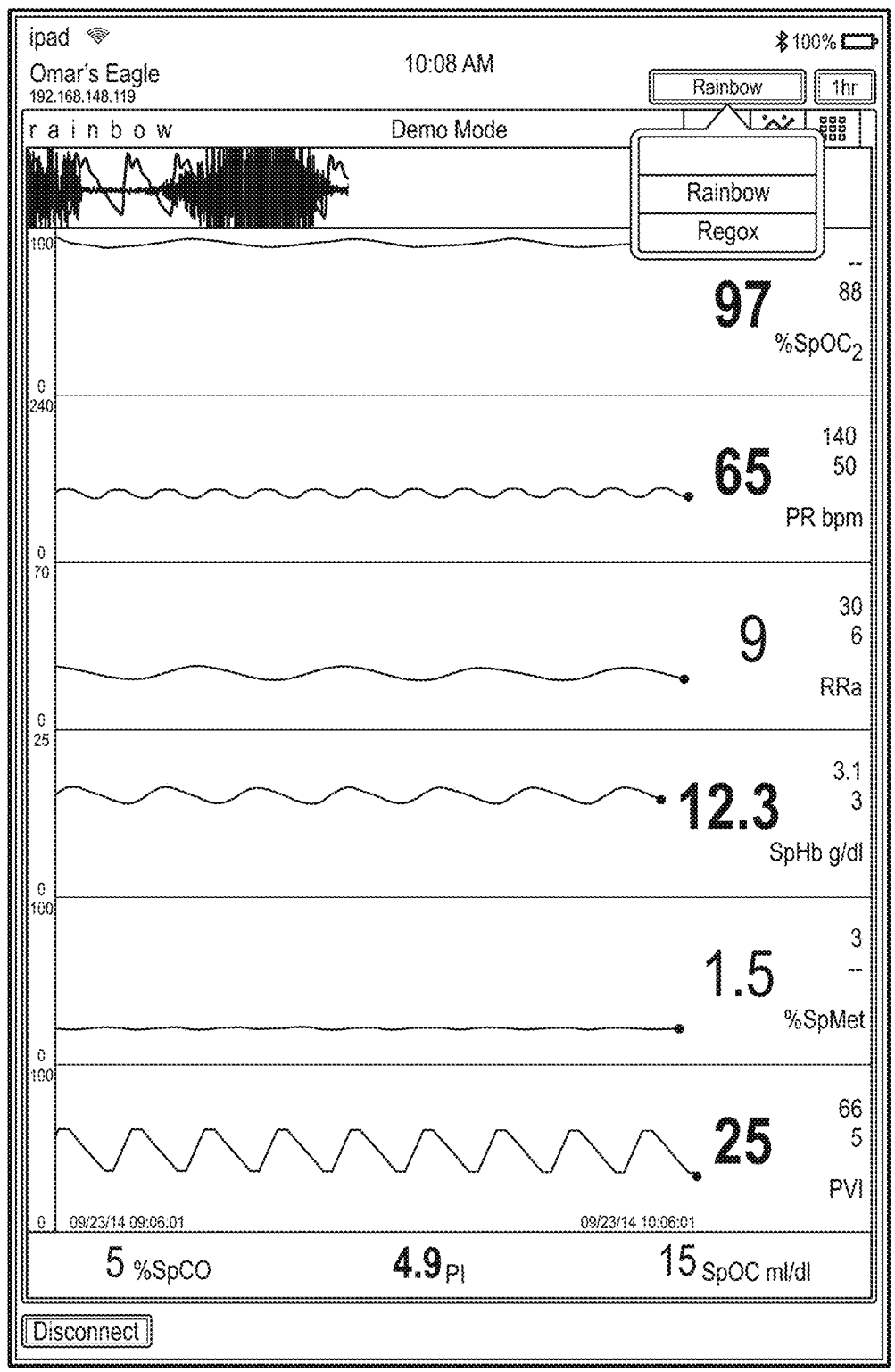
Figure 48:
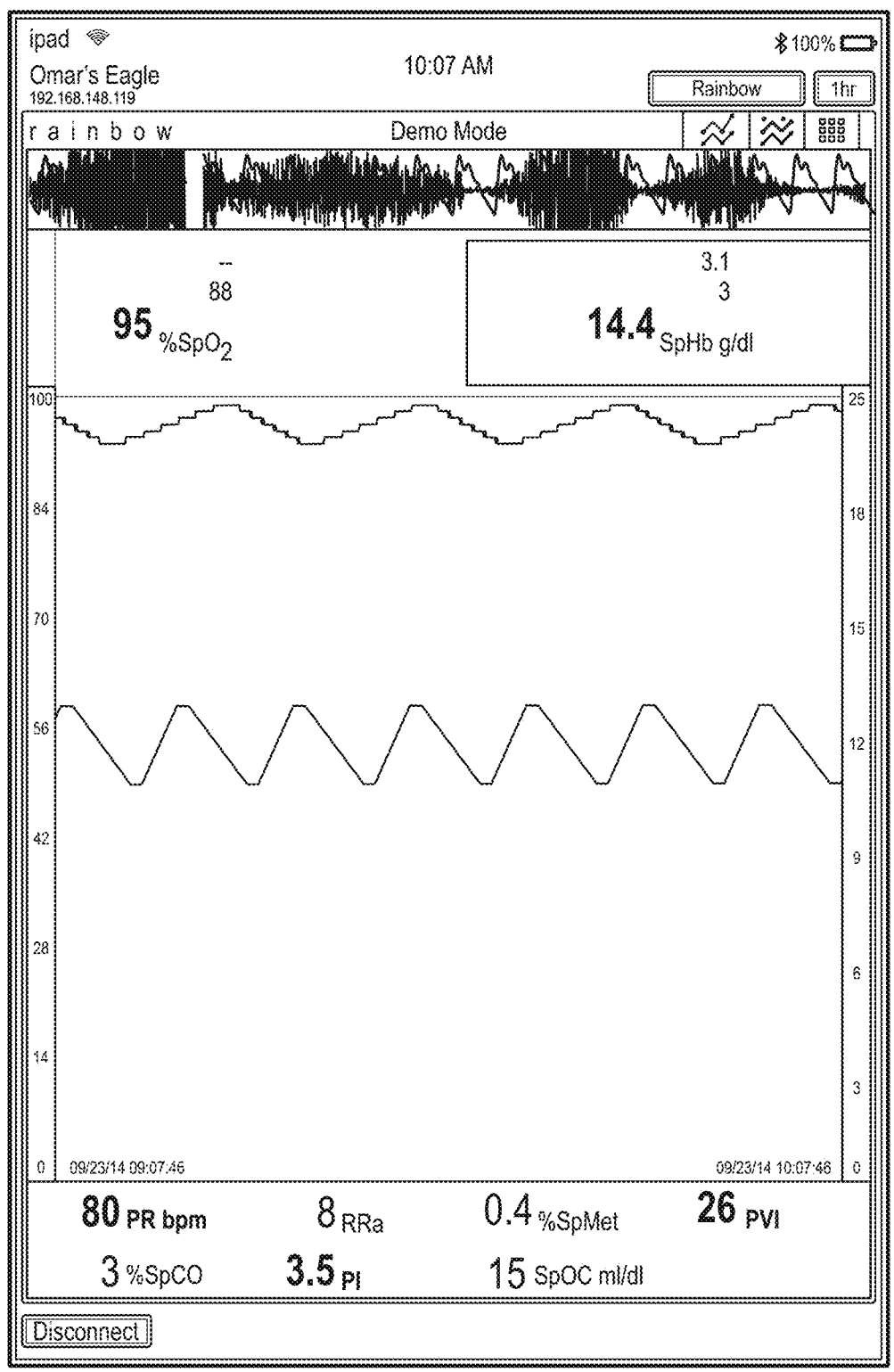
Figure 49:
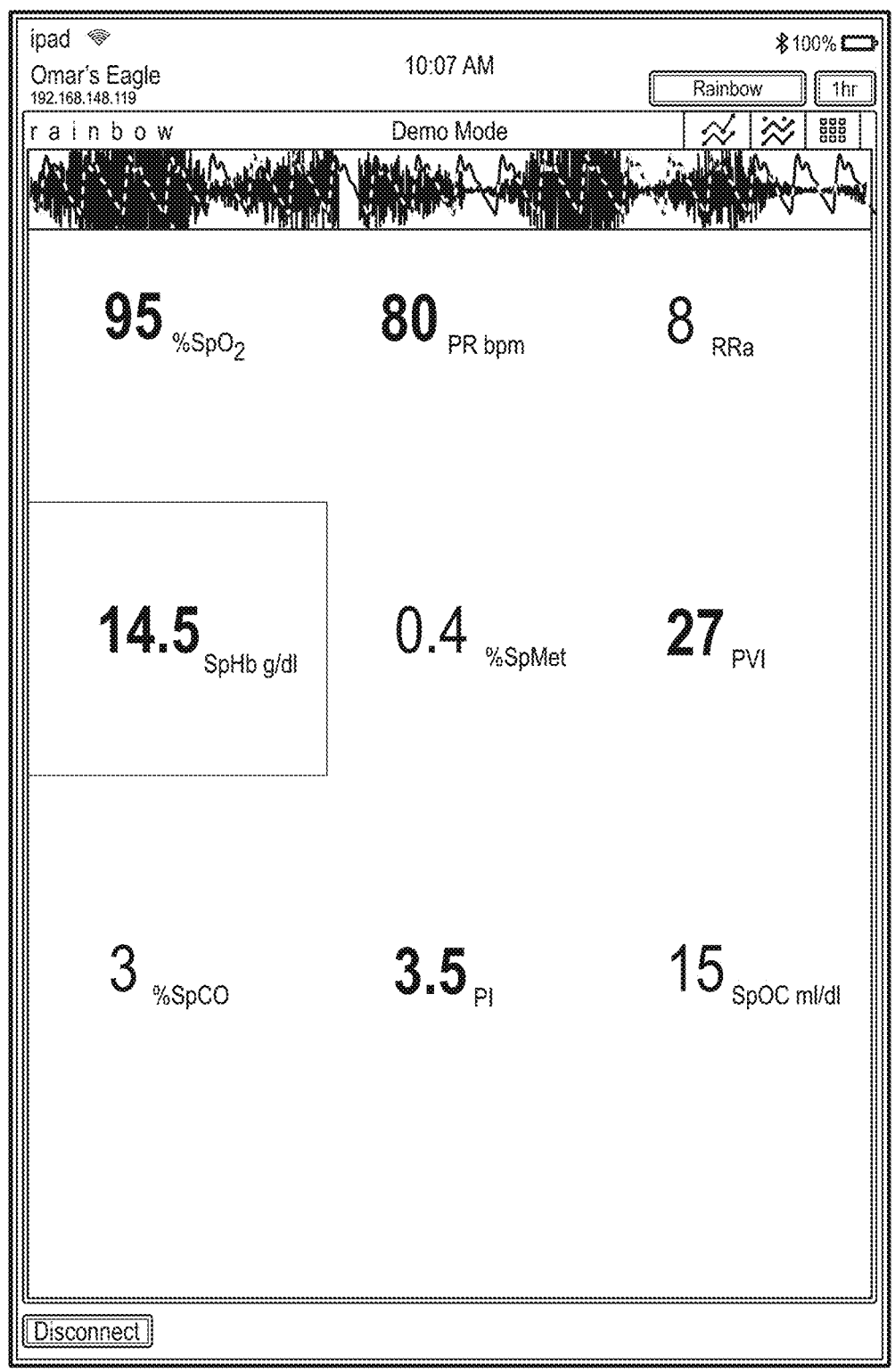
Figure 50:
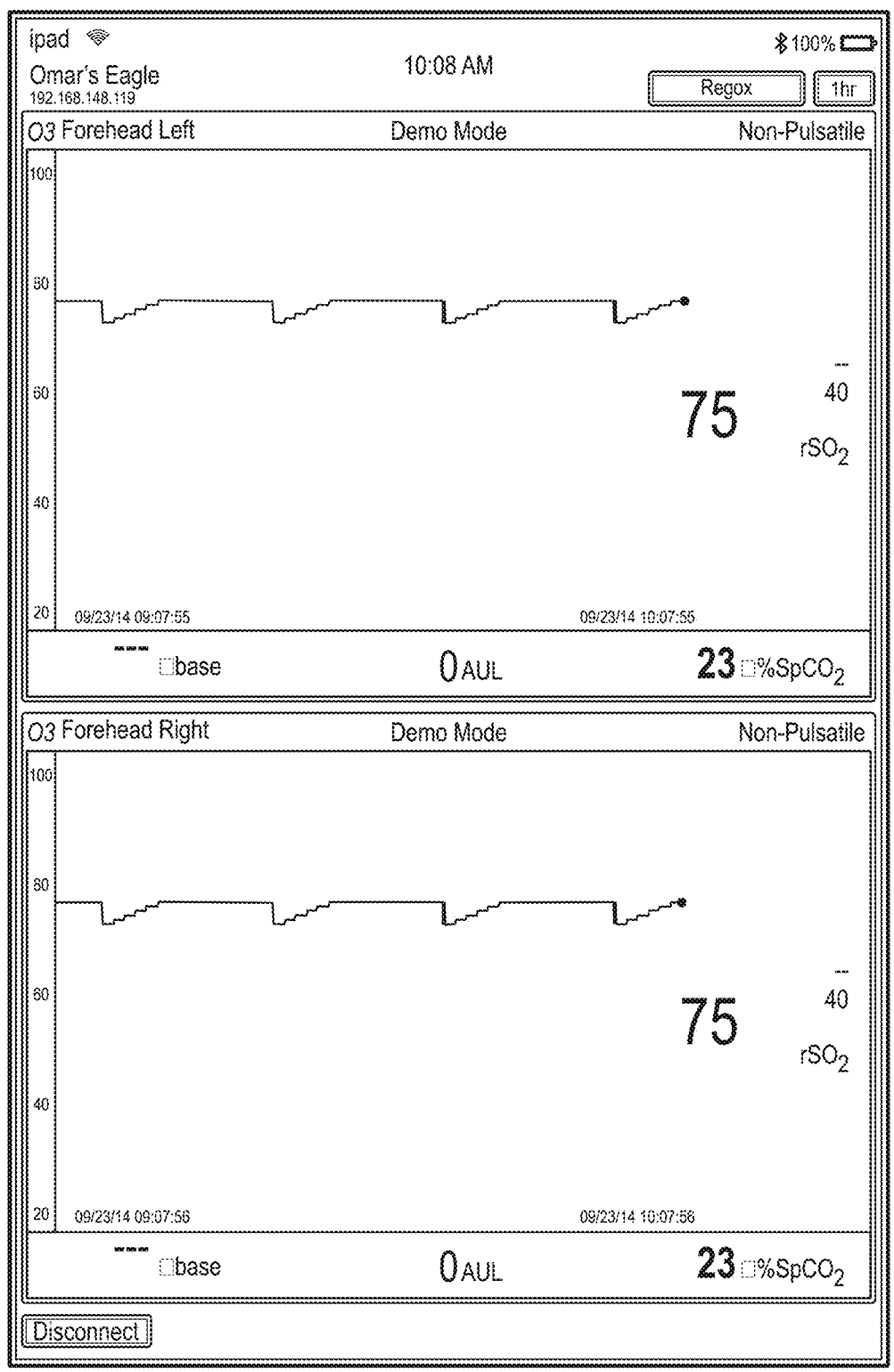
Figure 51:
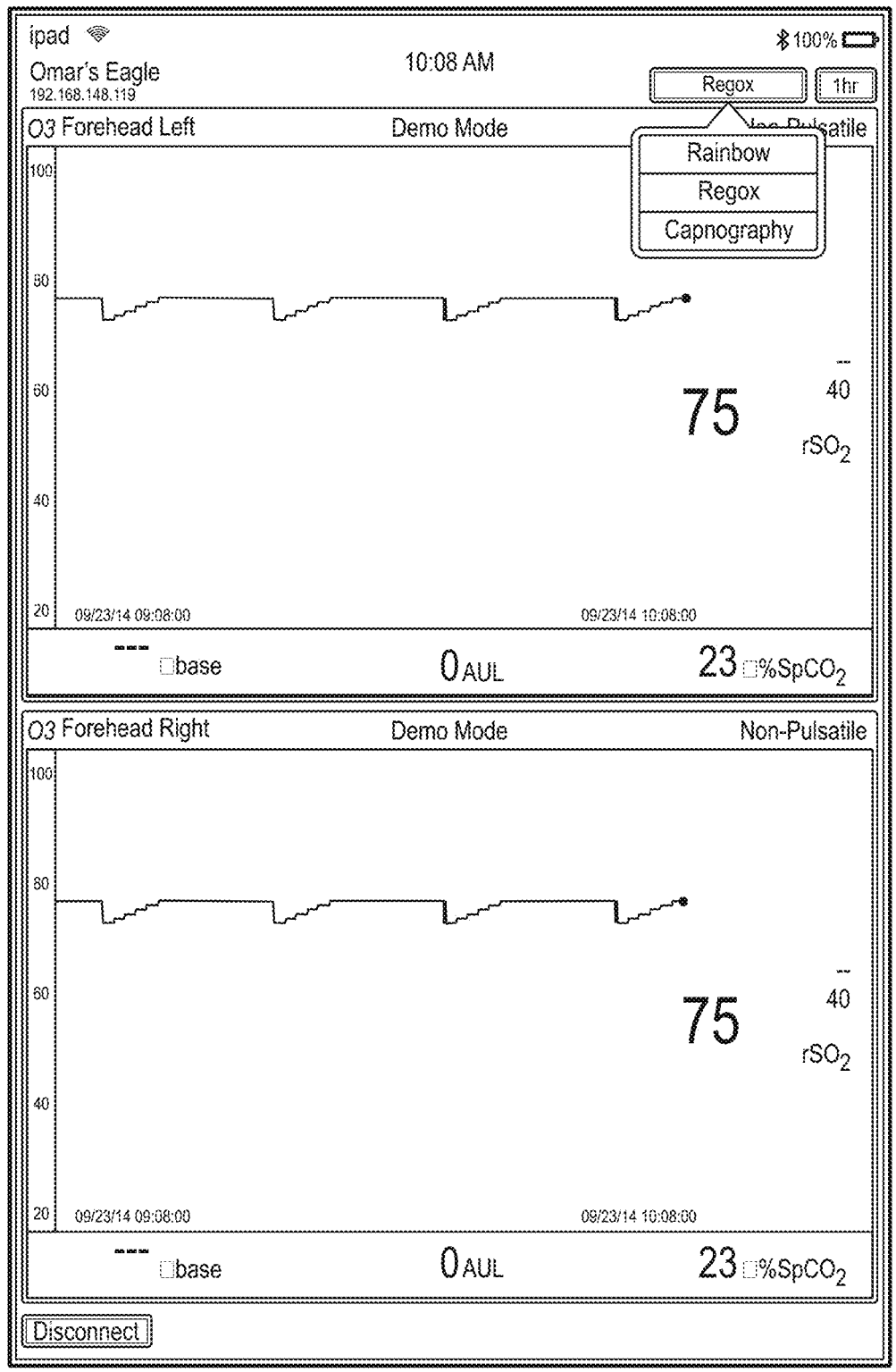
Figure 52:
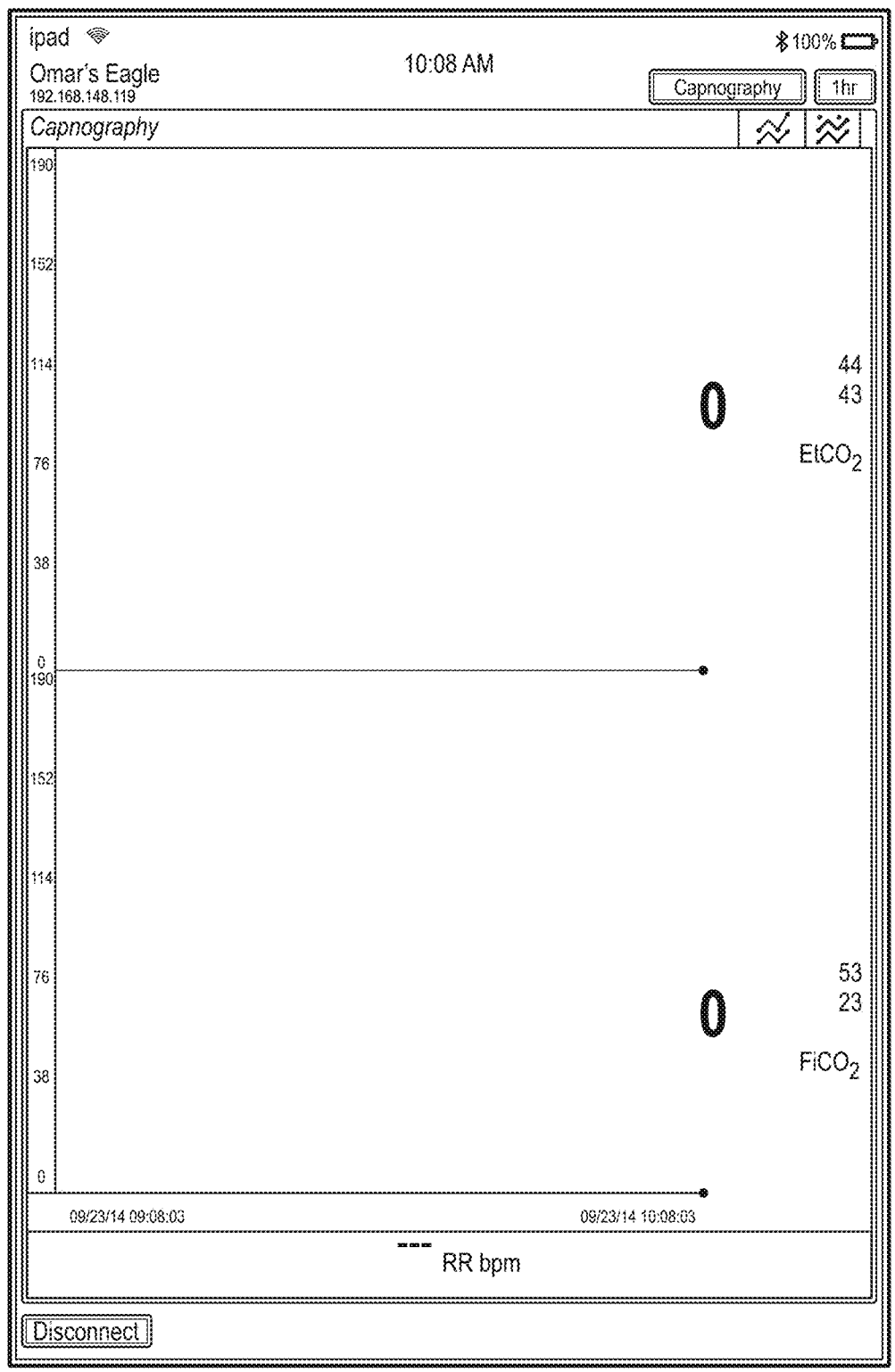
Figure 53:
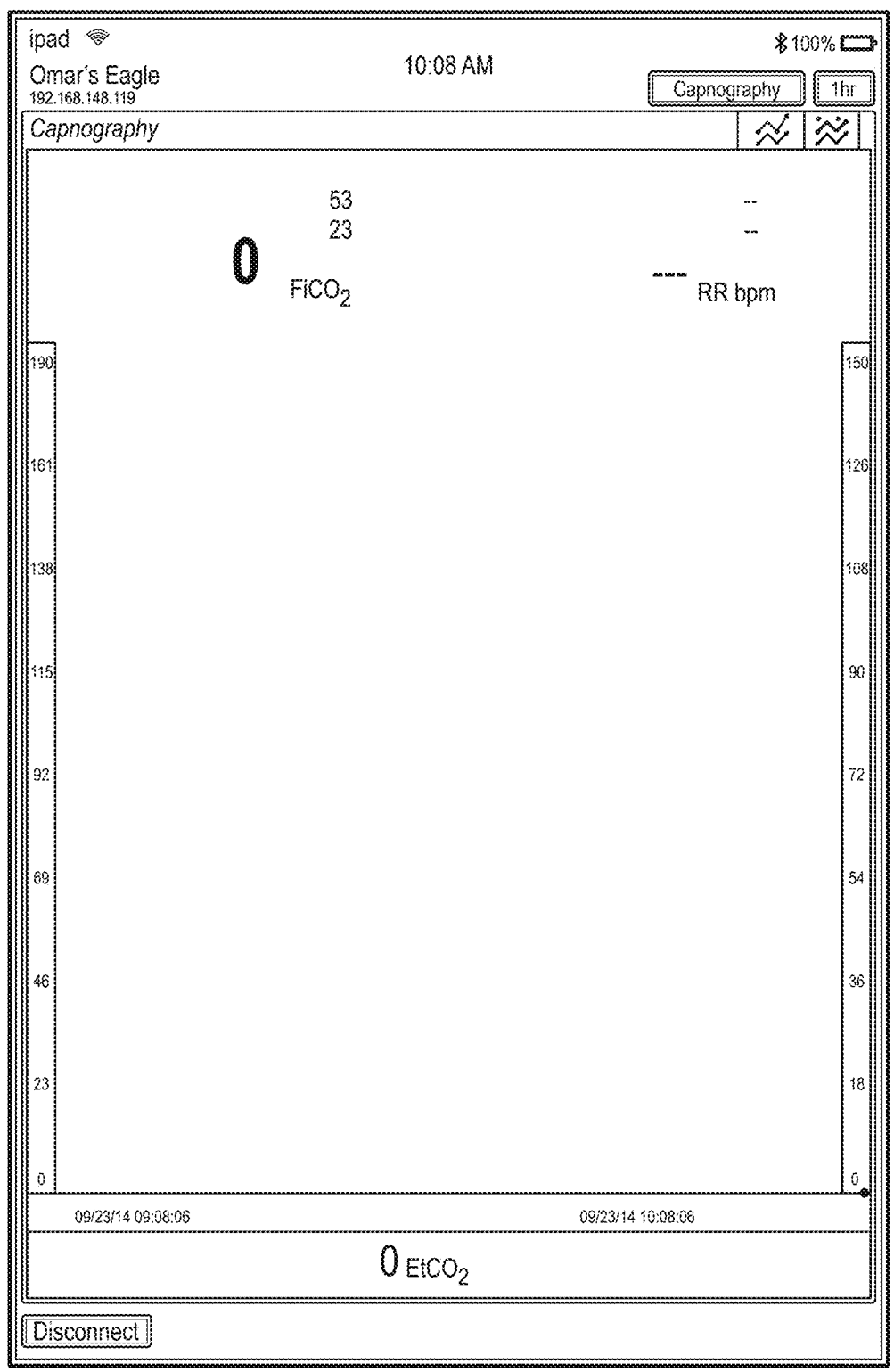
Figure 54:
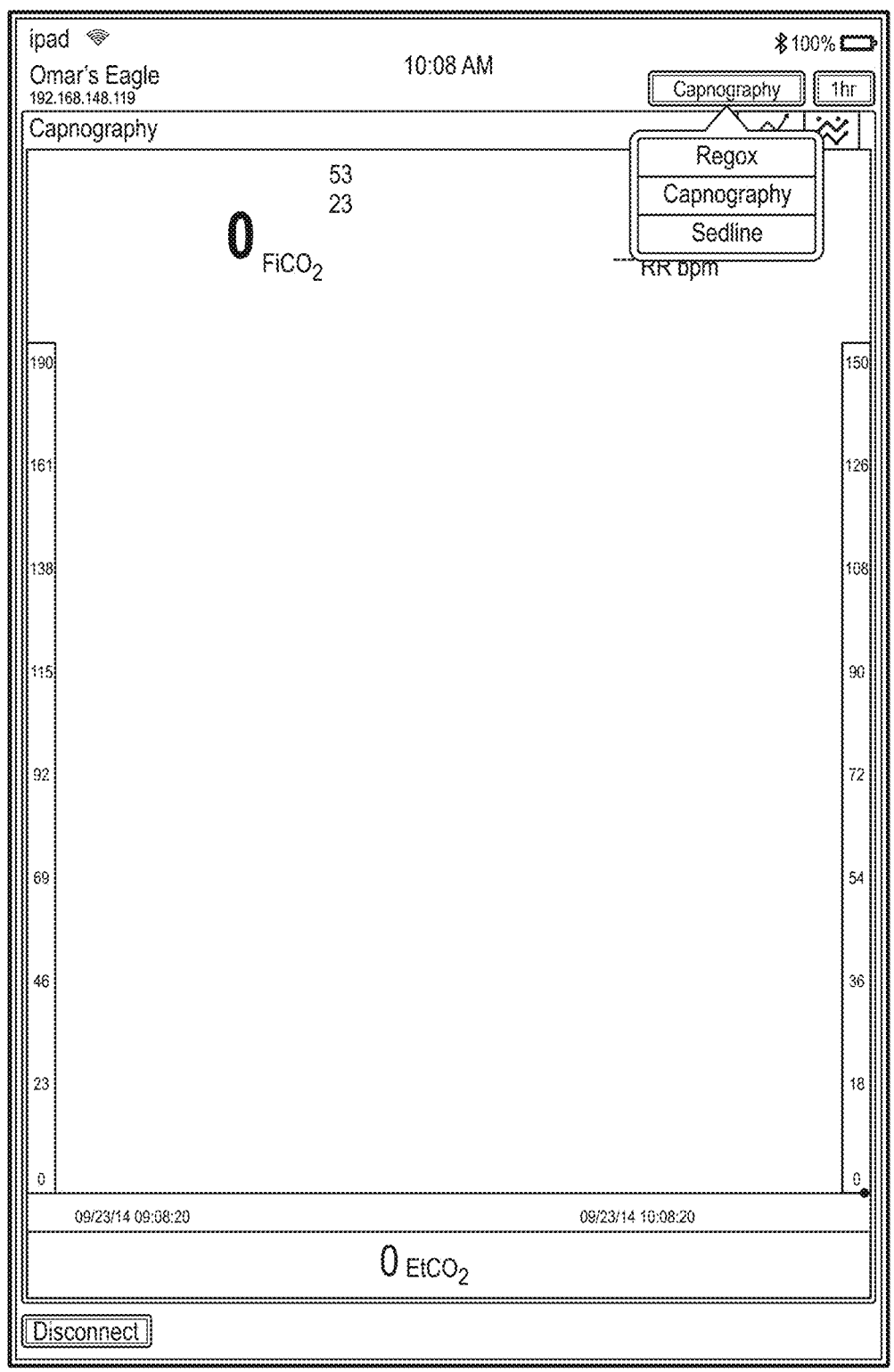
Figure 55:
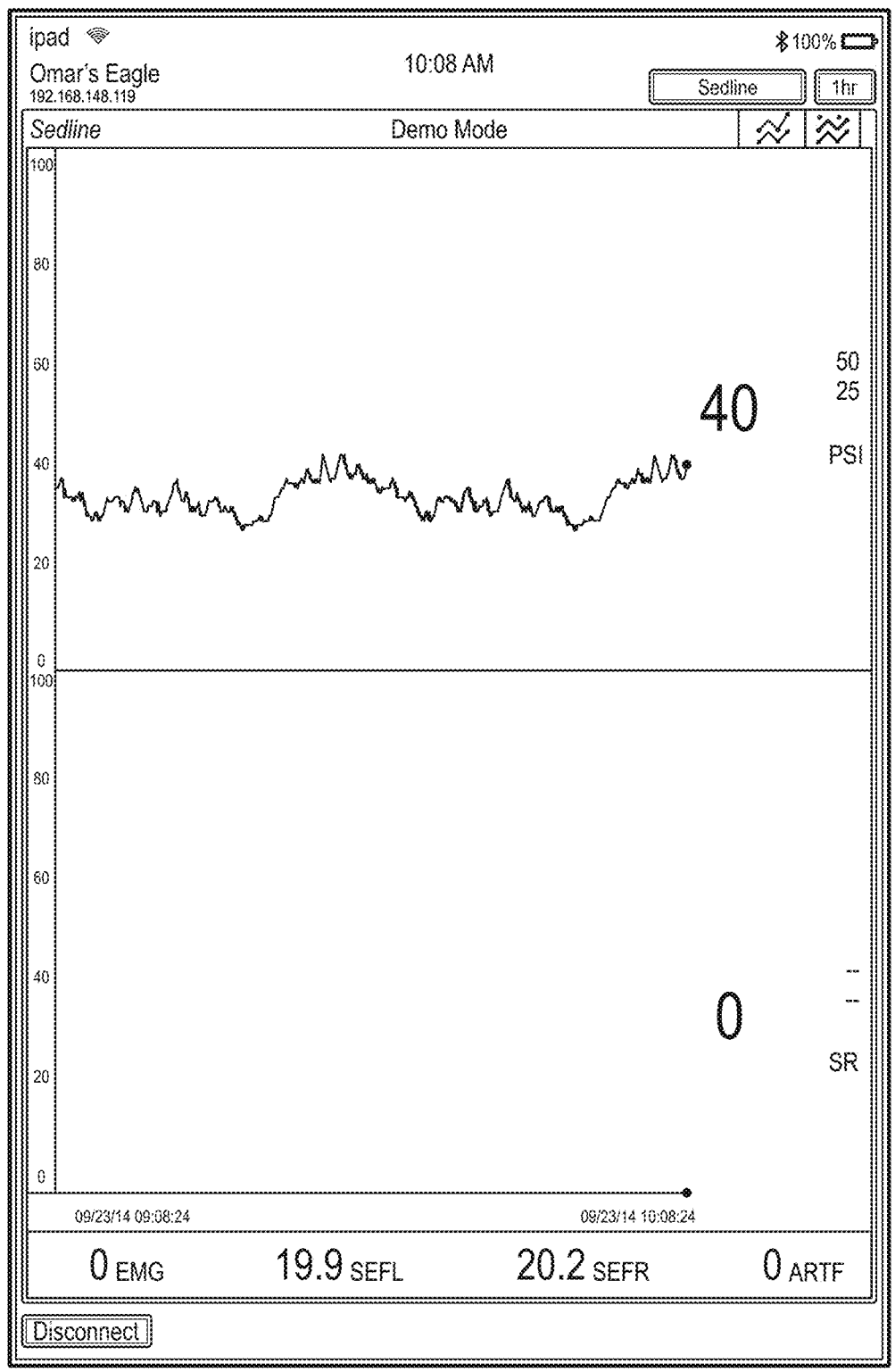
Figure 56:
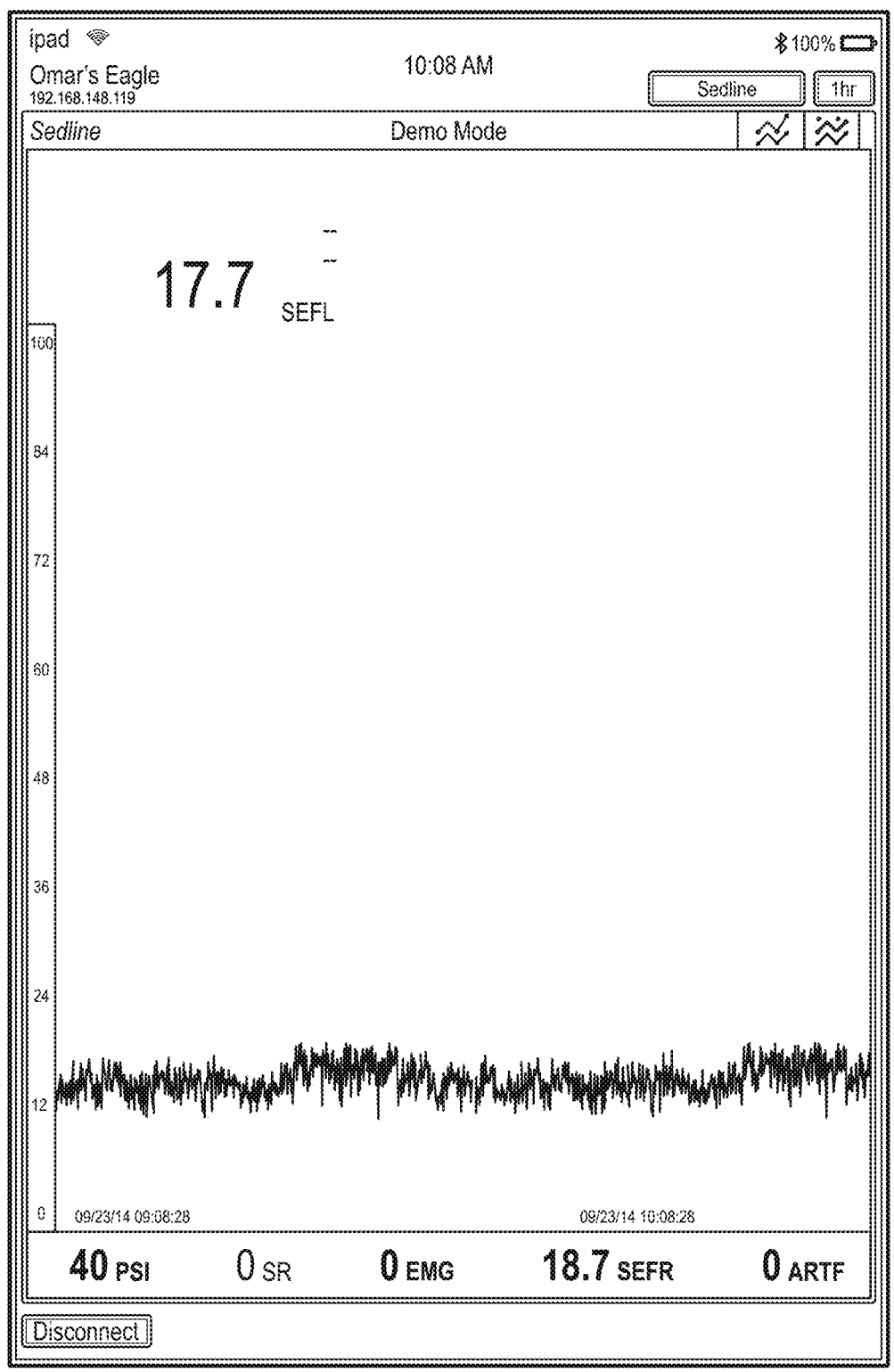
Figure 57:
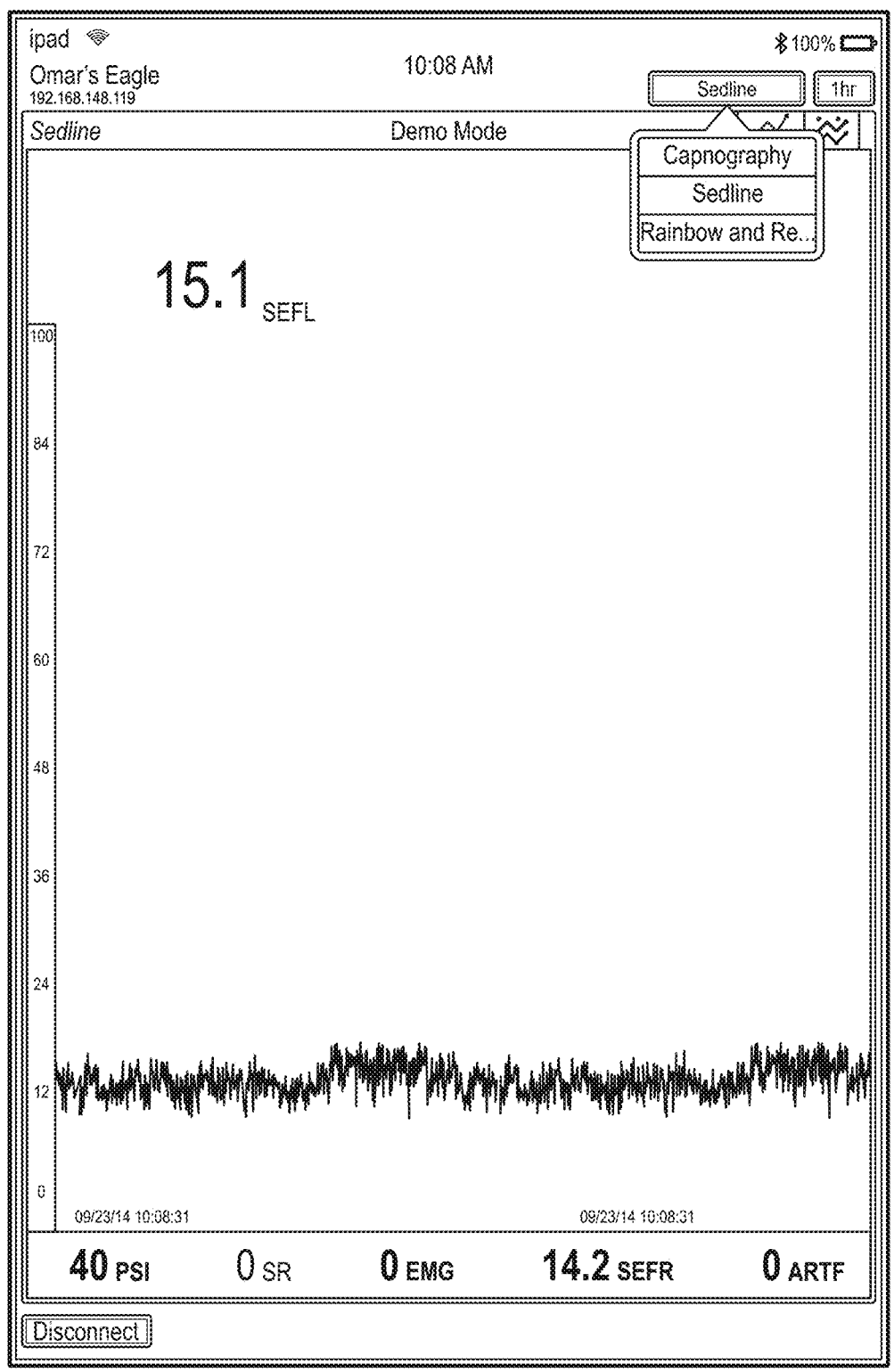
Figure 58:
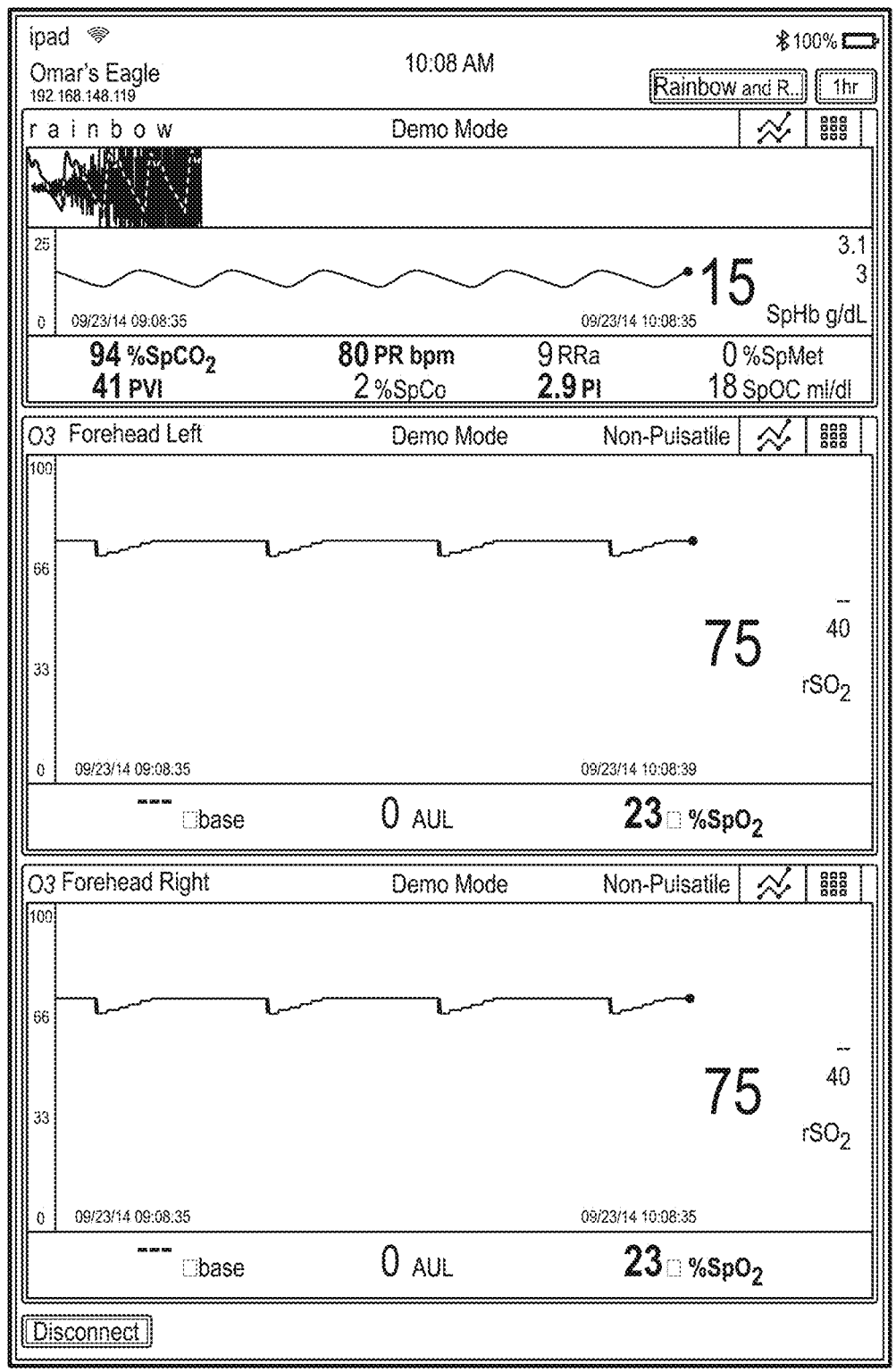
Figure 59:
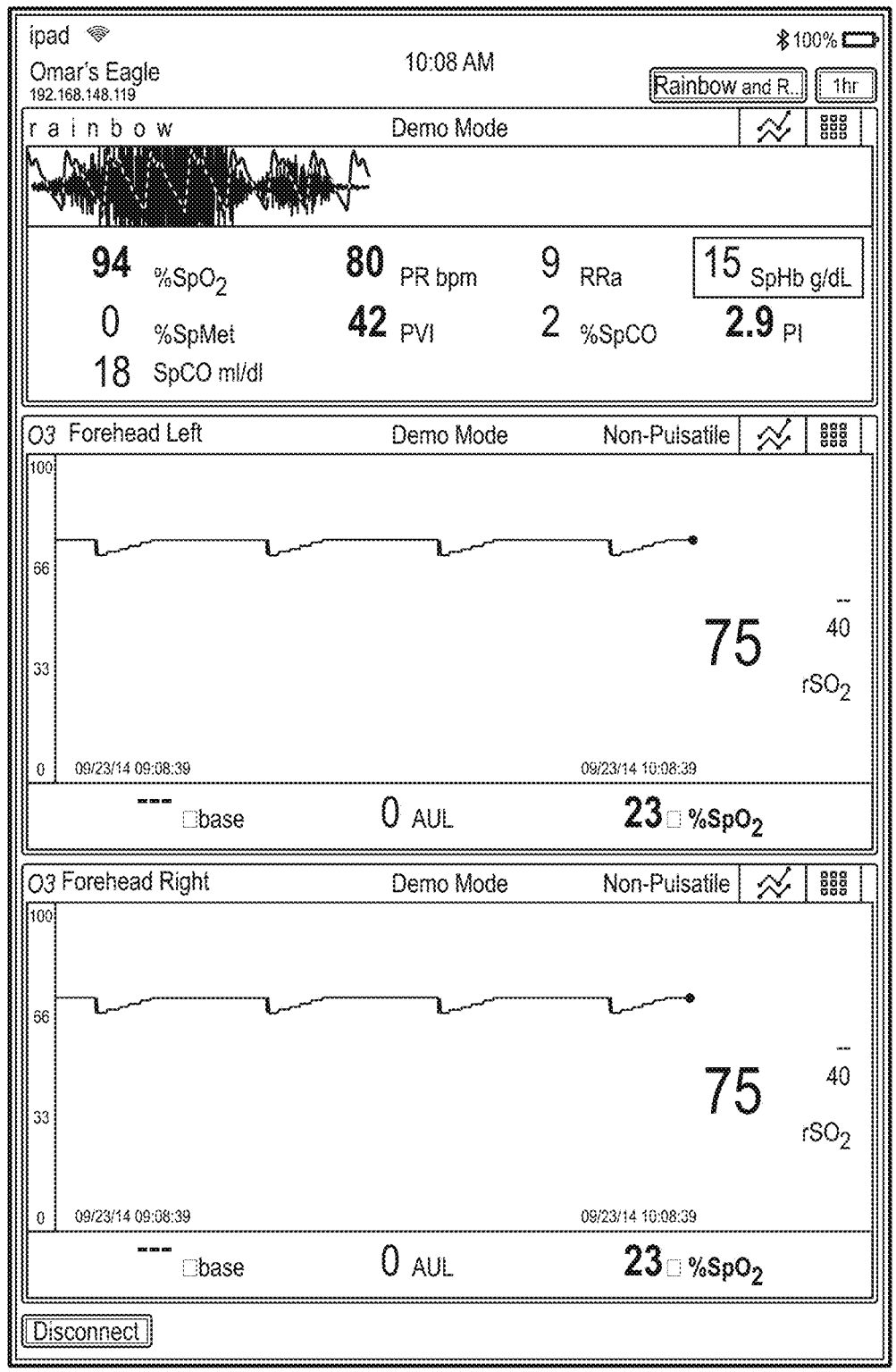
Figure 60:
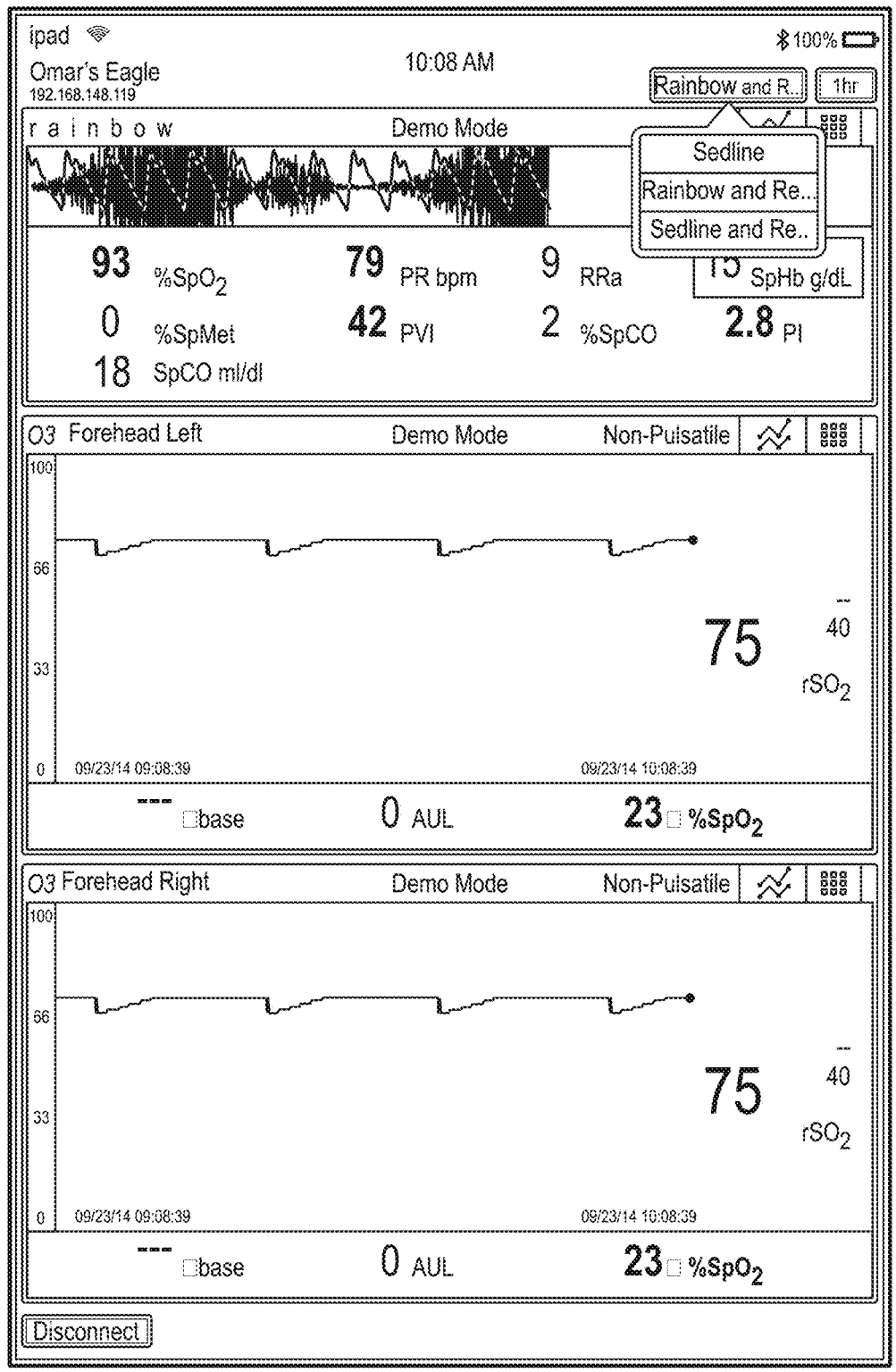
Figure 61:
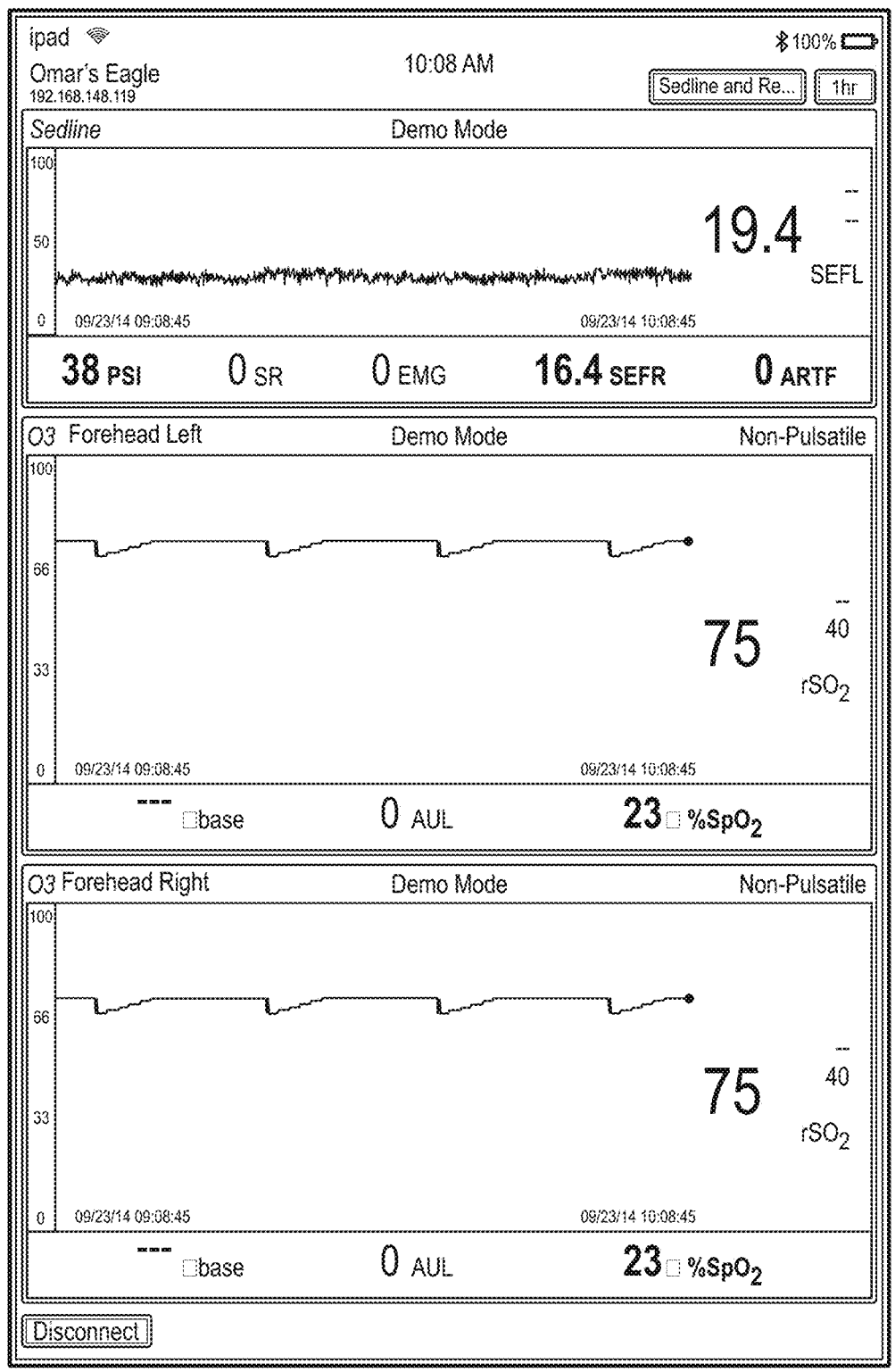
Figure 62:
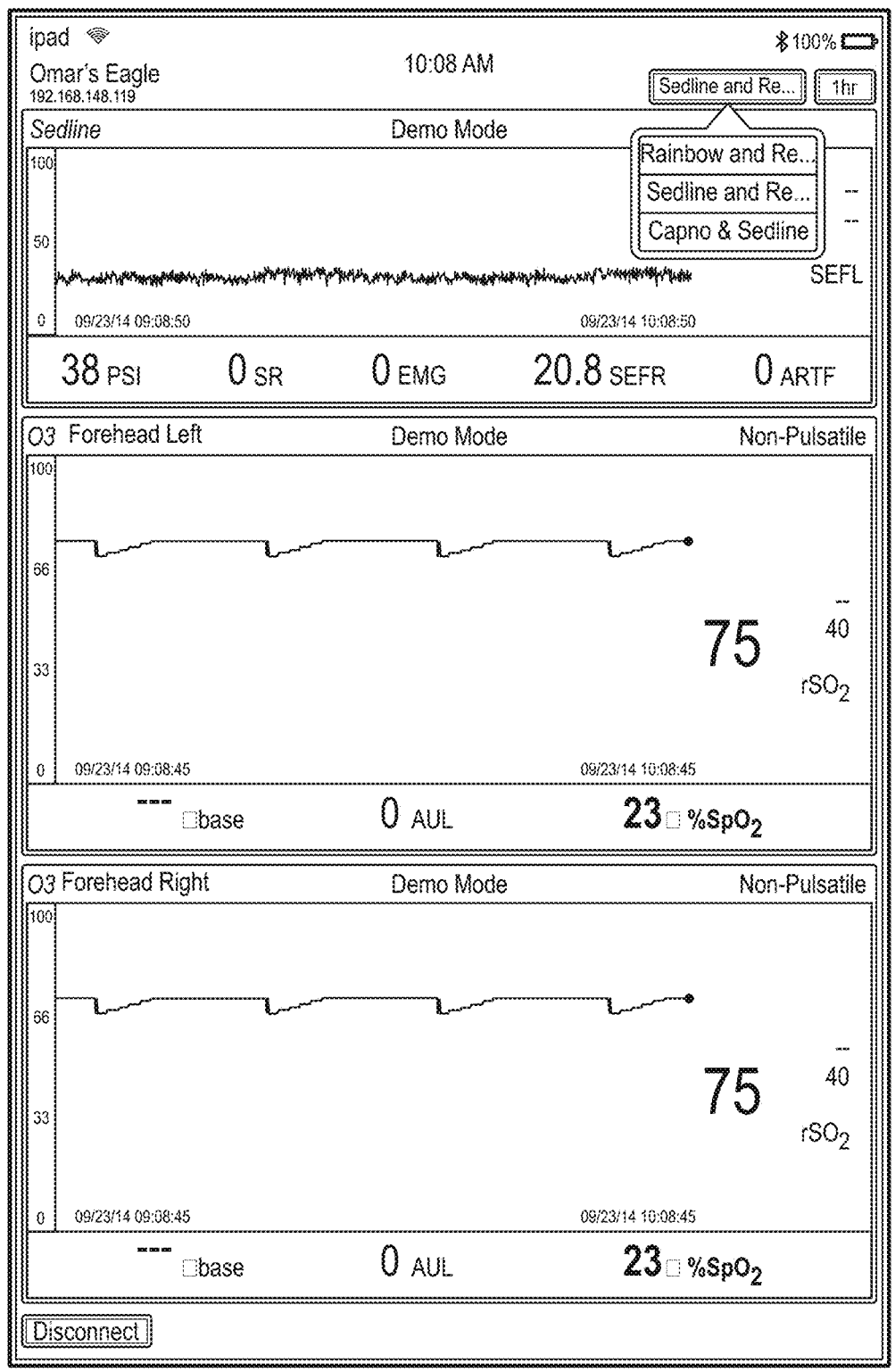
Figure 63:
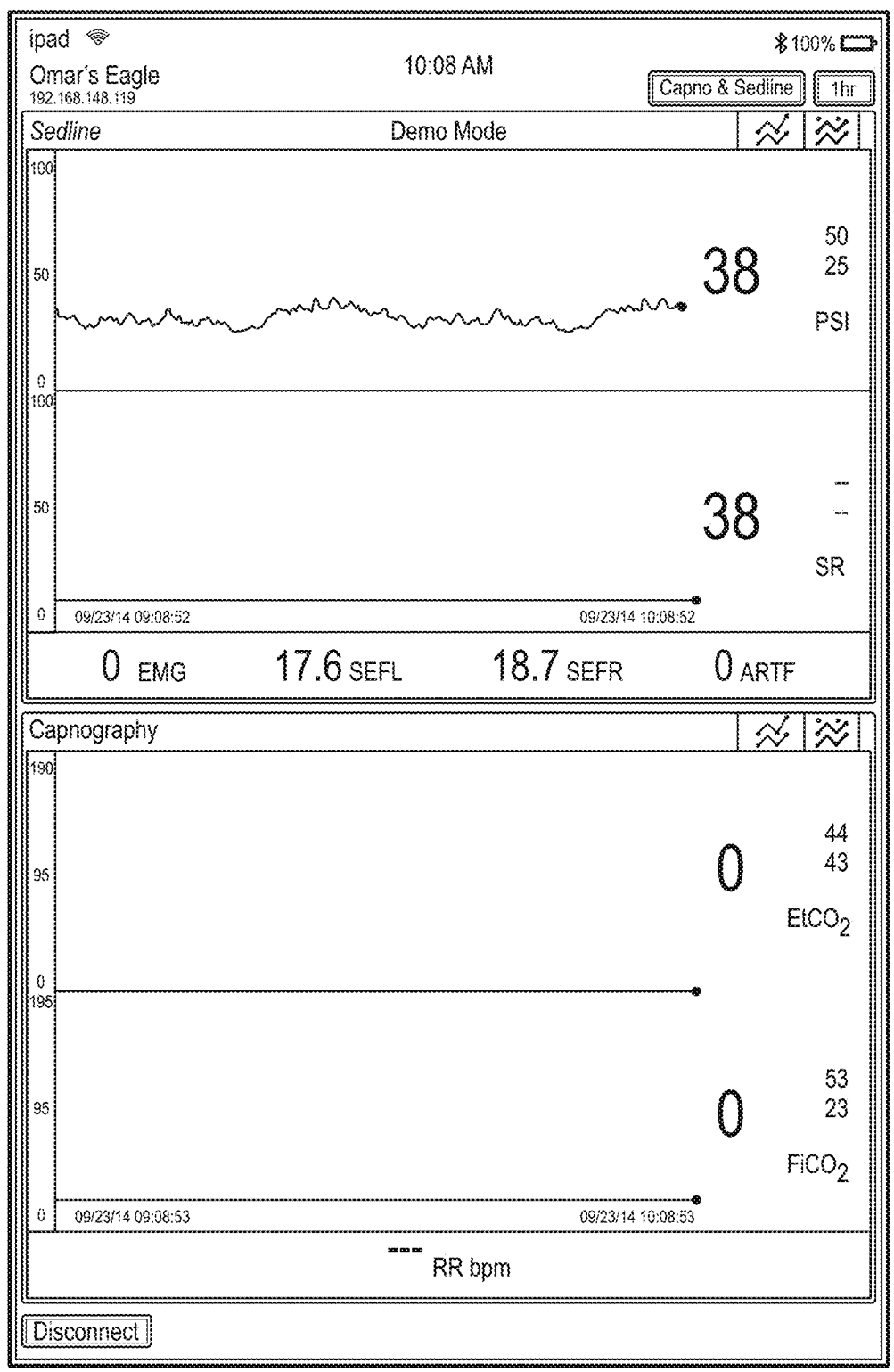
Figure 64:
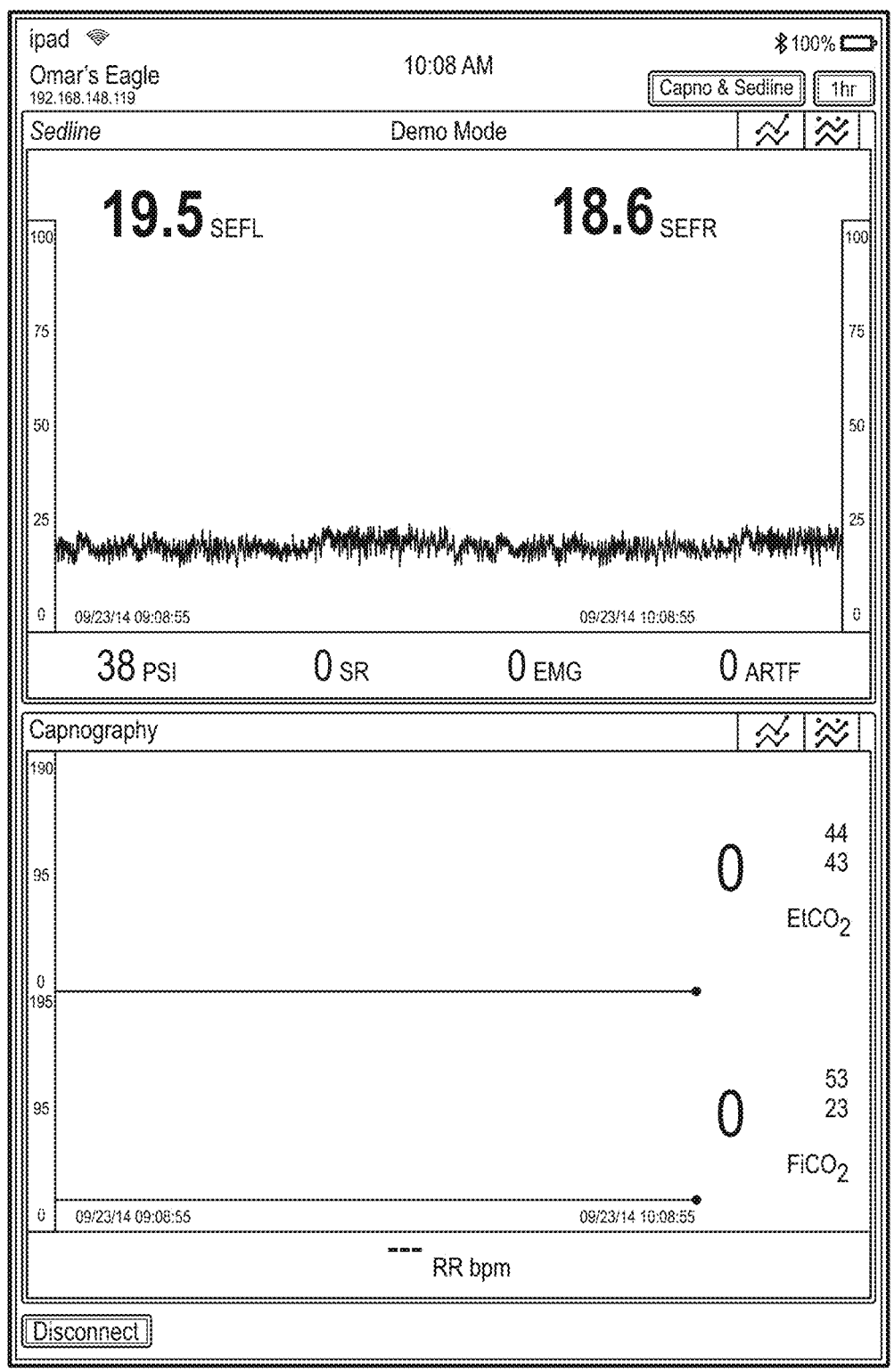
Figure 65:
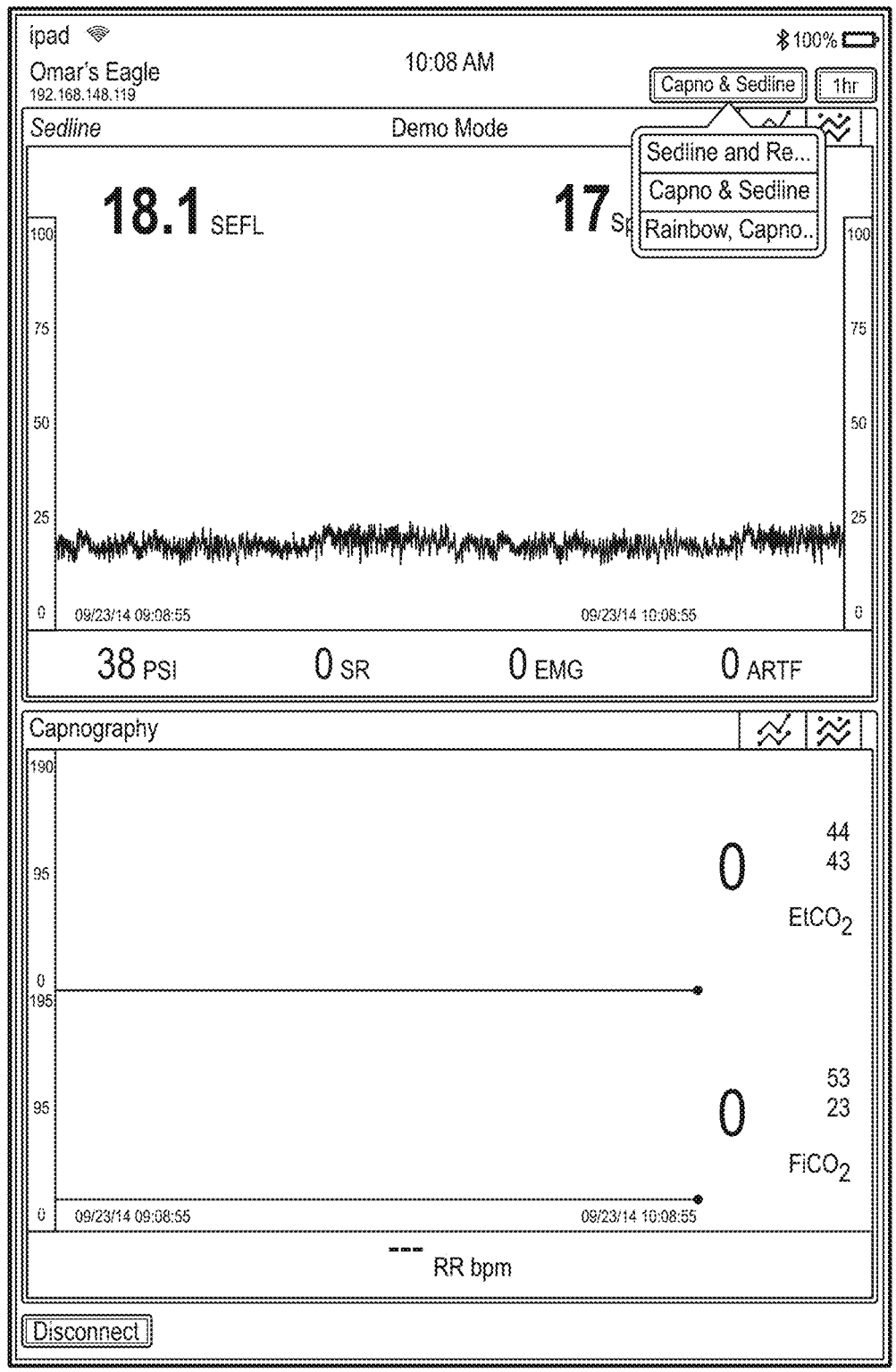
Figure 66:
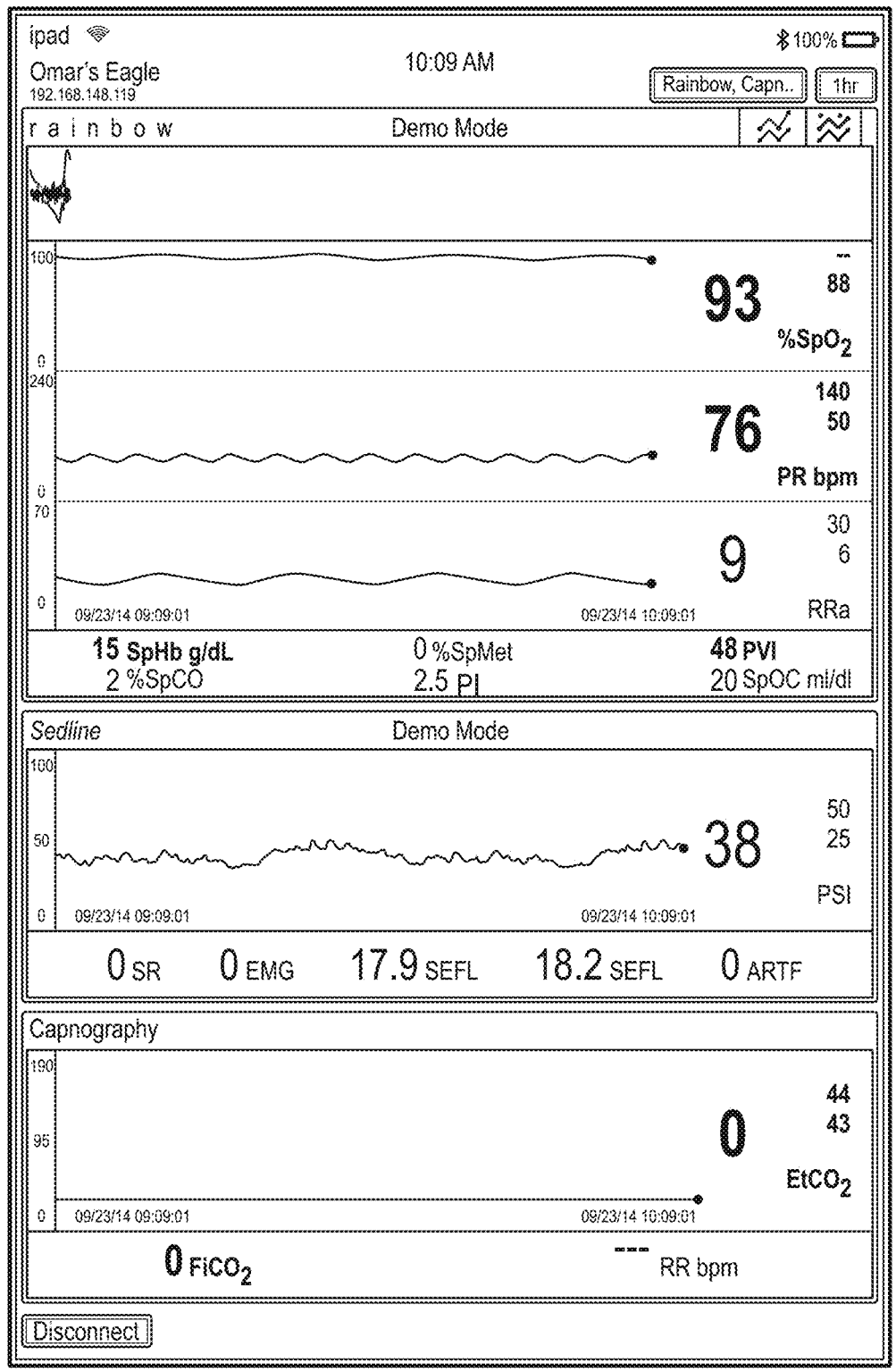
Figure 67:
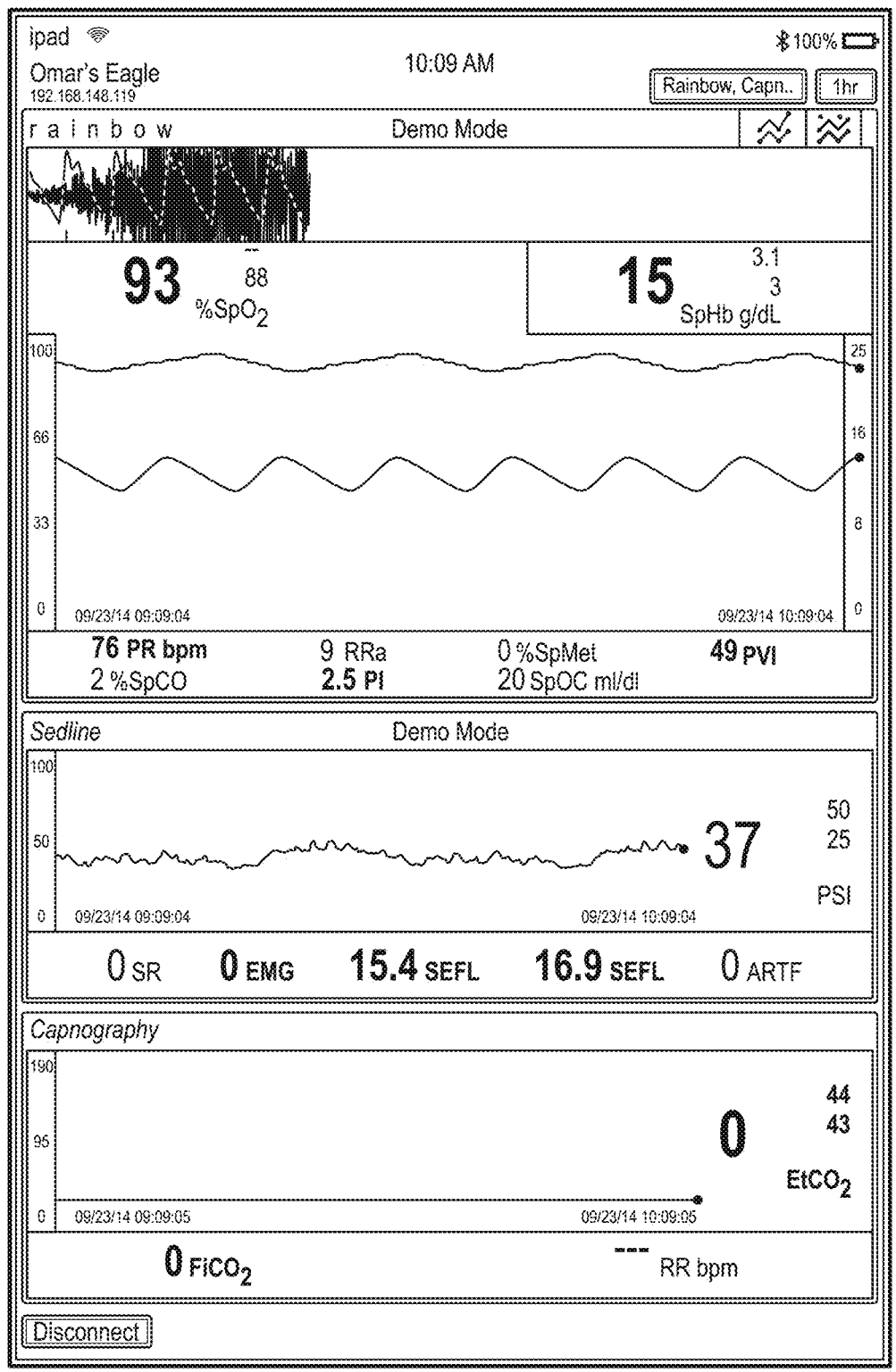
Figure 68:
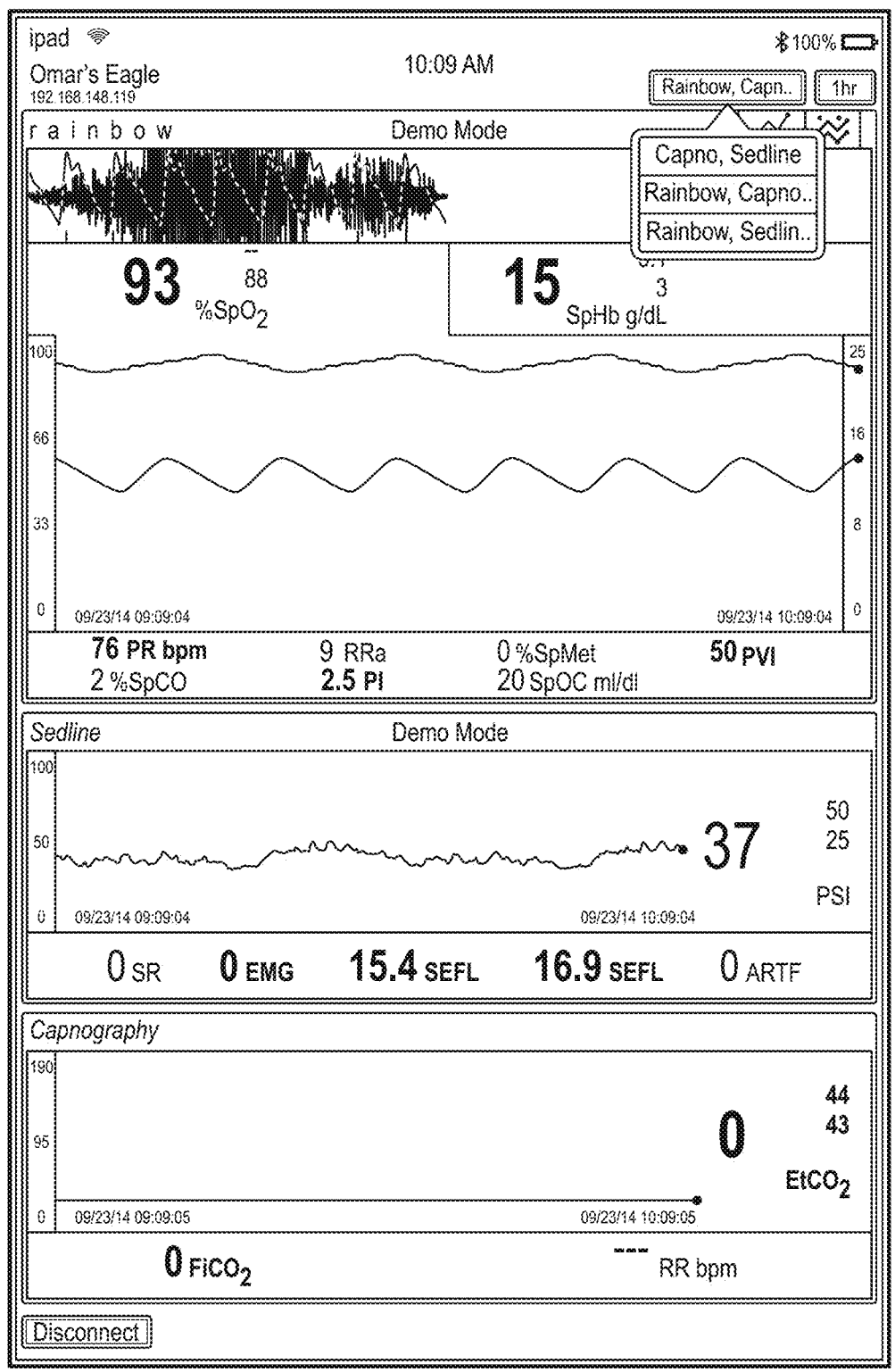
Figure 69:
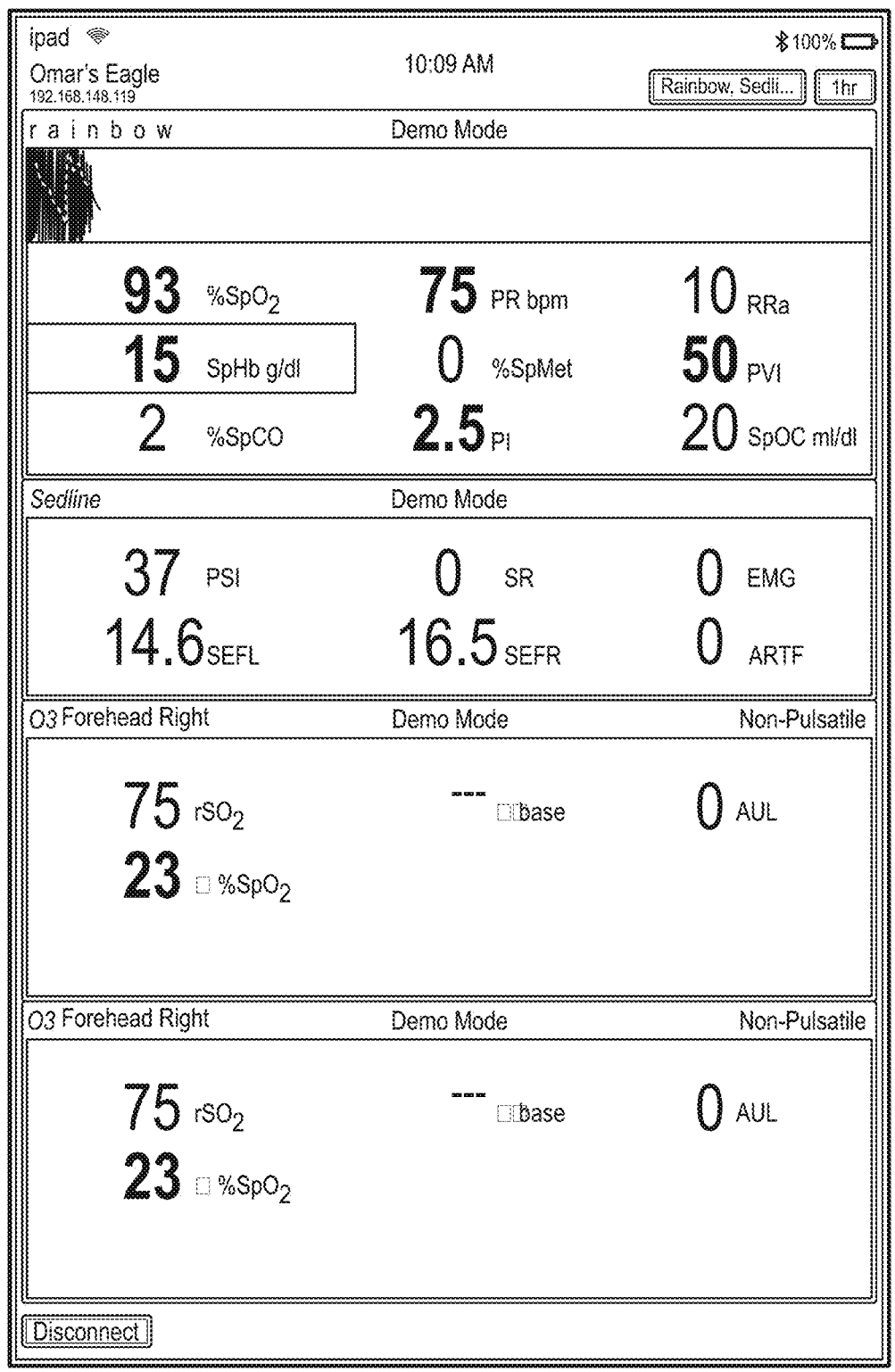
Figure 70:
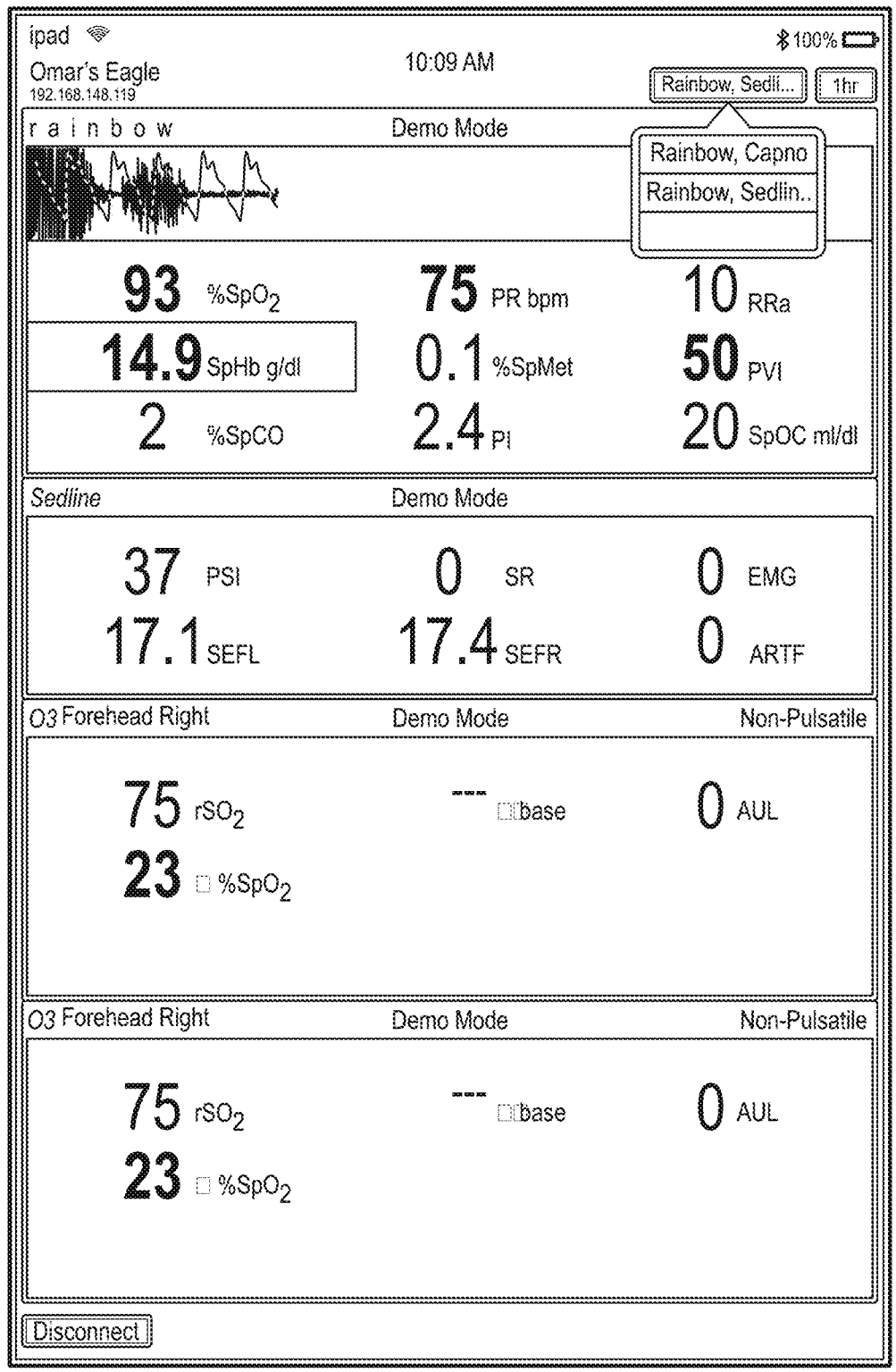
Figure 71:
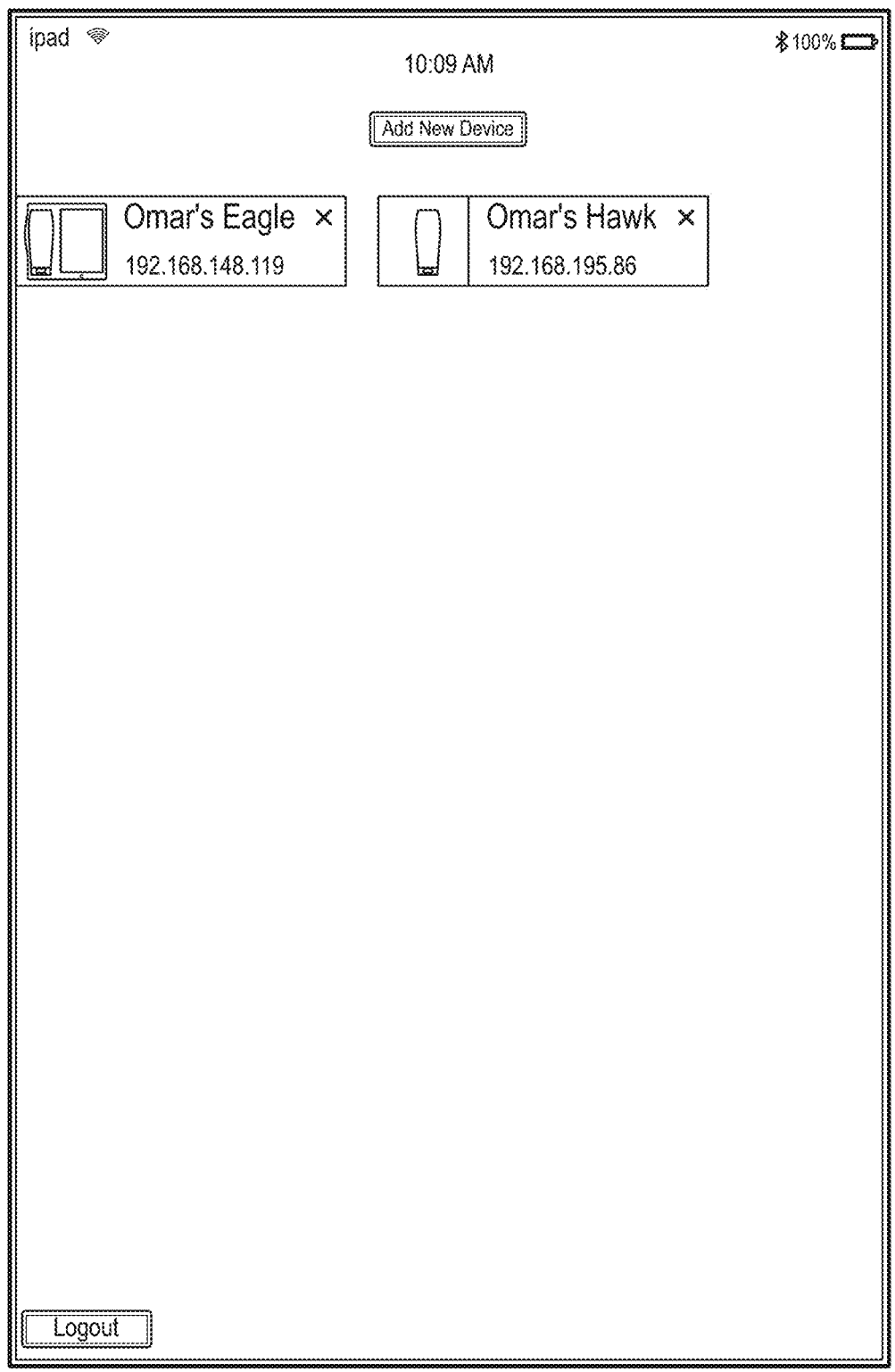

The automatic rule configuration process 2900D illustrated in FIG. 45D is similar to the process 2900B illustrated in FIG. 45B. At block 2912, the translation module 2415 can transmit one or more test, dummy, or initialization messages to an HL7 medical device. Additionally or optionally, the translation module 2415 can cause one or more test messages to be transmitted to the new HL7 medical device from another HL7 medical device. As described above, the test messages can include messages having known HL7 formats configured to determine whether the HL7 device understands the test messages. The test messages can include test ADT messages, for example.

At block 2914, the translation module 2415 queries the HL7 medical device to receive information regarding an action taken or information stored in response to the test message. At block 2916, the translation module 2415 determines the formatting implementation of the HL7 device based on the information received. The translation module 2415 can analyze the information received to determine whether the test message or messages were properly understood. If none of the test messages were properly understood, the translation module 2415 can send additional test messages having other known HL7 formats and repeat blocks 2914 and 2916.

At block 2918, the translation module 2415 configures one or more translation rules to handle messages received from and/or sent to the detected HL7 medical device. The configuration of the translation rules can involve the creation or generation of new translation rules. Additionally or optionally, the configuration of the rules can involve the alteration or updating of existing rules. If a set of translation rules already exists for the formatting implementation used by the new HL7 medical device, then the configuration of new translation rules may not be required. Instead, existing translation rules can be associated with the new HL7 medical device for use in communication involving that HL7 medical device.

The automatic rule configuration processes described above can be triggered by the detection of a network device or system by the translation module 2415. The medical devices referred to in FIGS. 45A-45D can include any of the devices or systems illustrated in FIG. 1 or 24.

The automatic generation of translation rules can advantageously occur post-installation and post-compilation of the messaging sub-system software, which includes the translation module 2415. The automatic generation or dynamic modification of the translation rules 2420 can occur without having to recompile or rebuild the translation module software. This feature can be advantageous in terms of efficiently complying with U.S. Food and Drug Administration ("FDA") requirements regarding validation of software used in healthcare environments.

Take, for example, a situation where a medical device manufacturer plans to use the translation module 2415 to facilitate communication between a particular medical device or system that is to be installed in a hospital (for example, a patient monitoring system, as described herein), or other patient care facility, and other devices or systems that are already installed at the hospital (for example, the HIS or CIS). Any software required for the operation of the new medical device to be installed may be at least partially validated for FDA compliance prior to installation at the hospital despite the fact that, for example, the HL7 implementations of other existing devices or systems at the hospital may still be unknown. For example, any aspects of the software for the new medical device that are dependent upon receiving messages from other hospital devices can be validated pre-installation as being capable of fully and correctly operating when the expected message format is received. Then, once the medical device is installed at the hospital, the validation of the software can be completed by showing that the translation module 2415 is able to provide messages of the expected format to the newly installed device. In this way, FDA validation tasks can be apportioned to a greater extent to the pre-installation timeframe where they can be more easily carried out in a controlled manner rather than in the field.

In addition, the translation module 2415 can further help streamline FDA validation, for example, when a medical device or system is expected to be installed at different hospitals whose existing devices use, for example, different implementations of the HL7 protocol. Normally, this type of situation could impose the requirement that the entire functionality of the software for the new medical device be completely validated at each hospital. However, if the translation module 2415 is used to interface between the new medical device and the hospital's existing devices, then much of the software functionality could possibly be validated a single time prior to installation, as just described. Then, once installed at each hospital, the software validation for the medical device can be completed by validating that correct message formats are received from the translation module (the translation rules for which are field-customizable). This may result in making on-site validation procedures significantly more efficient, which will advantageously enable more efficient FDA compliance in order to bring life-saving medical technology to patients more quickly by the use of field-customizable translation rules.

V. Example Connections with the Hub Via a Board-In-Cable

As described with reference to FIGS. 2 and 12, the monitoring hub 100 can be connected to medical systems and receive data acquired by various sensors such as, for example, sensors 202, 222, 224, 226. For example, with reference to FIG. 12, various sensors can be connected to the monitoring hub 100 via a Board-in-Cable (BIC) device. The BIC device of FIG. 12 may be a custom device, with hardware and software built at least in part by a third-party manufacturer other than the provider of the monitoring hub 100. For example, a third-party manufacturer may design and build the BIC device to be compatible with the monitoring hub 100. Such a custom BIC can beneficially expand the capability of the monitoring hub 100, for example, by adding new physiological parameter monitoring capability. However, designing a custom BIC for each parameter can be a labor-intensive process.

The BIC of FIG. 12 can also be an off-the-shelf device. The provider of the monitoring hub 100 can supply a BIC that can be programmed by any third-party to monitor a new parameter when connected to a third-party sensor. The BIC may, for instance, include a processor, memory, and a programming environment that enables rapid development of parameter calculation algorithms without having to reinvent the wheel to design a BIC. This type of BIC—which may be considered an off-the-shelf BIC—can beneficially reduce or eliminate the need for third parties to manufacturer their own hardware (other than perhaps sensors and cables) and design firmware.

As an example, a third party may desire to expand the functionality of the monitoring hub by adding noninvasive blood pressure (NIBP) monitoring capability. The third party can obtain an off-the-shelf BIC from the provider of the monitoring hub 100 (optionally together with an associated cable for attaching to the hub 100), rather than designing its own BIC that interfaces with the monitoring hub 100. The third party can then access an SDK (described above and in more detail below) from the provider of the monitoring hub and use this SDK to program the BIC with a NIBP monitoring application. The third party can then sell the BIC (and optionally cable), together with its sensors, to hospitals or other patient care providers, who can then connect the BIC to the monitoring hub 100 to add NIBP functionality to the monitoring hub 100.

The off-the-shelf BIC may include an operating system and applications, including an API, that permit interactions with the hub 100. For instance, the API can enable an application running on the BIC to expose settings of the application to the monitoring hub 100. Thus, the off-the-shelf BIC may not only output data to be displayed on the hub but may also permit the hub to control aspects of the BIC. For example, the third-party application on the BIC may access an API that causes the hub to expose a user interface with settings that can affect the BIC, such as an alarm limit user interface control (like a slider). A clinician can access the settings on the hub, change them, and thereby cause the hub to use an API call to transmit the settings update to the BIC.

Figure 72A:
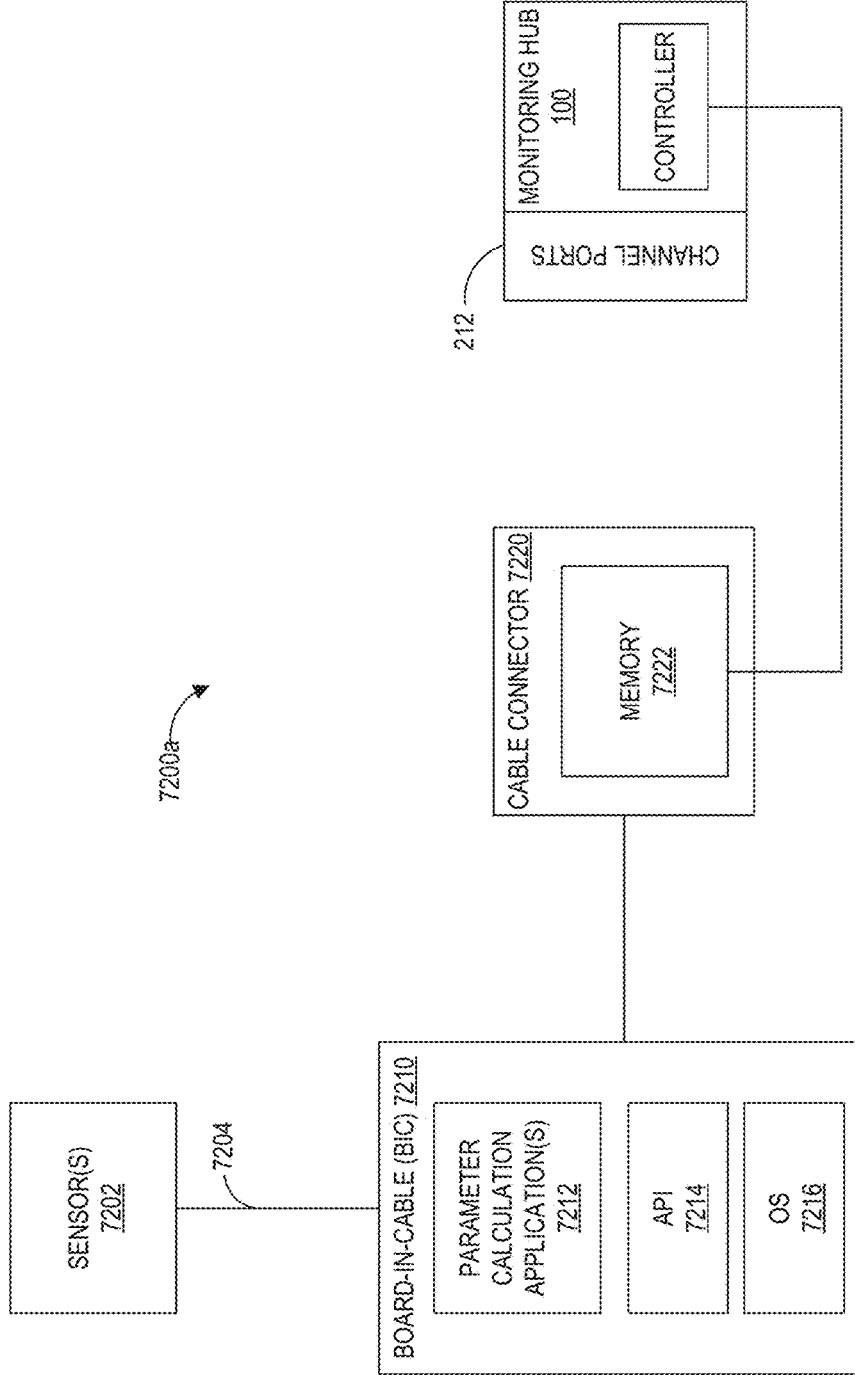
FIG. 72A illustrates an example of interfacing with the hub using a board-in-cable.

The above-described features are now described in more detail starting with FIG. 72A. FIG. 72A depicts a BIC and other associated components that can include any of the features described above, as well as optionally additional features. FIG. 72A illustrates an example of interfacing with the hub using an off-the-shelf BIC 7210. The computing environment 7200a can include sensor(s) 7202 and the monitoring hub 100. The sensors 7202 can be physiological sensors for measuring one or more of a patient's parameters. The sensor(s) 7202 can connect to the monitoring hub 100 via a sensor cable 7204 (also shown in FIG. 15) and a cable connector 7220. The sensor cable 7204 can include two ends where the first end can be connected to a sensor 7202 while the second end can be connected to the BIC 7210. The BIC 7210 may be connected to the cable connector 7220 which can connect to the monitoring hub 100.

The sensor cable 7204 can include the off-the-shelf BIC 7210, which can be programmed with algorithms for parameter calculations and for interfacing with the monitoring hub 100. The BIC 7210 can include a parameter calculation application(s) 7212 (optionally provided by a third party other than the hub 100 provider), an application programming interface (API) 7214 (e.g., provided by the hub 100 provider), and an operating system 7216 (e.g., provided by the hub 100 provider), although one or more of three components of BIC 7210 may be optional. Further, although not shown in FIG. 72A, the BIC 7210 can also include a hardware processor and a non-transitory memory to support the parameter calculation application 7212, the API 7214, and the operating system 7216.

The parameter calculation application can comprise executable code which implements algorithms for processing parameter data received from the sensor 7202. The executable code (such as, for example, the parameter calculation application(s) 7212, the API 7214, etc.) may be programmed by the SDK described above and in more detail below with reference to FIG. 74.

As an example of data processing by the BIC 7210, the BIC 7210 can be connected to the sensor 7202, which can measure a patient's blood pressure. The BIC 7210 can receive the patient's blood pressure data acquired from the sensor 7202 and generate data packets with the blood pressure changes over time. As another example, the BIC 7210 can additionally receive the patient's heart rate data from the monitoring hub 100 or another BIC associated with a different medical system. The parameter calculation application 7212 can use the blood pressure data and the heart rate data (among other data) to calculate a wellness index of the patient. The wellness index can be communicated to the monitoring hub 100 for display or further processing.

Additionally or optionally, the BIC 7210 can communicate display configurations associated with the sensor 7202 to the monitoring hub 100. Example display configurations can include the size of display, amount of information to be shown on the hub 100, frequency of display updates, color or font of the display, parameters to be displayed, and format of the display (for example, in graphical or numerical format), layout of information, etc. As an example of controlling the display setting of the monitoring hub 100 via the BIC 7210, the BIC 7210 can provide two, three, or more different sizes of display such as, for example, large, medium, and small sizes where the large size of the display may include more information associated with a patient parameter. For example, the large size may provide a graph showing heart rate changes over time while the small size may include a numerical number showing the current heart rate. The BIC 7210 may be configured to control a subdivision of monitoring hub's display. With reference to FIG. 23F, where the BIC 7210 communicates blood pressure data to the monitoring hub, the BIC 7210 may manage the settings for the bottom left region of the display (where the blood pressure is shown). Another BIC associated with a temperature sensor can be configured to manage the display settings on the bottom right region of the display in FIG. 23F.

The API 7214 can be configured to provide interfaces between the BIC 7210 and the hub 100. In this example, the API 7214 is illustrated separately from the parameter calculation application 7212. However, the API 7214 may be part of the parameter calculation application 7212. A user of the hub 100 (for example, a nurse or a doctor) can manage the BIC 7210 (for example, the parameter calculation application 7212) on the hub 100. A call to the API 7214 can be made for the BIC 7210 to implement the user inputs. For example, the BIC 7210 (for example, the parameter calculation application 7212) can provide an alert to the monitoring hub 100 when the patient's heart rate is above (or below) a certain threshold number. The monitoring hub 100 can present a user interface element (for example, a slider) for a user to configure the threshold number. A user of the monitoring hub 100 can actuate the user interface element to set or update the threshold number. The changes to the threshold number can be communicated by the monitoring hub 100 to the BIC 7210 such that the BIC 7210 will update the threshold to the new number and generate an alert when the new threshold number is met. The monitoring hub 100 can invoke one or more functions in the API 7214 to pass the threshold number to the BIC 7210.

When the hub 100 or the sensor 7202 is attached to a new patient, the hub 100 can automatically notify the BIC 7210 such that the BIC 7210 may automatically update the parameter calculation application 7212 or algorithms associated with how parameter data is interpreted. For example, once a new patient is attached to the monitoring hub 100 and the sensor 7202, the monitoring hub 100 can call the API 7214 to reset patient's baseline data for calculating the parameter associated with the sensor 7202. Although these examples are described with reference to changing the settings of the BIC 7210 by the hub 100, similar techniques can also be used to update other medical devices or components of medical systems.

The operating system (OS) 7216 can be configured to support the parameter calculation application(s) 7212, the API 7214, other components of the BIC 7210 that are not shown in FIG. 72A, individually or in combination. The OS 7216 can be a real-time operating system (RTOS), a non-RTOS, or other type of proprietary or non-proprietary OS (such as a form of Linux).

As shown in FIG. 72A, the sensor cable 7204 can connect to a cable connector 7220. The cable connector 7220 can include a cable which connects with the BIC 7210 to achieve connection with the sensor cable 7204. The cable connector 7220 can be connected to the monitoring hub 100 via the channel ports 212 (for example, by plugging into a channel port of the monitoring hub). In various other implementations, the cable connector can also connect to the monitoring hub 100 via other types of ports. For example, the sensor cable 7204 can also be connected to the monitoring hub 100 via the serial ports 210. Although not shown, the cable connector 7220 can also include a processor. Optionally, the BIC can be entirely located in the cable connector 7220 instead of in a separate board elsewhere in the cable.

The cable connector 7220 can include the example cable connectors shown in FIGS. 11A-11K. The cable connector 7220 can include a memory 7220 for storing information describing the type of data the hub 100 can expect to receive and how to receive the same. The memory 7220 can be the EPROM shown in FIG. 12. The cable connector 7220 can include software or firmware stored in the memory 7220. For example, the software or firmware may cause the cable connector 7220 to self-describe the type and order of incoming data using a self-describing language, as discussed above. The cable connector 7220 can also implement at least a portion of the functions for the parameter calculation application 7212 or the API 7214.

The sensor cable 7204 and/or the cable connector 7220 may be provided by a manufacturer or a supplier of the monitoring hub. The third-party provider may use the SDK described herein to program the BIC 7210 with various functionality. For example, the third-party provider can provide various functions of the parameter calculation application(s) 7212 and the API 7214 to expand the functionalities of the monitoring hub 100. Detailed descriptions related to functions that can be enabled by the SDK are further described below with reference to FIG. 74.

VI. Examples of Interfacing Sensors and the Hub Via a Dongle

Figure 72B:
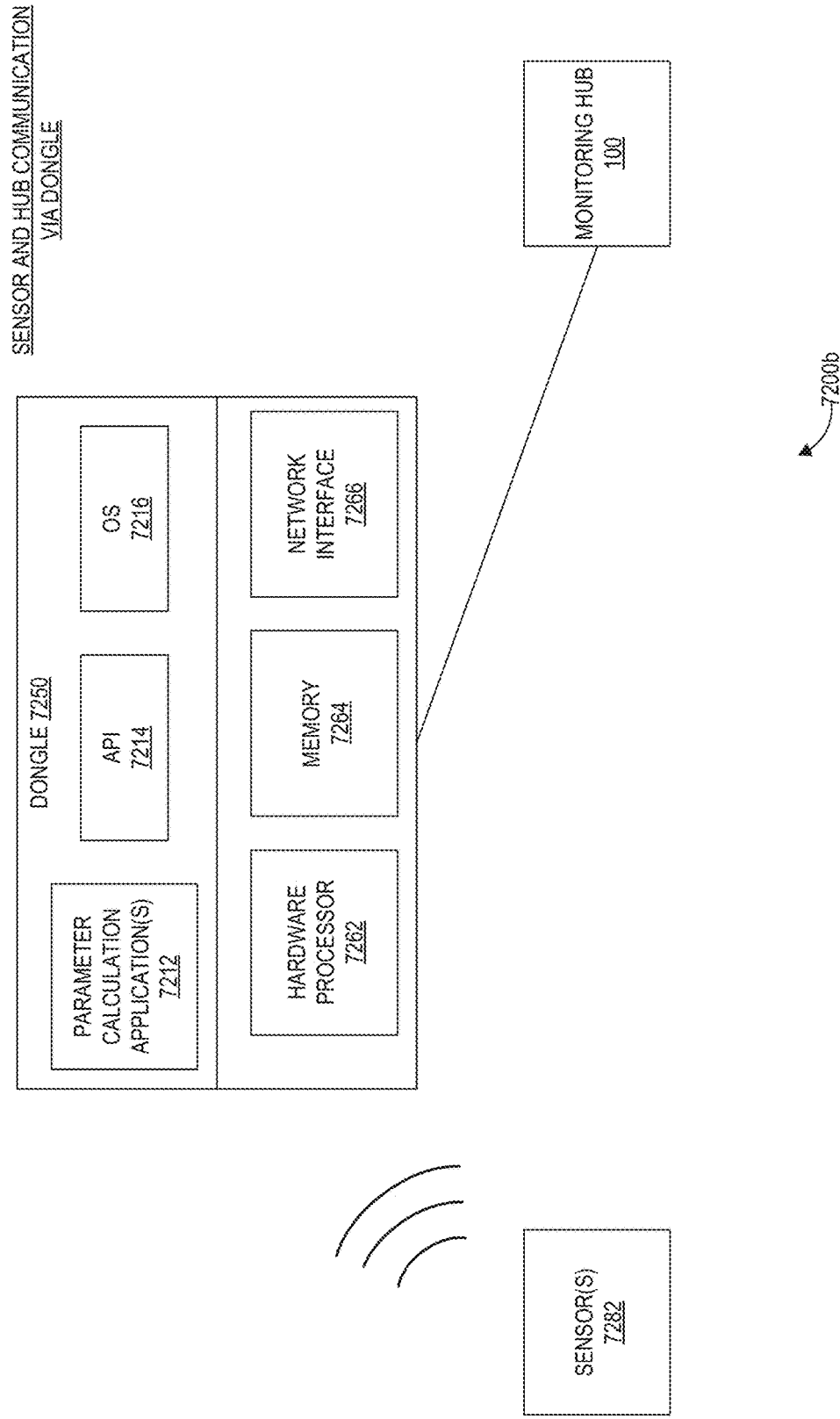
FIG. 72B illustrates an example of interfacing the hub with an external sensor using a dongle.

The monitoring hub 100 may be connected to the BIC or to other sensors or devices via a wireless connection. The wireless connections may involve Bluetooth, Wi-Fi, ZigBee, or other types of wireless connections. FIG. 72B illustrates an example of wireless connections to the monitoring hub. In the example computing environment 7200b, the wireless connection to the monitoring hub 100 is achieved through a dongle 7250. The dongle 7250 can be a wireless version of the BIC 7210 described above. The dongle 7250 can be connected to the monitoring hub via a connection port, such as, for example, a USB port, or other types of ports on the monitoring hub. The dongle can be paired with the monitoring hub 100 and the sensor 7282 (or the device associated with the sensor 7282). The dongle can receive patient data wirelessly from the sensor(s) 7282 and communicate the data to the monitoring hub 100.

The dongle 7250 can include a processing unit which may include a hardware processor 7262, a non-transitory memory 7264, and a network interface 7266. The processing unit can perform functions such as, for example, pairing, data receiving and transmissions, data processing, parameter calculations, and various other functions for the dongle 7250. The dongle 7250 can be configured to implement certain functions similar to those of the BIC 7210. For example, the dongle 7250 can be configured to execute the parameter calculation application(s) 7212, the API 7214, and the OS 7216.

As an example of data processing by the dongle 7250, the dongle 7250 can receive data for a patient parameter from the sensor 7282. The dongle 7250 can execute an algorithm in the parameter calculation application 7212 to generate a numerical value describing the patient parameter and communicate such numerical value to the monitoring hub 100 for further processing or display. As another example, the dongle 7250 can communicate display settings associated with the patient parameter to the monitoring hub 100 which may override or supplement a default setting of the display of the monitoring hub 100.

VII. Example Communications Between Sensors and the Hub

Figure 73A:
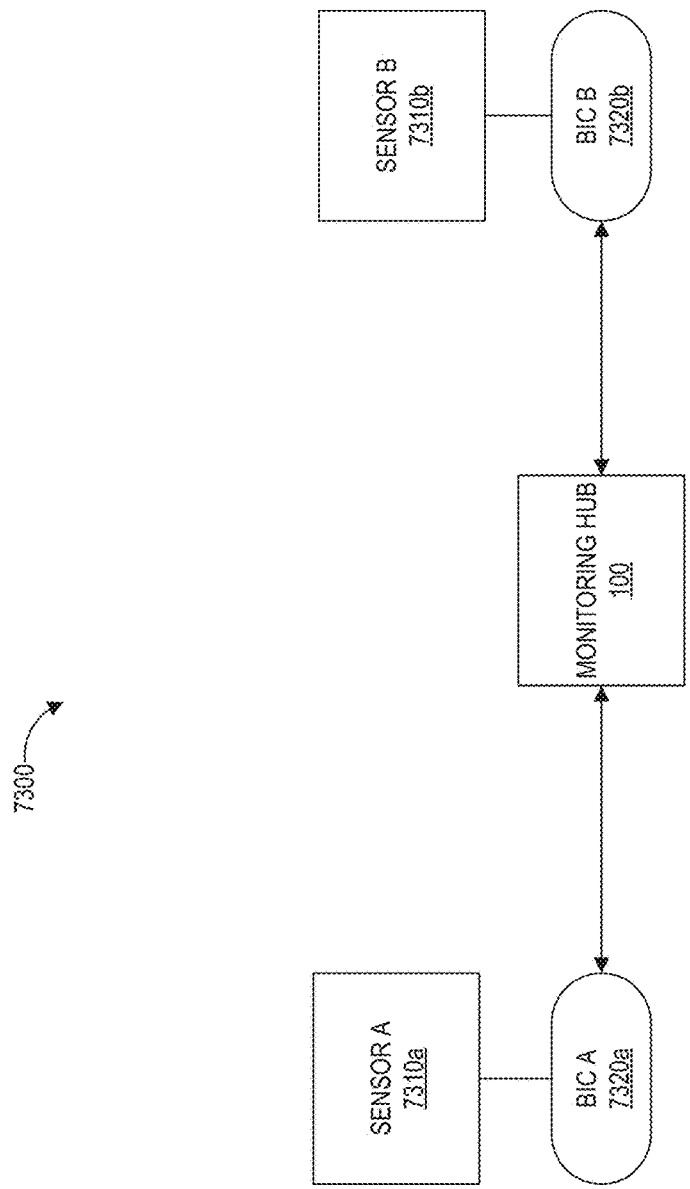
FIG. 73A illustrates an example computing environment of communications between sensors and the monitoring hub.

FIG. 73A illustrates an example computing environment for communications between BICs and the monitoring hub 100. The computing environment 7300 shown in FIG. 73A includes a sensor A 7310a and its corresponding BIC A 7320a, as well as a sensor B 7310b and its corresponding BIC B 7320b. The sensors A 7310a and B 7310b can be connected to the monitoring hub 100 via the respective BICs 7320a and 7320b. Although not shown, the sensors A and B may be part of a medical system or a patient device for monitoring one or more patient parameters. The BICs 7320 can include any of the functionality of the BICs described above.

The BICs 7320a and 7320b can pass data acquired by the sensors 7310a, 7310b respectively to the monitoring hub 100 where the monitoring hub 100 can perform data processing to derive patient parameter data, waveforms, alarms, and other results. The hub 100 can receive data from any BIC and incorporate the data in the calculation of one or more parameters. As an example, the monitoring hub 100 may calculate a respiratory rate from an acoustic sensor using an algorithm native to the monitoring hub 100 and may also calculate a heart rate from the respiratory rate data. If an external ECG device is attached to the monitoring hub 100 (for example, as a BIC connected to ECG sensors), the monitoring hub can use the ECG data (which may be more accurate than the acoustic data) to calibrate the acoustic heart rate algorithm or to update a confidence value for outputs generated based on the acoustic data (e.g., the closer the acoustic HR is to the ECG HR, the higher the confidence value output to the user).

In addition to or in alternative to communicating data acquired by the corresponding sensor, a BIC can also communicate display settings to the monitoring hub 100 to affect or control the graphical configurations of the monitoring hub 100. The monitoring hub 100 can provide a display framework for various patient parameters or other indices. For example, the hub 100 can provide standardized graphical interfaces depending on the display characteristics of the medical systems. The framework may include default location, layout, size, format associated with the display for various of parameters. The BIC can provide data to the hub 100 to populate the framework.

The BICs can self-define a numerical readout, a graph, or other specified display characteristics. The self-defined display characteristics can be programmed into the BICs associated with the respective medical systems (for example, via the SDK described in FIG. 75). The BICs can provide these display characteristics to the monitoring hub, which may override or supplement one or more display configurations of the monitoring hub 100. As an example, the monitoring hub 100 can initially be connected to the BIC 7320a. The BIC 7320b can be added to the monitoring hub 100 to provide data on a new parameter. When there is a new parameter to be added to the display, the BIC 7320b can provide the display characteristics for this parameter, such as, for example, the label to be shown on the hub 100, forms of how the values are to be displayed (for example, a numerical value, graphs, letter grades, etc.) color on the screen of the hub 100 (for example, a blue v. a green color), layout of information for the parameter, etc. The display characteristics can be published on the bus of the monitoring hub 100, and the monitoring hub 100 can implement the display characteristics for displaying the values received from the BIC 7320*b*.

The BICs can also send images or display graphics for use in place of monitoring hub's graphics. For example, the BIC can provide an image or an animation of a pumping heart to the hub 100 for displaying the heart rate measurements from the BIC. The heart may change color or increase in size in response to an alarm associated with the heart rate (for example, when the heart rate is too fast or too slow). As another example, the display characteristics received from the BIC can include a graphics command that accesses a graphics library (such as OpenGL). With reference to the preceding example, the command can cause the hub 100 to call one or more functions in the graphics library to draw a heart shape.

Advantageously, the BICs, once connected to the hub 100, can pull from or push to the hub any information. For example, a connected BIC A can pull measured parameters of connected BIC B from the hub 100. For example, the connected BIC A can notify the hub 100 to send data associated with a parameter labeled x. The hub 100 can accordingly communicate the data with label x to the connected BIC A as the hub 100 obtains such data. The BIC A can then use that information to generate a new measured parameter which can then be pushed to the hub for display or use by other connected medical systems. As an example, a BIC (or the monitoring hub) can calculate a wellness index (described above) based on any parameter data from any other BIC(s) and/or from the monitoring hub.

A BIC can perform data processing based on data acquired from its corresponding sensor (or medical system), other sensors (or medical systems), or the hub 100, alone or in combination. With continued reference to FIG. 73A, BIC 7320*a* can use data from the sensor 7310*a*, the sensor 7310*b*, the BIC B 7320*b*, or the monitoring hub 100, individually or as a combination, to perform data processing. As an example, sensor A 7310*a* can measure a patient's respiratory information and BIC A 7320*a* can calculate the respiratory rate from data acquired from sensor A 7310*a*. BIC A 7320*a* can also calculate the respiratory rate from the heart rate data (for example, where the heart rate modulates respiratory rate). BIC B 7320*b* can receive the ECG data from the sensor B 7310*b*. The BIC B 7320*b* can calculate the heart rate based on the ECG data and pass the heart rate to BIC A 7320*a* for the determination of the respiratory rate. The BIC B can also pass the ECG data to BIC A and BIC A can perform the calculation of the heart rate. The resulting respiratory rate and the heart rate can be communicated to the hub 100 for further processing or display.

The monitoring hub 100 may implement a restriction mechanism associated with types of data that can be obtained by a BIC. Or, the monitoring hub 100 may adopt an open port policy such that there is no restriction on what the BIC can obtain from the hub 100. In one example policy, the BIC can obtain all waveforms from the monitoring hub 100, such as those associated with SpO2, pulse rate. Every time when the BIC receives a message from the hub, in this example, the BIC can pull these waveforms out of the received message.

In addition to or in alternative to performing calculations based on data received from a BIC, the BIC can use the information received from the hub or other BICs for other types of actions. For example, the received data may be used to calibrate an algorithm used for processing data received from a sensor connected to the BIC. As another example, the BIC can restart its processing algorithm or establish a new baseline based on information received from the hub or other devices. In this example, a BIC may receive a message from the hub 100 which includes indications that the hub 100 or the sensor corresponding to the BIC is attached to a new patient. The BIC can accordingly reset the processing algorithm or calculated baseline value for different physiological parameters in response to this message. Additionally or optionally, the BIC may create a new profile for the new patient and may start monitoring of patient parameters or calculations associated with the patient parameters from scratch.

As another example, the BIC can calculate an alert for the patient and output the alert to the hub 100. The hub 100 can display a graphical user interface element for adjusting settings of an alert. For example, the user of the hub 100 can actuate the graphical user interface element to change the threshold condition for triggering the alert. The hub 100 can communicate the updated alarm setting to a BIC for incorporating in its calculation. For example, a user may increase the value of the heart rate for triggering the alarm by the BIC. Such increase can be sent to the BIC, which may no longer generate the alarm if the heart rate is below this updated value. The hub 100 can also remotely control other operations of the BIC in addition to or optionally changing the alarm settings, as will further be described with reference to FIG. 73D.

Although examples in FIG. 73A are described with reference to bidirectional communications between BICs and the monitoring hub 100, in various other situations, the similar data or communication techniques can also be applied for communications between the monitoring hub 100 and other types of medical devices. Further, similar techniques and functions can also be applicable when the sensor (or the BIC) is connected to the hub 100 via a dongle. For example, the dongle can pull information from the monitoring hub 100, such as, for example, patient's alert information, waveform, patient parameter data, medical event information, etc. Such information can be acquired from various channels such as, for example, via the monitoring hub 100 itself, or other external medical devices connected to the monitoring hub 100. The dongle can also communicate display settings, perform calculations on this information, and communicate the results of the calculations to the monitoring hub 100.

Figure 73B:
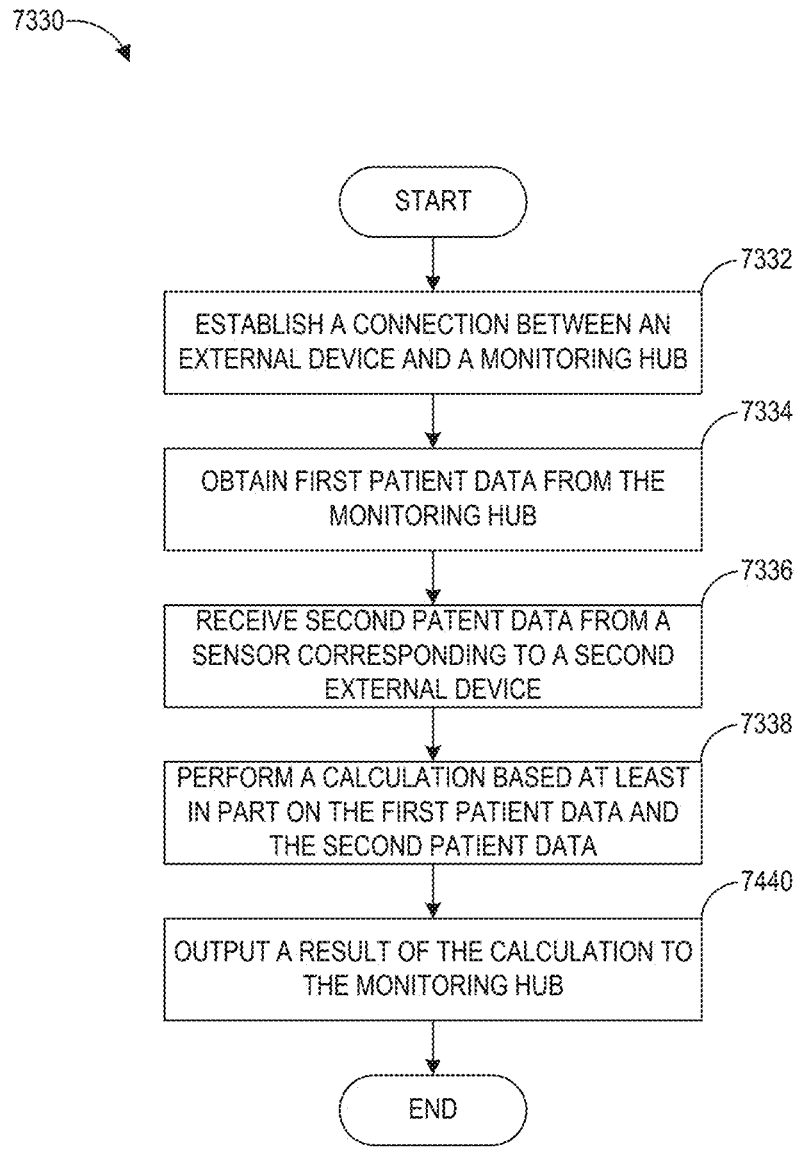
FIGS. 73B, 73C, and 73D illustrate example processes for various aspects of communications between the hub and external devices.
Figure 73C:
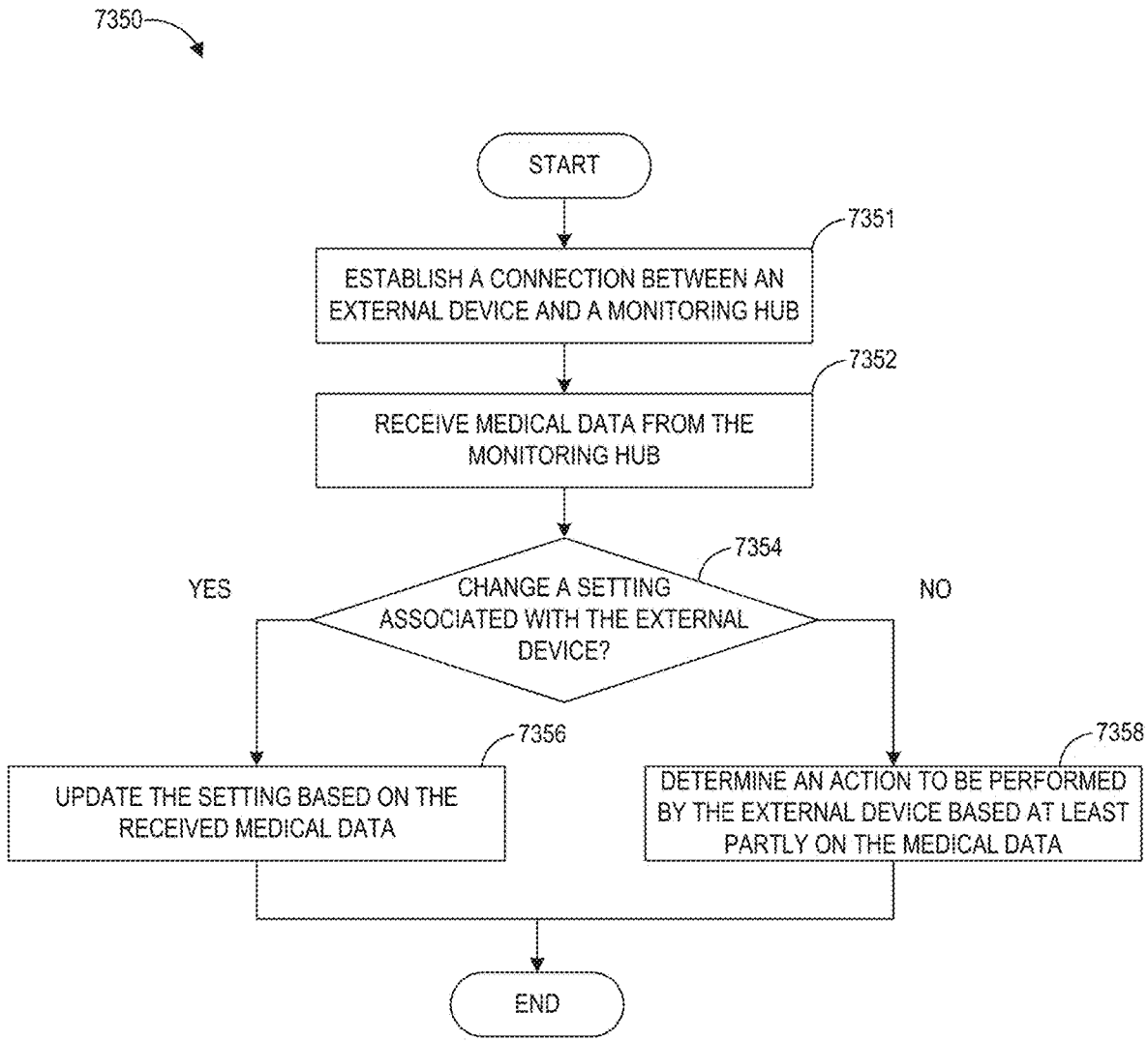
Figure 73D:
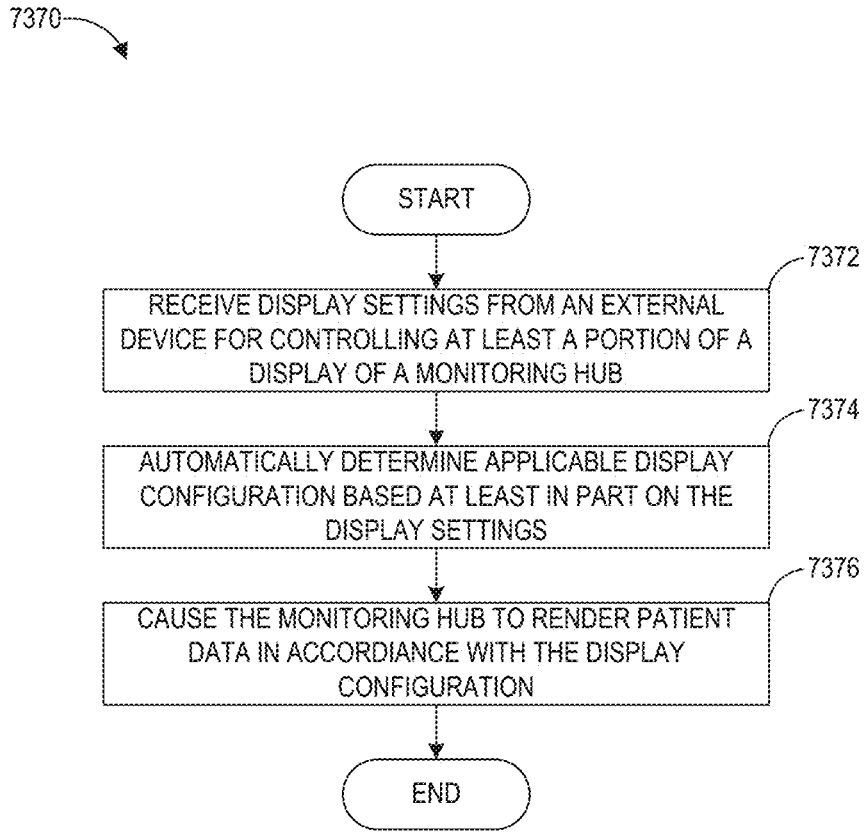

FIGS. 73B, 73C, and 73D illustrate example processes for various aspects of communications between the hub and external devices. The external devices may be the BIC 7210, the dongle 7250, or other patient devices described herein.

FIG. 73B illustrates an example process which an external device can perform data processing based on data acquired form the monitoring hub or other external devices. The example process 7330 in FIG. 73B may be performed by the external device.

At block 7332, a connection can be established between a first external device and the monitoring hub. The external device can implement the parameter calculation application 7212 described with reference to FIG. 72A to perform calculations on data received at the external device, where the data may come from a sensor, a monitoring hub, or another external device. The connection between the external device and the monitoring hub may be a wired or wireless connection. For example, the external device can connect wirelessly to the monitoring hub or in a wired connection through a BIC.

At block 7334, the external device can obtain patient data from the monitoring hub. The first patient data may include data acquired from one or more sensors native to the monitoring hub or another external device. Additionally or optionally, the first patient data may include results outputted by one or more algorithms derived by the monitoring hub or the other external device. For example, the first patient data can include values associated with one or more patient parameters, such as, for example, a value associated with the patient's blood pressure or heart rate. Although in this example, the external device can obtain the first patient data acquired by another external device through the monitoring hub, the external device can also acquire the first patient data directly from the other external device.

At block 7336, the external device can receive second patient data from a sensor corresponding to a second external device. The second external device can be a BIC, dongle, or other patient device. The sensor can monitor and acquire patient data and communicate the patient data to the second external device for further processing.

At block 7338, the first external device can perform a calculation based at least in part on the first patient data and the second patient data. For example, the first external device can calculate a wellness index based on heart rates and blood pressures.

At block 7440, the first external device can output the result of the calculation to the monitoring hub. The monitoring hub can further process the data from the first external device or display the result on a user interface of the monitoring hub. The first external device can also communicate the result to other external devices.

FIG. 73C illustrates an example process where the external device can initiate an action based on data received from a monitoring hub. The example process 7350 can be performed by an external device.

At block 7351, a connection is established between the external device and the monitoring hub. At block 7352, the external device can receive medical data from a monitoring ub. The medical data can include instructions to the external device to perform an action (for example, an instruction to reset a baseline in an algorithm or to set a threshold for an alarm) or data describing a triggering event (for example, a message informing that the new patient is linked). Additionally or optionally, the medical data can also include values associated with patient parameters as described with reference to FIG. 73B.

At block 7354, the third-party device can detect whether the medical data received from the monitoring hub includes an instruction to change a setting of the external device.

If the instruction to change the setting is present in the medical data, at block 7356, the external device can automatically update the setting based on the received medical data. For example, when a new patient is linked to the monitoring hub, the monitoring hub can send an instruction to the external device to reset the external device's calculations or baselines for algorithms. As another example, the instruction can include an adjustment to a threshold condition for triggering an alarm.

Additionally or optionally, the external device may analyze the medical data and generate one or more instructions for actions based on the medical data. For example, the monitoring hub can send information to the external device that a new patient is linked. Upon receiving this information, the external device can determine one or more actions to be taken due to the newly added patient. For example, the external device can reset the patient's baseline data or create a new profile for the patient.

FIG. 73D illustrates an example process of adjusting display settings of a monitoring hub by an external device. The example process 7370 can be performed by the monitoring hub described herein.

At block 7372, the monitoring hub can receive display settings from an external device, such as, for example, a dongle or a BIC. The display settings can be configured to manage display characteristics of at least a portion of the display for the monitoring hub. For example, the display settings can provide the labels, colors, images, layout, format of data presentation, etc., for values and parameters communicated from the external device. The display settings can override, set, or supplement existing user interface configurations for the monitoring hub as described with reference to FIG. 73A.

At block 7374, the monitoring hub can automatically determine applicable display configuration based at least in part on the display setting. For example, the monitoring hub may be connected to two external devices. The first external device can provide values for a first patient parameter while the second external device can provide values for a second patient parameter. The display setting received from the first external device may include several options for displaying information of the first patient parameter. The monitoring hub can select a display option for the first patient parameter in view of the display characteristics of the second patient parameter. For example, if the second patient parameter requires a large display region on the user interface, the monitoring hub may select a display setting which occupies a small amount of user interface space for the first patient parameter.

At block 7376, the monitoring hub can automatically render patient data in accordance with the display configuration. As the monitoring hub continuously receives values associated with the patient parameters, the monitoring hub can update the values on its user interface in accordance with the display configuration.

Figure 73E:
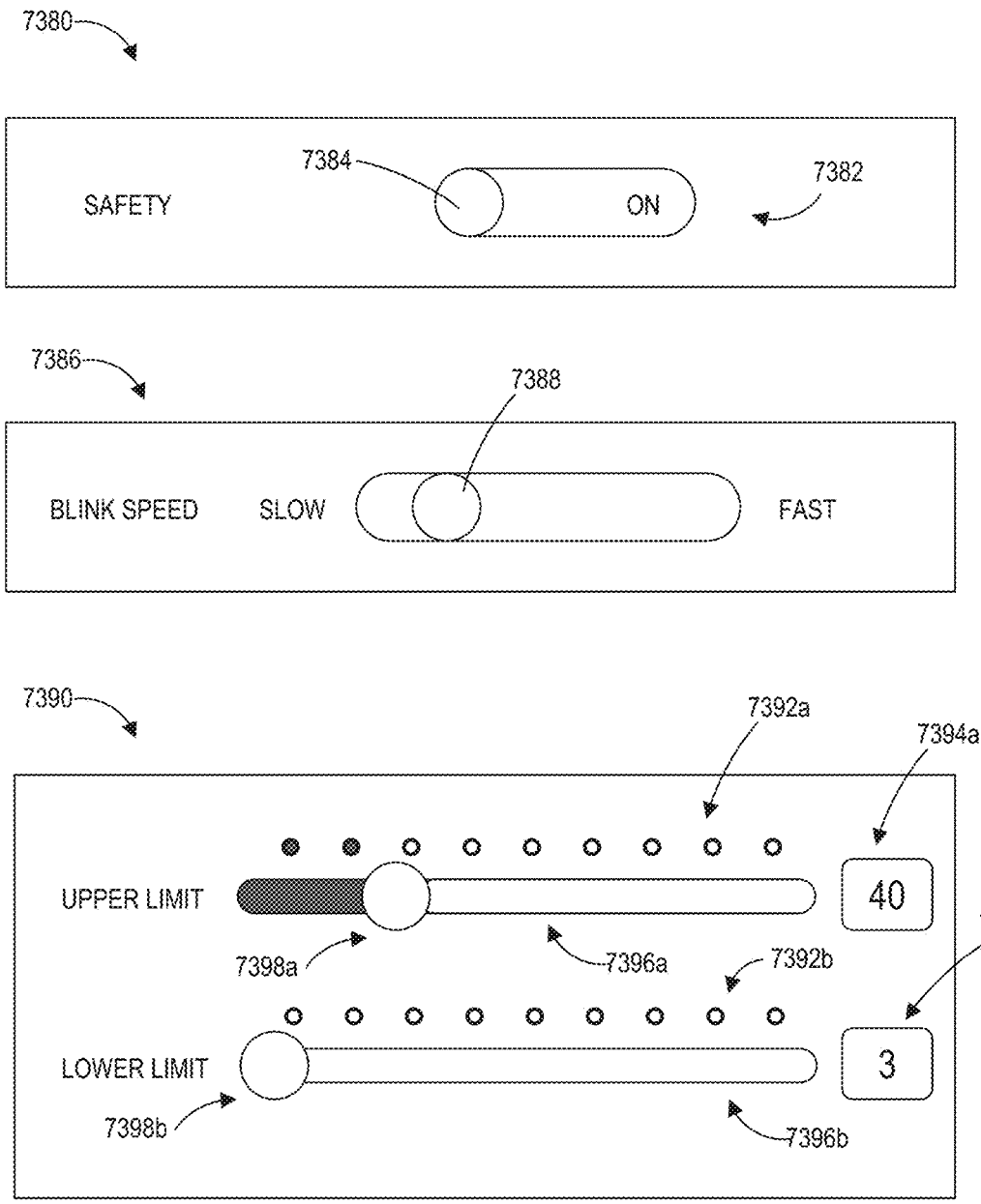
FIG. 73E illustrates example user interface elements of a monitoring hub for remotely controlling one or more operations of an external device.

FIG. 73E illustrates some example user interface elements for controlling an operation of a BIC or other external device remotely. Three user interface elements 7380, 7386, and 7390 are shown in FIG. 73E. These user interface elements can be output on the hub 100 and can receive a user input to control the operation of one or more medical devices connected to the hub 100.

The user interface 7380 shows an example slider bar 7382 for changing a safety feature between two states (for example the on and off states). As shown in FIG. 73E, the user interface element 7384 of the slider bar is all the way to the left of the slider bar which shows that the safety feature is currently turned off. The user can move the user interface element 7384 to the right side of the slider bar to enable the safety feature.

The user interface element 7384 controls the blink speed for information associated with a parameter. The blink speed feature may also have two states: an on state and an off state. Additionally or optionally, the blink speed feature can be adjusted based on numerical values. For example, a user can slide the user interface element 7388 on the slider bar of the user interface element 7386 to adjust the blink speed.

FIG. 73E also illustrates a user interface element 7390 where a user can adjust the limits of an alarm. The user interface element 7390 includes two slider bars 7396a and 7396b. The slider bar 7396a can be configured to adjust an upper limit of an alarm, whereas the slider bar 7396b can configured to adjust a lower limit for triggering the alarm. A user can move the user interface elements 7398a and 7398b to adjust the upper and lower limits respectively. The slider bars 7396a, 7396b may be associated with a row of user interface indicators 7392a, 7392b respectively. The user interface indicators 7392a, 7392b can provide visual cues on the values of the alarm limits in a spectrum of possible values. For example, the current position of the user interface element 7398a on the slider bar 7396a corresponds to two illuminated circles of the row of user interface indicator 7392a. Because there are nine circles in the row while two of them are illuminated, this can provide a cue that the upper limit for the alarm is set at a relatively low end. The slider bars 7396a and 7396b can also correspond to the user interface elements 7394a and 7394b which can which can show the numeric values of the current alarm limits. In addition to or in alternative to moving the user interface elements 7398a, 7398b to adjust the slider bars 7396a, 7396b respectively, a user may input the values of the alarm limits into the user interface elements 7394a, 7394b to adjust the alarm limits. The positions of the user interface elements 7398a, 7398b on the slider bars 7396a, 7396b may be automatically updated in response to the inputted values.

As will further be described with reference to FIG. 74, the adjustments on the user interface elements 7388, 7390 or the state change made on the user interface element 7380 can be communicated to the medical device by invoking the interface code 7430 associated with the medical device. Further, the hub 100 may communicate the adjustments to multiple connected medical devices where the adjustments on a user interface element affect more than more medical devices.

VIII. Example SDK Architecture for Enabling Functions of the Hub and Third-Party Devices As described above, the hub provider can provide an SDK to a device supplier. The SDK can define various aspects of the communications between the hub 100 and external device. The device supplier can use SDK to program various external devices, such as BICs, cable connector, or other medical devices.

As one example, the SDK can establish or define the behavior and meaning of the data output from the devices. The SDK can define communication protocols or the interpretations of the patient's parameter data (for example, formats, identifiers, etc.), display characteristics, waveforms, and alarms that can be communicated from the devices to the hub 100. The SDK can also allow the device supplier to specify display settings associated with data of the device. For example, the device supplier can use the SDK to specify available display format, layout for the data communicated to the monitoring hub 100 from the device. The data outputted by the device can be used as an input for the monitoring hub 100 and the monitoring hub 100 can apply one or more algorithms based on the data outputted by the device.

In addition to or in alternative to defining data output for communications from the device to the monitoring hub, the SDK can also support data acquisition by the external devices from the monitoring hub 100. For example, the SDK can be used to define an API 7214 which can receive messages from the hub and cause the device to perform one or more actions based on the information in the messages. For example, the monitoring hub can inform the device that there is a new patient or different patient connected to the monitoring hub. Based on this information, the device may restart its processing algorithm, create a new profile for the new user and start monitoring from scratch, or perform other actions that are suitable based on this new information.

The SDK can also be used to define the algorithms for performing calculations on data associated with the device. For example, the SDK can be used to implement an algorithm which calculates a value (for example, a wellness index) based on data received from devices or the monitoring hub 100.

Figure 74:
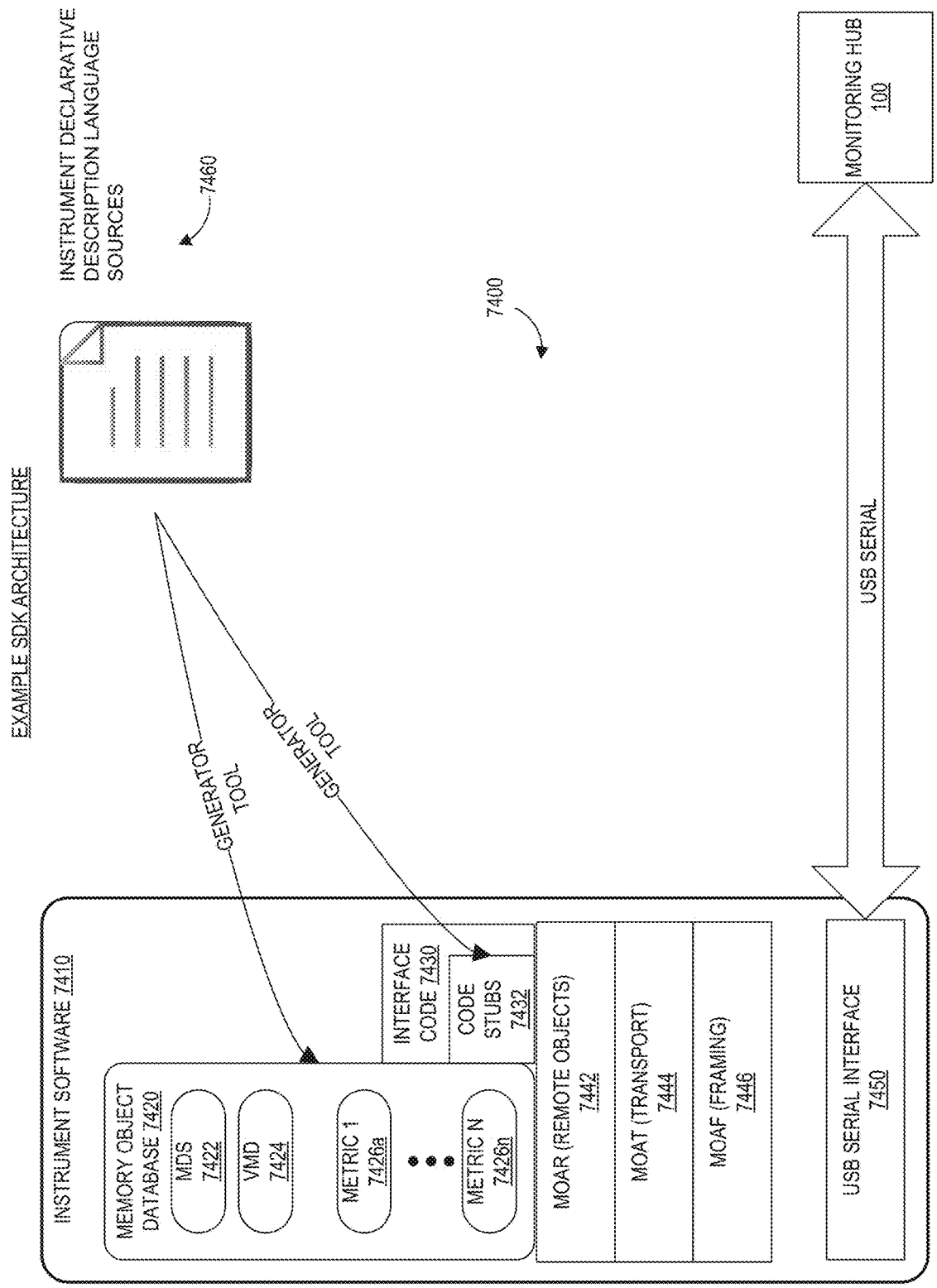
FIG. 74 illustrates some example features of a software development kit.

FIG. 74 illustrates some example features of an SDK software architecture. The computing environment 7400 includes a monitoring hub 100 and instrument software 7410 which can be implemented on the external device (which as described above, can be a BIC, dongle, or other patient device). The instrument software 7410 can be programmed using the instrument declarative description language sources 7460, which can provide tools and functions for creating the instrument software 7410.

The SDK may model an external device as a remotely accessible database of objects (illustrated as the object database 7420 in FIG. 74). This database of objects may be part of the parameter calculation application 7212 shown in FIGS. 72A and 72B. An object may be associated with an identity, an object class (which may be defined using the instrument declarative description language 7460), a set of attributes, a set of possible actions or methods that can be invoked remotely, a set of possible events that the object may signal to notify other devices, etc. The object database 7420 may include a set of predefined objects and/or new objects.

The object database 7420 is shown to have a medical device system (MDS) object 7422 which can be shown as an object representation of a medical device (e.g., an external device). A MDS object can include attributes, such as, for example, system type, system manufacturer and model name, unique identifiers (for example, serial number), system software and hardware version numbers, system status and operating mode, battery or power supply status, time, time zone, and clock synchronization information, etc.

Sometimes a single external device may include multiple relatively independent subsystems, either hardware or software. The virtual medical device (VMD) objects 7242 can model these subsystems. Attributes of a VMD object may include device status, device manufacturer and model name, software and hardware version numbers, principle or technology used to perform the measurement, etc.

Measurements for patient parameters (for example, vital signs) may be modeled as metrics class 7426a through 7426n. The measurements can include direct measurement values, as well as derived values that may depend on one or more vital signs measurements. The metrics class may include various metric characteristics such as, for example, update rate, relevance, whether it is directly measured or derived, measurement validity status, identifiers for the metric in nomenclature systems, unit of measure used, body site or sites involved in the measurement, other metrics used to compute a derived metric, calibration status, measurement times and periods, associated settings, etc. The metrics class can be further subdivided by the kind of data representation it uses. The measures can be represented as a numeric metric which may represent an ordinary scalar measurement value or as an array metric which may represent a series of measurements (for example, as a time series such as a waveform, or some other type of series such as histogram or spectrum distribution measurement).

Although not shown in FIG. 74, SDK can also configure conditions that trigger an alert by the medical device. The alert can be a patient alert representing some abnormal condition noted in the patient, or a technical alert representing some abnormal condition that may affect the operation of the device itself.

Certain aspects of the external device can be remotely changed by another device, such as, for example, the hub 100 or another external device. As an example, the SDK can configure a limit alert operation which can control the triggering condition for the alarm. For example, SDK can configure attributes for supporting high, low limits that will trigger the alert. The SDK can also configure a set value operation which can allow another device to control a numeric value of the external device (for example, a value for a patient parameter or a time that will trigger the alert). As another example, other types of operations of the medical device, such as, for example, blink speed (for example, of an indicator), safety mode, etc., can also be controlled remotely (for example, on a hub). The other device cannot directly access the object database 7420 within the medical device. The remote operations may be achieved by referencing the instance numbers of the operations through a service and control object which contains the operations.

Additionally or optionally, the SDK can also define control operations on the medical device for configuring display characteristics of the medical device's data on the monitoring hub. The SDK can define several attributes which can be communicated from the medical device to the monitoring hub as part of the display setting. As one example, the SDK can be used to configure a Vmo-Reference attribute of a control operation indicating what object the control is associated with (for example, a VMD object for device level controls, or a metric object for controls specific to a particular measured parameter). This association can control the layout of the hub's menus, so that VMD-related controls can be placed within sub-menus of the top-level menu for the device, and metric-level controls can be placed in sub-menus associated with the individual metrics. As another example, the placement of controls within the menus can also be configured by the SDK. For example, controls for the same group of operations can be placed within the same sub-menu.

A device remote to the medical device (for example, the hub 100) can control various settings and options via the interface code 7430. The interface code 7430 can be configured for controlling device-level, channel-level, and metric level functionalities of the medical device and can be configured to respond to requests for modifying the corresponding settings and options. The interface code 7430 can include code stubs 7432 which may be software executable code for controlling the settings and options. For example, the code stub 7432 can include software routines for a toggleflag operation which can enable, disable, or adjust a feature (for example, a blink speed or a safety mode of operation, etc.).

A user of the hub can adjust the user interface element (for example, the user interface elements 7380, 7386, or 7390 in FIG. 73E) to control the feature on the medical device. The software routines can be called in response to a user input on one or more user interface elements on the hub 100. As one example, the alert operation may include an upper limit and a lower limit (for example as shown in FIG. 73E) which can cause an alarm to be generated by the medical device. The upper limit can correspond to a first user interface element (for example, a slider bar or a box for inputting a value of the limit) while the lower limit can correspond to another user interface element. The actuation of either user interface element can cause the hub 100 to make a call to the interface code 7430 to implement changes to the upper or lower limit.

The instrument software 7410 can include one or more libraries for supporting functions associated with the memory object database 7420 and the interfaces between the hub 100 and the medical device. Some example libraries can include a MOAR library 7442 for dealing with functions associated with another device (for example, the hub 100), a MOAT library 7444 for transporting messages within the subsystems of the medical device or with another device, and a MOAF library 7446 which can be used in connection with the MOAT library 7444 and can frame data packets for message transportation.

The medical device can connect to the monitoring hub 100 via the USB serial interface 7450 although other types of interfaces can also be used. The serial interface 7450 may be part of the cable connector 7220 (which may have one or more pins supporting a USB interface).

IX. Examples of Display Management for the Monitoring Hub

As described in the preceding sections, the monitoring hub 100 can display patient data and alarms based on data received from various connected medical systems or sensors native to the hub 100. The connected medical systems can include BICs, dongles, medical devices, or sensors external to the hub 100, etc., alone or in combination. The sensors external to the hub 100 can be connected to the hub 100 using various connections described herein and do not have to be connected to the hub 100 via the BIC or the dongle described in the preceding sections.

The monitoring hub 100 can provide standardized graphical interfaces depending on the display characteristics of connected medical systems. The monitoring hub 100 can also receive display settings from the medical systems, where the display settings can be incorporated into the default graphical interfaces. For example, the medical systems can self-define to a numerical readout, a graph, or other specified display options which can be self-defined. The medical systems can also self-define display characteristic of the medical systems or parameters provided by the medical systems. For example, the medical systems can provide the size of the layout, the color of the layout, the parameters or graphics formats to be presented by the hub, etc. The attached medical system can also provide image data used by the hub to provide display graphics or provide instructions to call one or more graphics libraries on the hub to draw certain shapes. Based on the device information, parameter information, connected devices, or the display characteristics provided by the medical system, the hub can identify default graphical interface options. The hub can also modify or supplement default graphical interfaces based on the display setting received from the medical system.

The hub 100 can include a display layout manager that provides self-configurable display options. The hub 100 can determine which systems are connected to the hub 100 and what parameters or data will be provided by the systems. Such information may be obtained via the self-describing functions described in the preceding sections. The hub 100 can accordingly determine the self-configurable display options, such as, for example, how many rows or columns or subdivisions of the display that are needed to present the data from the connected system. Once the hub 100 obtains the display configuration information for each connected medical system, the hub 100 can automatically determine display real estate for each medical system parameter. The options for display real estate can be presented in the display layout manager. When a new system is linked or when an old system is removed, the hub 100 can automatically re-determine the display real estate. For example, when a sensor is removed from or connected to the hub 100, the hub 100 can automatically determine available display layouts based on changes or additions to parameters being displayed as a result of the removal or addition of the sensor.

The connected medical systems connected to the hub 100 can be preconfigured (for example, via the SDK described above) with a set of acceptable display layouts of various sizes. For example, a medical device can be configured to calculate and provide values for one or more patient parameters and the medical device can be pre-programmed with a set of display layouts for showing the values of the one or more parameters. As an example, the medical device may include an approximately rectangle-shaped display layout in which a label of a parameter and a value of the parameter are displayed on the top half of the rectangle while displaying a waveform of the parameter on the bottom half of the rectangle. The monitoring hub 100 can execute a display layout algorithm to determine different combinations of display layouts for the connected medical systems. The display layout algorithms can break display of the hub into known sizes, for example, a 2-column by 10-row grid. Because each connected system has a known set of layouts, a search engine of the display layout algorithms can use the know layouts for each connected system to find all possible combinations of layouts corresponding to the respective systems. The hub 100 can accordingly output the possible layouts and provide an option to a user to select any of the combined layouts. At least some of the combined layouts may cause the entire display or substantially the entire display to be occupied with data from the connected systems.

A display layout that uses the entire display may but need not use every pixel of the display to display data. Rather, such a display layout may allocate the entire display to the available parameters. For instance, if two parameters are displayed, each of the parameters may be allocated half of the display real estate (and each parameter may include waveforms and/or numerals that occupy a substantial portion of that allocated real estate). If ten parameters are displayed, each of the parameters may similarly be allocated ¹⁄₁₀th of the available display real estate. Thus, the same waveforms and/or numerals for a parameter may be larger if fewer other parameters are displayed or smaller if more other parameters are displayed. Optionally, instead of merely enlarging parameter numerals or waveforms, the display may provide additional data when additional real estate is available. For instance, a more detailed waveform or additional past trend values may be depicted. Of course, in other situations, at least some of the combined layouts may have unused or unallocated space on the display.

As further described with reference to FIGS. 76A-76C, a user may have the option to rearrange the layouts within the combined layout. The monitoring hub 100 can automatically select a default combination of layouts and the user can change the default using the display layout manager.

Additionally or optionally, the display layout management can also manage display options at a parameter-level. For example, each parameter may come with pre-configured spacing requirements or display requirements, for example, sizes of display options for the parameters, the amount of information provided for the parameter, etc. As an example, a parameter may come with two display options, where one display option requires two columns and two rows of the display and the other display option specifies two columns and four rows of the display. As another example, the display setting for the parameter may require two columns of space without specifying the number of rows.

As an example of managing display layouts at a parameter-level, a blood pressure sensor can be connected to the hub 100. The blood pressure sensor may have particular constraints, such as, for example, requirements for certain amount of space to display the blood pressure. The monitoring hub can look at all other parameters that need to be displayed and determine different configurations that can fit the blood pressure data. The monitoring hub 100 can use display layout algorithms similar to those described with reference to determining system-level display layouts to determine display layouts at the parameter-level. The monitoring hub 100 may display all variations of acceptable display layouts for the parameter and a user can automatically select a layout. The monitoring hub 100 can automatically select a default layout and the user can change the default layout using the display layout manager.

The hub 100 can consider both system-level layouts and parameter-level layouts. For example, the hub 100 can determine a set of combined layouts. One option in the set of combined layouts may include a first subdivision which includes a combined layout of two parameters from a first medical device and includes a second subdivision for a parameter from a second medical device. As another example, the set of combined layouts may include an option which has three subdivisions, where the subdivision one is for the first parameter from the first device, the subdivision two is for the second parameter from the first device, and the subdivision three is for the parameter from the second device.

The hub 100 can also support screen captures of current displays. For example, a user can capture a current screen by using hand gesture (for example, a three-finger swipe). The hub 100 can also provide an indication of the screen capture. For example, the screen can temporarily freeze and the background colors can be lightened momentarily to indicate the screen capture was successful. The screen captures can be time stamped and saved for later access or downloading from the hub 100.

Figure 75A:
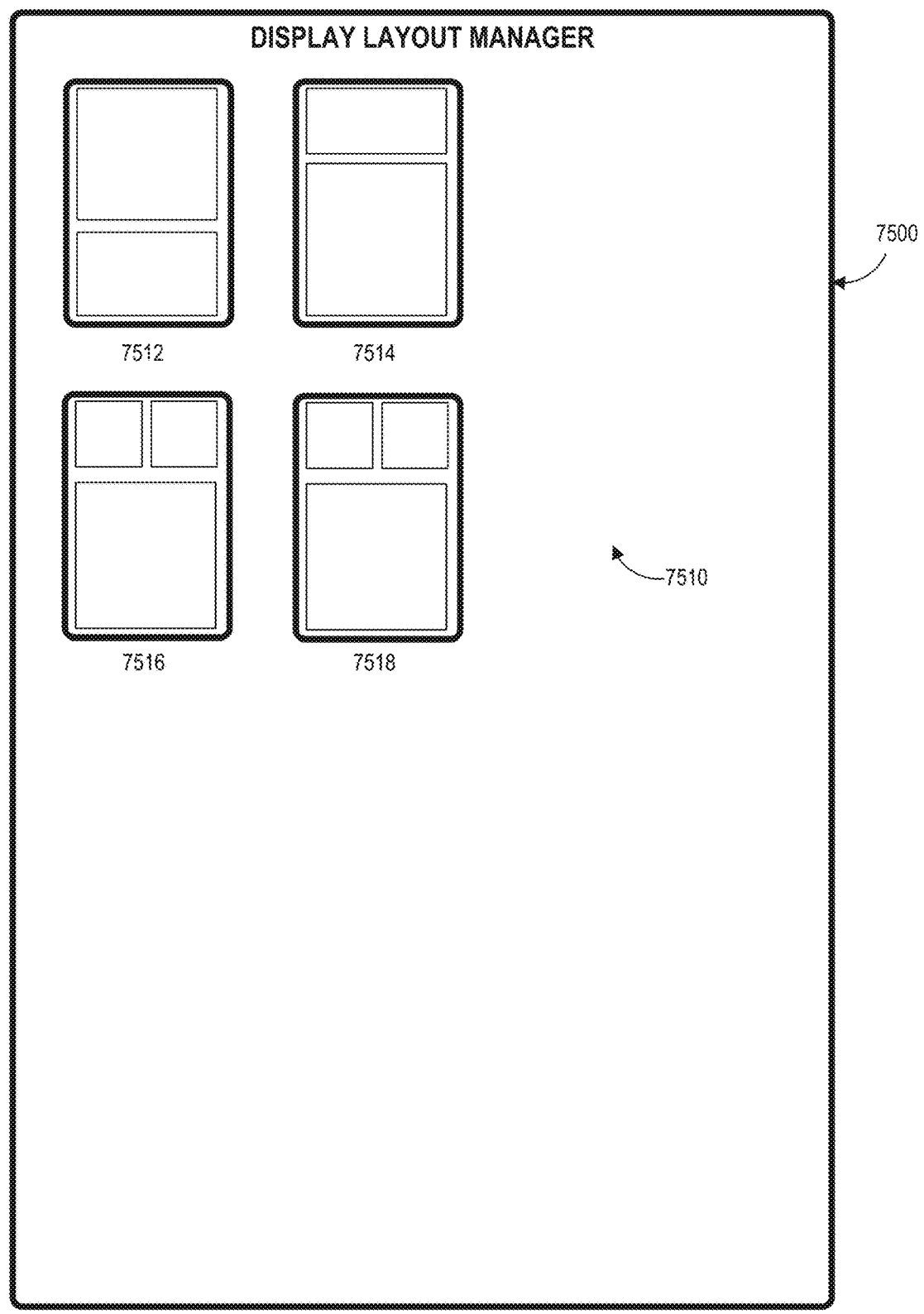
FIGS. 75A and 75B show example user interfaces of a display layout manager.
Figure 75B:
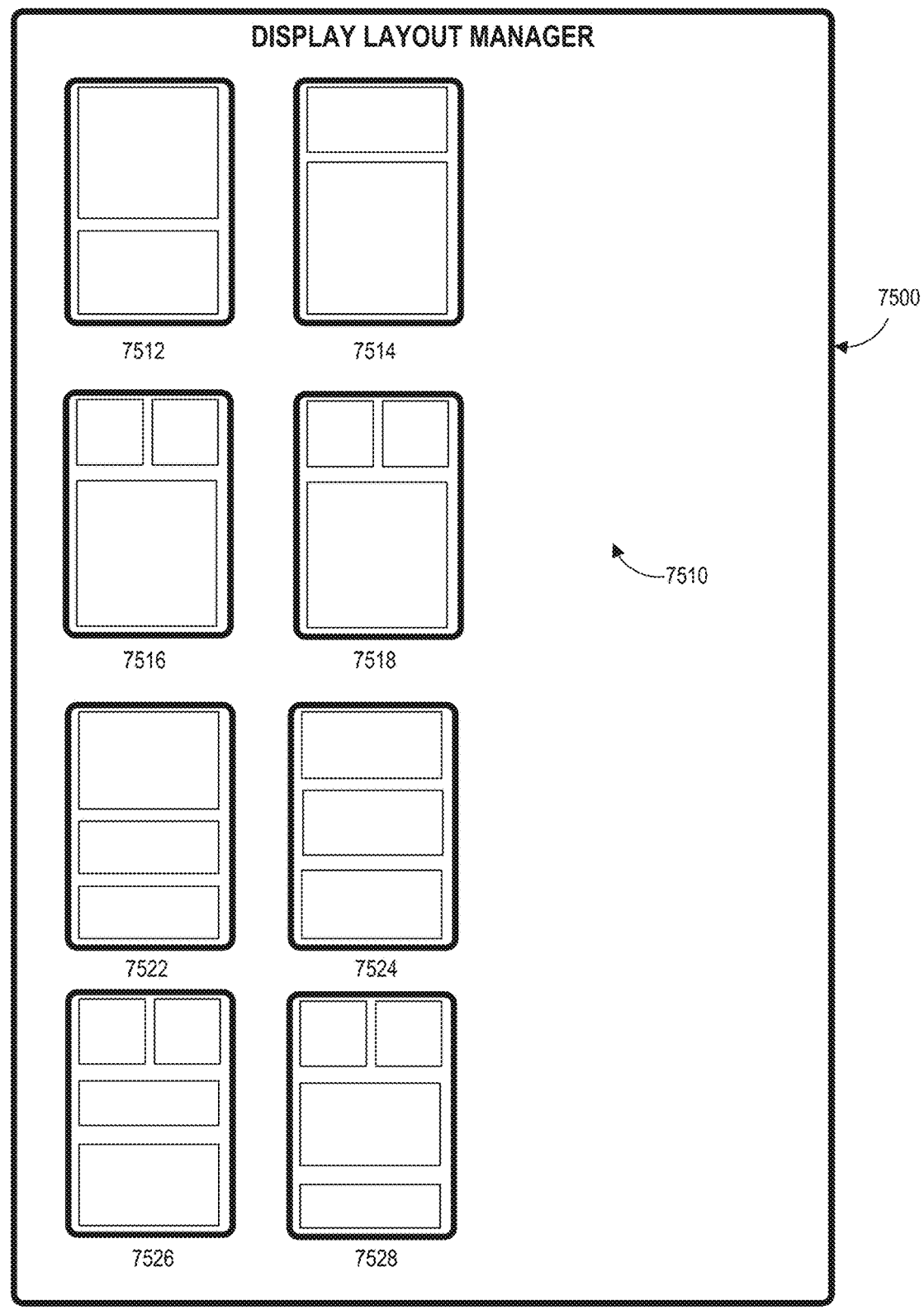

FIGS. 75A-75B shows example user interfaces of a display layout manager. In FIG. 75A, the hub's display 7500 can provide a display options menu 7510 which graphically illustrates a plurality of potential display configurations 7512, 7514, 7516, and 7518 (which schematically illustrate combined display layouts for each display configuration option). As described above, these layout options can be optimized and changed based on the types and number of connected systems or parameters.

FIG. 75B, for example, shows an alternative display layout manager screen with additional layout options when an additional medical system is connected to the hub. For example, the display 7500 of the hub additionally shows the layout options 7522, 7524, 7526, and 7528 when the additional device is connected. As more or different devices (or parameters) are linked to the hub, the hub automatically determines layout options and updates the layout options menu. Due to the display constraints of various devices or parameters, the number of layout options may decrease when additional systems or parameters are added to the hub.

The hub 100 can provide self-configuring options to the user such that the user can modify the display layouts. For example, when only one medical system is connected, the display configuration options can include a first plurality of display real estate allocation options to the user. When an additional medical system is connected, a second plurality of display real estate allocation options can be provided to the user that are different than, or in addition to, the first plurality of display real estate allocation options. The user can select an option or modify the layouts of subdivisions within the selected option.

Figure 76A:
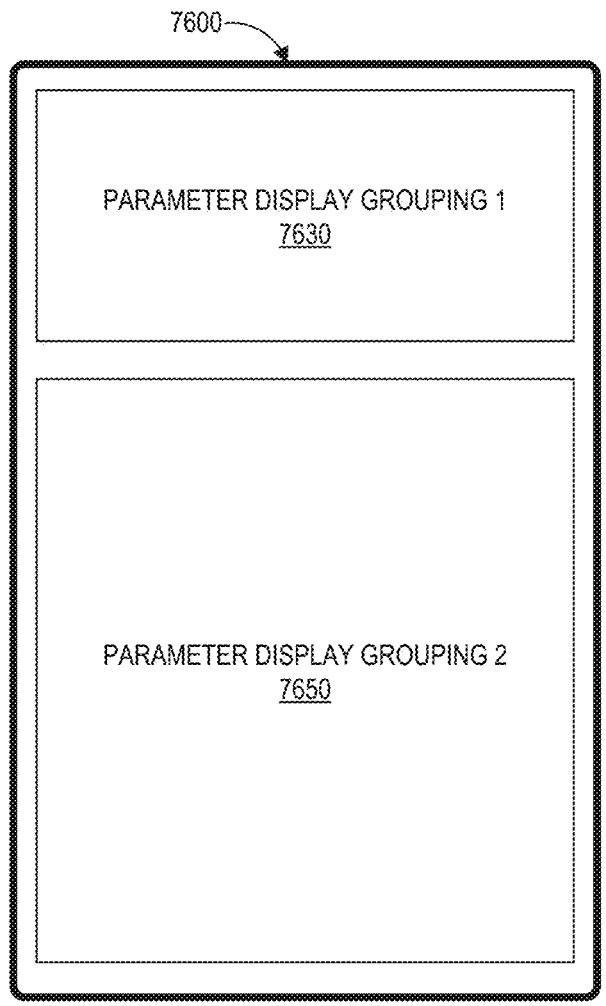
FIGS. 76A, 76B, 76C illustrate examples of a configurable display screen of the monitoring hub.

FIG. 76A illustrates an example of a configurable display screen of the monitoring hub. The screen 7600 of the hub 100 includes multiple different configurable display spaces (also referred to subdivisions) for different individual parameters or groups of parameters. The screen 7600 can include the display spaces 7630 and 7650 where each display space can present information of a parameter or a group of parameters. As an example, the parameter display grouping 1 7630 can correspond to the parameters SpO2, PR, SpHb, PVI, SpMet, SpCO shown in FIG. 23F whereas the parameter display grouping 2 7650 can correspond to the display of blood pressure and temperature shown in FIG. 23F. As an example, the parameter display grouping 1 7630 can be used to present data for SpO2, PR, SPHb, while the parameter display grouping 2 7650 is associated with the display of SEDLine shown in FIG. 23D.

Figure 76B:
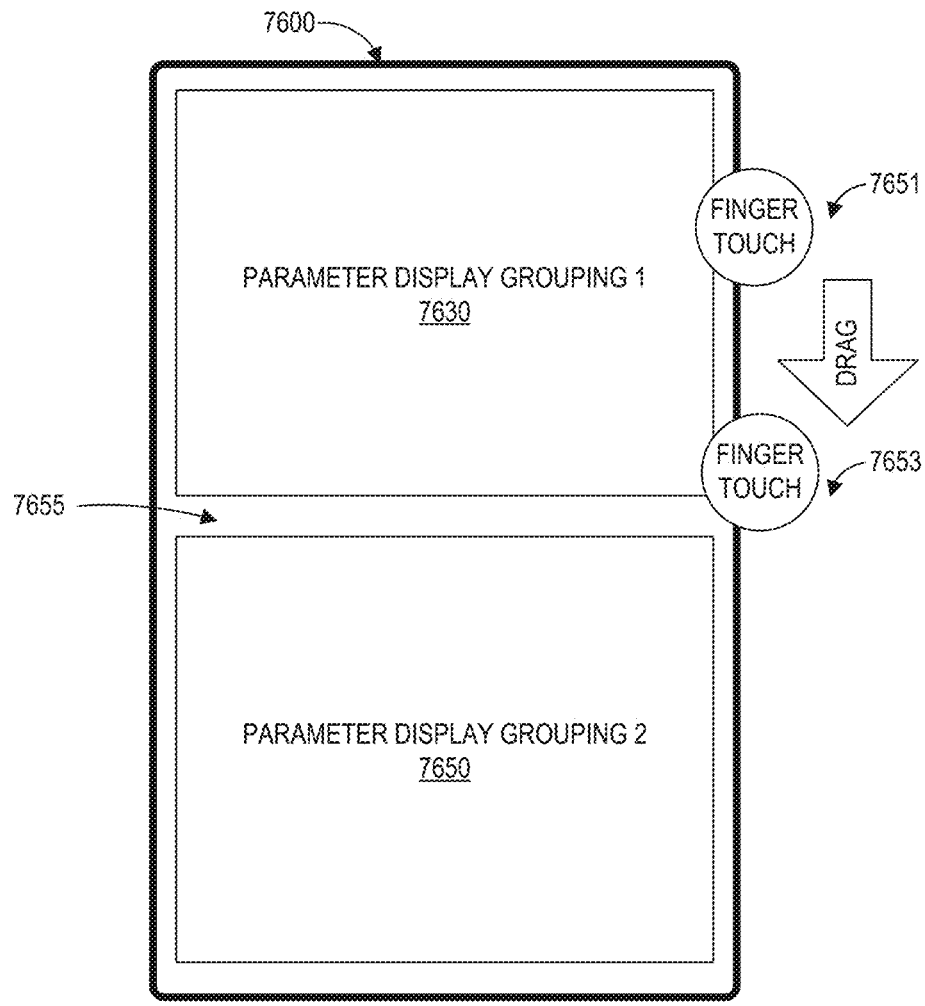
Figure 76C:
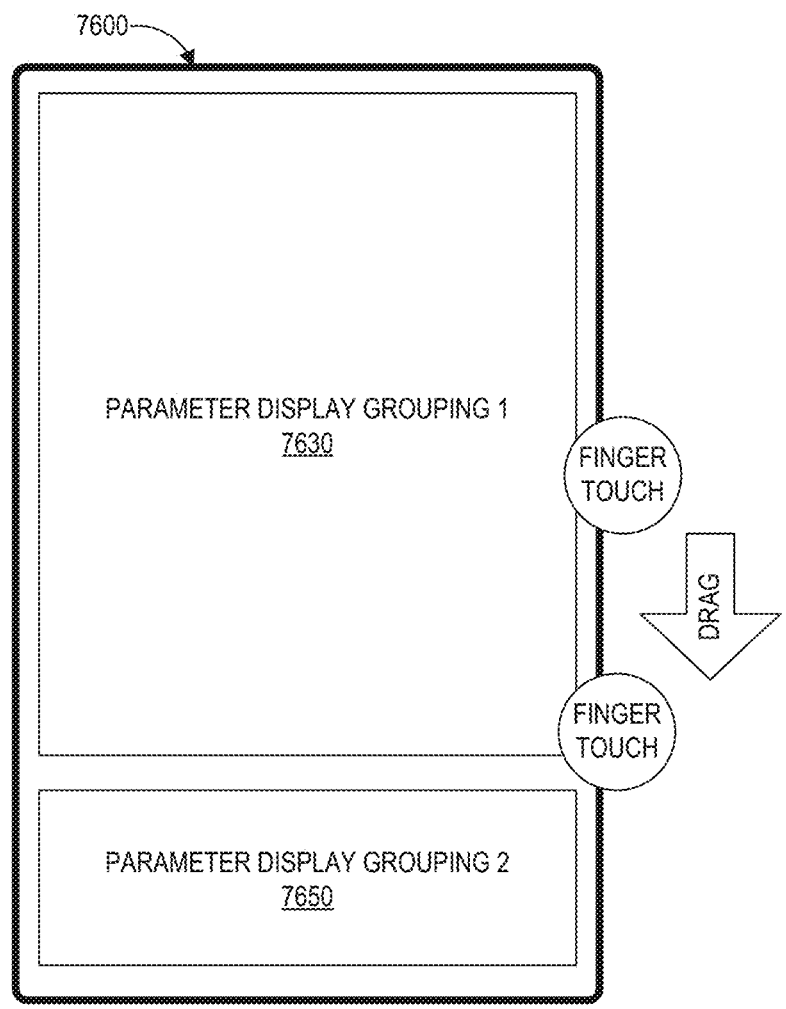

In the example in FIG. 76B, the display spaces can be dynamically adjustable by the user without having to enter a menu program. For example, a user can simple resize or reshape the display area using a touch screen monitor by dragging the display spaces to resize. As shown in FIG. 76B, the parameter display grouping 1 7630 can be adjusted to occupy larger space and the parameter display grouping 2 7650 can be adjusted to have less space at the same time. This can be done by using a finger touch 7651 to "grab" and resize the corners of the display by sliding a finger across the screen to the desired resized area and removing the finger touch 7653.

The hub 100 can optimize the display by resizing and/or adding or removing display features. For example, in addition to changing text size automatically through a reallocation of screen space, a trend display can be added when sufficient real estate space is provided. Additionally or optionally, the display areas 7630 and 7650 can be readjusted according to a snap grid operation. Thus, a user would need to adjust the display size until the display reaches the next snap grid for the adjustment to take place. FIG. 76C illustrates a further display change using the dynamic finger adjustments. In this figure, the area for the parameter display grouping 1 7630 is further enlarged through finger movements, and the hub 100 can automatically reduce the size for the parameter display grouping 2 7650 so as to fit both display groupings on the screen 7600.

As described above, a medical system (for example, a BIC, dongle, or a medical device, etc.) can use a function call through the API of the hub 100 to expose a user setting of the medical system on the hub's 100 display. This can be any settings—alarm settings, settings for inputting patient demographics, enabling or disabling monitoring functions or calculation of certain parameters, or any other settings. As one example, if the hub 100 is connected to a blood pressure device, it can connect to a neonate, child, or adult cuff. The blood pressure device can inform the monitoring hub (for example, via a BIC) to output user interface controls that allow a user to specify which type of cuff is connected to the hub 100 so that the blood pressure device (or the BIC) can apply the appropriate algorithm.

Figure 77:
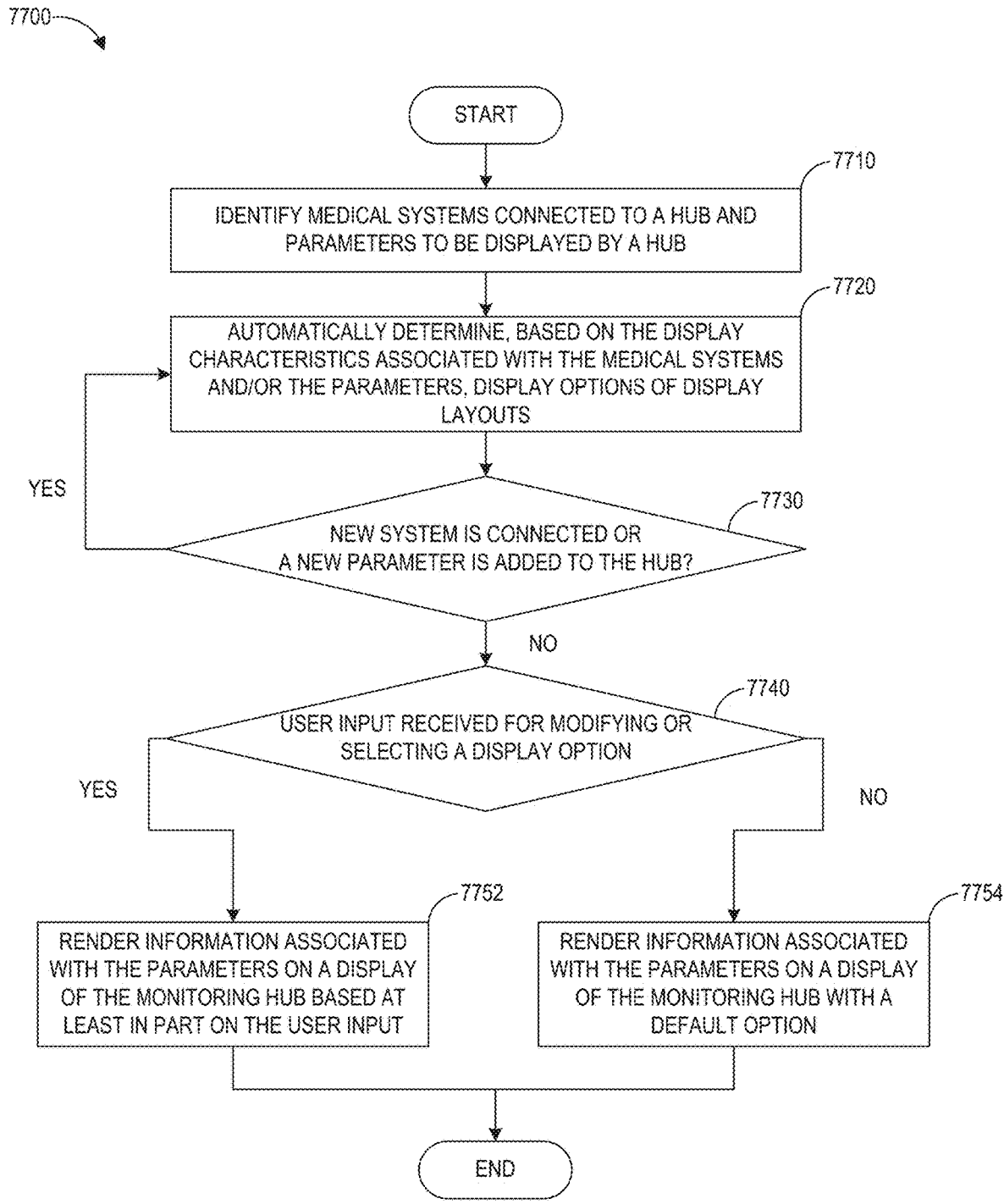
FIG. 77 illustrates an example process of configuring a monitoring hub's display.

FIG. 77 illustrates an example process of configuring a monitoring hub's display. The example 7700 can be performed by the monitoring hub 100 described herein.

At block 7710, the monitoring hub can identify medical systems connected to a hub and parameters to be displayed by the hub. The monitoring hub can obtain such information when the medical systems self-describe their functions to the monitoring hub upon connection. The self-description functions can be programmed using functions of the SDK described with reference to FIG. 74. The medical systems can also provide the monitoring hub display characteristics associated medical systems. For example, the medical systems can provide pre-configured display layout options for the parameters that will be communicated from the medical systems to the monitoring hub.

At block 7720, the monitoring hub can automatically determine display layout options based on the display characteristics associated with the medical systems and/or the parameters. For example, the monitoring hub can execute an algorithm which determines the display constraints of the medical systems or information associated with the parameters to be displayed. The output of the algorithms can include a set of potential display layout options for displaying the various parameters. The display characteristics can be supplied by the medical systems directly or can be determined by the monitoring hub 100 (for example, based on information of the medical systems and the parameters).

At block 7730, the monitoring hub can determine whether a new system is connected to the monitoring hub or a new parameter is added to the hub's display. For example, the monitoring hub can detect whether a new device is linked to the hub through the self-describing functions of the device. The monitoring hub can detect whether there are any new patient parameters based on the information provided by the newly connected device. A user of the monitoring hub can enable or disable the monitoring of some patient parameters. For example, the user can actuate a user interface element on the monitoring hub to cause a connected medical device to start monitoring a patient's parameter. As a result, the monitoring hub can automatically adjust the display layout options to accommodate the newly added parameter or device.

If there is no new system or parameter added to the hub, at block 7740, the monitoring hub 100 can determine whether a user input is received on the monitoring hub. A user can select a display layout among the display layout options. The user can also modify a display layout, for example, by changing the location or size subdivisions of the display layout or by adjusting display characteristics (for example, size, shape, location) of parameters within a subdivision.

If the user input is not received, at block 7754, the monitoring hub can automatically select a default option and render the display screen of the monitoring hub based on the default option. If the user input is received, at block 7752, the monitoring hub can automatically adjust the display screen and render the display screen based on the user input. Where the user changes a setting of a medical system (for example, by adjusting an alarm setting, or enabling/disabling a feature of the medical system, etc.), the monitoring hub 100 can also inform the medical system of the user's changes and the medical systems can take appropriate actions based on the user's changes.

Although the examples in FIGS. 72A through 77 are described with reference to a monitoring hub 100, similar functions and techniques described with reference to these figures can also be applied to an auxiliary device, such as, for example, the auxiliary device 2040 shown in FIG. 24.

X. Additional Examples

In certain aspects, a system for providing medical data translation for output on a medical monitoring hub can include a portable physiological monitor comprising a processor that can: receive a physiological signal associated with a patient from a physiological sensor, calculate a physiological parameter based on the physiological signal, and provide a first value of the physiological parameter to a monitoring hub for display. The monitoring hub can include a docking station that can receive the portable physiological monitor. The monitoring hub can: receive the first value of the physiological parameter from the portable physiological monitor; output the first value of the physiological parameter for display; receive physiological parameter data from a medical device other than the portable physiological monitor, the physiological parameter data formatted according to a protocol other than a protocol natively readable or displayable by the monitoring hub; pass the physiological parameter data to a translation module; receive translated parameter data from the translation module, where the translated parameter data can be readable and displayable by the monitoring hub; and output a second value from the translated parameter data for display.

The system of the preceding paragraph can be combined with any subcombination of the following features: the monitoring hub is further configured to output the first value of the physiological parameter and the second value from the translated parameter data on separate displays; the monitoring hub is further configured to output the second value from the translated parameter data to an auxiliary device having a separate display from a display of the monitoring hub; the auxiliary device is selected from the group consisting of a television, a tablet, a phone, a wearable computer, and a laptop; the physiological parameter data comprises data from an infusion pump; the physiological parameter data comprises data from a ventilator; and the translation module is configured to translate the physiological parameter data from a first Health Level 7 (HL7) format to a second HL7 format.

In certain aspects, a method of providing medical data translation for output on a medical monitoring hub can include: under the control of a first medical device comprising digital logic circuitry, receiving a physiological signal associated with a patient from a physiological sensor; obtaining a first physiological parameter value based on the physiological signal; outputting the first physiological parameter value for display; receiving a second physiological parameter value from a second medical device other than the first medical device, where the second physiological parameter value is formatted according to a protocol not used by the first medical device, such that the first medical device is not able to process the second physiological parameter value to produce a displayable output value; passing the physiological parameter data from the first medical device to a separate translation module; receiving translated parameter data from the translation module at the first medical device, the translated parameter data able to be processed for display by the first medical device; and outputting a second value from the translated parameter data for display.

The method of the preceding paragraph can be combined with any subcombination of the following features: further including translating the message by at least translating the message from a first Health Level 7 (HL7) format to a second HL7 format; the message can include data from a physiological monitor; the message can include data from an infusion pump or a ventilator; and the message can include data from a hospital bed.

In certain aspects, a system for providing medical data translation for output on a medical monitoring hub can include a first medical device including electronic hardware that can: obtain a first physiological parameter value associated with a patient; output the first physiological parameter value for display; receive a second physiological parameter value from a second medical device other than the first medical device, the second physiological parameter value formatted according to a protocol not used by the first medical device, such that the first medical device is not able to process the second physiological parameter value to produce a displayable output value; pass the physiological parameter data from the first medical device to a translation module; receive translated parameter data from the translation module at the first medical device, the translated parameter data able to be processed for display by the first medical device; and output a second value from the translated parameter data for display.

The system of the preceding paragraph can be combined with any subcombination of the following features: the first medical device can also output the first value of the physiological parameter and the second value from the translated parameter data on the same display; the first medical device can also output the first value of the physiological parameter and the second value from the translated parameter data on separate displays; the first medical device can also output the second value from the translated parameter data to an auxiliary device; the auxiliary device can be a television monitor; the auxiliary device can be selected from the group consisting of a tablet, a phone, a wearable computer, and a laptop; the first medical device can include the translation module; the first medical device can also pass the physiological parameter data to the translation module over a network; and the physiological parameter data can include data from an infusion pump or a ventilator.

XI. Terminology

Many other variations than those described herein will be apparent from this disclosure. For example, certain acts, events, or functions of any of the algorithms described herein can be performed in a different sequence, can be added, merged, or left out altogether (for example, not all described acts or events are necessary for the practice of the algorithms). Moreover, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular example of the examples disclosed herein. Thus, the examples disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the examples disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the examples disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another example, a processor can include an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the examples disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain examples include, while other examples do not include, certain features, elements and/or states. Thus, such conditional language is not generally intended to imply that features, elements and/or states are in any way required for one or more examples or that one or more examples necessarily include logic for deciding, with or without author input or prompting, whether these features, elements and/or states are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain examples require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various examples, it will be understood that various omissions, substitutions, and changes in the form and details of the devices or algorithms illustrated can be made without departing from the spirit of the disclosure. As will be recognized, the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A patient monitoring hub connectable to a plurality of physiological monitors, each physiological monitor configured to be in communication with one or more physiological sensors, the patient monitoring hub comprising:
  a plurality of ports operable to be in communication with the plurality of physiological monitors;
  a display; and
  a hardware processor configured to:
    identify a plurality of parameters to be displayed by the patient monitoring hub based at least in part on the plurality of physiological monitors connected to the patient monitoring hub, wherein each of the plurality of physiological monitors is configured to measure at least one parameter of the identified plurality of parameters and includes at least one preprogrammed display layout, wherein the plurality of physiological monitors comprise different types of independent medical devices each including their own displays that are configured to display the at least one parameter on the respective displays, the preprogrammed display layouts of the different types of independent medical devices being different from one another;
    generate a set of self-configurable display layout options based on layout restrictions, wherein the layout restrictions are based on the plurality of physiological monitors connected to the patient monitoring hub and the at least one preprogrammed display layout of each of the plurality of physiological monitors connected to the patient monitoring hub;

automatically populate a display layout manager on the display with the set of self-configurable display layout options;

output the plurality of parameters on the display according to a user selection of one of the self-configurable display layout options or a default selection by the hardware processor of one of the self-configurable display layout options in an absence of the user selection;

detect a change to the plurality of physiological monitors connected to the patient monitoring hub; and automatically update the set of self-configurable display layout options and the display layout manager based at least in part on the change.

2. The patient monitoring hub of claim 1, wherein the different types of independent medical devices comprise two or more of an oximetry monitor, a vital sign measurement system, an infusion pump system, a ventilator system, or an electronic patient bed system.

3. The patient monitoring hub of claim 1, wherein the set of self-configurable display layout options are based on layout restrictions, wherein the layout restrictions are based on a number and type of the plurality of physiological monitors, and the at least one preprogrammed display layout of each of the plurality of physiological monitors connected to the patient monitoring hub.

4. The patient monitoring hub of claim 3, wherein the layout restrictions are automatically provided to the patient monitoring hub by the plurality of physiological monitors while the plurality of physiological monitors and the patient monitoring hub are establishing a connection.

5. The patient monitoring hub of claim 4, wherein the layout restrictions further comprise at least one of:

an instruction to call a graphics library on the patient monitoring hub to draw a user interface element; or images or texts associated with displaying the at least one parameter.

6. The patient monitoring hub of claim 1, wherein the change comprises an addition or a removal of a physiological monitor connected to the hub.

7. The patient monitoring hub of claim 1, wherein the plurality of parameters comprise a parameter calculated by the patient monitoring hub.

8. The patient monitoring hub of claim 1, wherein the display is divided into a plurality of subdivisions wherein each subdivision comprises one or more parameters.

9. The patient monitoring hub of claim 8, wherein the hardware processor is further configured to:

receive a user input for adjusting a size or location of a subdivision; and automatically update displays of parameters in the plurality of subdivisions in response to the user input.

10. The patient monitoring hub of claim 1, wherein the hardware processor is further configured to receive a user input for adjusting settings of one or more medical systems.

11. The patient monitoring hub of claim 10, wherein the one or more medical systems comprise an alarm setting.

12. The patient monitoring hub of claim 10, wherein the user input comprises an instruction to enable a feature of the one or more medical systems.

13. The patient monitoring hub of claim 10, wherein the user input comprises an instruction to disable a feature of the one or more medical systems.

14. The patient monitoring hub of claim 10, wherein the hardware processor is further configured to inform the one or more medical systems of the user input.

15. The patient monitoring hub of claim 14, wherein one or more medical systems take one or more actions in response to the user input.

16. A method of managing displays of a patient monitoring hub connectable to a plurality of physiological monitors, each physiological monitor configured to be in communication with one or more physiological sensors, the method comprising:

under control of a hardware processor of the patient monitoring hub comprising a display:

identifying the plurality of physiological monitors connected to the patient monitoring hub;

identifying a plurality of parameters to be displayed by the patient monitoring hub based at least in part on information of the plurality of physiological monitors, wherein each of the plurality of physiological monitors is configured to measure at least one parameter of the identified plurality of parameters and includes at least one preprogrammed display layout, wherein the plurality of physiological monitors comprise different types of independent medical devices each including their own displays that are configured to display the at least one parameter on the respective displays, the preprogrammed display layouts of the different types of independent medical devices being different from one another;

generating a set of self-configurable display layout options based on layout restrictions, wherein the layout restrictions are based on the plurality of physiological monitors connected to the patient monitoring hub and the at least one preprogrammed display layout of each of the plurality of physiological monitors connected to the patient monitoring hub;

automatically populating a display layout manager on the display with the set of self-configurable display layout options;

outputting the plurality of parameters on the display according to a user selection of one of the self-configurable display layout options or a default selection by the hardware processor of one of the self-configurable display layout options in an absence of the user selection;

detecting a change to the plurality of physiological monitors connected to the patient monitoring hub; and automatically updating the set of self-configurable display layout options and the display layout manager based at least in part on the change.

* * * * *